US008691855B2

(12) United States Patent
Woo et al.

(10) Patent No.: US 8,691,855 B2
(45) Date of Patent: Apr. 8, 2014

(54) COMPOUNDS, ISOMER THEREOF, OR PHARMACEUTICALLY ACCEPTABLE SALTS THEREOF AS VANILLOID RECEPTOR ANTAGONIST AND PHARMACEUTICAL COMPOSITIONS CONTAINING THE SAME

(75) Inventors: Byoung Young Woo, Yongin-si (KR); Sun-Young Kim, Seoul (KR); Yeonjoon Kim, Yongin-si (KR); Song Seok Shin, Yongin-si (KR); Jin Kwan Kim, Suwon-si (KR); Ki-Wha Lee, Seoul (KR); Dong Hyun Kim, Uiwang-si (KR); Kyung Min Lim, Hwaseong-si (KR); Joo-Hyun Moh, Seoul (KR); Yeon Su Jeong, Yongin-si (KR); Jin Kyu Choi, Suwon-si (KR); Hyun Ju Koh, Anyang-si (KR); Jeongho Lee, Yongin-si (KR); Hyuk Kim, Yongin-si (KR); Jeong Hoon Yoon, Yongin-si (KR); Funan Li, Seoul (KR); Jee-Suk Kim, Pusan (KR); Young-Ger Suh, Gunpo-si (KR)

(73) Assignee: Amorepacific Corporation, Seoul (KR)

( * ) Notice: Subject to any disclaimer, the term of this patent is extended or adjusted under 35 U.S.C. 154(b) by 535 days.

(21) Appl. No.: 13/002,289

(22) PCT Filed: Jul. 2, 2009

(86) PCT No.: PCT/KR2009/003627
§ 371 (c)(1),
(2), (4) Date: Jan. 7, 2011

(87) PCT Pub. No.: WO2010/002209
PCT Pub. Date: Jan. 7, 2010

(65) Prior Publication Data
US 2011/0152318 A1 Jun. 23, 2011

Related U.S. Application Data

(60) Provisional application No. 61/077,600, filed on Jul. 2, 2008.

(51) Int. Cl.
C07D 263/42 (2006.01)
C07D 263/38 (2006.01)
C07D 307/52 (2006.01)
C07D 277/42 (2006.01)

(52) U.S. Cl.
CPC .......... C07D 263/42 (2013.01); C07D 263/38 (2013.01); C07D 307/52 (2013.01); C07D 277/42 (2013.01)
USPC ........... 514/374; 514/376; 514/365; 514/473; 548/200; 548/228; 548/236; 549/487

(58) Field of Classification Search
USPC .......... 514/365, 374, 448, 471; 548/188, 200, 548/236; 549/72, 487
See application file for complete search history.

(56) References Cited

U.S. PATENT DOCUMENTS

| 2004/0192728 A1 | 9/2004 | Codd et al. |
| 2006/0035882 A1 | 2/2006 | Koga et al. |
| 2006/0035939 A1 | 2/2006 | Koga et al. |
| 2006/0122231 A1 | 6/2006 | Lee et al. |
| 2006/0223868 A1 | 10/2006 | Besidski et al. |
| 2007/0149513 A1 | 6/2007 | Chen et al. |
| 2007/0149517 A1 | 6/2007 | Koga et al. |

FOREIGN PATENT DOCUMENTS

| WO | WO 02/16318 A1 | 2/2002 |
| WO | WO 02/16319 A1 | 2/2002 |
| WO | WO 02/061317 A2 | 8/2002 |
| WO | WO 02/090326 A1 | 11/2002 |
| WO | WO 03/029199 A1 | 4/2003 |
| WO | WO 03/049702 A2 | 6/2003 |
| WO | WO 03/053945 A2 | 7/2003 |
| WO | WO 03/070247 A1 | 8/2003 |
| WO | WO 03/099284 A1 | 12/2003 |
| WO | WO 2004/007495 A1 | 1/2004 |
| WO | WO 2004/014871 A1 | 2/2004 |
| WO | WO 2004/024154 A1 | 3/2004 |
| WO | WO 2004/024710 A1 | 3/2004 |
| WO | WO 2004/029031 A2 | 4/2004 |
| WO | WO 2004/035549 A1 | 4/2004 |
| WO | WO 2004/056823 A1 | 7/2004 |
| WO | WO 2004/072068 A1 | 8/2004 |
| WO | WO 2004/072069 A1 | 8/2004 |
| WO | WO 2004/089877 A1 | 10/2004 |
| WO | WO 2004/089881 A1 | 10/2004 |
| WO | WO 2004/111009 A1 | 12/2004 |
| WO | WO 2005/003084 A1 | 1/2005 |

(Continued)

OTHER PUBLICATIONS

Schafer et al. Drug Discovery Today 2008, 13 (21/22), 913-916.*
Horig et al. Journal of Translational Medicine 2004, 2(44).*
Akabori et al., "Transient receptor potential vanilloid I antagonist, capsazepine, improves survival in a rat hemorrhagic shock model," 2007, Ann. Surg., 245(6), pp. 964-970.

(Continued)

Primary Examiner — Michael Barker
(74) Attorney, Agent, or Firm — Merchant & Gould P.C.

(57) ABSTRACT

This present invention relates to novel compounds, isomer thereof or pharmaceutically acceptable salts thereof as vanilloid receptor (Vanilloid Receptor 1; VR1; TRPV1) antagonist; and a pharmaceutical composition containing the same. The present invention provides a pharmaceutical composition for preventing or treating a disease such as pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, heart disease and so on.

29 Claims, No Drawings

(56) References Cited

FOREIGN PATENT DOCUMENTS

| | | |
|---|---|---|
| WO | WO 2005/044786 A1 | 5/2005 |
| WO | WO 2005/044802 A2 | 5/2005 |
| WO | WO 2005/047279 A1 | 5/2005 |
| WO | WO 2005/047280 A1 | 5/2005 |
| WO | WO 2005/049601 A1 | 6/2005 |
| WO | WO 2005/049613 A1 | 6/2005 |
| WO | WO 2005/051390 A1 | 6/2005 |
| WO | WO 2005/703193 A1 | 8/2005 |
| WO | WO 2006/051378 A1 | 5/2006 |
| WO | WO 2006/095263 A1 | 9/2006 |
| WO | WO 2006/097817 A1 | 9/2006 |
| WO | WO 2006/098554 A1 | 9/2006 |
| WO | WO 2006/100520 A1 | 9/2006 |
| WO | WO 2006/101318 A1 | 9/2006 |
| WO | WO 2006/101321 A1 | 9/2006 |
| WO | WO 2006/102645 A1 | 9/2006 |
| WO | WO 2006/103503 A1 | 10/2006 |
| WO | WO 2006/111346 A1 | 10/2006 |
| WO | WO 2006/113769 A1 | 10/2006 |
| WO | WO 2006/116563 A1 | 11/2006 |
| WO | WO 2006/120481 A2 | 11/2006 |
| WO | WO 2006/122250 A2 | 11/2006 |
| WO | WO 2006/122799 A1 | 11/2006 |
| WO | WO 2006/129164 A1 | 12/2006 |
| WO | WO 2007/042906 A1 | 4/2007 |
| WO | WO 2007/045462 A2 | 4/2007 |
| WO | WO 2007/050732 A1 | 5/2007 |
| WO | WO 2007/054474 A1 | 5/2007 |
| WO | WO 2007/054480 A1 | 5/2007 |
| WO | WO 2007/063925 A1 | 6/2007 |
| WO | WO 2007/065662 A2 | 6/2007 |
| WO | WO 2007/065663 A1 | 6/2007 |
| WO | WO 2007/065888 A1 | 6/2007 |
| WO | WO 2007/067619 A2 | 6/2007 |
| WO | WO 2007/067710 A1 | 6/2007 |
| WO | WO 2007/067711 A2 | 6/2007 |
| WO | WO 2007/067756 A2 | 6/2007 |
| WO | WO 2007/067757 A2 | 6/2007 |
| WO | WO 2007/069773 A1 | 6/2007 |
| WO | WO 2007/133637 A2 | 11/2007 |

OTHER PUBLICATIONS

Akerman et al., "Anandamide acts as a vasodilator of dural blood vessels in vivo by activating TRPV1 receptors," 2004, Br. J. Pharmcol., 142, pp. 1354-1360.

Appendino et al., "Clinically useful vanilloid receptor TRPV1 antagonists: Just around the corner (or too early to tell)?" 2006, Progress in Medicinal Chemistry, 44, pp. 145-180.

Balaban et al., "Type 1 vanilloid receptor expression by mammalian inner ear ganglion cells," 2003, Hear Res. 175, pp. 165-170.

Birder et al., "Vanilloid receptor expression suggests a sensory role for urinary bladder epithelial cells," 2001, PNAS, 98, pp. 13396-13401.

Birder et al., "altered urinary bladder function in mice lacking the vanilloid receptor TRPV1," 2002, Nat. Neuroscience, 5, pp. 856-860.

Biro et al., "Hair cycle control by vanilloid receptor-1 (TRPV1): evidence from TRPV1 knockout mice," 2006, J. Invest. Dermatol, pp. 1-4.

Bodo et al., "Hot new twist to hair biology: Involvement of vanilloid receptor-1 (VR1/TRPV1) signaling in human hair growth control," 2005, Am. J. Patho. 166, pp. 985-998.

Caterina et al., "The capsaicin receptor: a heat-activated ion channel in the pain pathway," 1997, Nature, 389, pp. 816-824.

Caterina et al., "hnparied nociception and pain sensation in mice lacking the capsaicin receptor," 2000, Science, 288, pp. 306-313.

Chan et al., "Sensory fibres expressing capsaicin receptor TRPV1 in patients with rectal hypersensitivity and faecal urgency," 2003, Lancet, 361, pp. 385-391.

Correll et al., "Advances in the development of TRPV1 antagonists," 2006, Expert Opin. Ther. Patents, 16, pp. 783-795.

Cortright et al., "The tissue distribution and functional characterization of human VR1," 2001, Biochemical and Biophysical Research Communications, 281, pp. 1183-1189.

Davis et al., "Vanilloid receptor-1 is essential for inflammatory thermal hyperalgesia," 2000, Nature, 405, pp. 183-187.

Denda et al., "Immunoreactivity of VR1 on epidermal keratinocyte of human skin," 2001, Biochem. Biophys. Res. Commun., 285, pp. 1250-1252.

Dinis et al., "Anandamide-evoked activation of vanilloid receptor 1 contributes to the development of bladder hyperreflexia and nocicptive transmission to spinal dorsal hom neurons in cystitis," 2004, J. Neurosci., 24, pp. 11253-11263.

Dinis et al., "The distribution of sensor fibers immunoreactive for the TRPV1 (Capsaicin) receptor in the human prostate," 2005, Eur. Urol., 48, pp. 62-67.

Faucher et al., "Design, synthesis and evaluation of trifluormethane sulfonamide derivatives as new potent and selective peroxisome proliferator-activated receptor α agonists," 2008, Bioorganic & Medicinal Chemistry Letters, pp. 710-715.

Garcia-Martinez et al., "Attenuation of thermal nociception and hyperalgesia by VR1 blockers," 2002, PNAS, 99, pp. 2374-2379.

Geppetti et al., "Activation and sensitization of the vanilloid receptor: role in gastroinstestinal inflammation and function," 2004, Br. J. Pharmacol., 141, pp. 1313-1320.

Geppetti et al., "The transient receptor potential vanilloid I: Role in airway inflammation and disease," 2006, Eur. J. Pharmacol., 533, pp. 207-214.

Ghilardi et al., "Selective blockade of the capsaicin receptor TRPV1 attenuates bone cancer pain," 2005, J. Neurosci., 25, 3126-31.

Gopinath et al., "Increasedcapsaicin receptor TRPV1 in skin nerve fibres and related vanilloid receptors TRPV3 and TRPV4 in keratinocytes in human breast pain," 2005, BMC Womens Health, 5, 2-9.

Gram et al., "Capsaicin-sensitive sensory fibers in the islets of Langerhans contribute to defectie insulin secretion in Zucker diabetic rat, an animal model for some aspects of human type 2 diabetes," 2007, Eur. J. Neurosci., 25, pp. 213-223.

Gunthorpe et al., "Peripheral TRPV1 receptors as targets for drug development: New molecules and mechanisms," 2008, Curr. Pharm. Des., 14, pp. 32-41.

Holzer P, "TRPV1 and the gut: from a tasty receptor for a painful vanilloid to a key player in hyperalgesia,"2004, Eur. J. Pharm., 500, pp. 231-241.

Holzer P., "Capsaicin: cellular targets, mechanisms of action, and selectivity for thing sensory neurons," 1991, Pharmacological Reviews, 43, pp. 143-201.

Hutter et al., "Transient receptor potential vanilloid (TRPV-1) promotes neurogenic inflammation in the pancrease via activation of the neurokinin-1 receptor (NK-1R)," 2005, Pancreas, 30, pp. 260-265.

Hwang et al., "Direct activation of capsaicin receptors by products of lipoxygenases: Endogenous capsaicin-like substances," 2000, PNAS, 97, pp. 6155-6160.

Hwang et al., "Hot channels in airways: pharmacology of the vanilloid receptor," 2002, Curr. Opin. Pharmacol. pp. 235-242.

tmmke et al., "The TRPV1 receptor and nociception," 2006, Semin. Cell. Dev. Biol., 17(5), pp. 582-591.

Inoue et al., "Functional vanilloid receptors in cultured normal human epidermal keratinocytes," 2002, Biochem. Biophys. Res. Commun., 291, pp. 124-129.

Inoue et al., "Transient receptor potential channels in cardiovascular function and disease," 2006, Cir. Res., 99, pp. 119-131.

'Camel et al., "Role of vanniloid VR1 receptor in thermal allodynia and hyperalgesia in diabetic mice," 2001, Eur. J. Pharmacol. 422, pp. 83-86.

Karai et al., "Deletion of vanilloid receptor 1-expressing primary afferent neurons for pain control," 2004, J. Clin. Invest., 113, pp. 1344-1352.

Kim et al., "Transient receptor potential vanilloid subtype 1 mediates cell death of mesencephalic dopaminergic neurons In Vivo and In Vitro," 2005, J. Neurosci. 25(3), pp. 662-671.

Kyle et al., "TRPV1 antagonists: a survey of the patent literature," 2006, Expert Opin. Ther. Patents, 16, pp. 977-996.

(56) References Cited

OTHER PUBLICATIONS

Ma et al., "Inflammatory mediators modulating the transient receptor potential vanilloid I receptor: therapeutic targets to treat inflammatory and neuropathic pain," 2007, Expert Opin. Ther. Targets, 11(3), pp. 307-320.

Marsch et al., "Reduced anxiety, conditioned fear, and hippocampal long-term potentiation in transient receptor potential vanilloid type 1 receptor-deficient mice," 2007, J. Neurosci., 27(4), pp. 832-839.

McLeod et al., "TRPV1 antagonists attenuate antigen-provoked cough in ovalbumin sensitized guinea pigs," 2006, Cough, 2, 10.

Mezey et al., "Distribution of mRNA for vanilloid receptor subtype 1 (VR1), and VR1-like immunoreactivity, in the central nervous system of the rat and human," 2000, PNAS, 97, pp. 3655-3660.

Morgan et al., "Vanilloid receptor 1 expression in human tooth pulp in relation to caries and pain," 2005, J. Orofac. Pain, 19, pp. 248-260.

Motter et al., "TRPV1-null mice are protected from diet-induced obesity," 2008, FEBS lett., 582, pp. 2257-2262.

Nagy et al., "The role of vanilloid (capsaicin) receptor (TRPV1) in physiology and pathology," 2004, Eur. J. Pharmacol. 500, 351-369.

Pan et al., "Sensing tissue ischemia: Another new function for capsaicin receptors?" 2004, Circulation 110, pp. 1826-1831.

Park et al., "Nitric oxide mediates capsaicin-induced cytotoxicity in cultured dorsal root ganglion neurons," 1999, Arch. Pharm. Res. 22, pp. 432-434.

Petersen et al., "Capsaicin evoked pain and allodynia in post-herpetic neuralgia," 2000, Pain 88, pp. 125-133.

Rami et al., "The therapeutic potential of TRPV1 (VR1) antagonists: clinical answers await," 2004, Drug Discovery Today: Therapeutic Strategies, 1, pp. 97-104.

Razavi et al., "TRPV1$^+$ sensory neurons control β cell stress and islet inflammation in autoimmune diabetes," 2006, Cell, 127, pp. 1123-1135.

Scotland et al., "Vanilloid receptor TRPV1, sensory c-fibers, and vascular autoregulation," 2004, Circ. Res. 95, pp. 1027-1034.

Sculptoreanu et al., Protein kinase C contributes to abnormal capsaicin responses in DRG neurons from cats with feline interstitial cystitis, 2005, Neurosci. Lett. 381, pp. 42-46.

Seki et al., "Expression and localization of TRPV1 in human nasal mucosa," 2006, Rhinology, 44, pp. 128-134.

Southall et al., "Activation of epidermal vanilloid receptor-1 induces release of proinflmmatory mediators in human keratinocytes," 2003, J. Pharmacol. Exp. Ther., 304, pp. 217-222.

Spina et al., "Pharmacology of airway irritability," 2002, Curr. Opin. Pharmacol. pp. 264-272.

Stander et al., "Expression of vanilloid receptor subtype 1 in cutaneous sensory nerve fibers, mast cells, and epithelial cells of appendage structures," 2004, Exp. Dermatol. 13, pp. 129-139.

Suri et al., "The emerging role of TRPV1 in diabetes and obesity," 2008, Trends Pharmacol .1 Sci. 29(1), pp. 29-36.

Szallasi et al., "The vanilloid receptor TRPV1: 10 years from channel cloning to antagonists proof-of-concept," 2007, Nat. Rev. Drug Discov., 6, pp. 357-372.

Tominaga et al., "The cloned capsaicin receptor integrates multiple pain-producing stimuli," 1998, Neuron, 21 pp. 531-543.

Tympanidis et al., "Increased vanilloid receptor VR1 innervation in vulvodynia," 2004, Eur. J. Pain, 8, pp. 129-133.

Veronesi et al., "Neurogenic inflammation and particulate matter (PM) air pollutants," 2001, NeuroToxicology, 22, pp. 795-810.

Walker et al., "The VR1 antagonist capsazepine reverses mechanical hyperalgesia in models of inflammatory and neurpathic pain," 2003, J. Phammcol. Exp. Ther., 304, pp. 56-62.

Yiangou et al., "Vanilloid receptor 1 immunoreactivity in inflamed human bowel," 2001, Lancet 357, pp. 1338-1339.

Supplementary European Search Report for related EP Application No. 09773745.6 mailed Jun. 28, 2011.

International Search Report for corresponding International Application No. PCT/KR2009/003627 mailed Feb. 25, 2010.

Written Opinion for corresponding International Application No. PCT/KR2009/003627 mailed Feb. 25, 2010.

\* cited by examiner

(12) United States Patent
US 8,691,855 B2

COMPOUNDS, ISOMER THEREOF, OR PHARMACEUTICALLY ACCEPTABLE SALTS THEREOF AS VANILLOID RECEPTOR ANTAGONIST AND PHARMACEUTICAL COMPOSITIONS CONTAINING THE SAME

This application is a National Stage Application of PCT/KR2009/003627, filed Jul. 2, 2009, which claims benefit of Ser. No. 61/077,600, filed Jul. 2, 2008 in the United States and which applications are incorporated herein by reference. To the extent appropriate, a claim of priority is made to each of the above disclosed applications.

TECHNICAL FIELD

The present invention relates to novel compounds, isomer thereof or pharmaceutically acceptable salts thereof as TRPV1 antagonist; and a pharmaceutical composition containing the same.

BACKGROUND ART

The vanilloid receptor-1 (VR1, or transient receptor potential vanilloid-1, TRPV1) is the receptor for capsaicin (8-methyl-N-vanillyl-6-nonenamide), a pungent ingredient in hot peppers. The molecular cloning of TRPV1 was reported in 1997 (Caterina et al., 1997, Nature, 389, pp 816-824), which belongs to the TRP channel family of non-selective cation channel. TRPV1 is activated or sensitized by stimuli such as capsaicin, resin iferatoxin, heat, acid, anandamide, lipid metabolites or the like; thus it plays a crucial role as a molecular integrator of noxious stimuli in mammals (Tominaga et al., 1998, Neuron, 21 pp 531-543; Hwang et al., 2000, PNAS, 97, pp 6155-6160). The TRPV1 is highly expressed in primary afferent sensory neurons, and also reportedly expressed in various organs and tissues such as bladder, kidney, lung, intestine, skin, central nervous system (CNS), and non-neuronal tissues (Mezey et al., 2000, PNAS, 97, pp 3655-3660; Stander et al., 2004, Exp. Dermatol. 13, pp 129-139; Cortright et al., 2001, BBRC, 281, pp 1183-1189), and besides TRPV1 protein is upregulated in painful disease conditions. Activation of the TRPV1 by endogenous/exogenous stimuli leads to not only transmission of noxious stimuli, but also liberation of neuropeptides such as substance P, CGRP (Calcitonin Gene-Related Peptide) in the neurons, thereby causing neurogenic inflammation. TRPV1 knock-out mice show normal responses in a wide range of behavioural tests including noxious mechanical and acute thermal stimuli, but exhibit little thermal hypersensitivity in inflammation states. (Caterina et al., 2000, Science, 288, pp 306-313; Davis et al., 2000, Nature, 405, pp 183-187; Karai et al., 2004, J. Clin. Invest., 113, pp 1344-1352).

As mentioned above, the TRPV1 knock-out mice exhibit reduced responses to thermal or noxious stimuli, which has been supported by the effects of TRPV1 antagonists in various animal models of pain (Immke et al., 2006, Semin. Cell. Dev. Biol., 17(5), pp 582-91; Ma et al., 2007, Expert Opin. Ther. Targets, 11(3), pp 307-20). The well-known TRPV1 antagonist, capsazepine, decreases hyperalgesia caused by physical stimuli in several models of inflammatory and neuropathic pain (Walker et al., 2003, JPET, 304, pp 56-62; Garcia-Martinez et al., 2002, PNAS, 99, 2374-2379). In addition, treatment of the primary culture of afferent sensory neurons with the TRPV1 agonist, capsaicin etc., results in damage to nerve functions and furthermore death of nerve cells. The TRPV1 antagonist exerts defense actions against such damage to nerve functions and nerve cell death (Holzer P., 1991, Pharmacological Reviews, 43, pp 143-201; Mezey et al., 2000, PNAS, 97, 3655-3660). The TRPV1 is expressed on sensory neurons distributed in all regions of the gastrointestinal tract and is highly expressed in inflammatory disorders such as irritable bowel syndrome and inflammatory bowel disease (Chan et al., 2003, Lancet, 361, pp 385-391; Yiangou et al., 2001, Lancet, 357, pp 1338-1339). In addition, activation of the TRPV1 stimulates sensory nerves, which in turn causes release of neuropeptides which are known to play a critical role in pathogenesis of gastrointestinal disorders such as gastro-esophageal reflux disease (GERD) and stomach duodenal ulcer (Holzer P., 2004, Eur. J. Pharmacol. 500, pp 231-241; Geppetti et al., 2004, Br. J. Pharmacol., 141, pp 1313-1320).

The TRPV1-expressing afferent nerves are abundantly distributed in airway mucosa, and bronchial hypersensitivity is very similar mechanism to hyperalgesia. Protons and lipoxygenase products, known as endogenous ligands for the TRPV1, are well known as crucial factors responsible for development of asthma and chronic obstructive pulmonary diseases (Hwang et al., 2002, Curr. Opin. Pharmacol. pp 235-242; Spina et al., 2002, Curr. Opin. Pharmacol. pp 264-272). Moreover, it has been reported that air-polluting substances which are a kind of asthma-causing substances, i.e., particulate matter specifically acts on the TRPV1 and such action is inhibited by capsazepine (Veronesi et al., 2001, NeuroToxicology, 22, pp 795-810). Urinary bladder hypersensitiveness and urinary incontinence are caused by various central/peripheral nerve disorders or injury, and TRPV1 expressed in afferent nerves and urothelial cells play an important role in bladder inflammation. (Birder et al., 2001, PNAS, 98, pp 13396-13401). Further, TRPV1 knock-out mice are anatomically normal but have higher frequency of low-amplitude, non-voiding bladder contractions and reduced reflex voiding during bladder filling as compared to wild type mice, which is thus indicating that the TRPV1 affects functions of the bladder (Birder et al., 2002, Nat. Neuroscience, 5, pp 856-860). The TRPV1 is distributed in human epidermal keratinocytes as well as in primary afferent sensory nerves (Benda et al., 2001, Biochem. Biophys. Res. Commun., 285, pp 1250-1252; Inoue et al., 2002, Biochem. Biophys. Res. Commun., 291, pp 124-129), and it is then involved in transmission of various noxious stimuli and pains such as skin irritation and pruritus, thereby having close correlation with etiology of dermatological diseases and disorders, such as skin inflammation, due to neurogenic/non-neurogenic factors. This is supported by the report that the TRPV1 antagonist, capsazepine inhibits inflammatory mediators in human skin cells (Southall et al., 2003, J. Pharmacol. Exp. Ther., 304, pp 217-222). Over recent years, evidence has been accumulation on other roles of TRPV1. TRPV1 might be involved in the blood flow/pressure regulation via sensory vasoactive neuropeptide release and in the regulation of plasma glucose levels or in the pathogenesis of type 1 diabetes (Inoue et al., Cir. Res., 2006, 99, pp 119-31; Razavi et al., 2006, Cell, 127, pp 1123-35; Gram et al., 2007, Eur. J. Neurosci., 25, pp 213-23). Further, it is reported that TRPV1 knock-out mice show less anxiety-related behavior than their wild type littermates with no differences in locomotion (Marsch et al., 2007, J. Neurosci., 27(4), pp 832-9). Recently, it is also reported the relations between TRPV1 and obesity. TRPV1 null mice have reduced body mass and adiposity on a higher fat diet and wild-type in this report (Motter et al., 2008, FEBS lett., 582, pp 2257-2262). Further, it is reported that TRPV1 expressing nerves have a role in the type 1 diabetic mellitus (T1DM) and the blockade of TRPV1 by small molecule antagonists improves insulin resistance in murine model of type 2 diabetic mellitus (T2DM). (Suri et al., 2008, Trends Pharmacol.) Sci. 29(1), pp 29-36; Gunthorpe et al., 2008, Curr. Pharm. Des., 14, pp 32-41)

Based on the above-mentioned information, development of various TRPV1 antagonists is under way, and some patents and patent applications relating to TRPV1 antagonists under development were published. (Szallasi et al., 2007, Nat. Rev. Drug Discov., 6, pp 357-72; Appendino et al., 2006, Progress in Medicinal Chemistry, 44, pp 145-180; Rami et al., 2004, Drug Discovery Today: Therapeutic Strategies, 1, pp 97-104; Correll et al., 2006, Expert Opin. Ther. Patents, 16, pp 783-795; Kyle et al., 2006, Expert Opin. Ther. Patents, 16, pp 977-996; Gunthorpe et al., 2008, Curr. Pharm. Des., 14, pp 32-41)

Compounds of the present invention, are useful for prophylaxis and treatment of diseases associated with the activity of TRPV1 (Nagy et al., 2004, Eur. J. Pharmacol. 500, 351-369) including but not limited to, pain such as acute pain, chronic pain, neuropathic pain, post-operative pain, rheumatic arthritic pain, osteoarthritic pain, postherpetic neuralgia, neuralgia, headache, dental pain, pelvic pain, migraine, bone cancer pain, mastalgia and visceral pain (Petersen et al., 2000, Pain 88, pp 125-133; Walker et al., 2003, J. Pharmacol. Exp. Ther., 304, pp 56-62; Morgan et al., 2005, J. Orofac. Pain, 19, pp 248-60; Dinis et al., 2005, Eur. Urol., 48, pp 162-7; Akerman et al., 2004, Br. J. Pharmcol., 142, pp 1354-1360; Ghilardi et al., 2005, J. Neurosci., 25, 3126-31; Gopinath et al., 2005, BMC Womens Health, 5, 2-9); nerve-related diseases such as neuropathies, HIV-related neuropathy, nerve injury, neurodegeneration, and stroke (Park et al., 1999, Arch. Pharm. Res. 22, pp 432-434; Kim et al., 2005, J. Neurosci. 25(3), pp 662-671); diabetic neuropathy (Kamei et al., 2001, Eur. J. Pharmacol. 422, pp 83-86); fecal urgency; irritable bowel syndrome (Chan et al., 2003, Lancet, 361, pp 385-391); inflammatory bowel disease (Yiangou et al., 2001, Lancet 357, pp 1338-1339); gastrointestinal disorders such as gastro-esophageal reflux disease (GERD), stomach duodenal ulcer and Crohn's disease (Holzer P, 2004, Eur. J. Pharm., 500, pp 231-241; Geppetti et al., 2004, Br. J. Pharmacol., 141, pp 1313-1320); respiratory diseases such as asthma, chronic obstructive pulmonary disease, cough (Hwang et al., 2002, Curr. Opin. Pharmacol. pp 235-242; Spina et al., 2002, Curr. Opin. Pharmacol. pp 264-272; Geppetti et al., 2006, Eur. J. Pharmacol., 533, pp 207-214; McLeod et al., 2006, Cough, 2, 10); urinary incontinence (Birder et al., 2002, Nat. Neuroscience 5, pp 856-860); urinary bladder hypersensitiveness (Birder et al., 2001, PNAS, 98, pp 13396-13401); neurotic/allergic/inflammatory skin diseases such as psoriasis, pruritus, prurigo and dermatitis (Southall et al., 2003, J. Pharmacol. Exp. Ther., 304, pp 217-222); irritation of skin, eye or mucous membrane (Tominaga et al., 1998, Neuron 21 pp 531-543); hyperacusis; tinnitus; vestibular hypersensitiveness (Balaban et al., 2003, Hear Res. 175, pp 165-70); cardiac diseases such as myocardial ischemia (Scotland et al., 2004, Circ. Res. 95, pp 1027-1034; Pan et al., 2004, Circulation 110, pp 1826-1831); haemorrhagic shock (Akabori et al., 2007, Ann. Surg., 245(6), pp 964-70); hair growth-related disorders such as hirsutism, effluvium, alopecia (Bodo et al., 2005, Am. J. Patho. 166, pp 985-998; Biro et al., 2006, J. Invest. Dermatol. pp 1-4); rhinitis (Seki et al., 2006, Rhinology, 44, pp 128-34); pancreatitis (Mutter et al., 2005, Pancreas, 30, pp 260-5); cystitis (Dinis et al., 2004, J. Neurosci., 24, pp 11253-63; Sculptoreanu et al., 2005, Neurosci. Lett. 381, pp 42-6); vulvodynia (Tympanidis et al., 2004, Eur. J. Pain, 8, pp 12-33); psychiatric disorders such as anxiety or fear (Marsch et al., 2007, J. Neurosci., 27(4), pp 832-9); obesity (Motter et al., 2008, FEBS lett., 582, pp 2257-2262); T1DM and T2DM (Suri et al., 2008, Trends Pharmacol. Sci. 29(1), pp 29-36; Gunthorpe et al., 2008, Curr. Pharm. Des., 14, pp 32-41).

Compounds that are related to VR1 activities are discussed e.g. in WO 02/61317, WO 02/090326, WO 02/16318, WO 02/16319, WO 03/053945, WO 03/099284, WO 03/049702, WO 03/049702, WO 03/029199, WO 03/70247, WO 04/07495, WO 04/72068, WO 04/035549, WO 04/014871, WO 04/024154, WO 04/024710, WO 04/029031, WO 04/089877, WO 04/089881, WO 04/072069, WO 04/111009, WO 05/03084, WO 05/073193, WO 05/051390, WO 05/049613, WO 05/049601, WO 05/047280, WO 05/047279, WO 05/044802, WO 05/044786, WO 06/097817, WO 06/098554, WO 06/100520, WO 06/101321, WO 06/102645, WO 06/103503, WO 06/111346, WO 06/101321, WO 06/101318, WO 06/1113769, WO 06/116563, WO 06/120481, WO 06/122250, WO 06/122799, WO 06/129164, WO 06/51378, WO 06/95263, WO 07/42906, WO 07/45462, WO 07/50732, WO 07/54474, WO 07/54480, WO 07/63925, WO 07/65663, WO 07/65888, WO 07/67619, WO 07/67710, WO 07/67711, WO 07/67756, WO 07/67757, WO07/63925, WO07/65662, WO07/65663, WO07/65888, WO07/69773, US20070149517, or US20070149513.

DISCLOSURE

Technical Problem

It is an object of the present invention to provide novel compounds useful as a potent antagonist for a TRPV1, isomer thereof and pharmaceutically acceptable salts thereof; and a pharmaceutical composition comprising the same.

Technical Solution

The present invention provides a novel compound of the following formula (I), an isomer, or a pharmaceutically acceptable salt thereof:

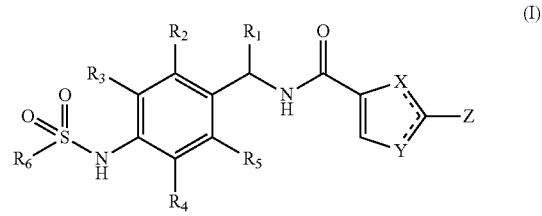

wherein,

X and Y are independently CH, N, O, or S;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;

$R_6$ is C1-C5 alkyl, halo(C1-C5) alkyl, or C2-C5 alkenyl; and

Z is

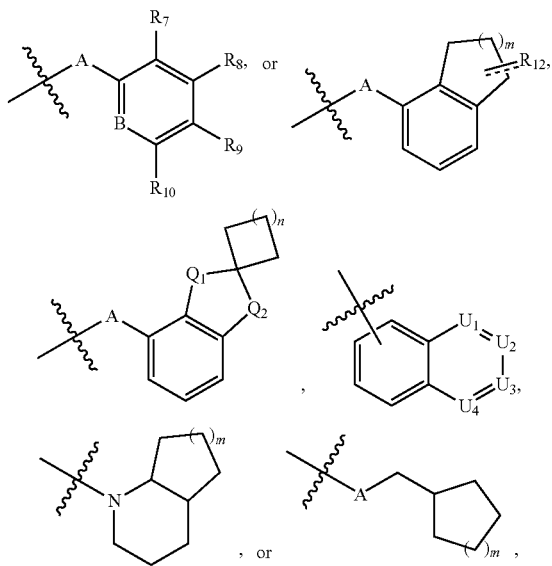

wherein,
A is a single bond, CH$_2$, NH, or O;
B is N or CR$_{11}$;
----- is a single bond or a double bond;
Q$_1$ and Q$_2$ are independently O or CH$_2$;
U$_1$, U$_2$, U$_3$, and U$_4$ are independently CH or N, and if anyone of U$_1$ to U$_4$ is N, the rest are independently CH;
m is 1 or 2;
n is 0, 1 or 2;
R$_7$, R$_8$, R$_9$, R$_{10}$, and R$_{11}$ are independently hydrogen, halogen, nitro, cyano, C1-C10 alkyl, C1-C10 alkoxy, halo(C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio;
R$_{12}$ is hydrogen, halogen, C1-C3 alkyl, or halo(C1-C3)alkyl wherein ----- is a single bond, and CH$_2$ or CHR$_{13}$ wherein ----- is a double bond; and
R$_{13}$ is C1-C5 alkyl.

One preferred aspect of the present invention is a compound of the formula (II), an isomer, or a pharmaceutically acceptable salt thereof;

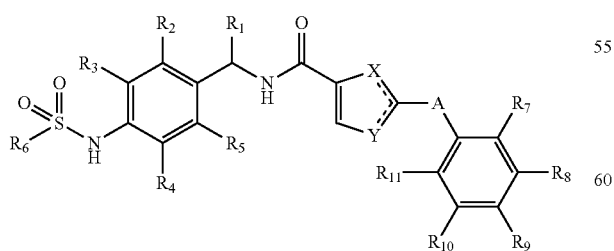

(II)

wherein,
X and Y are independently CH, N, O, or S;
A is CH$_2$, NH, or O;
R$_1$ is hydrogen, halogen, or C1-C5 alkyl;
R$_2$, R$_3$, R$_4$, and R$_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;
R$_6$ is C1-C5 alkyl, halo(C1-C5) alkyl, or C2-C5 alkenyl; and
R$_7$, R$_8$, R$_9$, R$_{10}$, and R$_{11}$ are independently hydrogen, halogen, nitro, cyano, C1-C10 alkyl, C1-C10 alkoxy, halo (C1-C10) alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

Another preferred aspect of the present invention is a compound of the formula (III), an isomer, or a pharmaceutically acceptable salt thereof;

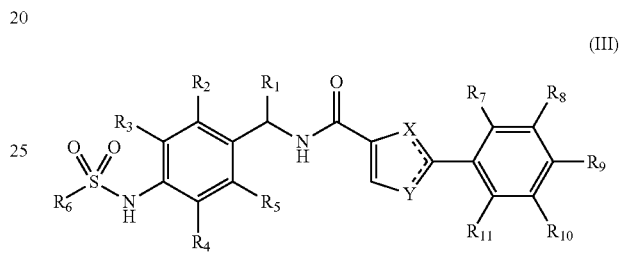

(III)

wherein,
X and Y are independently CH, N, O, or S;
R$_1$ is hydrogen, halogen, or C2-C5 alkyl;
R$_2$, R$_3$, R$_4$, and R$_5$ are independently hydrogen, halogen, nitro, cyano, C1-C5 alkyl, C2-C5 alkoxy, halo(C2-C5) alkyl, C2-C5 alkenyl, C2-C5 alkynyl, or carboxy;
R$_6$ is C2-C5 alkyl, halo(C2-C5) alkyl, or C2-C5 alkenyl; and
R$_7$, R$_8$, R$_9$, R$_{10}$, and R$_{11}$ are independently hydrogen, halogen, nitro, cyano, C1-C10 alkyl, C1-C10 alkoxy, halo (C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

One preferred aspect of the present invention is a compound of the formula (IV), an isomer, or a pharmaceutically acceptable salt thereof;

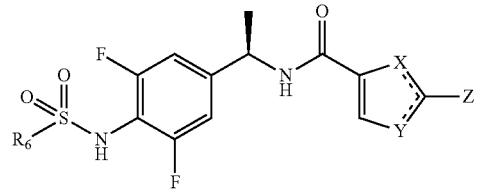

(IV)

wherein,
provided that if X is O, then Y is CH and if X is N, then Y is O;
R$_6$ is methyl, ethyl, or trifluoromethyl; and Z is

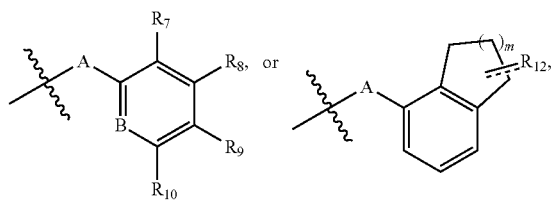

Wherein,

A is a single bond or O;

B is CH or $CR_{11}$;

----- is a single bond or double bond;

m is 1 or 2;

$R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, phenyl, di(C1-C5 alkyl)amino, C3-C6 cycloalkyl, or C1-C5 alkylthio;

$R_{12}$ is hydrogen, methyl, ethyl, or trifluoromethyl wherein ----- is a single bond, and $CH_2$ or $CHR_{13}$ wherein ----- is a double bond; and $R_{13}$ is C1-C5 alkyl.

One preferred aspect of the present invention is a pharmaceutical composition comprising the foregoing compound, an isomer, or a pharmaceutically acceptable salt thereof, as an active ingredient and a pharmaceutically acceptable carrier.

One preferred aspect of the present invention is use of the foregoing compound, an isomer, or a pharmaceutically acceptable salt thereof for the preparation of a medicament.

Advantageous Effects

The compound according to the present disclosure is useful to prevent or to treat pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis. More specifically, the compound according to the present disclosure is useful to preventing and treating of pain, which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, and other types of headaches.

Best Mode

The present invention provides a novel compound of the following formula (I), an isomer, or a pharmaceutically acceptable salt thereof:

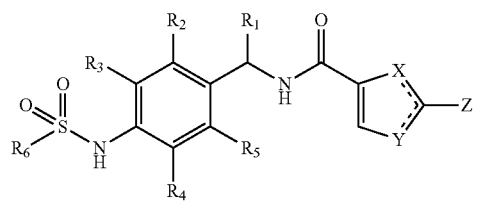

(I)

wherein,

X and Y are independently CH, N, O, or S;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;

$R_6$ is C1-C5 alkyl, halo(C1-C5) alkyl, or C2-C5 alkenyl; and

Z is

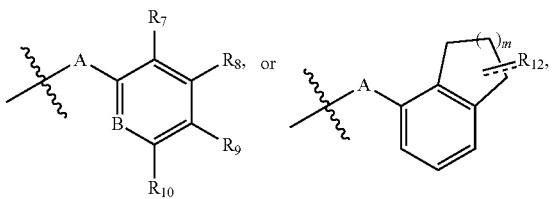

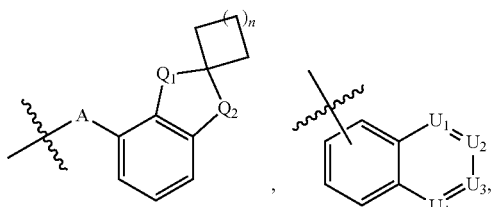

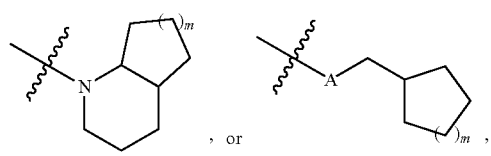

wherein,

A is a single bond, CH$_2$, NH, or O;

B is N or CR$_{11}$;

----- is a single bond or a double bond;

Q$_1$ and Q$_2$ are independently O or CH$_2$;

U$_1$, U$_2$, U$_3$, and U$_4$ are independently CH or N, and if anyone of U$_1$ to U$_4$ is N, the rest are independently CH;

m is 1 or 2;

n is 0, 1 or 2;

R$_7$, R$_8$, R$_9$, R$_{10}$, and R$_{11}$ are independently hydrogen, halogen, nitro, cyano, C1-C10 alkyl, C1-C10 alkoxy, halo(C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkylamino, C3-C8 cycloalkyl, or C1-C10 alkylthio;

R$_{12}$ is hydrogen, halogen, C1-C3 alkyl, or halo(C1-C3)alkyl wherein ----- is a single bond, and CH$_2$ or CHR$_{13}$ wherein ----- is a double bond; and R$_{13}$ is C1-C5 alkyl.

According to one embodiment of the present invention, in the compounds of formula I as further described herein, if X is O or S, then Y may be CH, and if X is N, then Y may be O or S.

According to another embodiment of the present invention, in the compounds of formula I as further described herein, R$_1$ is hydrogen, methyl, or ethyl;

R$_2$, R$_3$, R$_4$, and R$_5$ are independently hydrogen, halogen, nitro, cyano, C1-C5 alkyl, C1-C5 alkoxy, halo(C1-C5) alkyl, C2-C5 alkenyl, or C2-C5 alkynyl;

R$_6$ is C1-C3 alkyl, halo(C1-C3)alkyl, or vinyl; and

Z is

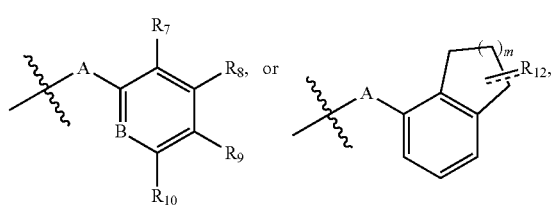

wherein,

A is a single bond, CH$_2$, NH, or O; B is CR$_{11}$;

----- is a single bond or a double bond; m is 1 or 2; R$_7$, R$_8$, R$_9$, R$_{10}$, and R$_{11}$ are independently hydrogen, halogen, nitro, cyano, C1-C10 alkyl, C1-C10 alkoxy, halo(C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio;

R$_{12}$ is hydrogen, C1-C3 alkyl, or halo(C1-C3)alkyl wherein ----- is a single bond, and CH$_2$ or CHR$_{13}$ wherein ----- is a double bond; and R$_{13}$ is C1-C5 alkyl.

According to another embodiment of the present invention, in the compounds of formula I as further described herein, R$_6$ is methyl, or trifluoromethyl; and Z is

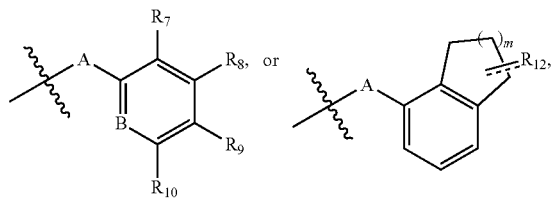

wherein,

A is a single bond or O;

B is CR$_{11}$;

m is 1 or 2;

R$_7$, R$_8$, R$_9$, R$_{10}$, and R$_{11}$ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, aryl, C1-C5 alkylamino, di(C1-C5 alkyl)amino, C3-C6 cycloalkyl, or C1-C5 alkylthio;

R$_{12}$ is hydrogen, methyl, ethyl, or trifluoromethyl wherein ----- is a single bond and CH$_2$ or CHR$_{13}$ wherein ----- is a double bond; and R$_{13}$ is C1-C3 alkyl.

According to another embodiment of the present invention, in the compounds of formula I as further described herein, R$_1$ is methyl;

R$_2$, R$_3$, R$_4$, and R$_5$ are independently hydrogen, fluoro, cyano, methyl, trifluoromethyl, vinyl, or acetylenyl;

R$_6$ is methyl; and

Z is

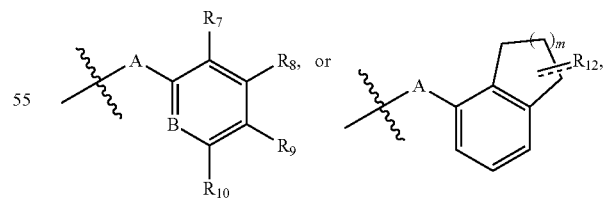

Wherein,

A is a single bond or O;

B is CR$_{11}$;

----- is a single bond or a double bond:

m is 1 or 2;

$R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkenyl, carboxy, C1-C5 alkoxycarbonyl, C1-C5 alkylcarbonyl, phenyl, di(C1-C5 alkyl)amino, C3-C6 cycloalkyl, or C1-C5 alkylthio; and $R_{12}$ is hydrogen, methyl, ethyl, or trifluoromethyl wherein ----- is a single bond, and $CH_2$ wherein ----- is a double bond.

One preferred aspect of the present invention is a compound of the formula (II), an isomer, or a pharmaceutically acceptable salt thereof;

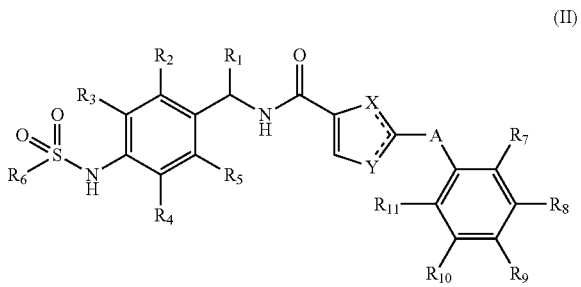

(II)

wherein,

X and Y are independently CH, N, O, or S;

A is $CH_2$, NH, or O;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;

$R_6$ is C1-C5 alkyl, halo(C1-C5) alkyl, or C2-C5 alkenyl; and $R_7$, $R_8$, $R_9$, $R_{10}$, and $R_{11}$ are independently hydrogen, halogen, nitro, cyano, C1-C10 alkyl, C1-C10 alkoxy, halo(C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

According to one embodiment of the present invention, in the compounds of formula II as further described herein, $R_2$, $R_3$, $R_4$, and $R_5$ are independently hydrogen, halogen, cyano, methyl, ethyl, trifluoromethyl, vinyl, or acetylenyl; and $R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, phenyl, di(C1-C5 alkyl)amino, C3-C6 cycloalkyl, or C1-C5 alkylthio.

According to another embodiment of the present invention, in the compounds of formula II as further described herein, $R_2$ and $R_5$ are hydrogen;

$R_3$ and $R_4$ are independently hydrogen, fluoro, chloro, cyano, methyl, trifluoromethyl, vinyl, or acetylenyl; and $R_7$, $R_8$, $R_9$, $R_{10}$, and $R_{11}$ are independently hydrogen, halogen, C1-C5 alkyl, C1-C5 alkoxy, halo(C1-C2)alkyl, C2-C5 alkenyl, C2-C5 alkynyl, phenyl, or C3-C5 cycloalkyl.

According to another embodiment of the present invention, in the compounds of formula II as further described herein, $R_2$ and $R_5$ are hydrogen;

$R_3$ and $R_4$ are independently hydrogen, fluoro, cyano, methyl, trifluoromethyl, vinyl, or acetylenyl; and $R_7$, $R_8$, $R_9$, $R_{10}$, and $R_{11}$ are independently hydrogen, fluoro, chloro, bromo, iodo, ethyl, isopropyl, tert-butyl, propoxy, butoxy, trifluoromethyl, 1-trifluoromethylethyl, or cyclopropyl.

According to another embodiment of the present invention, in the compounds of formula II as further described herein, provided that if X is O, then Y is CH and if X is N, then Y is O or S; A is, if present, O.

According to another embodiment of the present invention, in the compounds of formula II as further described herein, Wherein, provided that if X is O, then Y is CH and if X is N, then Y is O; and A is, if present, O.

According to another embodiment of the present invention, in the compounds of formula II as further described herein, $R_1$ is hydrogen, methyl, or ethyl; and $R_6$ is methyl, or trifluoromethyl.

According to another embodiment of the present invention, in the compounds of formula II as further described herein, $R_1$ is hydrogen, or methyl; $R_2$ and $R_5$ are hydrogen; $R_3$ and $R_4$ are independently hydrogen, fluoro, cyano, methyl, trifluoromethyl, vinyl, acetylenyl;

$R_6$ is methyl; and $R_7$, $R_8$, $R_9$, $R_{10}$, and $R_{11}$ are independently hydrogen, fluoro, chloro, bromo, iodo, ethyl, isopropyl, tert-butyl, butoxy, trifluoromethyl, or cyclopropyl.

Another preferred aspect of the present invention is a compound of the formula (III), an isomer, or a pharmaceutically acceptable salt thereof;

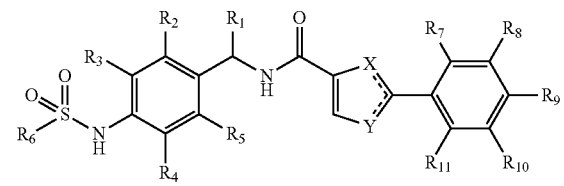

(III)

wherein,

X and Y are independently CH, N, O, or S;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;

$R_6$ is C1-C5 alkyl, halo(C1-C5) alkyl, or C2-C5 alkenyl; and $R_7$, $R_8$, $R_9$, $R_{10}$, and Ru are independently hydrogen, halogen, nitro, cyano, C1-C10 alkyl, C1-C10 alkoxy, halo (C1-C10)alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

According to one embodiment of the present invention, in the compounds of formula III as further described herein, $R_2$, $R_3$, $R_4$, and $R_5$ are independently hydrogen, halogen, cyano, methyl, ethyl, trifluoromethyl, vinyl, or acetylenyl; and $R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, phenyl, di(C1-C5 alkyl)amino, C3-C6 cycloalkyl, or C1-C5 alkylthio.

According to another embodiment of the present invention, in the compounds of formula III as further described herein, $R_2$ and $R_5$ are hydrogen;

$R_3$ and $R_4$ are independently hydrogen, fluoro, chloro, cyano, methyl, trifluoromethyl, vinyl, or acetylenyl; and $R_7$, $R_8$, $R_9$, $R_{10}$, and $R_{11}$ are independently hydrogen, halogen, C1-C5 alkyl, C1-C5 alkoxy, halo(C1-C2)alkyl, C2-C5 alkenyl, C2-C5 alkynyl, phenyl, or C3-C5 cycloalkyl.

According to another embodiment of the present invention, in the compounds of formula III as further described herein, $R_2$ and $R_5$ are hydrogen;

$R_3$ and $R_4$ are independently hydrogen, fluoro, cyano, methyl, trifluoromethyl, vinyl, or acetylenyl; and $R_7$, $R_8$, $R_9$, $R_{10}$, and $R_{11}$ are independently hydrogen, fluoro, chloro, bromo, iodo, ethyl, isopropyl, tert-butyl, propoxy, butoxy, trifluoromethyl, 1-trifluoromethyl-ethyl, or cyclopropyl.

According to another embodiment of the present invention, in the compounds of formula III as further described herein, provided that if X is O, then Y is CH and if X is N, then Y is O or S; A is, if present, O.

According to another embodiment of the present invention, in the compounds of formula III as further described herein, Wherein, provided that if X is O, then Y is CH and if X is N, then Y is O; and A is, if present, O.

According to another embodiment of the present invention, in the compounds of formula III as further described herein, $R_1$ is hydrogen, methyl, or ethyl; and $R_6$ is methyl, or trifluoromethyl.

According to another embodiment of the present invention, in the compounds of formula III as further described herein, $R_1$ is hydrogen, or methyl; $R_2$ and $R_5$ are hydrogen; $R_3$ and $R_4$ are independently hydrogen, fluoro, cyano, methyl, trifluoromethyl, vinyl, acetylenyl;

$R_6$ is methyl; and $R_7$, $R_8$, $R_9$, $R_{10}$, and $R_{11}$ are independently hydrogen, fluoro, chloro, bromo, iodo, ethyl, isopropyl, tert-butyl, butoxy, trifluoromethyl, or cyclopropyl.

One preferred aspect of the present invention is a compound of the formula (IV), an isomer, or a pharmaceutically acceptable salt thereof;

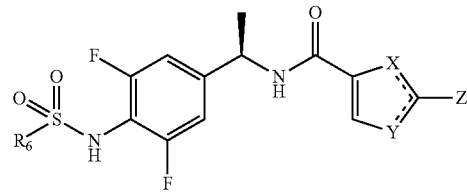

(IV)

wherein, provided that if X is O, then Y is CH and if X is N, then Y is O;

$R_6$ is methyl, ethyl, or trifluoromethyl; and

Z is

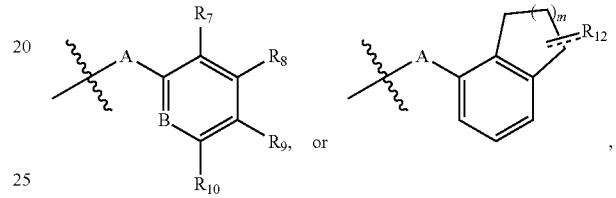

Wherein,

A is a single bond or O;

B is CH or $CR_{11}$;

----- is a single bond or double bond;

m is 1 or 2;

$R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, phenyl, di(C1-C5 alkyl)amino, C3-C6 cycloalkyl, or C1-C5 alkylthio;

$R_{12}$ is hydrogen, methyl, ethyl, or trifluoromethyl wherein ----- is a single bond, and $CH_2$ or $CHR_{13}$ wherein ----- is a double bond; and $R_{13}$ is C1-C5 alkyl.

According to one embodiment of the present invention, in the compounds of formula IV as further described herein, $R_6$ is methyl;

$R_7$, $R_8$, $R_9$, $R_{10}$, and $R_{11}$ are independently hydrogen, halogen, C1-C5 alkyl, C1-C5 alkoxy, halo(C1-C2) alkyl, C2-C5 alkenyl, C2-C5 alkynyl, phenyl, or C3-C5 cycloalkyl;

$R_{12}$ is hydrogen, methyl, or trifluoromethyl wherein ----- is a single bond, and $CH_2$ or $CHR_{13}$ wherein ----- is a double bond; and $R_{13}$ is C1-C3 alkyl.

According to another embodiment of the present invention, in the compounds of formula IV as further described herein, $R_6$ is methyl;

$R_7$, $R_8$, $R_9$, $R_{10}$, and $R_{11}$ are independently hydrogen, fluoro, chloro, bromo, iodo, ethyl, isopropyl, tert-butyl, butoxy, trifluoromethyl, or cyclopropyl; and $R_{12}$ is hydrogen, methyl, ethyl, or trifluoromethyl wherein ----- is a single bond, and $CH_2$ wherein ----- is a double bond.

Preferred examples of compounds according to the invention are selected from the group consisting of;

2-(3-tert-Butyl-phenoxy)-oxazole-4-carboxylic acid [1-(3,5-difluoro-4-methanesulfonylamino-phenyl)-ethyl]-amide, 2-(3-Trifluoromethyl-phenoxy)-oxazole-4-carboxylic acid [1-(3,5-difluoro-4-methanesulfonylamino-phenyl)-ethyl]-amide,
2-(2-Isopropyl-phenoxy)-oxazole-4-carboxylic acid [1-(3,5-difluoro-4-methanesulfonylamino-phenyl)-ethyl]-amide,
2-(3-Isopropyl-phenoxy)-oxazole-4-carboxylic acid [1-(3,5-difluoro-4-methanesulfonylamino-phenyl)-ethyl]-amide,
2-(3-Ethyl-phenoxy)-oxazole-4-carboxylic acid [1-(3,5-difluoro-4-methanesulfonylamino-phenyl)-ethyl]-amide,
2-(1-Methyl-indan-4-yloxy)-oxazole-4-carboxylic acid [1-(3,5-difluoro-4-methanesulfonylamino-phenyl)-ethyl]-amide,
2-(3-Cyclopropyl-phenoxy)-oxazole-4-carboxylic acid [1-(3,5-difluoro-4-methanesulfonylamino-phenyl)-ethyl]-amide,
2-(2,2-Dimethyl-2,3-dihydro-benzofuran-7-yloxy)-oxazole-4-carboxylic acid [1-(3,5-difluoro-4-methanesulfonylamino-phenyl)-ethyl]-amide,
2-(5-Methylene-5,6,7,8-tetrahydro-naphthalen-1-yloxy)-oxazole-4-carboxylic acid [1-(3,5-difluoro-4-methanesulfonylamino-phenyl)-ethyl]-amide,
2-(1-Ethyl-indan-4-yloxy)-oxazole-4-carboxylic acid [1-(3,5-difluoro-4-methanesulfonylamino-phenyl)-ethyl]-amide,
2-(5-Methyl-5,6,7,8-tetrahydro-naphthalen-1-yloxy)-oxazole-4-carboxylic acid [1-(3,5-difluoro-4-methanesulfonylamino-phenyl)-ethyl]-amide,
2-(2-Propyl-5-trifluoromethyl-phenoxy)-oxazole-4-carboxylic acid [1-(3,5-difluoro-4-methanesulfonylamino-phenyl)-ethyl]-amide,
2-(2-Propyl-3-trifluoromethyl-phenoxy)-oxazole-4-carboxylic acid [1-(3,5-difluoro-4-methanesulfonylamino-phenyl)-ethyl]-amide,
2-(2-Cyclopropyl-3-trifluoromethyl-phenoxy)-oxazole-4-carboxylic acid [1-(3,5-difluoro-4-methanesulfonylamino-phenyl)-ethyl]-amide,
2-(5,6,7,8-Tetrahydro-naphthalen-1-yloxy)-oxazole-4-carboxylic acid [1-(3,5-difluoro-4-methanesulfonylamino-phenyl)-ethyl]-amide,
2-(3-Cyclobutyl-phenoxy)-oxazole-4-carboxylic acid [1-(3,5-difluoro-4-methanesulfonylamino-phenyl)-ethyl]-amide,
2-(1-Trifluoromethyl-indan-4-yloxy)-oxazole-4-carboxylic acid [1-(3,5-difluoro-4-methanesulfonylamino-phenyl)-ethyl]-amide,
2-(3-Iodo-phenoxy)-oxazole-4-carboxylic acid [1-(3,5-difluoro-4-methanesulfonylamino-phenyl)-ethyl]-amide,
5-(4-Bromo-phenyl)-2-trifluoromethyl-furan-3-carboxylic acid [1-(3,5-difluoro-4-methanesulfonylamino-phenyl)-ethyl]-amide,
2-(3-Trifluoromethyl-phenyl)-oxazole-4-carboxylic acid [1-(3,5-difluoro-4-methanesulfonylamino-phenyl)-ethyl]-amide,
2-(3-Isopropyl-phenyl)-oxazole-4-carboxylic acid [1-(3,5-difluoro-4-methanesulfonylamino-phenyl)-ethyl]-amide,
2-(4-Trifluoromethyl-phenyl)-oxazole-4-carboxylic acid [1-(3,5-difluoro-4-methanesulfonylamino-phenyl)-ethyl]-amide,
2-(3-Isopropyl-phenyl)-thiazole-4-carboxylic acid [1-(3,5-difluoro-4-methanesulfonylamino-phenyl)-ethyl]-amide,
2-(3,5-Bis-trifluoromethyl-phenyl)-oxazole-4-carboxylic acid [1-(3,5-difluoro-4-methanesulfonylamino-phenyl)-ethyl]-amide,
2-(4-Chloro-3-trifluoromethyl-phenyl)-oxazole-4-carboxylic acid [1-(3,5-difluoro-4-methanesulfonylamino-phenyl)-ethyl]-amide,
2-(3-Trifluoromethyl-phenyl)-thiazole-4-carboxylic acid [1-(3,5-difluoro-4-methanesulfonylamino-phenyl)-ethyl]-amide,
2-(3-Cyclopropyl-phenyl)-oxazole-4-carboxylic acid [1-(3,5-difluoro-4-methanesulfonylamino-phenyl)-ethyl]-amide,
2-(3-Cyclopropyl-phenyl)-thiazole-4-carboxylic acid [1-(3,5-difluoro-4-methanesulfonylamino-phenyl)-ethyl]-amide,
5-(3-Cyclopropyl-phenyl)-furan-2-carboxylic acid [1-(3,5-difluoro-4-methanesulfonylamino-phenyl)-ethyl]-amide,
5-(3-Trifluoromethyl-phenyl)-furan-2-carboxylic acid 3-fluoro-4-methanesulfonylamino-5-methyl-benzylamide,
5-(3-Trifluoromethyl-phenyl)-furan-2-carboxylic acid 3-ethynyl-5-fluoro-4-methanesulfonylamino-benzylamide,
5-(3-Trifluoromethyl-phenyl)-furan-2-carboxylic acid 3-fluoro-4-methanesulfonylamino-5-vinyl-benzylamide,
5-(3,5-Dicyclopropyl-phenyl)-furan-2-carboxylic acid [1-(3,5-difluoro-4-methanesulfonylamino-phenyl)-ethyl]-amide,
(S)-5-(3-Trifluoromethyl-phenyl)-furan-2-carboxylic acid [1-(3,5-difluoro-4-methanesulfonylamino-phenyl)-ethyl]-amide,
5-(3-Trifluoromethyl-phenyl)-furan-2-carboxylic acid [1-(3-fluoro-4-methanesulfonylamino-phenyl)-ethyl]-amide,
5-(3-Trifluoromethyl-phenyl)-furan-2-carboxylic acid 4-methanesulfonylamino-3-methyl-benzylamide,
5-(3-Trifluoromethyl-5-vinyl-phenyl)-furan-2-carboxylic acid [1-(3,5-difluoro-4-methanesulfonylamino-phenyl)-ethyl]-amide,
5-(3-Ethyl-5-trifluoromethyl-phenyl)-furan-2-carboxylic acid [1-(3,5-difluoro-4-methanesulfonylamino-phenyl)-ethyl]-amide,
5-(3-Trifluoromethyl-phenyl)-furan-2-carboxylic acid 3-fluoro-4-methanesulfonylamino-benzylamide,
5-(2-Trifluoromethyl-phenyl)-furan-2-carboxylic acid [1-(3,5-difluoro-4-methanesulfonylamino-phenyl)-ethyl]-amide,
(R)-5-(3-Trifluoromethyl-phenyl)-furan-2-carboxylic acid [1-(3,5-difluoro-4-methanesulfonylamino-phenyl)-ethyl]-amide,
5-(3-Trifluoromethyl-phenyl)-furan-2-carboxylic acid 3-cyano-5-fluoro-4-methanesulfonylamino-benzylamide,
5-(3,5-Bis-trifluoromethyl-phenyl)-furan-2-carboxylic acid [1-(3,5-difluoro-4-methanesulfonylamino-phenyl)-ethyl]-amide,
5-(4-Fluoro-3-trifluoromethyl-phenyl)-furan-2-carboxylic acid [1-(3,5-difluoro-4-methanesulfonylamino-phenyl)-ethyl]-amide, and
5-(4-Fluoro-3-trifluoromethyl-phenyl)-furan-2-carboxylic acid 3-fluoro-4-methanesulfonylamino-benzylamide.

Preferred examples of compounds according to the invention are selected from the group consisting of;
2-(3-tert-Butyl-phenoxy)-oxazole-4-carboxylic acid [1-(3,5-difluoro-4-methanesulfonylamino-phenyl)-ethyl]-amide,
2-(3-Isopropyl-phenoxy)-oxazole-4-carboxylic acid [1-(3,5-difluoro-4-methanesulfonylamino-phenyl)-ethyl]-amide,
2-(1-Methyl-indan-4-yloxy)-oxazole-4-carboxylic acid [1-(3,5-difluoro-4-methanesulfonylamino-phenyl)-ethyl]-amide,
2-(3-Cyclopropyl-phenoxy)-oxazole-4-carboxylic acid [1-(3,5-difluoro-4-methanesulfonylamino-phenyl)-ethyl]-amide, 2-(2-Propyl-5-trifluoromethyl-phenoxy)-oxazole-4-carboxylic acid [1-(3,5-difluoro-4-methanesulfonylamino-phenyl)-ethyl]-amide, 2-(2-Propyl-3-trifluoromethyl-phenoxy)-oxazole-4-carboxylic acid [1-(3,5-difluoro-4-methanesulfonylamino-phenyl)-ethyl]-amide, 2-(3-Iodo-phenoxy)-oxazole-4-carboxylic acid [1-(3,5-difluoro-4-methanesulfonylamino-phenyl)-ethyl]-amide, 2-(3-Isopropyl-phenyl)-oxazole-4-carboxylic acid [1-(3,5-difluoro-4-methanesulfonylamino-phenyl)-ethyl]-amide, 2-(3-Isopropyl-phenyl)-thiazole-4-carboxylic acid [1-(3,5-difluoro-4-methanesulfonylamino-phenyl)-ethyl]-amide 2-(3,5-Bis-trifluoromethyl-phenyl)-oxazole-4-carboxylic acid [1-(3,5-difluoro-4-methanesulfonylamino-phenyl)-ethyl]-amide, 2-(4-Chloro-3-trifluoromethyl-phenyl)-oxazole-4-carboxylic acid [1-(3,5-difluoro-4-methanesulfonylamino-phenyl)-ethyl]-amide, 2-(3-Cyclopropyl-phenyl)-oxazole-4-carboxylic acid [1-(3,5-difluoro-4-methanesulfonylamino-phenyl)-ethyl]-amide, 2-(3-Cyclopropyl-phenyl)-thiazole-4-carboxylic acid [1-(3,5-difluoro-4-methanesulfonylamino-phenyl)-ethyl]-amide, 5-(3-Cyclopropyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid 3-ethynyl-5-fluoro-4-methanesulfonylamino-benzylamide, 5-(3-Trifluoromethyl-phenyl)-furan-2-carboxylic acid 3-fluoro-4-methanesulfonylamino-5-vinyl-benzylamide, 5-(3-Trifluoromethyl-phenyl)-furan-2-carboxylic acid [1-(3-fluoro-4-methanesulfonylamino-phenyl)-ethyl]-amide, 5-(3-Trifluoromethyl-5-vinyl-phenyl)-furan-2-carboxylic acid [1-(3,5-difluoro-4-methanesulfonylamino-phenyl)-ethyl]-amide, 5-(3-Ethyl-5-trifluoromethyl-phenyl)-furan-2-carboxylic acid [1-(3,5-difluoro-4-methanesulfonylamino-phenyl)-ethyl]-amide, 5-(2-Trifluoromethyl-phenyl)-furan-2-carboxylic acid [1-(3,5-difluoro-4-methanesulfonylamino-phenyl)-ethyl]-amide, (R)-5-(3-Trifluoromethyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid 3-cyano-5-fluoro-4-methanesulfonylamino-benzylamide, 5-(3,5-Bis-trifluoromethyl-phenyl)-furan-2-carboxylic acid [1-(3,5-difluoro-4-methanesulfonylamino-phenyl)-ethyl]-amide, and 5-(4-Fluoro-3-trifluoromethyl-phenyl)-furan-2-carboxylic acid [1-(3,5-difluoro-4-methanesulfonylamino-phenyl)-ethyl]-amide.

The compounds of the formula (I), (II), (III), or (IV) of the present invention can chemically be synthesized by the following reaction schemes. However, these are given only for illustration of the invention and not intended to limit to them.

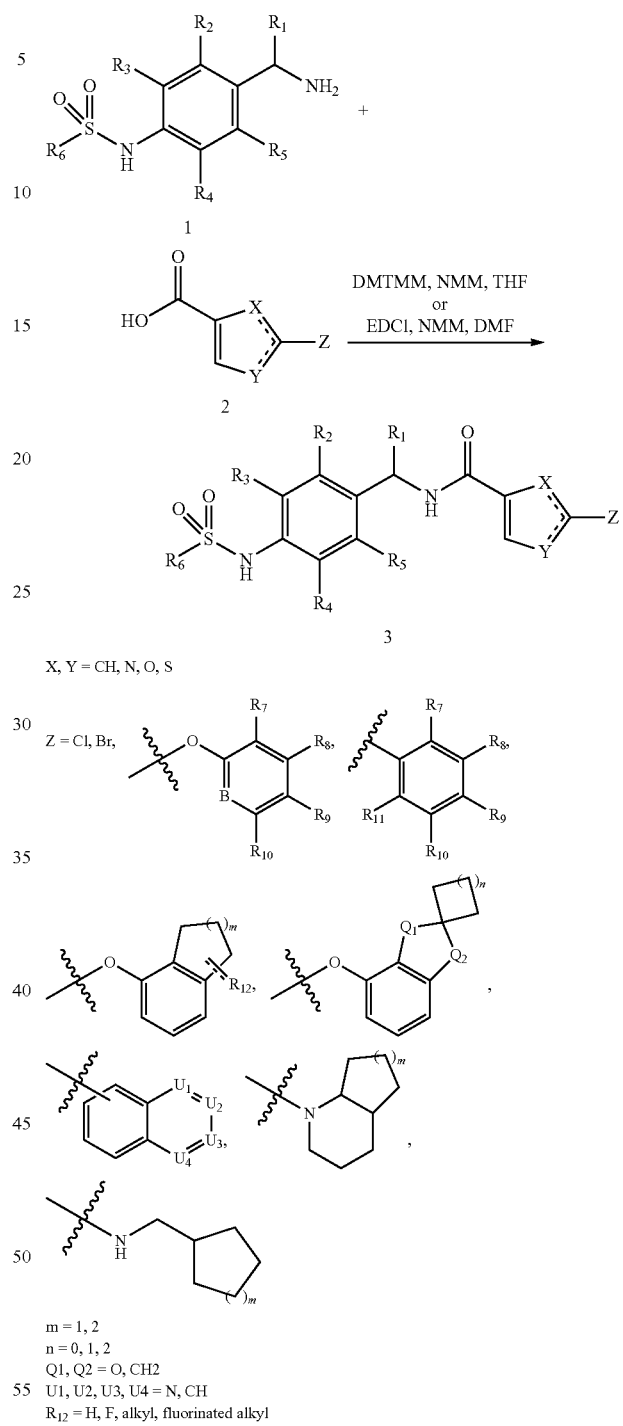

The Scheme 1 shows a proposed process for synthesizing amide compound with various substituents. Substituted benzylamine (1) is reacted with 5-membered heterocycle carboxylic acid (2) to yield benzyl amide (3) using DMTMM {4-(4,6-dimethoxy-1,3,5-triazin-2-yl)-4-methylmorpholinium chloride} (Tetrahedron Lett., 1999, 40, 5327) or EDCI {N-ethyl-N'-(3-dimethylaminoprophyl)-carbodimide, HCl salt.

[Scheme 2]

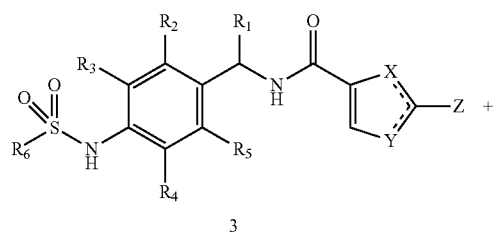

3

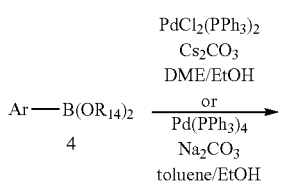

[Scheme 3]

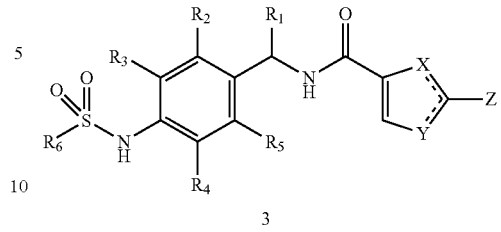

3

6

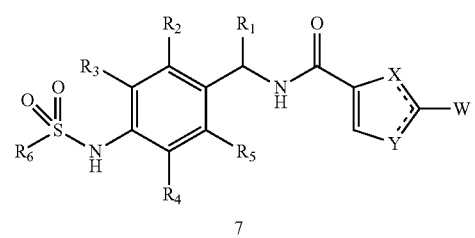

7

X, Y = CH, N, O, S
Z = Cl, Br

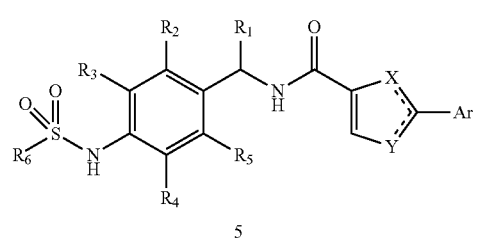

5

X, Y = CH, N, O, S
Z = Cl, Br

R$_{14}$ = H,

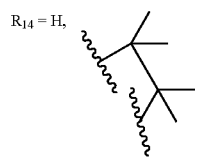

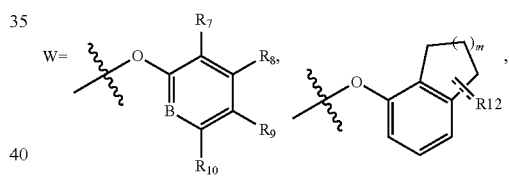

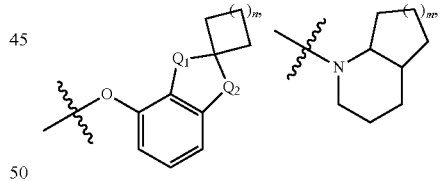

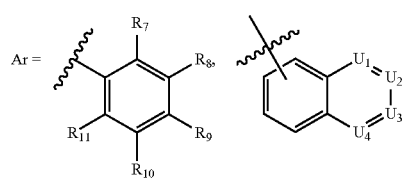

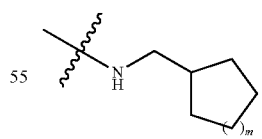

U1, U2, U3, U4 = N, CH m = 1, 2
n = 0, 1, 2
Q1, Q2 = O, CH2

The Scheme 2 shows a proposed process for synthesizing amide compound (5) with various substituents. Benzyl amide with various substituents (3) is reacted with boronic acid or boronic ester (4) in the presence of palladium catalyst and a base in a suitable solvent system by irradiating the microwave to give the amide compound (5).

The Scheme 3 shows a proposed process for synthesizing amide compound (7) with various substituents. Benzyl amide with various substituents (3) is reacted with phenol or amine (6) in the presence of a base in a suitable solvent system by irradiating the microwave to give the amide compound (7).

[Scheme 4]

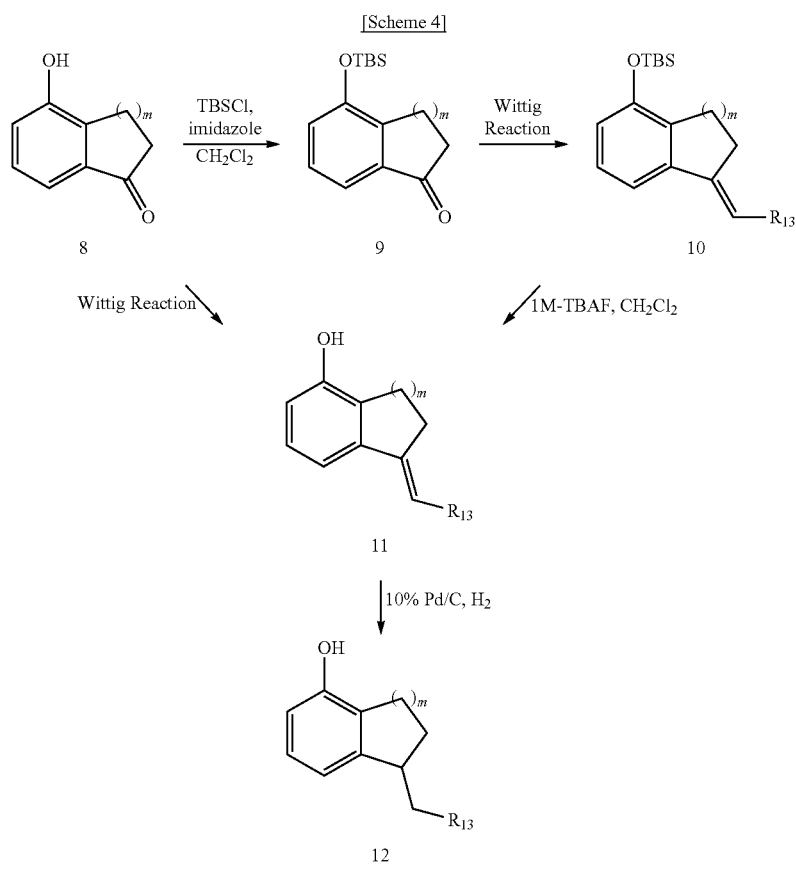

m = 1, 2

The Scheme 4 shows a proposed process for synthesizing phenol compound (12). Phenol compound (11) is obtained by the reaction of compound (8) with various Wittig reagents. Alternatively, compound (8) is reacted with TBSCl in the presence of imidazole to yield compound (9), which undergoes Wittig reaction followed by deprotection reaction using 1M-TBAF to give phenol compound (11). Compound (11) is hydrogenated under hydrogen atmosphere with 10% Pd/C in a suitable solvent to afford compound (12).

[Scheme 5]

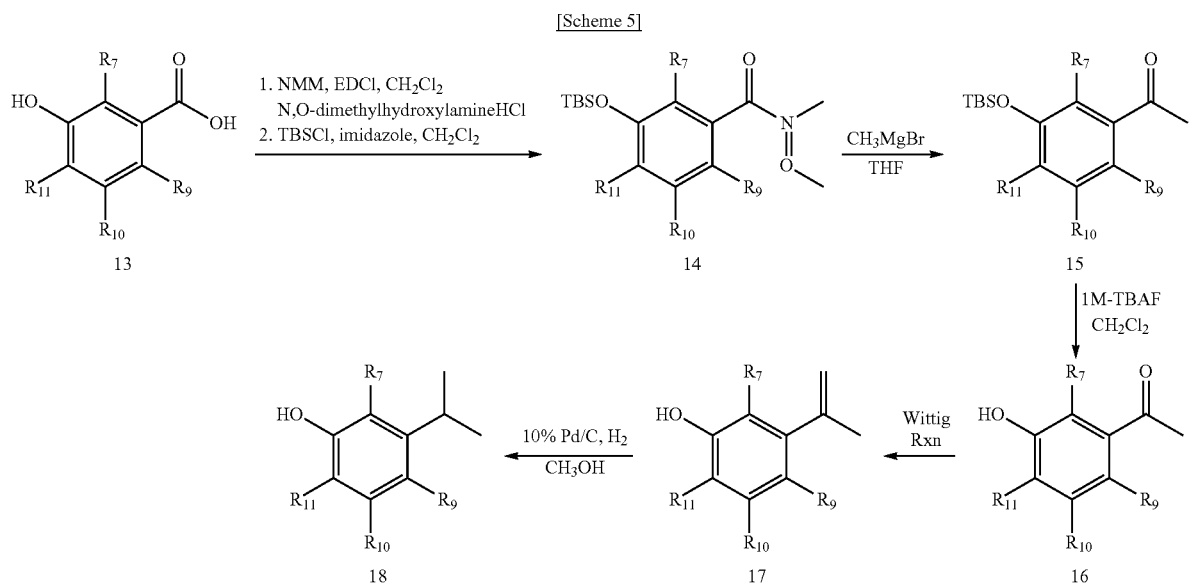

The Scheme 5 shows a proposed process for synthesizing phenol compound with isopropyl substituent (18). Compound (13) is reacted with N,O-dimethylhydroxylamie hydrochloride followed by protection using TBSC1 and imidazole to give compound (14). Compound (14) is reacted with methylmagnesiumbromide to afford compound (15). Phenol group of the compound (15) is deprotected with TBAF to give compound (16), which is converted to olefin (17) by Wittig reaction. Compound (17) is hydrogenated under hydrogen atmosphere with 10% Pd/C in a suitable solvent to afford compound (18).

The Scheme 6 shows a proposed process for synthesizing phenol compound (22) or phenol compound (24) with propyl substituent. Compound (19) is reacted with allylbromide to give compound (20). Compound (20) is reacted with NMP by irradiating in the microwave reactor to give both compound (21) and compound (23). Compound (21) and compound (23) is separated and then hydrogenated under hydrogen atmosphere with 10% Pd/C in a suitable solvent to afford compound (22) and compound (24), respectively.

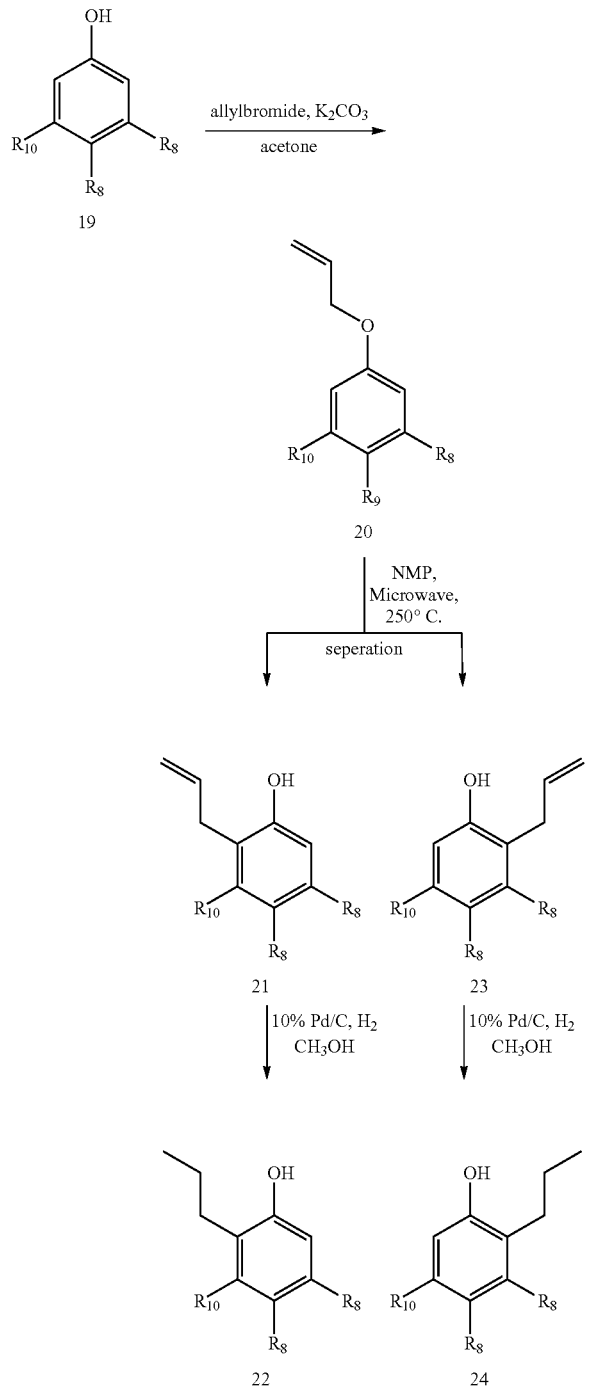

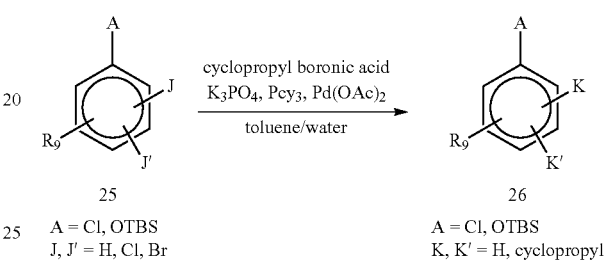

The Scheme 7 shows a proposed process for synthesizing compound (26) with cyclopropyl substituent. Compound (25) is reacted with cyclopropylboronic acid in the presence of palladium catalyst and a base in a suitable solvent system to give the amide compound (26).

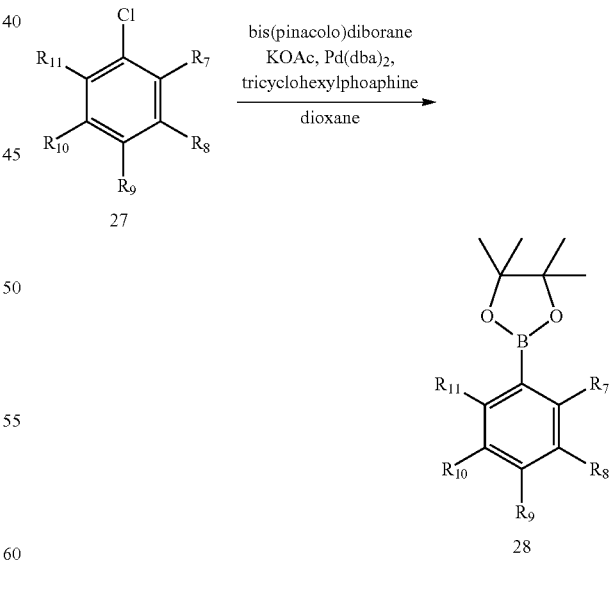

The Scheme 8 shows a proposed process for synthesizing boronic ester compound (28) with various substituents. Compound (27) is reacted with bis(pinacolo)diborane in the presence of palladium catalyst and a base in a suitable solvent system to give the boronic ester compound (28)

[Scheme 9]

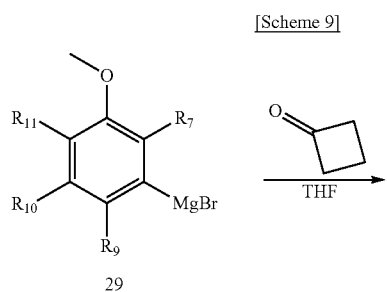

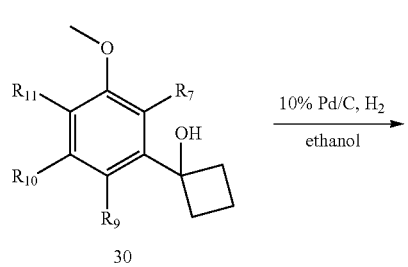

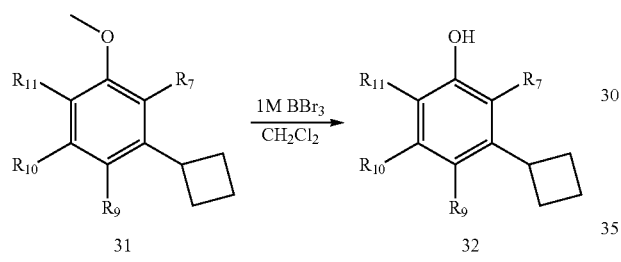

The Scheme 9 shows a proposed process for synthesizing phenol compound (32) with cyclobutyl substituent. Grignard compound (29) is reacted with cyclobutanone to give compound (30). Compound (30) is hydrogenated under hydrogen atmosphere with 10% Pd/C in a suitable solvent to afford compound (31). Compound (31) is deprotected by BBr$_3$ to give phenol compound (32).

[Scheme 10]

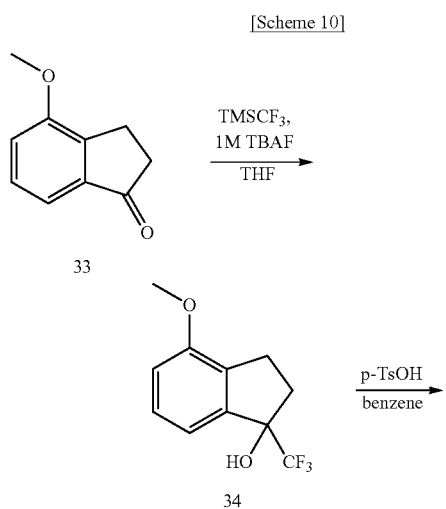

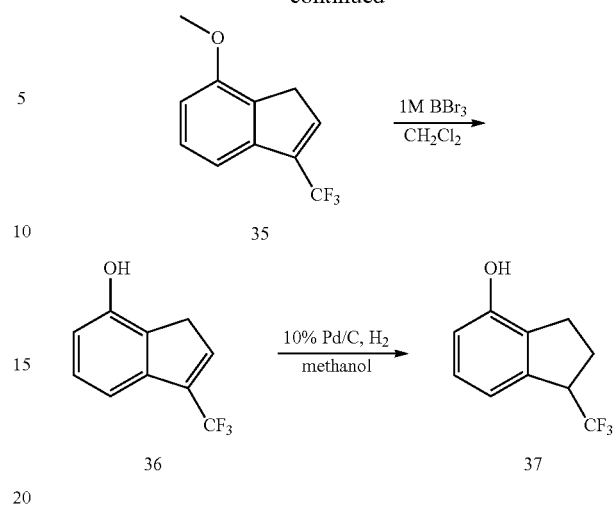

The Scheme 10 shows a proposed process for synthesizing alcohol compound (37). Compound (33) is reacted with TBSCF$_3$ to give compound (34). Compound (34) is reacted with p-TsOH to afford compound (35), which is deprotected by BBr$_3$ to give compound (36). Compound (36) is hydrogenated under hydrogen atmosphere with 10% Pd/C in a suitable solvent to afford compound (37).

[Scheme 11]

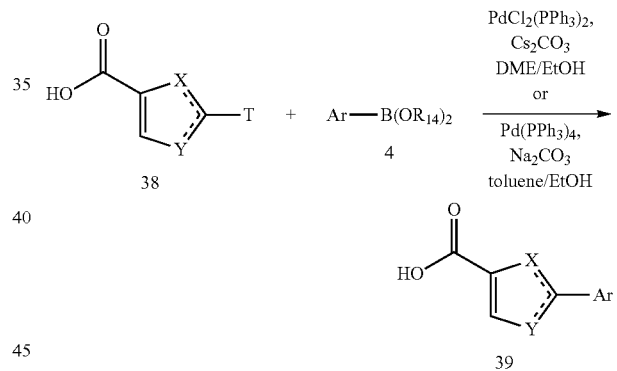

X, Y = CH, N, O, S
T = Cl, Br
R$_{14}$ = H, 

Ar = 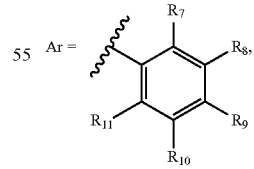

U1, U2, U3, U4 = N, CH

The Scheme 11 shows a proposed process for synthesizing acid compound (39) with various substituents. Acid compound (38) is reacted with boronic acid or boronic ester (4) in the presence of palladium catalyst and a base in a suitable solvent system by irradiating the microwave to give the acid compound (39).

27

[Scheme 12]

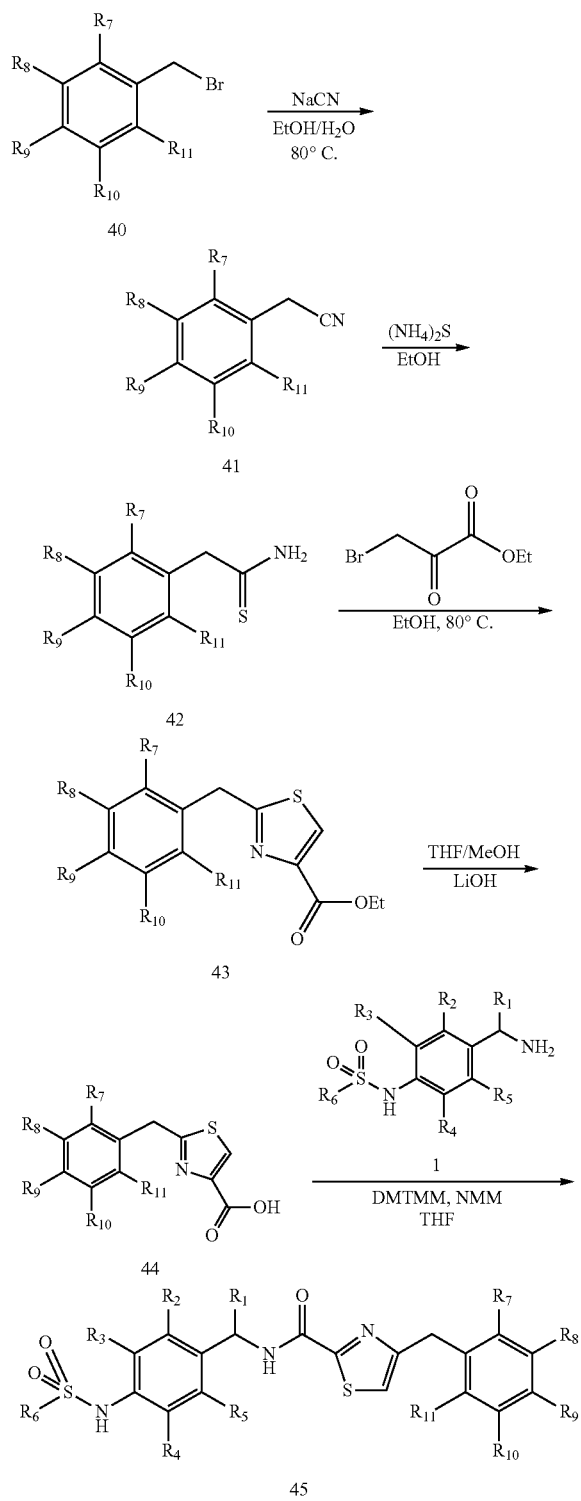

28 hydrolyzed to the acid compound (44), which is reacted with benzyl amine (1) in the presence of DMTMM to yield thiazole compound (45).

[Scheme 13]

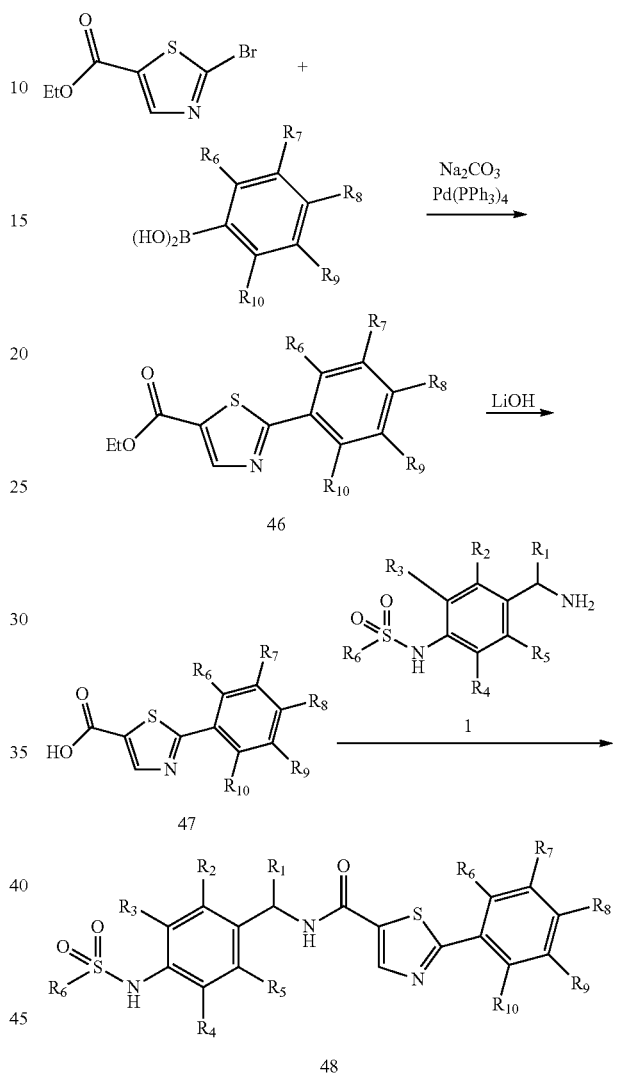

The Scheme 12 shows a proposed process for synthesizing thiazole compound (45) with various substituents. Benzyl bromice (38) is reacted with NaCN to yield the benzyl cyanide 41, which is converted to thioamide compound (42) using ammonium sulfide. Thiazole ester 43 obtained by reacting thioamide compound (42) with ethyl bromopyruvate is The Scheme 13 shows a proposed process for synthesizing another thiazole compound (48) with various substituents. Ethyl 2-bromothiazole-5-carboxylate is reacted with various phenylboronic acid in the presence of a base and a catalyst to yield thiazole compound (46), which is hydrolyzed using a base such as LiOH to give the acid compound (47). The acid compound (47) is reacted with benzyl amine (1) in the presence of DMTMM to yield thiazole compound (48).

The present invention also provides a compound of formula (I), (II), (III), or (IV), an isomer thereof, or a pharmaceutically acceptable salt thereof for preventing or treating a disease associated with the pathological stimulation and/or aberrant expression of vanilloid receptor.

In one preferred aspect, the present invention provides a compound of formula (I), (II), (III), or (IV), an isomer thereof, or a pharmaceutically acceptable salt thereof for treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear.

In a particularly preferred aspect, the present invention relates to a compound of formula (I), (II), (III), or (IV) an isomer thereof, or a pharmaceutically acceptable salt thereof, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia and visceral pain.

The present invention also provides a pharmaceutical composition comprising a compound of formula (I), (II), (III), or (IV), an isomer thereof, or a pharmaceutically acceptable salt thereof as an active ingredient together with a pharmaceutically acceptable carrier.

The present invention also provides a pharmaceutical composition for preventing or treating a disease associated with the pathological stimulation and/or aberrant expression of vanilloid receptor, wherein said composition comprises the compound of formula (I), (II), (III), or (IV), an isomer thereof or a pharmaceutically acceptable salt thereof; and pharmaceutically acceptable carrier.

In one preferred aspect, the present invention provides a pharmaceutical composition comprising a compound of formula (I), (II), (III), or (IV), an isomer thereof, or a pharmaceutically acceptable salt thereof, for treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear.

In a particularly preferred aspect, the present invention relates to the pharmaceutical composition comprising a compound of formula (I), (II), (III), or (IV), an isomer thereof, or a pharmaceutically acceptable salt thereof for treating pain as described above, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

The present invention also provides a pharmaceutical composition comprising a compound of formula (I); (II), (III), or (IV), an isomer thereof, or a pharmaceutically acceptable salt thereof, which is characterized in that it is adapted for oral administration.

In another aspect, the present invention relates to a method for inhibiting vanilloid ligand from binding to vanilloid receptor in a patient, comprising contacting cells expressing vanilloid receptor in the patient with the compound of formula (I), (II), (III), or (IV), an isomer thereof, or a pharmaceutically acceptable salt thereof.

In another aspect, the present invention also provides a method for preventing or treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear, which comprises administering to a mammal including a person in need thereof a therapeutically effective amount of the compound of formula (I), (II), (III), or, (IV), an isomer thereof, or a pharmaceutically acceptable salt thereof.

In a particularly preferred aspect, the present invention relates to the method of treating pain by administering a compound of formula (I), (II), (III), or (IV), an isomer thereof, or a pharmaceutically acceptable salt thereof as described above, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

In another aspect, the present invention relates to the use of a compound of formula (I), (II), (III), or (IV), an isomer thereof, or a pharmaceutically acceptable salt thereof for the preparation of a medicament for the prevention or treatment of a condition that is associated with the aberrant expression and/or aberrant activation of a vanilloid receptor.

In another aspect, the present invention relates to the use of a compound of formula (I), (II), (III), or (IV), an isomer thereof, or a pharmaceutically acceptable salt thereof, in preparation of a medicament for the prevention or treatment of a condition that is selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemic, hair growth-related disorders such as effluvium, alopecia, rhinitis, pancreatitis, vulvodynia, haemorrhagic shock, and psychiatric disorders such as anxiety or fear.

In a particularly preferred aspect, the present invention relates to the use of the compound of formula (I), (II), (III), or (IV), an isomer thereof, for preparing a medicament for preventing or treating pain as described above, wherein the condition is pain or which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

Hereinafter, the formulating methods and kinds of excipients will be described, but the present invention is not limited to them.

A compound of formula (I), (II), (III), or (IV), an isomer thereof or a pharmaceutically acceptable salt thereof according to the present invention can be prepared as a pharmaceutical composition containing pharmaceutically acceptable carriers, adjuvants, diluents and the like. For instance, the compounds of the present invention can be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. For topical administration, the compounds of the present invention can be formulated in the form of ointment or cream.

The compound according to the present invention may also be used in the forms of pharmaceutically acceptable salts thereof, and may be used either alone or in combination or in admixture with other pharmaceutically active compounds.

The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient, severity of the particular disease, dosage form, and route and period of administration, but may appropriately be chosen by those skilled in the art. The compounds of the present invention are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present invention are used in a pharmaceutical composition in an amount of 0.0001-10% by weight, and preferably 0.001-1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

When describing the compounds, pharmaceutical compositions containing such compounds, methods of using such compounds and compositions, and use of such compounds and compositions, all terms used in the present application shall have the meaning usually employed by a relevant person skilled in the art, e.g. by a medicinal chemists, pharmacist or physician. By the way of example some definitions of specific groups are given below:

"Alkyl" includes monovalent saturated aliphatic hydrocarbyl groups. The hydrocarbon chain may be either straight-chained or branched. "Alkyl" has preferably 1-15 carbon atoms ("C1-C15 alkyl"), more preferably 1-10 carbon atoms ("C1-C10 alkyl"), even more preferably 1-8 carbon atoms ("C1-C8 alkyl") or 1-6 carbon atoms ("C1-C6 alkyl"), and in some instances even more preferably 1-5 carbon atoms ("C1-C5 alkyl"), 1-4 carbon atoms ("C1-C4 alkyl"), or only 1-3 carbon atoms ("C1-C3 alkyl"). This term is exemplified by groups such as methyl, ethyl, n-propyl, isopropyl, n-butyl, iso-butyl, tert-butyl, t-amyl, and the like.

"Alkoxy" includes the group —OR wherein R is "alkyl" as defined further above. Particular alkoxy groups include, by way of example, methoxy, ethoxy, n-propoxy, isopropoxy, n-butoxy, tert-butoxy, sec-butoxy, n-pentoxy, 1,2-dimethyl-butoxy, and the like.

"Alkoxycarbonyl" refer to the radical —C(=O)—O—R, wherein R is an alkyl group as defined herein.

"Alkenyl" includes monovalent olefinically unsaturated hydrocarbyl groups being straight-chained or branched and having at least 1 double bond. "Alkenyl" has preferably 2-15 carbon atoms ("C2-C15 alkenyl"), more preferably 2-10 carbon atoms ("C2-C10 alkenyl"), even more preferably 2-8 carbon atoms ("C2-C8 alkenyl") or 2-6 carbon atoms ("C2-C6 alkenyl"), and in some instances even more preferably 2-5 carbon atoms ("C1-C5 alkenyl"), 2-4 carbon atoms ("C2-C4 alkenyl"), or only 2-3 carbon atoms ("C2-C3 alkenyl"). Particular alkenyl groups include ethenyl (—CH=CH$_2$), n-propenyl (—CH$_2$CH=CH$_2$), isopropenyl (C(CH$_3$)=CH$_2$), and the like. A preferred "alkenyl" group is ethenyl (vinyl).

"Alkynyl" includes acetylenically unsaturated hydrocarbyl groups being straight-chained or branched and having at least 1 triple bond. "Alkynyl" has preferably 2-15 carbon atoms ("C2-C15 alkynyl"), more preferably 2-10 carbon atoms ("C2-C10 alkynyl"), even more preferably 2-8 carbon atoms ("C2-C8 alkynyl") or 2-6 carbon atoms ("C2-C6 alkynyl"), and in some instances even more preferably 2-5 carbon atoms ("C1-C5 alkynyl"), 2-4 carbon atoms ("C2-C4 alkynyl"), or only 2-3 carbon atoms ("C2-C3 alkynyl"). A preferred alkynyl group is ethynyl (acetylenyl).

"Alkylamino" includes the group —NHR', wherein R' is alkyl group as defined herein.

"Dialkylamino" includes the group —NR'R", wherein R' and R" are alkyl group as defined herein.

"Amino" refers to the radical —NH$_2$.

"Aryl" refers to an aromatic hydrocarbyl radical. Examples of "aryl" radicals are phenyl, naphthyl, indenyl, azulenyl, fluorine or anthracene, wherein phenyl is preferred.

"Carboxy" refers to the radical —C(=O)OH.

"Cycloalkyl" refers to cyclic saturated aliphatic hydrocarbyl groups. The numbers of C-atoms referenced in connection with a given cycloalkyl group corresponds to the number of ring forming carbon atoms, e.g. "C3-C6 cycloalkyl" refers to a cycloalkyl with between three and six ring-forming C atoms. Examples of "cycloalkyl" are cyclopropyl, cyclobutyl, cyclopentyl, cyclohexyl etc. If indicated, a "cycloalkyl" group may be unsubstituted or substituted with one or more alkyl groups, e.g. with C1-C6 alkyl groups, preferably with C1-C3 alkyl groups, particularly preferably with methyl groups. If a "cycloalkyl" carries more than one alkyl substituent these substituents may be attached to the same or to different ring-forming carbon atoms.

"Cyano" refers to the radical —C≡N.

"Ethenyl" refers to —CH=CH$_2$ which is also designated "vinyl" in the present application.

"Ethynyl" refers to —C≡CH.

"Halo" or "halogen" refers to fluoro, chloro, bromo and iodo. Preferred halo groups are either fluoro or chloro.

"Haloalkyl" includes an "alkyl" group as defined further above which is substituted with one or more halogens which may be the same, e.g. in trifluoromethyl or pentafluoroethyl, or which may be different.

"Heteroaryl" refers to aromatic ring system containing at least one heteroatom such as O, S or N. Examples of heteroaryl radicals are furanyl, thienyl, pyrollyl, thiazolyl, oxazolyl, imidazolyl, pyrazolyl, isoxazolyl, isothiazolyl, triazolyl, oxadiazolyl, thiadiazolyl, pyranyl, pyridinyl, pyridazinyl, pyrimidinyl, pyrazinyl, triazinyl, tetrazinyl, indolinyl, indolyl, isoindolyl, benzofuranyl, benzothiophenyl, benzoimidazolyl, benzthiazolyl, purinyl, quinazolinyl, quinolinyl, isoquinolinyl, quinolizinyl, pteridinyl, carbazolyl, wherein one ring sytems, and in particular pyridinyl and imidazolyl are preferred.

"Nitro" refers to the radical-$NO_2$.

"Isomer" includes especially optical isomers (for example essentially pure enantiomers, essentially pure diastereomers, and mixtures thereof) as well as conformation isomers (i.e. isomers that differ only in their angles of at least one chemical bond), position isomers (particularly tautomers), and geometric isomers (e.g. cis-trans isomers).

"Essentially pure", e.g. in connection with enantiomers or diastereomers means at least about 90%, preferably at least about 95%, more preferably at least about 97 or at least about 98%, even more preferably at least about 99%, and particularly preferably at least about 99.5% (w/w) of a specified compound, e.g. a particular enantiomer or diastereomer.

"Pharmaceutically acceptable" means being devoid of substantial toxic effects when used in doses usually employed in a medicinal dosage, and thereby being approvable or preferably being approved by a regulatory agency of the Federal or a state government or being listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

"Pharmaceutically acceptable carrier" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

MODE FOR INVENTION

The present invention is more specifically explained by following examples and experimental examples. However, it should be understood that the extent of the present invention is not limited to the following examples and experimental examples.

Example 1

2-(3-tert-Butyl-phenoxy)-oxazole-4-carboxylic acid [1-(3,5-difluoro-4-methanesulfonylamino-phenyl)-ethyl]-amide

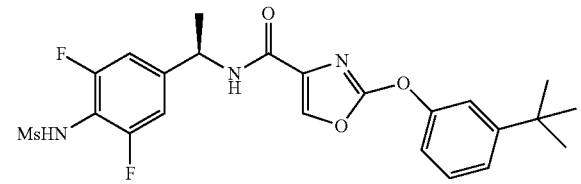

In a 5 ml glass tube were placed 2-chloro-oxazole-4-carboxylic acid [1-(3,5-difluoro-4-methanesulfonylamino-phenyl)-ethyl]-amide (40 mg, 0.10 mmol), $K_2CO_3$ (17 mg, 0.12 mmol), 3-tert-butyl phenol (18 mg, 0.12 mmol), DMF (1 mL), and a magnetic stir bar. The vial was sealed with septum and placed into the Microwave cavity. The vial was irradiated in a Microwave synthesizer at 130° C. for 10 min. The reaction mixture was diluted with EtOAc, and washed with saturated ammonium chloride and water. The organic layer was dried over anhydrous $MgSO_4$ and concentrated under reduced pressure. The crude residue was purified by column chromatography (gradient 12% to 100% EtOAc in n-hexane) to give title compound (90 mg, 80%).

$^1$H NMR (300 MHz, $CDCl_3$): δ7.91 (s, 1H), 7.40~7.30 (m, 3H), 7.16~7.12 (m, 1H), 7.00~6.93 (m, 3H), 6.58 (s, 1H), 5.20~5.12 (m, 1H), 3.16 (s, 3H), 1.50 (d, 3H, J=7.2 Hz), 1.34 (s, 9H).

Example 2

2-(3-Trifluoromethyl-phenoxy)-oxazole-4-carboxylic acid [1-(3,5-difluoro-4-methanesulfonylamino-phenyl)-ethyl]-amide

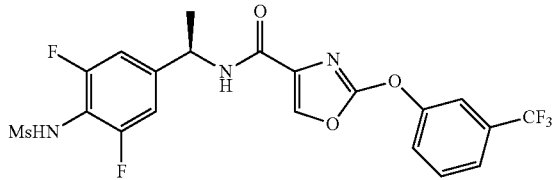

This compound was prepared according to the method of example 1.

2-Chloro-oxazole-4-carboxylic acid [1-(3,5-difluoro-4-methanesulfonylamino-phenyl)-ethyl]-amide (40 mg, 0.11 mmol) was reacted with 3-trifluoromethyl phenol (20 mg, 0.12 mmol) to give the title compound (42 mg, 82%) after purification by column chromatography (gradient 12% to 100% EtOAc in n-hexane).

$^1$H NMR (300 MHz, CDCl$_3$): δ7.96 (s, 1H), 7.62~7.53 (m, 3H), 6.95~6.88 (m, 3H), 5.20~5.12 (m, 1H), 3.16 (s, 3H), 1.51 (d, 3H, J=6.9 Hz)

Example 3

2-(2-Isopropyl-phenoxy)-oxazole-4-carboxylic acid [1-(3,5-difluoro-4-methanesulfonylamino-phenyl)-ethyl]-amide

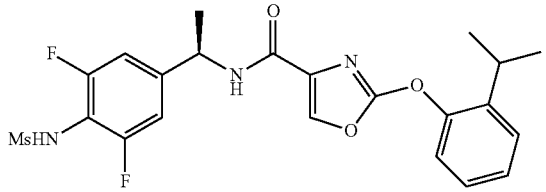

This compound was prepared according to the method of example 1.

2-Chloro-oxazole-4-carboxylic acid [1-(3,5-difluoro-4-methanesulfonylamino-phenyl)-ethyl]-amide (40 mg, 0.11 mmol) was reacted with 2-isopropyl phenol (18 mg, 0.12 mmol) to give the title compound (49 mg, 97%) after purification by column chromatography (gradient 12% to 100% EtOAc in n-hexane).

$^1$H NMR (300 MHz, CDCl$_3$): δ7.85 (s, 1H), 7.36~7.34 (m, 1H), 7.24~7.16 (m, 3H), 6.90~6.88 (m, 3H), 6.45 (s, 1H), 5.12~5.07 (m, 1H), 3.20~3.05 (m, 1H), 3.11 (s, 3H), 1.44 (d, 3H, J=7.2 Hz), 1.19 (d, 6H, J=6.9 Hz).

Example 4

2-(3-Isopropyl-phenoxy)-oxazole-4-carboxylic acid [1-(3,5-difluoro-4-methanesulfonylamino-phenyl)-ethyl]-amide

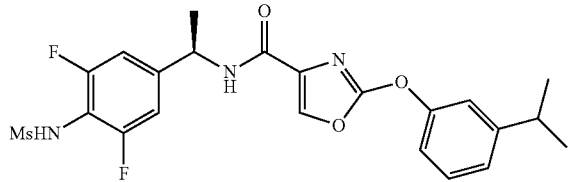

This compound was prepared according to the method of example 1.

2-Chloro-oxazole-4-carboxylic acid [1-(3,5-difluoro-4-methanesulfonylamino-phenyl)-ethyl]-amide (40 mg, 0.11 mmol) was reacted with 3-isopropyl phenol (18 mg, 0.12 mmol) to give the title compound (42 mg, 83%) after purification by column chromatography (gradient 12% to 100% EtOAc in n-hexane).

$^1$H NMR (300 MHz, CDCl$_3$): δ7.86 (s, 1H), 7.31 (t, 1H, J=8.4 Hz), 7.13~7.07 (m, 3H), 6.94 (d, 1H, J=7.8 Hz), 6.89 (d, 2H, J=8.4 Hz), 6.53 (s, 1H), 5.20~5.07 (m, 1H), 3.11 (s, 3H), 2.95~2.86 (m, 1H), 1.45 (d, 3H, J=6.9 Hz), 1.23 (d, 6H, J=6.9 Hz).

Example 5

2-(4-Isopropyl-phenoxy)-oxazole-4-carboxylic acid [1-(3,5-difluoro-4-methanesulfonylamino-phenyl)-ethyl]-amide

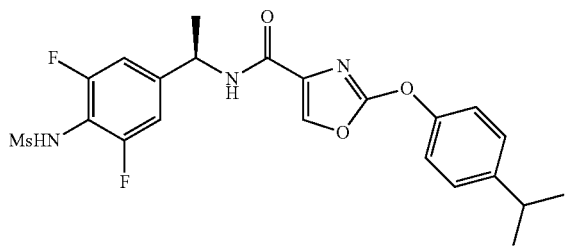

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 4-isopropyl phenol (36 mg, 0.26 mmol) to give the title compound (46 mg, 73%) after purification by column chromatography (gradient 12% to 100% EtOAc in n-hexane).

$^1$H NMR (300 MHz, CDCl$_3$): δ7.89 (s, 1H), 7.31~7.21 (m, 4H), 6.96 (d, 2H, J=8.7 Hz), 6.93 (d, 1H, J=5.7 Hz). 6.41 (s, 1H), 5.21~5.13 (m, 1H), 3.17 (s, 3H), 3.00~2.90 (m, 1H), 1.51 (d, 3H, J=6.9 Hz), 1.27 (d, 6H, J=6.9 Hz).

Example 6

2-(4-Trifluoromethyl-phenoxy)-oxazole-4-carboxylic acid [1-(3,5-difluoro-4-methanesulfonylamino-phenyl)-ethyl]-amide

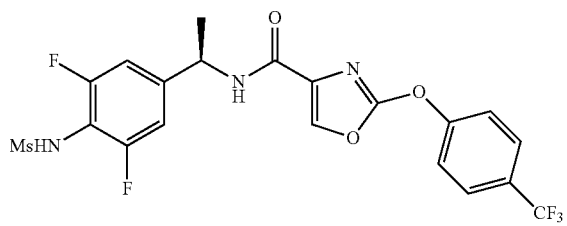

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 4-trifluoromethyl phenol (43 mg, 0.26 mmol) to give the title compound (45 mg, 67%) after purification by column chromatography (gradient 12% to 100% EtOAc in n-hexane).

$^1$H NMR (300 MHz, CDCl$_3$): δ7.95 (s, 1H), 7.73 (d, 2H, J=8.7 Hz), 7.47 (d, 2H, J=8.7 Hz), 6.97 (d, 2H, J=8.1 Hz), 6.86 (d, 1H, J=7.8 Hz), 6.44 (s, 1H), 5.22~5.14 (m, 1H), 3.17 (s, 3H), 1.52 (d, 3H, J=7.2 Hz).

Example 7

2-(4-tert-Butyl-phenoxy)-oxazole-4-carboxylic acid [1-(3,5-difluoro-4-methanesulfonylamino-phenyl)-ethyl]-amide

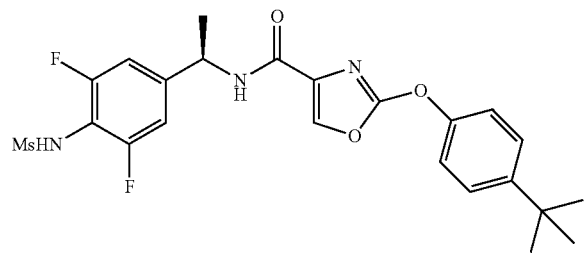

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 4-tert-butyl phenol (40 mg, 0.26 mmol) to give the title compound (33 mg, 51%) after purification by column chromatography (gradient 12% to 100% EtOAc in n-hexane).

$^1$H NMR (300 MHz, CDCl$_3$): δ7.86 (s, 1H), 7.44 (d, 2H, J=9.0 Hz), 7.23 (d, 2H, J=9.0 Hz), 6.97 (d, 2H, J=8.7 Hz), 6.91 (d, 1H, J=7.8 Hz), 6.11 (s, 1H), 5.20~5.15 (m, 1H), 3.18 (s, 3H), 1.52 (d, 3H, J=6.9 Hz), 1.34 (s, 9H).

Example 8

2-(3-Diethylamino-phenoxy)-oxazole-4-carboxylic acid [1-(3,5-difluoro-4-methanesulfonylamino-phenyl)-ethyl]-amide

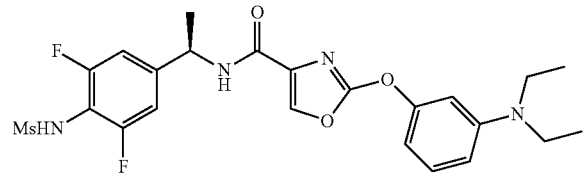

This compound was prepared according to the method of example 1

2-Chloro-oxazole-4-carboxylic acid [1-(3,5-difluoro-4-methanesulfonylamino-phenyl)-ethyl]-amide (50 mg, 0.13 mmol) was reacted with 3-diethylamino phenol (44 mg, 0.26 mmol) to give the title compound (26 mg, 39%) after purification by column chromatography (gradient 12% to 100% EtOAc in n-hexane).

$^1$H NMR (300 MHz, CDCl$_3$): δ7.90 (s, 1H), 7.25~7.18 (m, 1H), 7.02 (d, 1H, J=7.5 Hz), 6.93 (d, 2H, J=8.4 Hz), 6.57~6.51 (m, 4H), 5.17~5.12 (m, 1H), 3.35 (q, 4H, J=7.2 Hz), 3.15 (s, 3H), 1.49 (d, 3H, J=6.9 Hz), 1.72 (t, 6H, J=7.2 Hz).

Example 9

2-(3-Isopropyl-phenoxy)-oxazole-4-carboxylic acid 3,5-difluoro-4-methanesulfonylamino-benzylamide

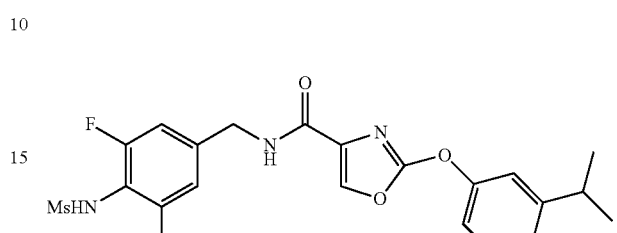

This compound was prepared according to the method of example 1.

2-Chloro-oxazole-4-carboxylic acid 3,5-difluoro-4-methanesulfonylamino-benzylamide (38 mg, 0.11 mmol) was reacted with 3-isopropyl phenol (18 mg, 0.12 mmol) to give the title compound (37 mg, 70%) after purification by column chromatography (gradient 12% to 100% EtOAc in n-hexane).

$^1$H NMR (300 MHz, CDCl$_3$): δ7.85 (s, 1H), 7.29 (t, 1H, J=8.4 Hz), 7.10~7.08 (m, 3H), 6.92 (d, 1H, J=7.8 Hz), 6.84 (d, 2H, J=8.4 Hz), 6.50 (s, 1H), 4.42 (d, 2H, d=6.0 Hz), 3.11 (s, 3H), 2.93~2.87 (m, 1H), 1.24 (d, 6H, J=6.9 Hz).

Example 10

(R)—N-[1-(3,5-Difluoro-4-methanesulfonylamino-phenyl)-ethyl]-2-(4-t-butylbenzyl)-thiazole-4-amide

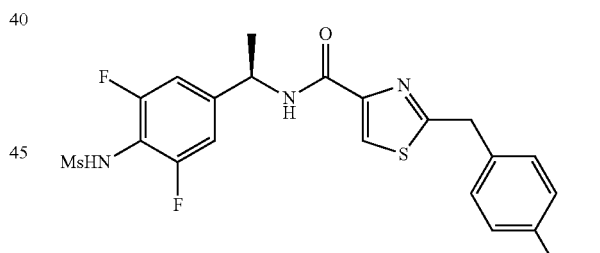

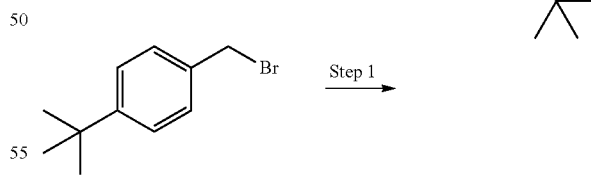

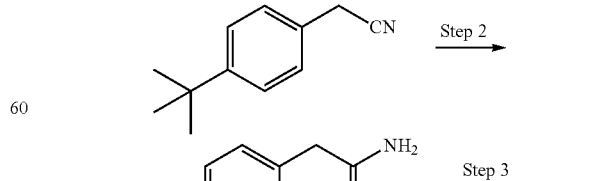

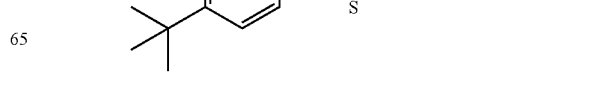

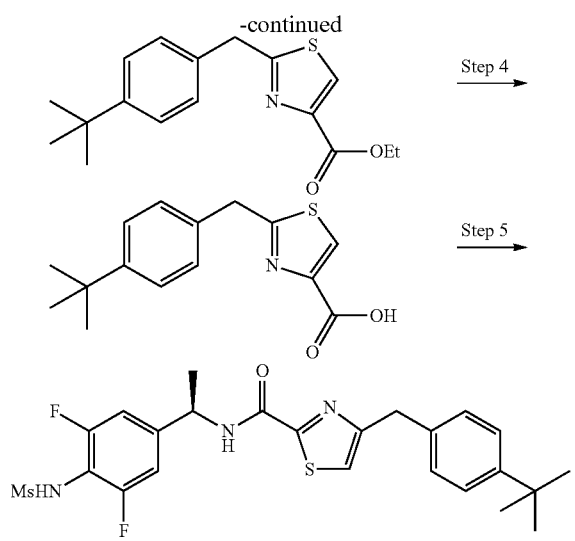

Step 1: (4-t-Butylphenyl)acetonitrile 4-t-Butylbenzylbromide (903 mg, 3.98 mmol) was reacted with NaCN (210 mg, 4.30 mmol) in ethanol (10 ml) and H₂O (2 ml) at 80° C. The reaction solvent was removed in vacuo. The residue was diluted with EtOAc and H₂O and the aqueous layer was extracted with EtOAc. The combined organic layer was dried over MgSO₄ and then concentrated in vacuo. The residue was purified with column chromatography to yield title compound (797 mg)

¹H NMR (300 MHz, CDCl₃): δ7.42 (d, 2H, J=8.4 Hz), 7.27 (d, 2H, J=8.4 Hz), 3.72 (s, 2H), 1.32 (s, 9H)

Step 2: 2-(4-tert-Butylbenzyl)thioacetamide 2-(4-t-Butylphenyl)acetonitrile (797 mg, 4.60 mmol) was reacted with ammonium sulfide solution (2 ml) in ethanol. The reaction solvent was removed in vacuo. The residue was diluted with EtOAc and H₂O and the aqueous layer was extracted with EtOAc. The combined organic layer was dried over MgSO₄ and then concentrated in vacuo. The residue was purified with column chromatography to yield title compound (173 mg)

¹H NMR (300 MHz, CDCl₃): δ7.42 (d, 2H, J=8.1 Hz), 7.20 (d, 2H, J=8.1 Hz), 4.09 (s, 2H), 1.32 (s, 9H)

Step 3: 2-(4-tert-Butylphenyl)thiazole-4-carboxylic acid ethyl ester 2-(4-tert-Butylbenzyl)thioacetamide (173 mg, 0.84 mmol) was reacted with ethyl bromopyruvate (0.12 ml) in ethanol at 80° C. The reaction solvent was removed in vacuo. The residue was diluted with EtOAc and H₂O and the aqueous layer was extracted with EtOAc. The combined organic layer was dried over MgSO₄ and then concentrated in vacuo. The residue was purified with column chromatography to yield title compound (177 mg)

¹H NMR (300 MHz, CDCl₃): δ8.04 (s, 1H), 7.34 (d, 2H, J=8.1 Hz), 7.25 (d, 2H, J=8.1 Hz), 4.44 (q, 2H, J=7.2 Hz), 4.35 (s, 2H), 1.43 (t., 3H, J=7.2 Hz), 1.32 (s, 9H)

Step 4: 2-(4-tert-Butylbenzyl)thiazole-4-carboxylic acid 2-(4-tert-Butylbenzyl)thiazole-4-carboxylic acid ethyl ester was hydrolysized with 1M LiOH (5 ml). The reaction solvent was removed in vacuo. The residue was diluted with EtOAc and H₂O and the aqueous layer was extracted with EtOAc. The combined organic layer was washed with brine, dried over MgSO₄ and then concentrated in vacuo.

¹H NMR (300 MHz, CDCl₃): δ8.04 (s, 1H), 7.34 (d, 2H, J=8.1 Hz), 7.25 (d, 2H, J=8.1 Hz), 4.98 (s, 2H), 1.25 (s, 9H)

Step 5: (R)—N-[1-(3,5-Difluoro-4-methanesulfonylamino-phenyl)-ethyl]-2-(4-t-butylbenzyl)-thiazole-4-amide (R)—N-(4-Aminoethyl-2,6-difluoro-phenyl)-methanesulfonamide, HCl salt (57 mg, 0.198 mmol) was reacted with 2-(4-tert-butylbenzyl)thiazole-4-carboxylic acid (49 mg, 0.178 mmol), NMM (0.2 ml) and DMTMM (60 mg, 0.23 mmol) to give the title compound (19 mg) after purification by column chromatography (Hex/EtOAc=1/1).

¹H NMR (300 MHz, CDCl₃): δ8.01 (s, 1H), 7.62 (d, 1H, J=7.8 Hz), 7.38 (d, 1H, J=8.1 Hz), 7.25 (d, 1H, J=8.1 Hz), 7.03 (d, 1H, J=8.7 Hz), 6.53 (br, 1H), 5.28 (t, 1H, J=7.5 Hz), 4.28 (s, 2H), 3.20 (s, 3H), 1.58 (d, 3H, J=6.9 Hz), 1.32 (s, 9H).

Example 11

(R)—N-[1-(3,5-Difluoro-4-methanesulfonylaminophenyl)-ethyl]-2-(3,4-difluorobenzyl)-thiazole-4-amide

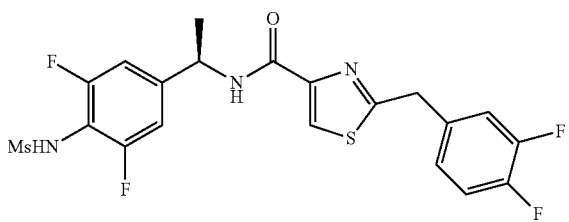

2-(3,4-Difluorobenzyl)thiazole-4-carboxylic acid was prepared as described in example 10.

(R)—N-(4-Aminoethyl-2,6-difluoro-phenyl)-methanesulfonamide, HCl salt (60 mg, 0.209 mmol) was reacted with 2-(3,4-difluorobenzyl)thiazole-4-carboxylic acid (49.3 mg, 0.193 mmol), NMM (0.2 ml) and DMTMM (65 mg, 0.23 mmol) to give the title compound (15 mg) after purification by column chromatography (Hex/EtOAc=1/1).

¹H NMR (300 MHz, CDCl₃): δ8.03 (s, 1H), 7.52 (d, 1H, J=7.8 Hz), 7.13 (m, 2H) 7.04 (m, 3H), 6.22 (br, 1H), 5.22 (t, 1H, J=7.5 Hz), 4.28 (s, 2H), 3.20 (s, 3H), 1.58 (d, 3H, J=6.9 Hz).

Example 12

N-[1-(3,5-Difluoro-4-methanesulfonylamino)-benzyl]-2-(3,4-difluorobenzyl)-thiazole-4-amide

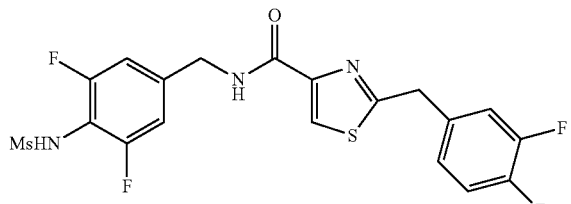

N-(4-Aminomethyl-2,6-difluoro-phenyl)-methanesulfonamide, HCl salt (57 mg) was reacted with 2-(3,4-difluorobenzyl)thiazole-4-carboxylic acid (46 mg, 0.193 mmol), NMM (0.2 ml) and DMTMM (67 mg, 0.24 mmol) to give the title compound (51 mg) after purification by column chromatography (Hex/EtOAc=1/1).

$^1$H NMR (300 MHz, CDCl$_3$): δ8.06 (s, 1H), 7.71 (t, 1H, J=7.5 Hz), 7.13 (m, 2H), 6.06 (br, 1H), 4.61 (d, 2H, J=6.3 Hz), 4.26 (s, 2H), 3.21 (s, 3H).

Example 13

2-(Cyclohexylmethyl-amino)-oxazole-4-carboxylic acid [1-(3,5-difluoro-4-methanesulfonylamino-phenyl)-ethyl]-amide

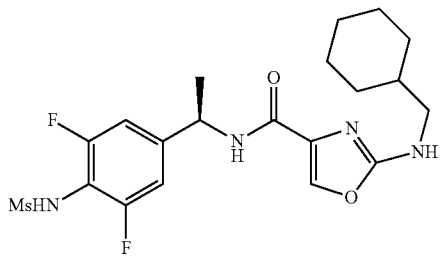

This compound was prepared according to the method of example 1.

2-Chloro-oxazole-4-carboxylic acid [1-(3,5-difluoro-4-methanesulfonylamino-phenyl)-ethyl]-amide (50 mg, 0.131 mmol) was reacted with cyclohexyl methylamine (33 mg, 0.29 mmol) to give the title compound (30 mg, 50%) after purification by column chromatography (gradient 12% to 100% EtOAc in n-hexane).

$^1$H NMR (300 MHz, CDCl$_3$): δ7.69 (s, 1H), 7.02 (d, 1H, J=8.1 Hz), 6.97 (d, 2H, J=8.7 Hz), 6.59 (s, 1H), 5.19~5.14 (m, 1H), 4.71 (t, 1H, J=6.0 Hz), 3.22~3.16 (m, 2H), 3.18 (s, 3H), 1.78~1.67 (m, 5H), 1.53 (d, 3H, J=7.2 Hz), 1.27~1.18 (m, 4H), 1.02~0.88 (m, 2H).

Example 14

2-(4-Trifluoromethyl-phenoxy)-thiazole-4-carboxylic acid 3,5-difluoro-4-methanesulfonylamino-benzylamide

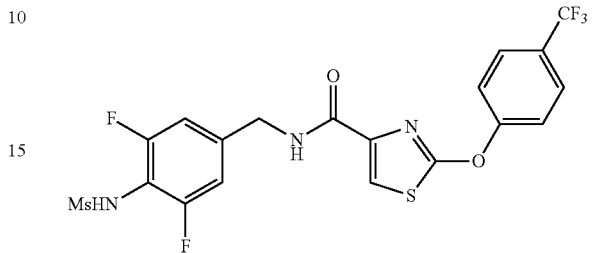

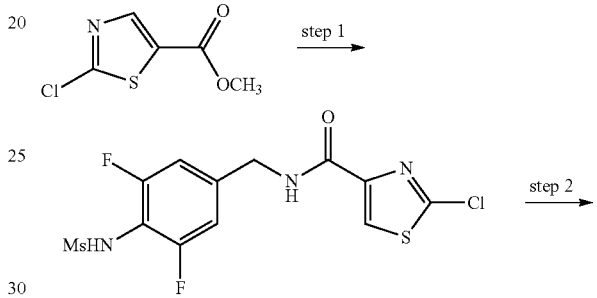

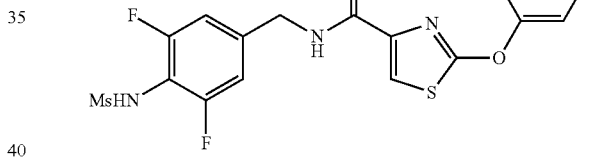

Step 1: 2-Chloro-thiazole-4-carboxylic acid 3,5-difluoro-4-methanesulfonylamino-benzylamide Methyl-2-chlorothiazole-4-carboxylate (2 g, 11.26 mmol) was dissolved in ethanol solution, to which was added excess c-HCl, and the resulting mixture was refluxed for 30 minutes. The reaction mixture was concentrated, and the crude acid (151 mg, 0.92 mmol) was dissolved in THF. To the resulting solution was added N-(4-aminomethyl-2,6-difluoro-phenyl)-methanesulfonamide, HCl salt (250 mg, 0.92 mmol) followed by DMTMM. The reaction mixture was stirred overnight at room temperature, and then diluted with EtOAc and water. The aqueous layer was extracted with EtOAc and the combined organic layer was washed with brine, dried over anhydrous magnesium sulfate, filtered, and concentrated under reduced pressure. The crude residue was purified by column chromatography (Hex/EtOAc=1:1) to give the title product (263 mg, 0.69 mmol).

$^1$H NMR (300 MHz, DMSO-d$_6$): δ9.43 (s, 1H), 9.20 (s, 1H), 8.24 (s, 1H), 7.15 (s, 1H), 7.09 (s, 1H), 4.41 (d, 2H, J=6.0 Hz), 3.03 (s, 3H).

Step 2: 2-(4-Trifluoromethyl-phenoxy)-thiazole-4-carboxylic acid 3,5-difluoro-4-methanesulfonylamino-benzylamide 2-Chloro-thiazole-4-carboxylic acid 3,5-difluoro-4-methanesulfonylamino-benzylamide (62 mg, 0.16 mmol), anhyd. K$_2$CO$_3$ (49 mg, 0.20 mmol) was reacted with 3-trifluoromethylphenol (40 µl, 0.19 mmol) as described above to give the title compound (42 mg, 51%) after purification by column chromatography (Hex/EtOAc=3:2)

$^1$H NMR (300 MHz, DMSO-d$_6$): δ9.47 (s, 1H), 8.89 (t, 1H, J=5.7 Hz), 7.81 (m, 5H), 7.07 (d, 2H, J=8.1 Hz), 4.39 (d, 2H, d=6.0 Hz), 3.03 (s, 3H).

Example 15

2-(3-Bromo-phenoxy)-oxazole-4-carboxylic acid [1-(3,5-difluoro-4-methanesulfonylamino-phenyl)-ethyl]-amide

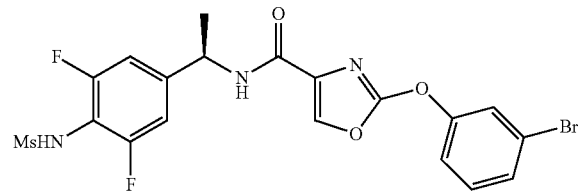

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-bromophenol (45 mg, 0.26 mmol) to give the title compound (38 mg, 56%) after purification by column chromatography (gradient 12% to 100% EtOAc in n-hexane).

$^1$H NMR (300 MHz, CDCl$_3$): δ7.94 (s, 1H), 7.50 (s, 1H), 7.44 (d, 1H, J=7.5 Hz), 7.35~7.26 (m, 2H), 6.96 (d, 2H, J=8.7 Hz), 6.92 (d, 1H, J=8.7 Hz), 6.60 (s, 1H), 5.18~5.13 (m, 1H), 3.16 (s, 3H), 1.52 (d, 3H, J=7.2 Hz).

Example 16

2-(3-Chloro-phenoxy)-oxazole-4-carboxylic acid [1-(3,5-difluoro-4-methanesulfonylamino-phenyl)-ethyl]-amide

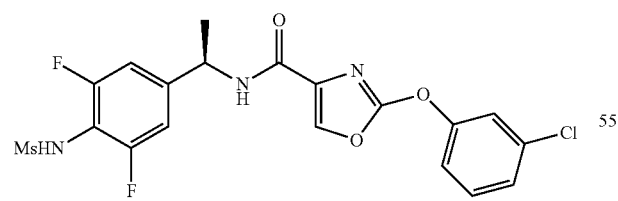

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-chlorophenol (34 mg, 0.26 mmol) to give the title compound (18 mg, 29%) after purification by column chromatography (gradient 12% to 100% EtOAc in n-hexane).

$^1$H NMR (300 MHz, CDCl$_3$): δ7.93 (s, 1H), 7.42~7.22 (m, 4H), 6.95 (d, 2H, J=8.4 Hz), 6.93 (d, 1H, J=10.2 Hz), 6.49 (s, 1H), 5.20~5.11 (m, 1H), 3.17 (s, 3H), 1.52 (d, 3H, J=6.9 Hz).

Example 17

2-(3-Cyano-phenoxy)-oxazole-4-carboxylic acid [1-(3,5-difluoro-4-methanesulfonylamino-phenyl)-ethyl]-amide

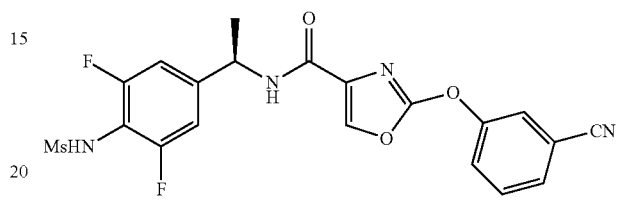

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-cyanophenol (31 mg, 0.26 mmol) to give the title compound (44 mg, 73%) after purification by column chromatography (gradient 12% to 100% EtOAc in n-hexane).

$^1$H NMR (300 MHz, CDCl$_3$): δ7.96 (s, 1H), 7.70 (s, 1H), 7.60 (m, 3H), 6.96 (d, 2H, J=8.7 Hz), 6.85 (d, 1H, J=7.8 Hz), 6.56 (s, 1 Hz), 5.20~5.14 (m, 1H), 3.17 (s, 3H), 1.54 (d, 3H, J=7.2 Hz).

Example 18

2-(3-Nitro-phenoxy)-oxazole-4-carboxylic acid [1-(3,5-difluoro-4-methanesulfonylamino-phenyl)-ethyl]-amide

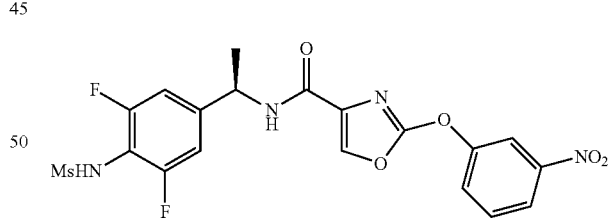

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-nitrophenol (36 mg, 0.26 mmol) to give the title compound (31 mg, 49%) after purification by column chromatography (gradient 12% to 100% EtOAc in n-hexane).

$^1$H NMR (300 MHz, CDCl$_3$): δ8.31 (d, 1H, J=2.4 Hz), 8.20 (d, 1H, J=7.5 Hz), 7.96 (s, 1H), 7.72~7.64 (m, 2H), 6.96 (d, 2H, J=8.4 Hz), 6.83 (d, 1H, J=7.8 Hz), 6.33 (s, 1H), 5.20~5.14 (m, 1H), 3.18 (s, 3H), 1.53 (d, 3H, J=6.9 Hz).

Example 19

2-(Octahydro-quinolin-1-yl)-oxazole-4-carboxylic acid [1-(3,5-difluoro-4-methanesulfonylamino-phenyl)-ethyl]-amide

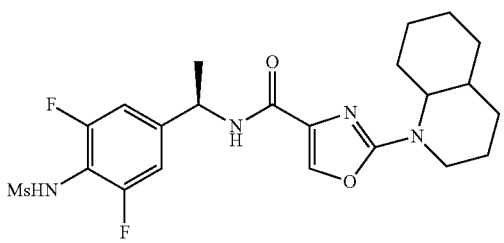

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with decahydroquinoline (26 mg, 0.26 mmol) to give the title compound (57 mg, 90%) after purification by column chromatography (gradient 12% to 100% EtOAc in n-hexane).

$^1$H NMR (300 MHz, CDCl$_3$): δ7.74 (s, 1H), 7.08 (d, 1H, J=7.5 Hz), 6.98 (d, 2H, J=8.4 Hz), 6.59 (s, 1H), 5.18~5.13 (m, 1H), 3.82~3.81 (m, 1H), 3.67~3.63 (m, 1H), 3.26~3.21 (m, 1H), 3.17 (s, 3H), 1.85~1.78 (m, 4H), 1.59~1.25 (m, 9H), 1.53 (d, 3H, J=6.9 Hz).

Example 20

2-(3-Trifluoromethyl-benzyl)-thiazole-4-carboxylic acid [1-(3,5-difluoro-4-methanesulfonylamino-phenyl)-ethyl]-amide

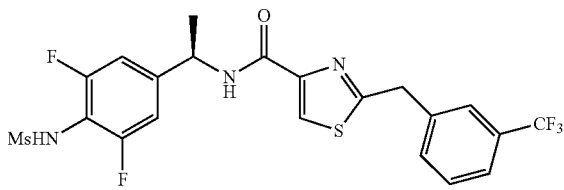

To a suspension of N-[4-(1-amino-ethyl)-2,6-difluoro-phenyl]-methanesulfonamide, HCl salt (143 mg, 0.50 mmol) in THF (3 mL) was added N-methylmorpholine (110 μL, 1.00 mmol). The mixture was stirred for 5 minutes, to which were added 2-(3-trifluoromethyl-benzyl)-1,3-thiazole-4-carboxylic acid (115 mg, 0.40 mmol) and DMTMM (138 mg, 0.50 mmol). The mixture was stirred overnight at room temperature and was diluted with EtOAc and water. The aqueous layer was extracted with EtOAc and the combined organic layer was washed with brine, dried over anhydrous magnesium sulfate, filtered, and concentrated under reduced pressure. The crude residue was purified by column chromatography (gradient 12% to 100% EtOAc in n-hexane) to give title compound (39 mg, 19%).

$^1$H NMR (300 MHz, CDCl$_3$): δ8.05 (s, 1H), 7.54 (m, 4H), 7.01 (d, 2H, J=8.7 Hz), 6.52 (s, 1H), 5.21 (m, 1H), 4.39 (s, 2H), 3.18 (s, 3H), 1.58 (d, 3H, J=6.9 Hz)

Example 21

5-(3-Isopropyl-phenoxy)-thiophene-2-carboxylic acid [1-(3,5-difluoro-4-methanesulfonylamino-phenyl)-ethyl]-amide

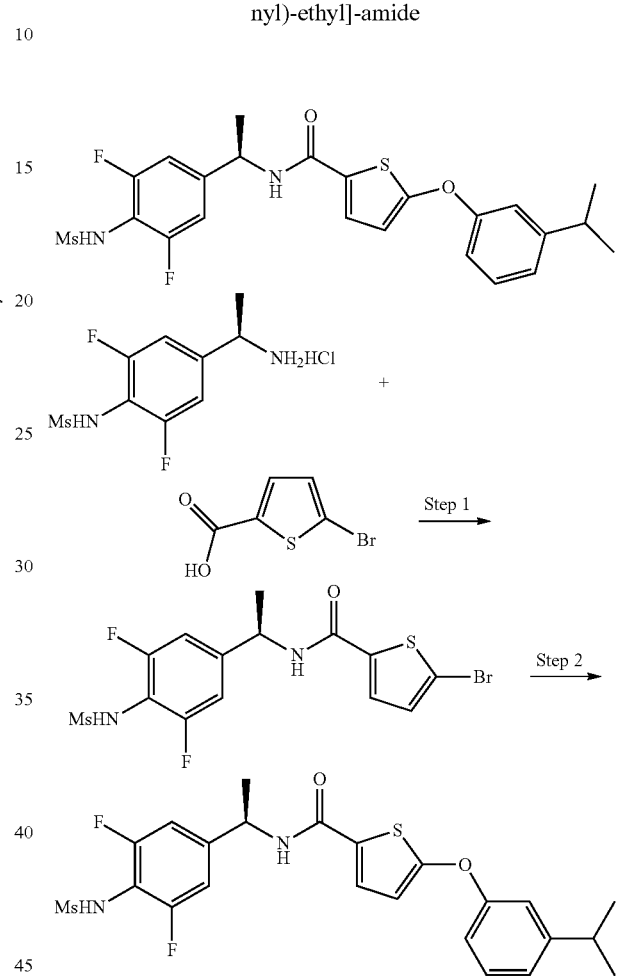

Step 1: 5-Bromo-thiophene-2-carboxylic acid 3,5-difluoro-4-methanesulfonylamino-benzylamide To a suspension of N-(4-aminomethyl-2,6-difluoro-phenyl)-methanesulfonamide, HCl salt (1.45 g, 5.31 mmol) in DMF (20 mL) was added N-methylmorpholine (548 μL, 5.31 mmol). The mixture was stirred for 5 minutes, to which were added 5-bromo-thiophene-2-carboxylic acid (1.0 g, 4.83 mmol) and N-(3-dimethylaminopropyl)-N'-ethylcarbodiimide HCl salt (1.05 g, 5.31 mmol). The mixture was stirred overnight at room temperature and was diluted with EtOAc and water. The organic layer was washed with saturated sodium bicarbonate, 1N HCl and brine, dried over anhydrous magnesium sulfate, filtered, and concentrated under reduced pressure. The crude residue was purified by recrystallization from n-Hex/EtOAc to give title compound (848 mg, 41%).

$^1$H NMR (300 MHz, DMSO-d$^6$): δ9.49 (s, 1H), 9.17 (t, 1H, J=6.0 Hz), 7.64 (d, 1H, J=3.6 Hz), 7.30 (d, 1H, J=3.6 Hz), 7.11 (d, 2H, J=8.7 Hz), 4.43 (d, 2H, J=6.0 Hz), 3.04 (s, 3H).

Step 2: 5-(3-Isopropyl-phenoxy)-thiophene-2-carboxylic acid [1-(3,5-difluoro-4-methanesulfonylamino-phenyl)-ethyl]-amide In a 5 ml glass tube were placed 5-bromo-thiophene-2-carboxylic acid [1-(3,5-difluoro-4-methanesulfonylaminophenyl)-ethyl]-amide (50 mg, 0.14 mmol), 3-isopropylphenol (62 mg, 0.27 mmol), CuI (5 mg, weight of 10%), $Cs_2CO_3$ (88 mg, 0.27 mmol), NMP (1 mL), ethanol (1 mL), and a magnetic stir bar. The vial was sealed with septum and placed into the Microwave cavity. The vial was irradiated in a Microwave synthesizer at 195° C. for 120 min. The mixture was diluted with EtOAc and washed with 1N HCl and water. The organic layer was dried over anhydrous $MgSO_4$ and concentrated under reduced pressure. The crude residue was purified by column chromatography (gradient 12% to 100% EtOAc in n-hexane) to give title compound (2.5 mg, 4.5%).

$^1$H NMR (300 MHz, $CDCl_3$): δ7.29 (d, 1H, J=6.0 Hz), 7.11~7.06 (m, 1H), 6.98~6.85 (m, 2H), 6.73 (d, 1H, J=9.9 Hz), 6.65 (d, 1H, J=8.1 Hz), 6.47 (s, 1H), 6.00 (s, 1H), 5.88 (d, 1H, J=9.9 Hz), 4.98~4.48 (m, 1H), 3.05 (s, 3H), 2.73~2.64 (m, 1H), 1.29 (d, 3H, J=6.9 Hz) 1.03 (d, 6H, J=6.6 Hz).

Example 22

2-(Indan-5-yloxy)-oxazole-4-carboxylic acid [1-(3,5-difluoro-4-methanesulfonylamino-phenyl)-ethyl]-amide

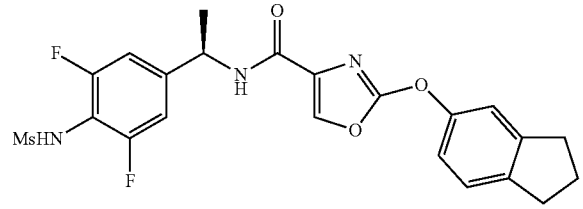

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with indan-5-ol (35 mg, 0.26 mmol) to give the title compound (42 mg, 67%) after purification by column chromatography (gradient 12% to 100% EtOAc in n-hexane).

$^1$H NMR (300 MHz, $CDCl_3$): δ7.86 (s, 1H), 7.25 (t, 1H, J=6.9 Hz), 7.12 (s, 1H), 7.04 (d, 1H, J=8.1 Hz), 6.95 (d, 2H, J=8.7 Hz), 6.91 (d, 1H, J=7.8 Hz), 6.23 (s, 1H), 5.19~5.13 (m, 1H), 3.17 (s, 3H), 2.95 (d, 2H, J=7.5 Hz), 2.90 (d, 2H, J=7.5 Hz), 2.20~2.04 (m, 2H), 1.50 (d, 3H, J=6.9 Hz).

Example 23

2-(Quinolin-6-yloxy)-oxazole-4-carboxylic acid [1-(3,5-difluoro-4-methanesulfonylamino-phenyl)-ethyl]-amide

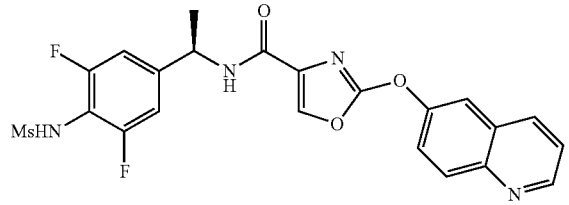

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with quinolin-6-ol (38 mg, 0.26 mmol) to give the title compound (27 mg, 42%) after purification by column chromatography (gradient 12% to 100% EtOAc in n-hexane).

$^1$H NMR (300 MHz, $CDCl_3$): δ8.96~8.94 (m, 1H), 8.22~8.17 (m, 2H), 7.95 (s, 1H), 7.76 (d, 1H, J=2.4 Hz), 7.69 (dd, 1H, J=9.3, 2.7 Hz), 7.48 (q, 1H, J=4.2 Hz), 6.95 (d, 2H, J=8.4 Hz), 6.86 (d, 1H, J=7.8 Hz), 6.51 (s, 1H), 5.19~5.14 (m, 1H), 3.17 (s, 3H), 1.49 (d, 3H, J=7.2 Hz).

Example 24

2-(Quinolin-8-yloxy)-oxazole-4-carboxylic acid [1-(3,5-difluoro-4-methanesulfonylamino-phenyl)-ethyl]-amide

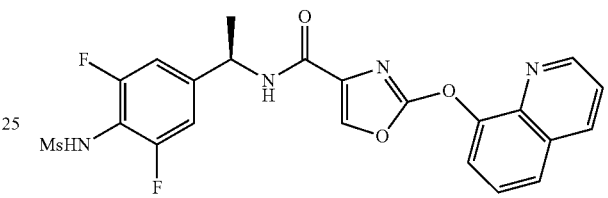

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with quinolin-8-ol (38 mg, 0.26 mmol) to give the title compound (37 mg, 58%) after purification by column chromatography (gradient 12% to 100% EtOAc in n-hexane).

$^1$H NMR (300 MHz, $CDCl_3$): δ8.88~8.86 (m, 1H), 8.24~8.21 (m, 1H), 7.86 (s, 1H), 7.80 (d, 1H, J=8.1 Hz), 7.71~7.69 (m, 1H), 7.62~7.57 (m, 1H), 7.49~7.45 (m, 1H), 6.92~6.90 (m, 3H), 6.51 (s, 1H), 5.14~5.09 (m, 1H), 3.16 (s, 3H), 1.45 (d, 3H, J=6.9 Hz).

Example 25

2-(4-Tri fluoromethyl-pyridin-2-yloxy)-oxazole-4-carboxylic acid [1-(3,5-difluoro-4-methanesulfonylamino-phenyl)-ethyl]-amide

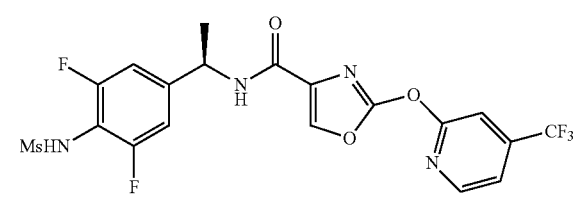

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 4-trifluoromethyl-pyridin-2-ol (43 mg, 0.26 mmol) to give the title compound (20 mg, 30%) after purification by column chromatography (gradient 12% to 100% EtOAc in n-hexane).

$^1$H NMR (300 MHz, CDCl$_3$): δ8.27 (s, 1H), 7.70 (d, 1H, J=7.2 Hz), 7.03-6.96 (m, 4H), 6.43 (d, 1H, J=7.2 Hz), 6.15 (s, 1H), 5.25~5.20 (m, 1H), 3.21 (s, 3H), 1.58 (d, 3H, J=5.4 Hz).

Example 26

2-(8-Chloro-pyridin-2-yloxy)-oxazole-4-carboxylic acid [1-(3,5-difluoro-4-methanesulfonylamino-phenyl)-ethyl]-amide

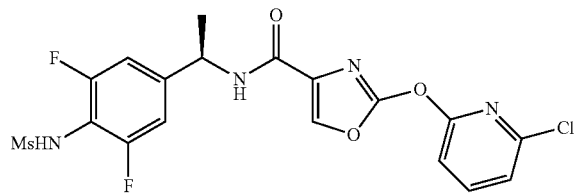

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 6-chloro-pyridin-2-ol (34 mg, 0.26 mmol) to give the title compound (50 mg, 82%) after purification by column chromatography (gradient 12% to 100% EtOAc in n-hexane).

$^1$H NMR (300 MHz, CDCl$_3$): δ8.03 (s, 1H), 7.80 (t, 1H, J=7.8 Hz), 7.27 (d, 1H, J=6.9 Hz), 7.10 (d, 1H, J=8.1 Hz), 7.02~6.96 (m, 3H), 6.51 (s, 1H), 5.20~5.15 (m, 1H), 3.18 (s, 3H), 1.53 (d, 3H, J=6.9 Hz).

Example 27

2-(3-Ethynyl-phenoxy)-oxazole-4-carboxylic acid [1-(3,5-difluoro-4-methanesulfonylamino-phenyl)-ethyl]-amide

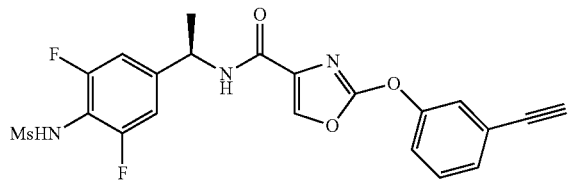

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-ethynyl-phenol (31 mg, 0.26 mmol) to give the title compound (55 mg, 91%) after purification by column chromatography (gradient 12% to 100% EtOAc in n-hexane).

$^1$H NMR (300 MHz, CDCl$_3$): δ7.90 (s, 1H), 7.42~7.40 (m, 3H), 7.33~7.29 (m, 1H), 6.96 (d, 2H, J=8.7 Hz), 6.87 (d, 1H, J=7.5 Hz), 6.29 (s, 1H), 5.21~5.11 (m, 1H), 3.17 (s, 3H), 1.51 (d, 3H, J=6.9 Hz).

Example 28

2-(1-Methylene-indan-4-yloxy)-oxazole-4-carboxylic acid [1-(3,5-difluoro-4-methanesulfonylamino-phenyl)-ethyl]-amide

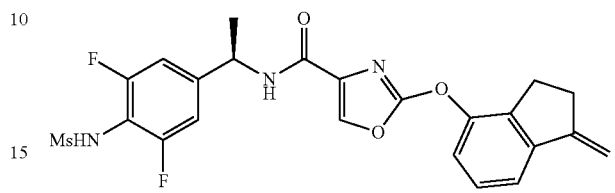

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 1-methylene-indan-4-ol (38 mg, 0.26 mmol) prepared as in example 30 to give the title compound (49 mg, 77%) after purification by column chromatography (gradient 12% to 100% EtOAc in n-hexane).

$^1$H NMR (300 MHz, CDCl$_3$): δ7.89 (s, 1H), 7.44 (d, 1H, J=7.5 Hz), 7.32~7.27 (m, 2H), 7.16 (d, 1H, J=7.8 Hz), 6.94 (d, 1H, J=8.1 Hz), 6.90 (d, 1H, J=7.8 Hz), 6.38 (s, 1H), 5.52 (t, 1H, J=2.4 Hz), 5.19~5.12 (m, 1H), 5.12 (s, 1H), 3.17 (s, 3H), 2.94~2.81 (m, 4H), 1.50 (d, 3H, J=6.9 Hz).

Example 29

2-(3-Ethyl-phenoxy)-oxazole-4-carboxylic acid [1-(3,5-difluoro-4-methanesulfonylamino-phenyl)-ethyl]-amide

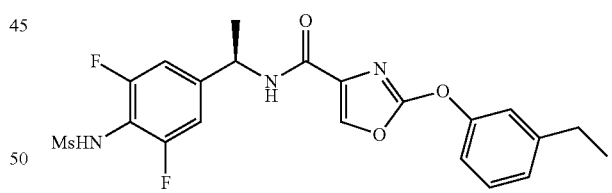

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-ethyl-phenol (32 mg, 0.26 mmol) to give the title compound (49 mg, 80%) after purification by column chromatography (gradient 12% to 100% EtOAc in n-hexane).

$^1$H NMR (300 MHz, CDCl$_3$): δ7.91 (s, 1H), 7.35 (t, 1H, J=7.8 Hz), 7.15~7.12 (m, 3H), 6.96~6.93 (m, 3H), 6.54 (s, 1H), 5.20~5.12 (m, 1H), 3.16 (s, 3H), 2.70 (q, 2H, J=7.5 Hz), 1.50 (d, 3H, J=6.6 Hz), 1.26 (t, 3H, J=7.5 Hz).

Example 30

2-(1-Methyl-indan-4-yloxy)-oxazole-4-carboxylic acid [1-(3,5-difluoro-4-methanesulfonylamino-phenyl)-ethyl]-amide

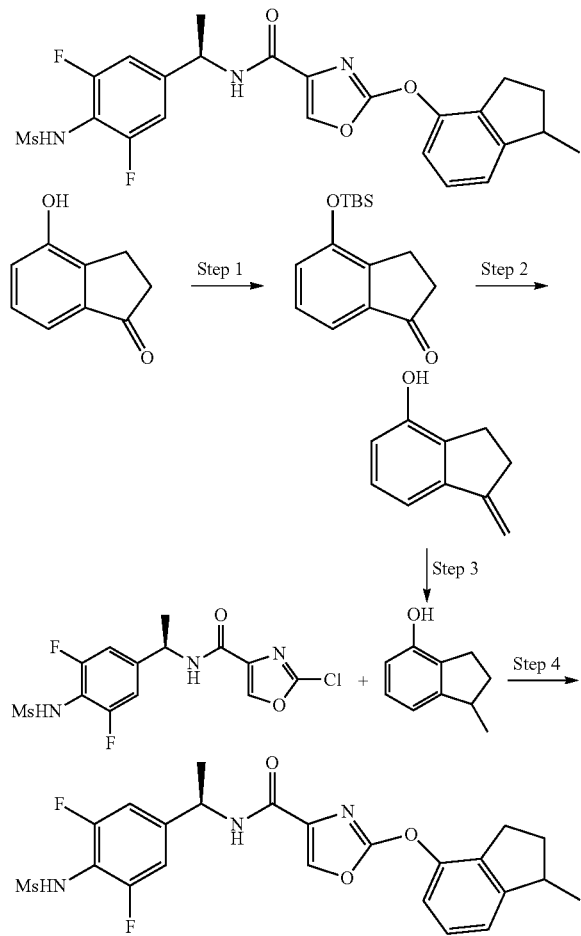

Step 1:
4-(tert-Butyl-dimethyl-silanyloxy)-indan-1-one

To a solution of 4-hydroxy-indan-1-one (1.0 g, 6.75 mmol) in CH$_2$Cl$_2$ (20 mL) was added imidazole (690 mg, 10.12 mmol). The mixture was stirred for 5 minutes, to which was added portionwise tert-butyldimethylsilyl chloride (1.05 g, 5.31 mmol). The mixture was stirred for 3 hours at room temperature and was diluted with EtOAc. The organic layer was washed with 1N HCl, water and brine, dried over anhydrous magnesium sulfate, filtered, and concentrated under reduced pressure. The crude residue was purified by column chromatography to give 4-(tert-butyl-dimethyl-silanyloxy)-indan-1-one (1600 mg, 90%).

$^1$H NMR (300 MHz, CDCl$_2$): δ7.27 (d, 1H, J=7.5 Hz), 7.15 (t, 1H, J=7.5 Hz), 6.89 (d, 1H, J=7.5 Hz), 2.93 (t, 2H, J=5.7 Hz), 2.57 (t, 2H, J=5.7 Hz), 0.81 (s, 9H), 0.15 (s, 6H).

Step 2: 1-Methylene-indan-4-ol

To a suspension of CH$_3$PPh$_3$I (924 mg, 2.29 mmol) in Et$_2$O (20 mL) was added t-BuOK (256 mg, 2.29 mmol). The mixture was stirred for 15 minutes, to which was added dropwise 4-(tert-butyl-dimethyl-silanyloxy)-indan-1-one (500 mg, 1.91 mmol). The mixture was stirred at room temperature overnight and then diluted with diethylether. The mixture was filtered on a pad of celite. The remaining precipitate was washed with diethylether. The combined filtrate was concentrated under reduced pressure. The crude compound was dissolved in THF and then was added 1M-TBAF (in THF, 1.2 eq). The reaction mixture was stirred for 30 min at room temperature, treated with saturated ammonium chloride, and then extracted with EtOAc. The organic layer was dried over magnesium sulfate and concentrated in vacuo. The crude product was purified by column chromatography to give 1-methylene-indan-4-ol (200 g, 72%).

1H NMR (300 MHz, CDCl$_3$): δ7.10 (d, 2H, J=3.9 Hz), 6.69 (t, 1H, J=4.2 Hz), 5.43 (s, 1H), 5.03 (s, 1H), 2.92~2.82 (m, 4H).

Step 3: 1-Methyl-indan-4-ol

A mixture of 1-methylene-indan-4-ol (200 mg, 1.37 mmol) and 10% Pd/C (60 mg, 10% weight) in methanol (6 ml) was hydrogenated under 50 psi hydrogen atmosphere for 1 hour. The mixture was dissolved in EtOAc, filtered through a celite pad. The filtrate was concentrated under reduced pressure, and dried to give 1-methyl-indan-4-ol (190 g, 94%)

1H NMR (300 MHz, CDCl$_3$): δ7.08 (t, 1H, J=7.5 Hz), 6.79 (d, 1H, J=7.5 Hz), 6.64 (d, 1H, J=7.5 Hz), 5.02 (s, 1H), 3.23~3.16 (m, 1H), 2.96~2.84 (m, 1H), 2.79~2.68 (m, 1H), 2.39~2.29 (m, 1H), 1.70~1.60 (m, 1H), 1.28 (d, 3H, J=6.9 Hz).

Step 4: 2-(1-Methyl-indan-4-yloxy)-oxazole-4-carboxylic acid [1-(3,5-difluoro-4-methanesulfonylamino-phenyl)-ethyl]-amide 2-Chloro-oxazole-4-carboxylic acid [1-(3,5-difluoro-4-methanesulfonylamino-phenyl)-ethyl]-amide (50 mg, 0.13 mmol) was reacted with 1-methyl-indan-4-ol (39 mg, 0.26 mmol) to give the title compound (40 mg, 63%) after purification by column chromatography (gradient 12% to 100% EtOAc in n-hexane).

1H NMR (300 MHz, CDCl$_3$): δ7.90 (s, 1H), 7.26 (t, 1H, J=7.8 Hz), 7.14-7.08 (m, 2H), 6.98~6.92 (m, 3H), 5.19~5.12 (m, 1H), 3.25~3.16 (m, 1H), 3.17 (s, 3H), 2.93~2.83 (m, 1H), 2.79~2.71 (m, 1H), 2.40~2.31 (m, 1H), 1.71~1.58 (m, 1H), 1.49 (d, 3H, J=6.6 Hz), 1.31 (d, 3H, J=6.9 Hz).

Example 31

2-(3-Isopropyl-phenoxy)-thiazole-4-carboxylic acid [1-(3,5-difluoro-4-methanesulfonylamino-phenyl)-ethyl]-amide

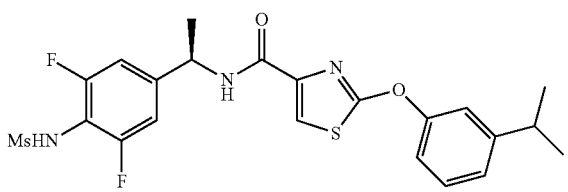

This compound was prepared according to the method of example 1.

2-Chloro-thiazole-4-carboxylic acid [1-(3,5-difluoro-4-methanesulfonylamino-phenyl)-ethyl]-amide (50 mg, 0.13 mmol) was reacted with 3-isopropyl phenol (34 mg, 0.25 mmol) to give the title compound (42 mg, 67%) after purification by column chromatography (gradient 12% to 100% EtOAc in n-hexane).

$^1$H NMR (300 MHz, CDCl$_3$): δ7.67 (s, 1H), 7.43~7.34 (m, 2H), 7.20~7.15 (m, 3H), 7.00~6.97 (m, 2H), 6.48 (s, 1H), 5.22~5.15 (m, 1H), 3.18 (s, 3H), 3.01~2.90 (m, 1H), 1.56 (d, 3H, J=7.2 Hz), 1.26 (d, 6H, J=6.6 Hz).

Example 32

2-(3-Cyclopropyl-phenoxy)-oxazole-4-carboxylic acid [1-(3,5-difluoro-4-methanesulfonylamino-phenyl)-ethyl]-amide

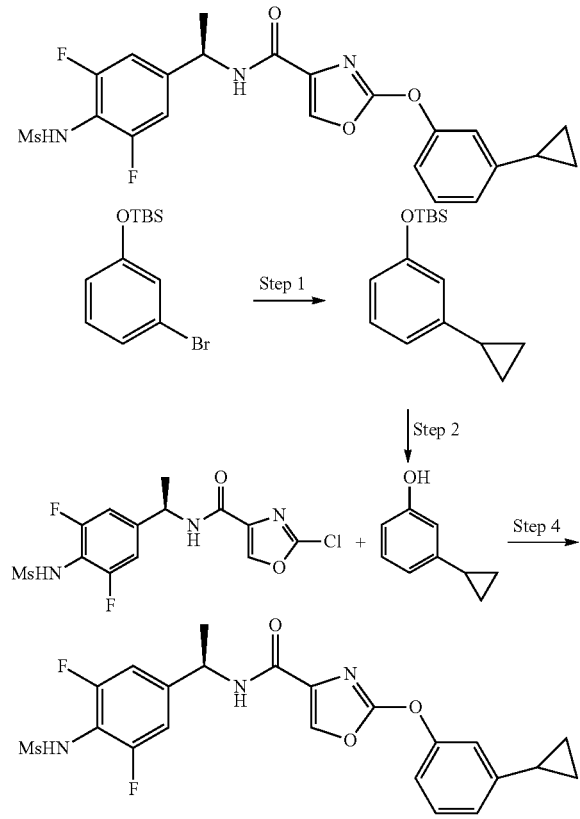

Step 1: tert-Butyl-(3-cyclopropyl-phenoxy)-dimethyl-silane

A suspension of (3-bromo-phenoxy)-tert-butyl-dimethyl-silane (500 mg, 0.1.74 mmol), cyclopropyl boronic acid (194 mg, 2.26 mmol), K$_3$PO$_4$ (1.3 g, 6.1 mmol), PCy$_3$ (49 mg, 0.17 mmol), and Pd(OAc)$_2$ (20 mg, 0.087 mmol) in toluene/water (8 ml/0.4 ml) was stirred 3 hours at 110° C. and then diluted with Et$_2$O. The organic layer was washed with water and brine, dried over anhydrous magnesium sulfate, filtered, and concentrated under reduced pressure. The crude residue was purified by column chromatography (gradient 12% to 100% EtOAc in n-hexane) to give tert-butyl-(3-cyclopropyl-phenoxy)-dimethyl-silane (390 mg, 90%).

$^1$H NMR (300 MHz, CDCl$_3$): δ7.15~7.09 (m, 1H), 6.71 (d, 1H, J=7.8 Hz), 6.47 (dd, 1H, J=7.8, 1.5 Hz), 6.56 (s, 1H), 1.91~1.84 (m, 1H), 1.01 (s, 9H), 0.98~0.94 (m, 2H), 0.72~0.68 (m, 2H), 0.22 (s, 6H).

Step 2: 3-Cyclopropyl-phenol

To a solution of tert-butyl-(3-cyclopropyl-phenoxy)-dimethyl-silane (390 mg, 1.57 mmol) in THF (5 mL) was added a solution of 1M-TBAF (in THF, 2 mL, 1.3 mmol), and the mixture was stirred for 30 min at room temperature. The residue was diluted with EtOAc and water. The organic layer was washed with saturated ammonium chloride, water and brine, dried over anhydrous magnesium sulfate, filtered, and concentrated under reduced pressure. The crude residue was purified by column chromatography to give 3-cyclopropyl-phenol (200 mg, 95%).

1H NMR (300 MHz, CDCl$_3$): δ7.10 (t, 1H, J=7.8 Hz), 6.66 (d, 1H, J=7.5 Hz), 6.60 (dd, 1H, J=8.1, 2.1 Hz), 6.52 (s, 1H), 1.88~1.79 (m, 1H), 0.96~0.85 (m, 2H), 0.96~0.85 (m, 2H), 0.69~0.65 (m, 2H).

Step 3: 2-(3-Cyclopropyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-cyclopropyl-phenol (35.2 mg, 0.26 mmol) to give the title compound (52 mg, 83%) after purification by column chromatography (gradient 12% to 100% EtOAc in n-hexane).

1H NMR (300 MHz, CDCl$_3$): δ7.92 (s, 1H), 7.31 (t, 1H, J=8.1 Hz), 7.10~6.92 (m, 6H), 6.43 (s, 1H), 5.20~5.11 (m, 1H), 3.17 (s, 3H), 1.96~1.88 (m, 1H), 1.50 (d, 3H, J=7.2 Hz), 1.05~0.99 (m, 2H), 0.75~0.69 (m, 2H).

Example 33

2-(2-Propyl-4-trifluoromethyl-phenoxy)-oxazole-4-carboxylic acid [1-(3,5-difluoro-4-methanesulfonylamino-phenyl)-ethyl]-amide

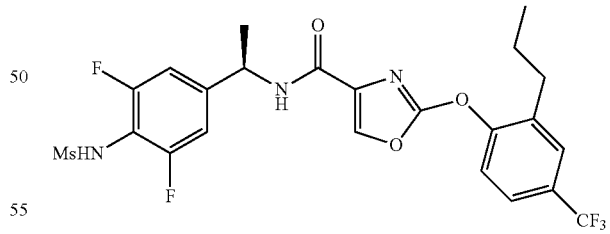

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 2-propyl-4-trifluoromethylphenol (37 mg, 0.18 mmol) to give the title compound (40 mg, 55%) after purification by flash chromatography on silica gel (gradient 12% to 100% EtOAc in n-hexane).

$^1$H NMR (300 MHz, CDCl$_3$): δ7.94 (m, 2H), 7.30 (d, 1H, J=8.7 Hz), 6.99-6.89 (m, 4H), 6.57 (s, 1H), 5.15 (m, 1H), 3.17

(s, 3H), 2.66 (t, 2H, J=7.7 Hz), 1.67 (m, 2H), 1.52 (d, 3H, J=6.9 Hz), 0.97 (t, 2H, J=7.2 Hz)

Example 34

2-(2,2-Dimethyl-2,3-dihydro-benzofuran-7-yloxy)-oxazole-4-carboxylic acid [1-(3,5-difluoro-4-methanesulfonylamino-phenyl)-ethyl]-amide

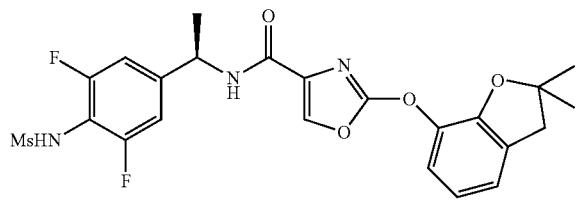

This compound was prepared according to the method of example 1.

2-Chloro-oxazole-4-carboxylic acid [1-(3,5-difluoro-4-methanesulfonylamino-phenyl)-ethyl]-amide (40 mg, 0.11 mmol) was reacted with 2,3-dihydro-2,2-dimethyl-7-benzofuranol (22 mg, 0.13 mmol) to give the title compound (50 mg, 94%) after purification by flash chromatography on silica gel (gradient 12% to 100% EtOAc in n-hexane).

$^1$H NMR (300 MHz, CDCl$_3$): δ7.86 (s, 1H), 7.08 (m, 2H), 6.94 (d, 3H, J=8.1 Hz), 6.85 (t, 1H, J=7.8 Hz), 6.35 (s, 1H), 5.15 (m, 1H), 3.17 (s, 3H), 3.07 (s, 2H), 1.50~1.44 (m, 9H)

Example 35

2-[3-(2,2,2-Trifluoro-1-methyl-ethyl)-phenoxy]-oxazole-4-carboxylic acid [1-(3,5-difluoro-4-methanesulfonylamino-phenyl)-ethyl]-amide

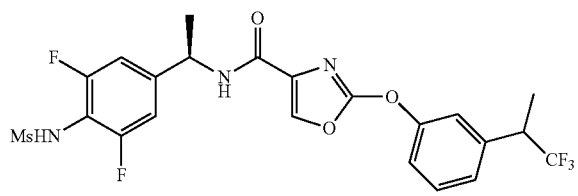

This compound was prepared according to the method of example 1.

2-Chloro-oxazole-4-carboxylic acid [1-(3,5-difluoro-4-methanesulfonylamino-phenyl)-ethyl]-amide (30 mg, 0.08 mmol) was reacted with 3-(1-trifluoromethylethyl)phenol (20 mg, 0.11 mmol) to give the title compound (37 mg, 88%) after purification by flash chromatography on silica gel (gradient 12% to 100% EtOAc in n-hexane).

$^1$H NMR (300 MHz, CDCl$_3$): δ7.90 (s, 1H), 7.44 (t, 1H, J=7.8 Hz), 7.34-7.25 (m, 3H), 6.96 (d, 2H, J=8.1 Hz), 6.90 (d, 1H, J=7.8 Hz), 6.25 (s, 1H), 5.15 (m, 1H), 3.49 (m, 1H), 3.18 (s, 3H), 1.53 (m, 6H)

Example 36

2-(3,5-Bis-trifluoromethyl-phenoxy)-oxazole-4-carboxylic acid [1-(3,5-difluoro-4-methanesulfonylamino-phenyl)-ethyl]-amide

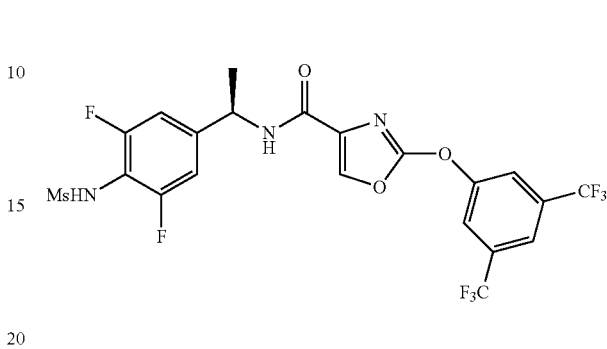

This compound was prepared according to the method of example 1.

2-Chloro-oxazole-4-carboxylic acid [1-(3,5-difluoro-4-methanesulfonylamino-phenyl)-ethyl]-amide (30 mg, 0.08 mmol) was reacted with 3,5-bis(trifluoromethyl)-phenol (30 mg, 0.13 mmol) to give the title compound (30 mg, 65%) after purification by flash chromatography on silica gel (gradient 12% to 100% EtOAc in n-hexane).

$^1$H NMR (300 MHz, CDCl$_3$): δ7.96 (s, 1H), 7.88 (s, 1H), 7.86 (d, 2H, J=10.8 Hz), 6.96 (d, 2H, J=8.1 Hz), 6.80 (d, 1H, J=7.8 Hz), 6.20 (s, 1H), 5.16 (m, 1H), 3.19 (s, 3H), 1.53 (d, 3H, J=6.9 Hz)

Example 37

2-(5-Methylene-5,6,7,8-tetrahydro-naphthalen-1-yloxy)-oxazole-4-carboxylic acid [1-(3,5-difluoro-4-methanesulfonylamino-phenyl)-ethyl]-amide

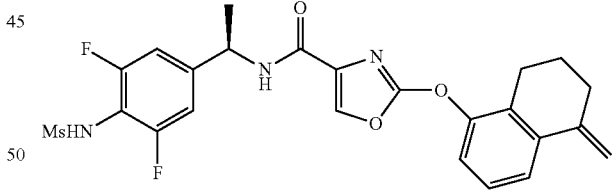

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 5-methylene-5,6,7,8-tetrahydro-naphthalen-1-ol (43 mg, 0.26 mmol, example 39) to give the title compound (52 mg, 85%) after purification by column chromatography (gradient 12% to 100% EtOAc in n-hexane).

$^1$H NMR (300 MHz, CDCl$_3$): δ7.91 (s, 1H), 7.60 (d, 1H, J=7.8 Hz), 7.23 (t, 1H, J=7.8 Hz), 7.15 (d, 1H, J=8.1 Hz), 6.95~6.92 (m, 3H), 6.64 (s, 1H), 5.53 (s, 1H), 5.16~5.09 (m, 1H), 5.04 (s, 1H), 3.15 (s, 3H), 2.76 (d, 2H, J=6.3 Hz), 2.52 (d, 2H, J=6.0 Hz), 1.92~1.84 (m, 2H), 1.49 (d, 3H, J=6.9 Hz).

Example 38

2-(1-Ethyl-indan-4-yloxy)-oxazole-4-carboxylic acid [1-(3,5-difluoro-4-methanesulfonylamino-phenyl)-ethyl]-amide

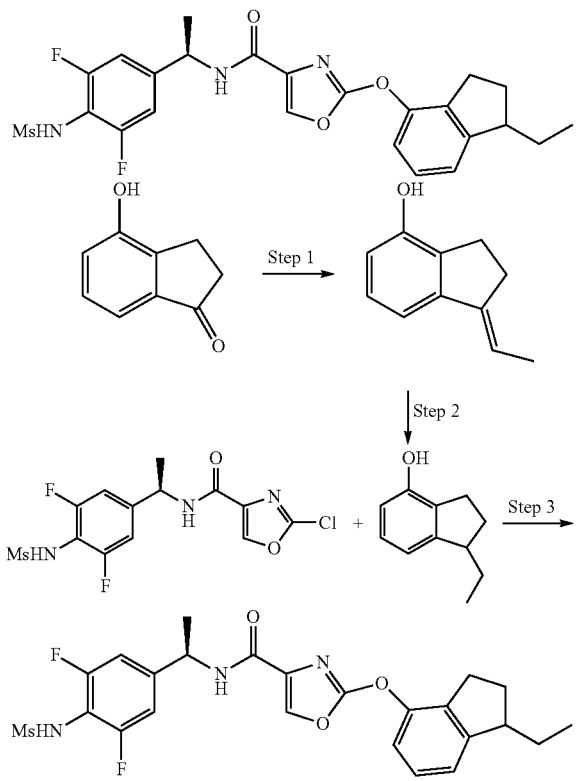

Step 1: 1-Ethylidene-indan-4-ol

To a suspension of $CH_3CH_2PPh_3I$ (677 mg, 1.62 mmol) in $Et_2O$ (10 mL) was added t-BuOK (181 mg, 1.62 mmol). The mixture was stirred for 15 minutes, to which was added dropwise 4-hydroxy-indan-1-one (200 mg, 1.35 mmol). The mixture was stirred at room temperature overnight and then diluted with diethylether. The mixture was filtered on a pad of celite, and the filtrate was concentrated. The crude residue was purified by column chromatography to give 1-ethylidene-indan-4-ol (37 mg, 17%).

$^1$H NMR (300 MHz, $CDCl_3$): δ7.75 (d, 1H, J=8.1 Hz), 6.94 (t, 1H, J=7.8 Hz), 6.50 (d, 1H, J=7.8 Hz), 5.85~5.77 (m, 1H), 4.53 (s, 1H), 2.76~2.58 (m, 4H), 1.62 (d, 3H, J=6.9 Hz).

Step 2: 1-Ethyl-indan-4-ol

A mixture of 1-ethylidene-indan-4-ol (37 mg, 0.23 mmol) and 10% Pd/C (12 mg, 10% weight) in methanol (4 ml) was hydrogenated under 50 psi hydrogen atmosphere for 1 hour. The mixture was dissolved in EtOAc, filtered through a celite pad. The filtrate was concentrated under reduced pressure, and dried to 1-ethyl-indan-4-ol (36 g, 97%)

$^1$H NMR (300 MHz, $CDCl_3$): δ7.05 (t, 1H, J=7.5 Hz), 6.79 (d, 1H, J=7.2 Hz), 6.62 (d, 1H, J=7.8 Hz), 4.90 (s, 1H), 3.06~3.02 (m, 1H), 2.91~2.78 (m, 1H), 2.75~2.67 (m, 1H), 2.35~2.24 (m, 1H), 1.90~1.79 (m, 1H), 1.74~1.64 (m, 1H), 1.48~1.38 (m, 1H), 0.97 (t, 3H, J=7.5 Hz).

Step 3: 2-(1-Ethyl-indan-4-yloxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 1-ethyl-indan-4-ol (43 mg, 0.26 mmol) to give the title compound (40 mg, 60%) after purification by column chromatography (gradient 12% to 100% EtOAc in n-hexane).

$^1$H NMR (300 MHz, $CDCl_3$): δ7.88 (s, 1H), 7.27~7.22 (m, 1H), 7.15~7.08 (m, 2H), 6.96~6.93 (m, 3H), 6.42 (s, 1H), 5.19~5.12 (m, 1H), 3.16 (s, 3H), 3.16~3.09 (m, 1H), 2.93~2.69 (m, 2H), 2.37~2.28 (m, 1H), 1.94-1.86 (m, 1H), 1.79~1.66 (m, 1H), 1.51~1.40 (m, 1H), 1.49 (d, 3H, J=6.9 Hz), 1.00 (t, 3H, J=7.8 Hz).

Example 39

2-(5-Methyl-5,6,7,8-tetrahydro-naphthalen-1-yloxy)-oxazole-4-carboxylic acid [1-(3,5-difluoro-4-methanesulfonylamino-phenyl)-ethyl]-amide

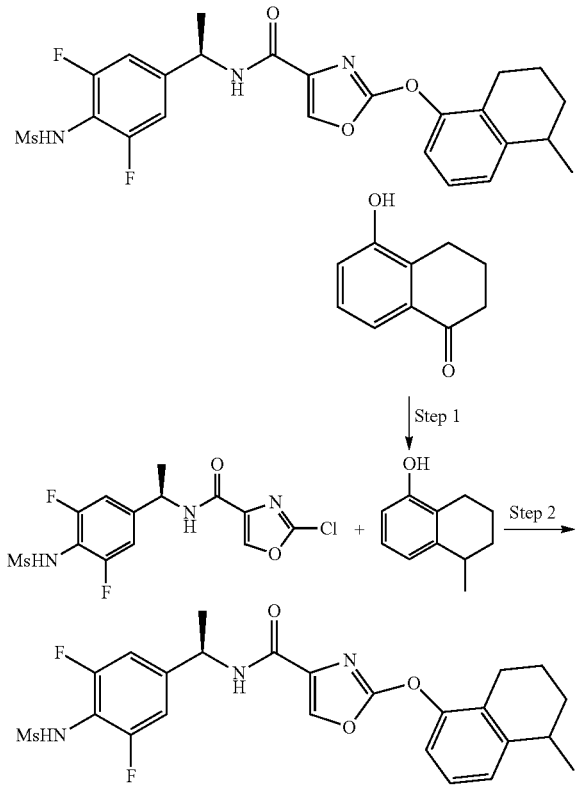

Step 1: 5-Hydroxy-3,4-dihydro-2H-naphthalen-1-one

To a suspension of $CH_3PPh_3I$ (897 mg, 2.22 mmol) in $Et_2O$ (10 mL) was added t-BuOK (249 mg, 2.22 mmol). The mixture was stirred for 15 minutes, to which was added dropwise 5-hydroxy-3,4-dihydro-2H-naphthalen-1-one (300 mg, 1.85 mmol). The mixture was stirred at room temperature overnight, diluted with diethylether, and then filtered through a celite pad. The filtrate was concentrated under reduced pressure. The crude residue was purified by short column chromatography and was concentrated under reduced pressure to give 5-methylene-5,6,7,8-tetrahydro-naphthalen-1-ol. A mixture of 5-methylene-5,6,7,8-tetrahydro-naphthalen-1-ol and 10% Pd/C (40 mg) in methanol (10 ml) was hydrogenated under 50 psi hydrogen atmosphere for 1 hour. The mixture was dissolved in EtOAc, filtered through a celite pad. The filtrate was concentrated under reduced pressure, and dried to give 5-methyl-5,6,7,8-tetrahydro-naphthalen-1-ol (110 mg, 36%).

$^1$H NMR (300 MHz, CDCl$_3$): δ7.01 (t, 1H, J=7.8 Hz), 6.80 (d, 1H, J=7.8 Hz), 6.59 (d, 1H, J=7.8 Hz), 4.81 (s, 1H), 2.92~2.86 (m, 1H), 2.68~2.55 (m, 2H), 1.93~1.85 (m, 2H), 1.78~1.70 (m, 1H), 1.57~1.49 (m, 1H), 1.27 (d, 3H, J=7.2 Hz).

Step 2: 2-(5-Methyl-5,6,7,8-tetrahydro-naphthalen-1-yloxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 5-methyl-5,6,7,8-tetrahydro-naphthalen-1-ol (43 mg, 0.26 mmol) to give the title compound (56 mg, 92%) after purification by column chromatography (gradient 12% to 100% EtOAc in n-hexane).

$^1$H NMR (300 MHz, CDCl$_3$): δ7.87 (s, 1H), 7.25~7.18 (m, 2H), 7.07~7.04 (m, 1H), 6.96~6.93 (m, 3H), 6.45 (s, 1H), 5.17~5.12 (m, 1H), 3.16 (s, 3H), 2.97~2.95 (m, 1H), 2.73~2.63 (m, 2H), 1.90~1.75 (m, 3H), 1.59-1.49 (m, 1H), 1.50 (d, 3H, J=6.9 Hz), 1.32 (d, 3H, J=7.2 Hz).

Example 40

2-(3-Isopropyl-5-trifluoromethyl-phenoxy)-oxazole-4-carboxylic acid [1-(3,5-difluoro-4-methanesulfonylamino-phenyl)-ethyl]-amide

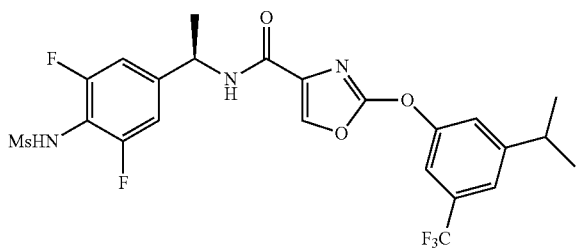

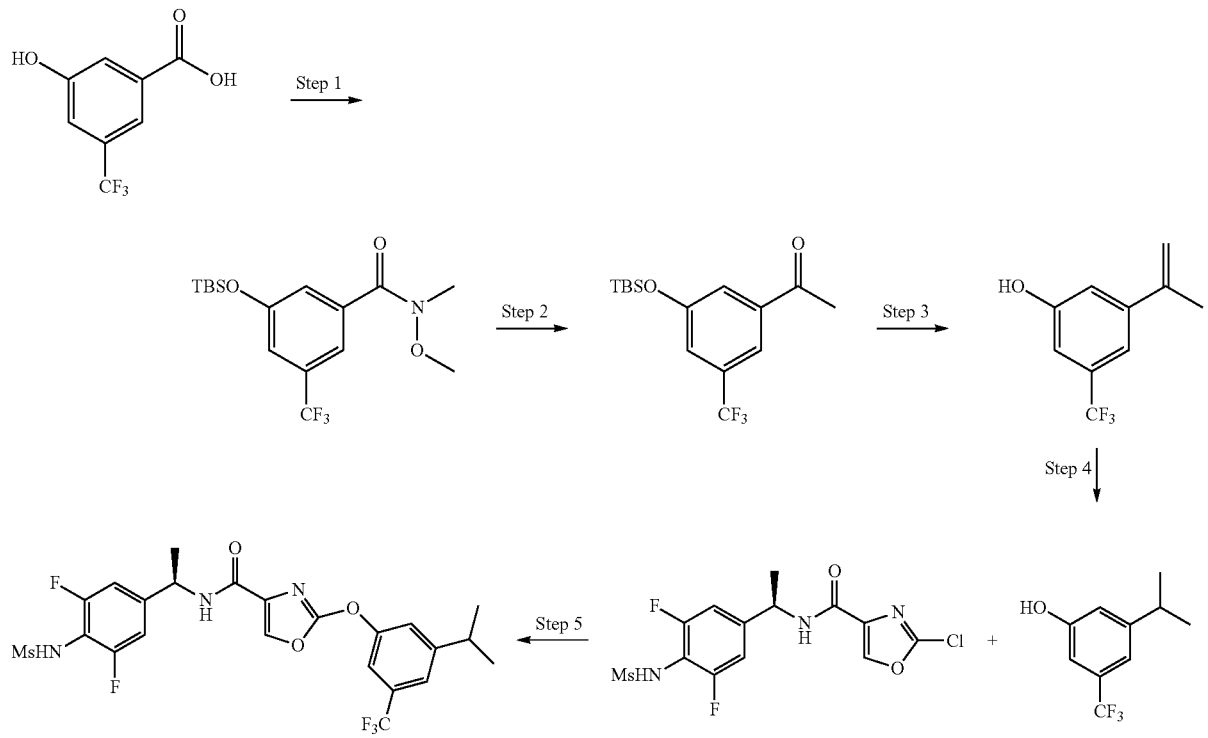

Step 1: 3-(tert-Butyl-dimethyl-silanyloxy)-N-methoxy-N-methyl-5-trifluoromethyl-benzamide To an ice-cold suspension of 3-hydroxy-5-trifluoromethyl-benzoic acid (1.0 mg, 4.85 mmol) and N,O-dimethylhydroxylamine hydrochloride (520 mg, 5.33 mmol) in CH$_2$Cl$_2$ (20 mL) was added N-methylmorpholine (586 μl, 5.33 mmol). The mixture was stirred for 5 minutes, to which were added N-(3-dimethylaminopropyl)-N'-ethylcarbodiimide hydrochloride (1.05 g, 5.33 mmol). The mixture was stirred for 3 hours at room temperature, and then diluted with EtOAc. The organic layer was washed with 1N HCl, water and brine, dried over anhydrous magnesium sulfate, filtered and concentrated under reduced pressure. The product was vacuum-dried to give the 3-hydroxy-N-methoxy-N-methyl-5-trifluoromethyl-benzamide. To a suspension of 3-hydroxy-N-methoxy-N-methyl-5-trifluoromethyl-benzamide (13.7 g, 44.8 mmol) and imidazole (495 mg, 7.27 mmol) in $CH_2Cl_2$ (20 mL) was added portionwise tert-butyldimethylsilyl chloride (877 mg, 5.82 mmol) at 0° C. The mixture was stirred for 3 hours at room temperature, and then diluted with EtOAc. The organic layer was washed with 1N HCl, water and brine, dried over anhydrous magnesium sulfate, filtered and concentrated under reduced pressure. The crude residue was purified by column chromatography to give 3-(tert-butyl-dimethyl-silanyloxy)-N-methoxy-N-methyl-5-trifluoromethyl-benzamide (1.71 g, 97%).

$^1$H NMR (300 MHz, $CDCl_2$): δ7.54 (s, 1H), 7.32 (s, 1H), 7.14 (s, 1H), 3.54 (s, 3H), 3.36 (s, 3H), 0.99 (s, 9H), 0.23 (s, 6H).

Step 2: 1-[3-(tert-Butyl-dimethyl-silanyloxy)-5-trifluoromethyl-phenyl]-ethanone To an ice-cold suspension of 3-(tert-butyl-dimethyl-silanyloxy)-N-methoxy-N-methyl-5-trifluoromethyl-benzamide (500 mg, 1.37 mmol) in THF (5 mL) was added dropwise 3.0M $CH_3MgCl$ (687 mL, 2.06 mmol) at 0° C. The mixture was stirred for 3 hours at room temperature, and then diluted with $Et_2O$. The reaction mixture was washed with saturated ammonium chloride, water and brine, dried over anhydrous magnesium sulfate, filtered and concentrated under reduced pressure. The crude residue was purified by column chromatography to give 1-[3-(tert-butyl-dimethyl-silanyloxy)-5-trifluoromethyl-phenyl]-ethanone (436 g, 99%).

$^1$H NMR (300 MHz, $CDCl_3$): δ7.77 (s, 1H), 7.56 (s, 1H), 7.25 (s, 1H), 2.61 (s, 3H), 1.00 (s, 9H), 0.25 (s, 6H).

Step 3: 3-Isopropenyl-5-trifluoromethyl-phenol

To a suspension of $CH_3PPh_3I$ (664 mg, 1.64 mmol) in $Et_2O$ (20 mL) was added t-BuOK (184 mg, 1.64 mmol). The mixture was stirred for 15 minutes, to which was added dropwise 1-[3-(tert-butyl-dimethyl-silanyloxy)-5-trifluoromethyl-phenyl]-ethanone (436 mg, 1.37 mmol). The mixture was stirred at room temperature overnight and then diluted with $Et_2O$. The mixture was filtered on a pad of celite. The residue compound was concentrated under reduced pressure. The crude residue was dissolved in THF and was added 1M-TBAF (in THF, 1.2 eq, 1.0M in $CH_2Cl_2$). The reaction mixture was stirred for 30 min at room temperature, treated with saturated ammonium chloride, and then extracted with EtOAc. The organic layer was dried over magnesium sulfate and concentrated in vacuo. The crude product was purified by column chromatography to give 3-isopropenyl-5-trifluoromethyl-phenol (220 mg, 79%).

$^1$H NMR (300 MHz, $CDCl_3$): δ7.27 (s, 1H), 7.07 (s, 1H), 6.67 (s, 1H), 5.39 (s, 1H), 5.16 (s, 1H), 2.13 (s, 3H).

Step 4: 3-Isopropyl-5-trifluoromethyl-phenol

A mixture of 3-isopropenyl-5-trifluoromethyl-phenol and 10% Pd/C (40 mg) in methanol (10 ml) was hydrogenated under 50 psi hydrogen atmosphere for 1 hour. The mixture was dissolved in EtOAc, filtered through a celite pad. The filtrate was concentrated under reduced pressure, and dried to give 3-isopropyl-5-trifluoromethyl-phenol (120 mg, 99%).

$^1$H NMR (300 MHz, $CDCl_3$): δ7.04 (s, 1H), 6.89 (s, 1H), 6.87 (s, 1H), 4.62 (s, 1H), 2.95~2.85 (m, 1H), 1.24 (d, 6H, J=6.9 Hz).

Step 5: 2-(3-Isopropyl-5-trifluoromethyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-isopropyl-5-trifluoromethyl-phenol (54 mg, 0.26 mmol) to give the title compound (58 mg, 81%) after purification by column chromatography (gradient 12% to 100% EtOAc in n-hexane).

$^1$H NMR (300 MHz, $CDCl_3$): δ7.95 (s, 1H), 7.43 (s, 1H), 7.41 (s, 1H), 7.35 (s, 1H), 6.93 (d, 2H, J=8.1 Hz) 6.91 (d, 1H, J=4.8 Hz), 5.18~5.09 (m, 1H), 3.15 (s, 3H), 3.09~2.97 (m, 1H), 1.50 (d, 3H, J=6.9 Hz), 1.29 (d, 6H, J=6.9 Hz).

Example 41

2-(2-Propyl-5-trifluoromethyl-phenoxy)-oxazole-4-carboxylic acid [1-(3,5-difluoro-4-methanesulfonylamino-phenyl)-ethyl]-amide

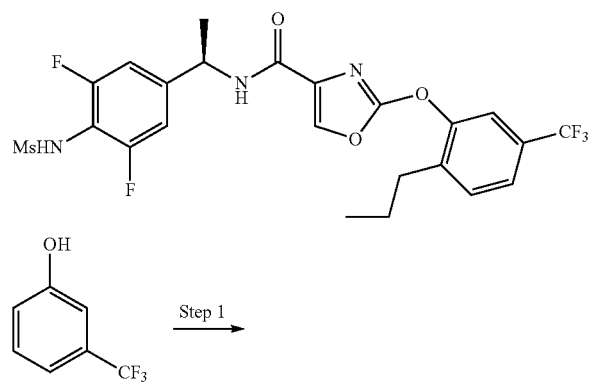

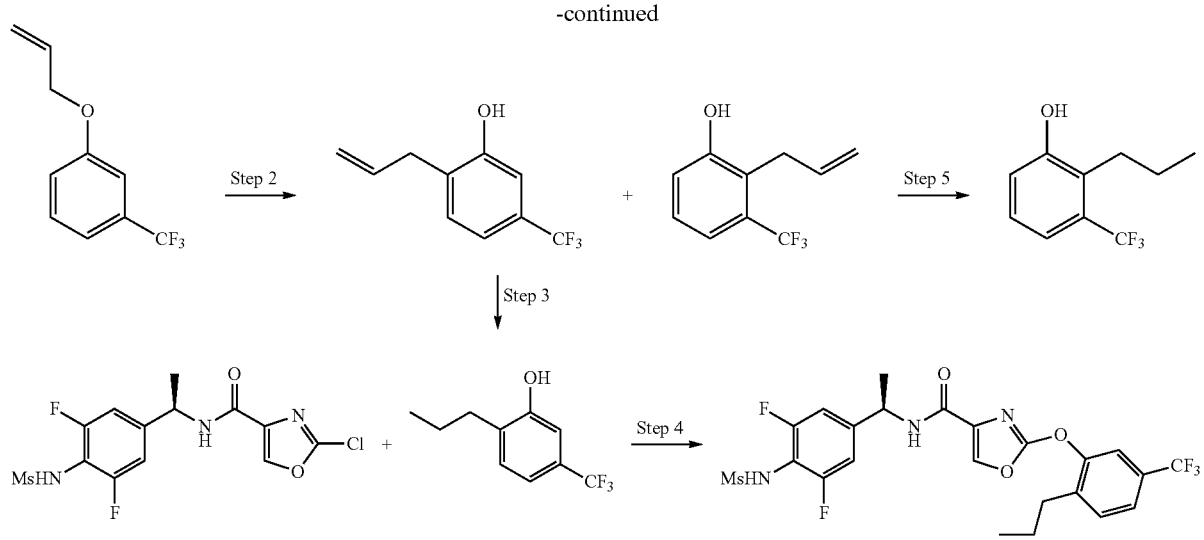

Step 1: 1-Allyloxy-3-trifluoromethyl-benzene

To a suspension of 3-trifluoromethyl phenol (4.05 g, 0.025 mol) and allyl bromide in acetone (50 mL) was added $K_2CO_3$ (3.5 g, 0.025 mol). The mixture was stirred overnight at 60° C. and was diluted with n-hexane. The solution was washed with water, dried over anhydrous magnesium sulfate, filtered, and concentrated under reduced pressure. The crude residue was purified by column chromatography to 1-alkyloxy-3-trifluoromethyl-benzene (4.0 mg, 79%).

$^1$H NMR (300 MHz, CDCl$_3$): δ7.20 (t, 1H, J=8.1 Hz), 7.03 (d, 1H, J=7.8 Hz), 6.97 (s, 1H), 6.91 (d, 1H, J=7.8 Hz), 5.93~5.81 (m, 1H), 5.25 (dd, 1H, J=17.1, 1.6 Hz), 5.14 (dd, 1H, J=10.2, 1.6 Hz), 4.39 (d, 2H, J=5.1 Hz).

Step 2: 2-Allyl-5-trifluoromethyl-phenol

In a 5 ml glass tube were placed 1-allyloxy-3-trifluoromethyl-benzene (500 mg, 0.26 mmol), and a magnetic stir bar. The vial was sealed with septum and placed into the Microwave cavity. The vial was irradiated in a Microwave synthesizer at 250° C. for 1 hour. The crude residue was purified by column chromatography to give 2-allyl-5-trifluoromethyl-phenol (60 mg, 12%) and 2-allyl-3-trifluoromethyl-phenol (60 mg, 12%).

$^1$H NMR (300 MHz, CDCl$_3$) δ7.24 (d, 1H, J=7.2 Hz), 7.20 (s, 1H), 7.14 (d, 1H, J=7.8 Hz), 7.06 (s, 1H), 6.06~5.93 (m, 1H), 5.25~5.14 (m, 2H), 3.45 (d, 2H, J=6.0 Hz).

Step 3: 2-Propyl-5-trifluoromethyl-phenol

A mixture of 2-allyl-5-trifluoromethyl-phenol (60 mg, 12%) and 2-allyl-3-trifluoromethyl-phenol and 10% Pd/C (20 mg) in methanol (4 ml) was hydrogenated under 50 psi hydrogen atmosphere for 1 hour. The mixture was dissolved in EtOAc, filtered through a celite pad. The filtrate was concentrated under reduced pressure, and dried to give 2-propyl-5-trifluoromethyl-phenol (53 mg, 87%).

$^1$H NMR (300 MHz, CDCl$_3$): δ7.21 (d, 1H, J=8.1 Hz), 7.12 (d, 1H, J=8.1 Hz), 7.00 (s, 1H), 5.15 (s, 1H), 2.62 (t, 2H, J=7.5 Hz), 1.71~1.59 (m, 2H), 0.97 (t, 3H, J=7.5 Hz).

Step 4: 2-(2-Propyl-5-trifluoromethyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with give 2-propyl-5-trifluoromethyl-phenol (54 mg, 0.26 mmol) to give the title compound (38 mg, 54%) after purification by column chromatography (gradient 12% to 100% EtOAc in n-hexane).

$^1$H NMR (300 MHz, CDCl$_3$): δ7.91 (s, 1H), 7.58 (s, 1H), 7.51 (d, 1H, J=8.4 Hz), 7.43 (d, 1H, J=8.1 Hz), 6.96 (d, 2H, J=8.7 Hz), 6.84 (d, 1H, J=7.5 Hz), 6.23 (s, 1H), 5.19~5.00 (m, 1H), 3.18 (s, 3H), 2.66 (t, 2H, J=7.5 Hz), 1.69~1.61 (m, 2H), 1.51 (d, 3H, J=6.9 Hz), 0.95 (t, 3H, J=7.5 Hz).

Example 42

2-(2-Propyl-3-trifluoromethyl-phenoxy)-oxazole-4-carboxylic acid [1-(3,5-difluoro-4-methanesulfonylamino-phenyl)-ethyl]-amide

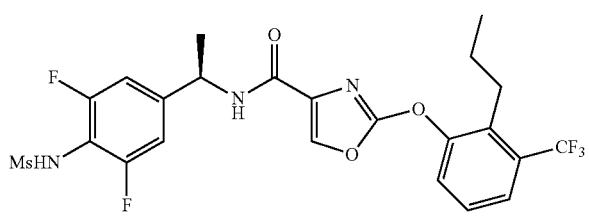

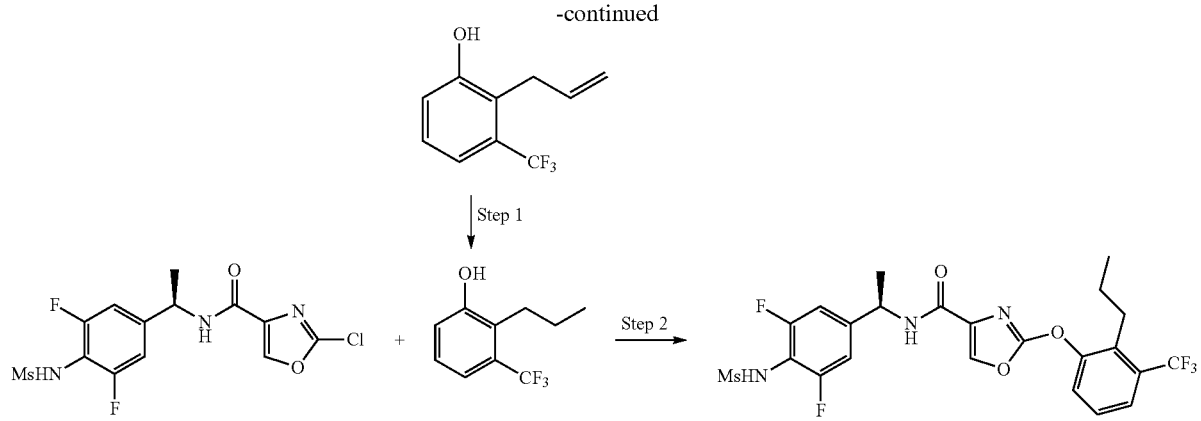

Step 1: 2-Allyl-3-trifluoromethyl-phenol

A mixture of 2-allyl-3-trifluoromethyl-phenol and 10% Pd/C (20 mg) in methanol (4 ml) was hydrogenated under 50 psi hydrogen atmosphere for 1 hour. The mixture was dissolved in EtOAc, filtered through a celite pad. The filtrate was concentrated under reduced pressure, and dried to give 2-propyl-3-trifluoromethyl-phenol (53 mg, 87%).

$^1$H NMR (300 MHz, CDCl$_3$): δ7.25~7.08 (m, 2H), 6.93 (d, 1H, J=7.8 Hz), 5.17 (s, 1H), 2.74~2.69 (m, 2H), 1.64~1.56 (m, 2H), 1.02 (t, 3H, J=7.5 Hz).

Step 2: 2-Propyl-3-trifluoromethyl-phenol

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 2-propyl-3-trifluoromethyl-phenol (54 mg, 0.26 mmol) to give the title compound (38 mg, 54%) after purification by column chromatography (gradient 12% to 100% EtOAc in n-hexane).

$^1$H NMR (300 MHz, CDCl$_3$): δ7.91 (s, 1H), 7.60 (d, 1H, J=7.2 Hz), 7.49-7.36 (m, 2H), 6.96 (d, 1H, J=8.7 Hz), 6.83 (d, 1H, J=7.5 Hz), 6.15 (s, 1H), 5.21~5.14 (m, 1H), 3.18 (s, 3H), 2.78~2.73 (m, 2H), 1.71~1.50 (m, 2H), 1.51 (d, 3H, J=6.9 Hz), 1.02 (t, 3H, J=7.5 Hz).

Example 43

2-(3-Isopropenyl-5-trifluoromethyl-phenoxy)-oxazole-4-carboxylic acid [1-(3,5-difluoro-4-methanesulfonylamino-phenyl)-ethyl]-amide

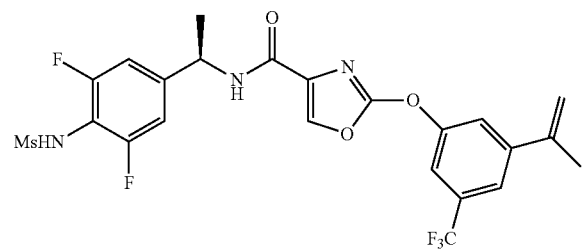

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-isopropenyl-5-trifluoromethyl-phenol (54 mg, 0.26 mmol) to give the title compound (60 mg, 85%) after purification by column chromatography (gradient 12% to 100% EtOAc in n-hexane).

$^1$H NMR (300 MHz, CDCl$_3$): δ7.96 (s, 1H), 7.63 (s, 1H), 7.57 (s, 1H), 7.51 (s, 1H), 6.93 (d, 2H, J=8.7 Hz), 6.90 (d, 1H, J=9.6 Hz), 5.48 (s, 1H), 5.26 (s, 1H), 5.18~5.09 (m, 1H), 3.16 (s, 3H), 2.18 (s, 3H), 1.50 (d, 3H, J=6.9 Hz).

Example 44

2-(3-Trifluoromethyl-phenylamino)-oxazole-4-carboxylic acid [1-(3,5-difluoro-4-methanesulfonylamino-phenyl)-ethyl]-amide

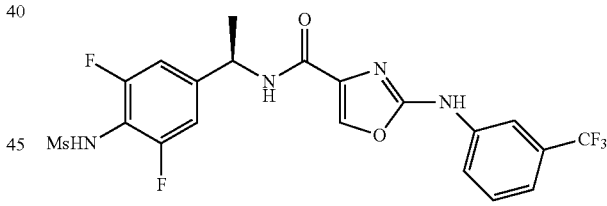

In a 5 ml glass tube were placed 2-chloro-oxazole-4-carboxylic acid [1-(3,5-difluoro-4-methanesulfonylamino-phenyl)-ethyl]-amide (100 mg, 0.26 mmol), 3-trifluoromethyl aniline (170 mg, 1.05 mmol), t-BuOK (30 mg, 0.26 mmol), 2,2'-bis(diphenylphosphino)-1,1'-binaphthalene (BINAP, 8.1 mg, 0.013 mmol), Pd(OAc)$_2$ (2.9 mg, 0.013 mmol), DMF (1 mL), and a magnetic stir bar. The vial was sealed with septum and placed into the Microwave cavity. The vial was irradiated in a Microwave synthesizer at 130° C. for 4 min. The mixture was diluted with EtOAc and washed with 1N HCl and water. The organic layer was dried over anhydrous MgSO$_4$ and concentrated under reduced pressure. The crude residue was purified by column chromatography (gradient 12% to 100% EtOAc in n-hexane) to give title compound (10 mg, 7.5%).

$^1$H NMR (300 MHz, CDCl$_3$): δ7.86 (s, 1H), 7.83 (s, 1H), 7.66 (d, 1H, J=8.1 Hz), 7.47 (t, 1H, J=8.1 Hz), 7.34~7.29 (m, 2H), 7.09 (d, 1H, J=7.8 Hz), 6.99 (d, 2H, J=8.1 Hz), 5.22~5.15 (m, 1H), 3.19 (s, 3H), 1.57 (d, 3H, J=6.9 Hz).

Example 45

2-(2-Chloro-3-trifluoromethyl-phenoxy)-oxazole-4-carboxylic acid [1-(3,5-difluoro-4-methanesulfonylamino-phenyl)-ethyl]-amide

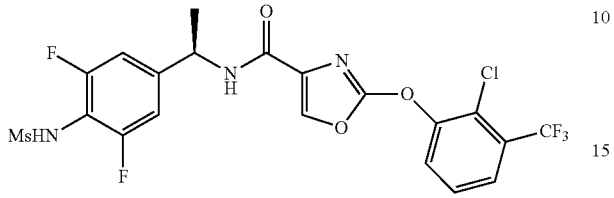

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 2-chloro-3-trifluoromethyl-phenol (53 mg, 0.26 mmol) to give the title compound (52 mg, 74%) after purification by column chromatography (gradient 12% to 100% EtOAc in n-hexane).

$^1$H NMR (300 MHz, CDCl$_3$): δ7.94 (s, 1H), 7.70 (d, 1H, J=7.8 Hz), 7.63 (d, 1H, J=7.8 Hz), 7.51 (d, 1H, J=8.1 Hz), 6.95 (d, 2H, J=8.4 Hz), 6.80 (d, 1H, J=7.5 Hz), 6.41 (s, 1H), 5.19~5.09 (m, 1H), 3.17 (s, 3H), 1.50 (d, 3H, J=7.2 Hz).

Example 46

2-(2-Cyclopropyl-3-trifluoromethyl-phenoxy)-oxazole-4-carboxylic acid [1-(3,5-difluoro-4-methanesulfonylamino-phenyl)-ethyl]-amide

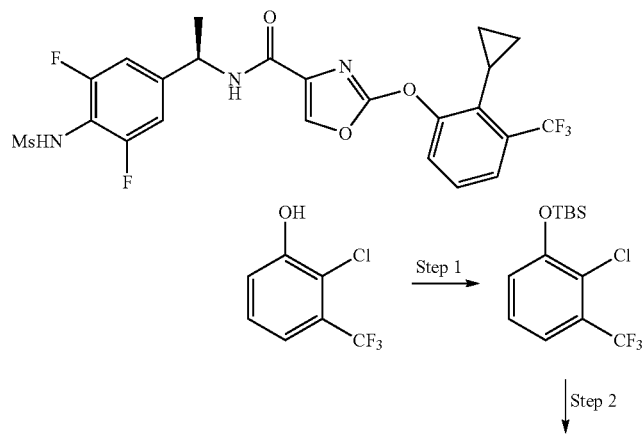

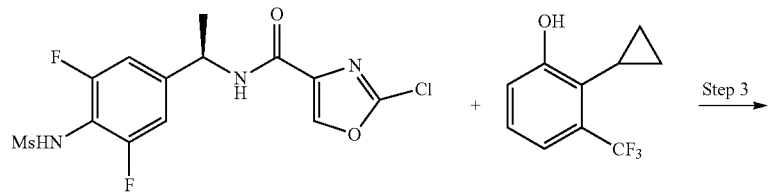

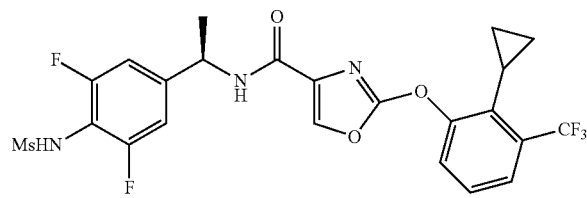

Step 1: tert-Butyl-(2-chloro-3-trifluoromethyl-phenoxy)-dimethyl-silane

To a solution of 2-chloro-3-trifluoromethyl-phenol (509 mg, 2.59 mmol) in $CH_2Cl_2$ (20 mL) was added imidazole (264 mg, 3.88 mmol). The mixture was stirred for 5 minutes, to which was added portionwise tert-butyldimethylsilyl chloride (467 g, 3.1 mmol). The mixture was stirred for 2 hours at room temperature and was diluted with EtOAc. The crude mixture was washed with 1N HCl, water and brine, dried over anhydrous magnesium sulfate, filtered, and concentrated under reduced pressure. The crude residue was purified by column chromatography to give tert-butyl-(2-chloro-3-trifluoromethyl-phenoxy)-dimethyl-silane (800 mg, 99%).

$^1$H NMR (300 MHz, $CDCl_3$): δ7.30~7.18 (m, 2H), 7.06 (d, 1H, J=8.1 Hz), 1.04 (s, 9H), 0.24 (s, 6H).

Step 2: 2-Cyclopropyl-3-trifluoromethyl-phenol

To a solution of tert-butyl-(2-chloro-3-trifluoromethyl-phenoxy)-dimethyl-silane (268 mg, 0.862 mmol), cyclopropyl boronic acid (96 mg, 1.12 mmol), $K_3PO_4$ (641 mg, 3.02 mmol), $Pcy_3$ (24.2 mg, 0.086 mmol), and $Pd(OAc)_2$ (9.7 mg, 0.043 mmol) in toluene/water (4 ml/0.2 ml) was stirred 3 hours at 110° C. and was diluted with $Et_2O$. The residue was washed with water and brine, dried over anhydrous magnesium sulfate, filtered, and concentrated under reduced pressure to give the tert-butyl-(2-cyclopropyl-3-trifluoromethyl-phenoxy)-dimethyl-silane. To a suspension of tert-butyl-(2-cyclopropyl-3-trifluoromethyl-phenoxy)-dimethyl-silane in THF (5 mL) was added a solution of 1M-TBAF (1.12 mL, 1.3 eq), and then was stirred for 30 min at room temperature. The residue was diluted with EtOAc and water. The organic layer was washed with saturated ammonium chloride, water and brine, dried over anhydrous magnesium sulfate, filtered, and concentrated under reduced pressure. The crude residue was purified by column chromatography to give tert-butyl-(2-chloro-3-trifluoromethyl-phenoxy)-dimethyl-silane (53 mg, 30%).

$^1$H NMR (300 MHz, $CDCl_3$): δ7.25~7.20 (m, 2H), 7.07~7.04 (m, 1H), 6.20 (s, 1H), 4.16~4.08 (m, 1H), 1.80~1.73 (m, 1H), 1.17~1.12 (m, 2H), 0.78~0.75 (m, 2H).

Step 3: 2-(2-Cyclopropyl-3-trifluoromethyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 2-cyclopropyl-3-trifluoromethyl-phenol (53 mg, 0.26 mmol) to give the title compound (41 mg, 58%) after purification by column chromatography (gradient 12% to 100% EtOAc in n-hexane).

$^1$H NMR (300 MHz, $CDCl_3$): δ7.92 (s, 1H), 7.64~7.61 (m, 1H), 7.44~7.41 (m, 2H), 6.96 (d, 2H, J=9.9 Hz), 6.84 (d, 1H, J=7.8 Hz), 6.48 (s, 1H), 5.18~5.12 (m, 1H), 3.17 (s, 3H), 1.77~1.70 (m, 1H), 1.50 (d, 3H, J=6.9 Hz), 0.97~0.93 (m, 2H), 0.79~0.78 (m, 2H).

Example 47

2-(5-Isopropyl-2-methyl-phenoxy)-oxazole-4-carboxylic acid [1-(3,5-difluoro-4-methanesulfonylamino-phenyl)-ethyl]-amide

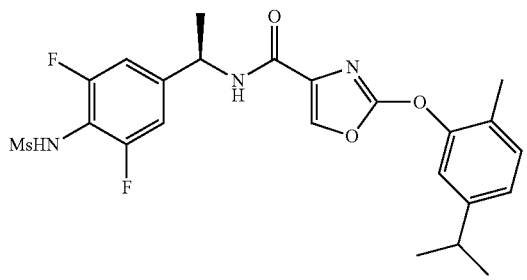

This compound was prepared according to the method of example 1.

Carvacrol (25 mg, 0.16 mmol) and 2-chloro-oxazole-4-carboxylic acid [1-(3,5-difluoro-4-methanesulfonylamino-phenyl)-ethyl]-amide (40 mg, 0.11 mmol) was reacted using $K_2CO_3$ (50 mg, 0.36 mmol) as described above to give the title compound (40 mg, 77%) after purification by flash chromatography on silica gel (hexane: EtOAc=1:1).

$^1$H NMR (300 MHz, $CDCl_3$): δ7.86 (s, 1H), 7.21 (d, 1H, J=8.1 Hz), 7.10 (d, 1H, J=8.1 Hz), 7.09 (s, 1H), 6.96 (d, 2H, J=8.4 Hz), 6.94 (m, 1H), 6.14 (s, 1H), 5.15 (m, 1H), 3.18 (s, 3H), 2.92 (m, 1H), 2.23 (s, 3H), 1.50 (d, 3H, J=6.9 Hz), 1.25 (d, 6H, J=6.9 Hz)

Example 48

2-(3-Isopropoxy-phenoxy)-oxazole-4-carboxylic acid [1-(3,5-difluoro-4-methanesulfonylamino-phenyl)-ethyl]-amide

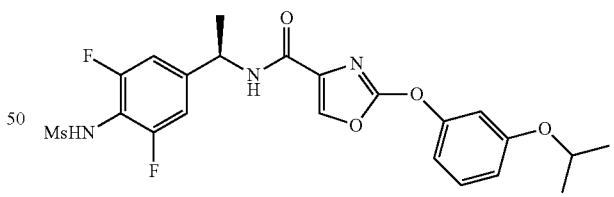

This compound was prepared according to the method of example 1.

3-Isopropoxyphenol (80 mg, 0.53 mmol) and 2-chloro-oxazole-4-carboxylic acid [1-(3,5-difluoro-4-methanesulfonylamino-phenyl)-ethyl]-amide (35 mg, 0.09 mmol) was reacted using $K_2CO_3$ (60 mg, 0.43 mmol) as described above to give the title compound (28 mg, 61%) after purification by flash chromatography on silica gel (hexane: EtOAc=1:1).

$^1$H NMR (300 MHz, $CDCl_3$): δ7.92 (s, 1H), 7.31 (t, 1H, J=8.4 Hz), 6.96 (m, 3H), 6.84 (m, 3H), 6.73 (s, 1H), 5.15 (m, 1H), 4.55 (m, 1H), 3.16 (s, 3H), 1.51 (d, 3H, J=6.6 Hz), 1.35 (d, 6H, J=6.3 Hz)

Example 49

2-(2,3-Dihydroxy-phenoxy)-oxazole-4-carboxylic acid [1-(3,5-difluoro-4-methanesulfonylamino-phenyl)-ethyl]-amide, cyclopentanone ketal

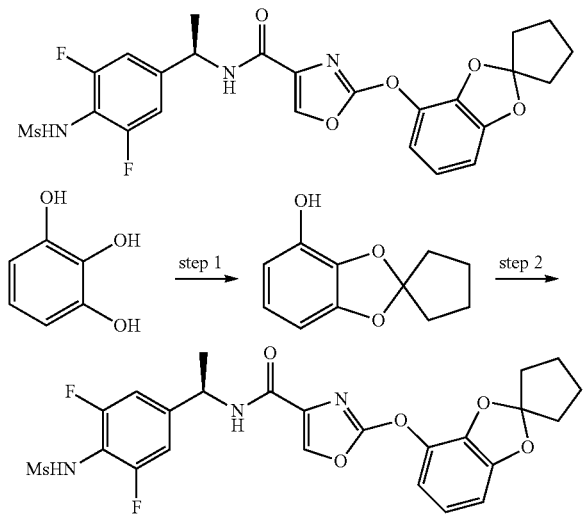

Step 1: Pyrogallol, cyclopentanone ketal

A mixture of pyrogallol (1.51 g, 12 mmol), cyclopentanone (1.1 g, 13.1 mmol), and pyridinium p-toluenesulfonate (100 mg) in toluene was heated to reflux with Dean-Stark apparatus for 24 hours. The mixture was cooled to room temperature, poured into water, and extracted with EtOAc. The organic layer was dried over anhydrous MgSO$_1$, filtered, and concentrated under reduced pressure. The residue was purified with flash column chromatography to give the title compound (450 mg, 20%)

$^1$H NMR (300 MHz, CDCl$_3$): δ6.67 (t, 1H, J=7.8 Hz), 6.44 (d, 1H, J=7.8 Hz), 6.39 (d, 1H, J=7.8 Hz), 4.83 (s, 1H), 2.94 (m, 1H), 2.11 (m, 4H), 1.84 (m, 4H).

Step 2: 2-(2,3-Dihydroxy-phenoxy)-oxazole-4-carboxylic acid [1-(3,5-difluoro-4-methanesulfonylamino-phenyl)-ethyl]-amide, cyclopentanone ketal This compound was prepared according to the method of example 1.

Pyrogallol, cyclopentanone ketal (28 mg, 0.15 mmol) and 2-chloro-oxazole-4-carboxylic acid [1-(3,5-difluoro-4-methanesulfonylamino-phenyl)-ethyl]-amide (40 mg, 0.11 mmol) was reacted using K$_2$CO$_3$ (50 mg, 0.36 mmol) as described above to give the title compound (45 mg, 80%) after purification by flash chromatography on silica gel (hexane:EtOAc=1:1).

$^1$H NMR (300 MHz, CDCl$_3$): δ7.89 (s, 1H), 6.95 (d, 3H, J=8.4 Hz), 6.81 (m, 2H), 6.71 (m, 1H), 6.33 (s, 1H), 5.16 (m, 1H), 3.18 (s, 3H), 2.09 (m, 4H), 1.81 (m, 4H), 1.50 (d, 3H, J=7.2 Hz)

Example 50

2-(2-Cyclohexyl-5-methyl-phenoxy)-oxazole-4-carboxylic acid [1-(3,5-difluoro-4-methanesulfonylamino-phenyl)-ethyl]-amide

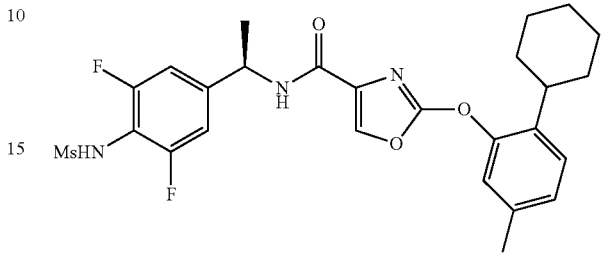

This compound was prepared according to the method of example 1.

2-Cyclohexyl-5-methylphenol (28 mg, 0.15 mmol) and 2-chloro-oxazole-4-carboxylic acid [1-(3,5-difluoro-4-methanesulfonylamino-phenyl)-ethyl]-amide (40 mg, 0.11 mmol) was reacted using K$_2$CO$_3$ (50 mg, 0.36 mmol) as described above to give the title compound (40 mg, 71%) after purification by flash chromatography on silica gel (hexane:EtOAc=1:1).

$^1$H NMR (300 MHz, CDCl$_3$): δ7.91 (s, 1H), 7.24 (d, 1H, J=8.1 Hz), 7.09 (d, 1H, J=8.1 Hz), 6.96 (m, 4H), 6.53 (s, 1H), 5.15 (m, 1H), 3.17 (s, 3H), 2.74 (m, 1H), 2.35 (s, 3H), 1.79 (m, 4H), 1.59~1.24 (m, 6H), 1.50 (d, 3H, J=6.9 Hz)

Example 51

2-(3-Cyclopentyl-phenoxy)-oxazole-4-carboxylic acid [1-(3,5-difluoro-4-methanesulfonylamino-phenyl)-ethyl]-amide

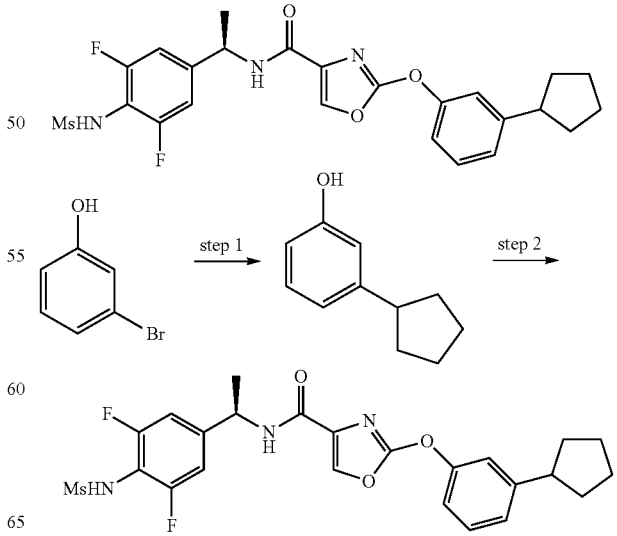

Step 1: 3-Cyclopentylphenol

A mixture of 3-bromophenol (730 mg, 4.22 mmol), TBSCl (700 mg, 4.64 mmol), and imidazole (330 mg, 4.85 mmol) in DMF was stirred for 3 hours at room temperature. The mixture was poured into water and extracted with Et$_2$O. The organic layer was dried over anhydrous MgSO$_4$, filtered, and concentrated under reduced pressure to give a TBS ether with a quantitative yield. A mixture of the TBS ether (720 mg, 2.5 mmol), magnesium (120 mg, 4.94 mmol), and small amount of iodine in Et$_2$O was heated to reflux to generate Grignard reagent. To the mixture was added cyclopentanone (230 mg, 2.7 mmol). After 1 h stirring, the mixture was poured into aq. HCl and extracted with EtOAc. The organic layer was dried over anhydrous MgSO$_4$, filtered, and concentrated under reduced pressure. The residue (200 mg) was dissolved in benzene and heated to reflux with pyridinium p-toluenesulfonate for overnight. The mixture was poured into aq. NaHCO$_3$ and extracted with EtOAc. The organic layer was dried over anhydrous MgSO$_4$, filtered, and concentrated under reduced pressure. The residue was purified with flash column chromatography to give 3-cyclopentenylphenoxy-tert-butyldimethylsilylether (100 mg, 15% for 2 steps). A mixture of the ether (100 mg, 0.36 mmol) and 5% Pd/C (30 mg) in EtOH was hydrogenated under 40 psi hydrogen atmosphere for 5 hours. The mixture was filtered through a silica pad and washed with EtOAc. The filtrate was concentrated under reduced pressure, and the residue was dissolved in THF and treated with TBAF (1M, 0.5 ml). The mixture was stirred for 1 h and poured into aq. NH$_4$Cl and extracted with EtOAc. The organic layer was dried over anhydrous MgSO$_4$, filtered, and concentrated under reduced pressure. The residue was purified with flash column chromatography to give the title compound (40 mg, 68% for 2 steps).

$^1$H NMR (300 MHz, CDCl$_3$): δ7.14 (t, 1H, J=7.8 Hz), 6.82 (d, 1H, J=7.8 Hz), 6.72 (d, 1H, J=2.1 Hz), 6.64 (dd, 1H, J=7.8, 2.1 Hz), 4.79 (s, 1H), 2.94 (m, 1H), 2.05 (m, 2H), 1.79 (m, 2H); 1.72~1.50 (m, 4H).

Step 2: 2-(3-Cyclopentyl-phenoxy)-oxazole-4-carboxylic acid [1-(3,5-difluoro-4-methanesulfonylamino-phenyl)-ethyl]-amide This compound was prepared according to the method of example 1.

3-Cyclopentylphenol (40 mg, 0.25 mmol) and 2-chloro-oxazole-4-carboxylic acid [1-(3,5-difluoro-4-methanesulfonylamino-phenyl)-ethyl]-amide (40 mg, 0.11 mmol) was reacted using K$_2$CO$_3$ (50 mg, 0.36 mmol) as described above to give the title compound (40 mg, 75%) after purification by flash chromatography on silica gel (hexane: EtOAc=1:1).

$^1$H NMR (300 MHz, CDCl$_3$): δ7.88 (s, 1H), 7.35 (t, 1H, J=8.0 Hz), 7.17 (m, 3H), 6.97 (d, 2H, J=8.4 Hz), 6.95 (m, 1H), 6.17 (s, 1H), 5.17 (m, 1H), 3.18 (s, 3H), 3.05 (m, 1H), 2.10 (m, 2H), 1.84 (m, 2H), 1.76-1.53 (m, 4H), 1.51 (d, 3H, J=7.2 Hz)

Example 52

2-(2-Iodo-5-isopropyl-phenoxy)-oxazole-4-carboxylic acid [1-(3,5-difluoro-4-methanesulfonylamino-phenyl)-ethyl]-amide

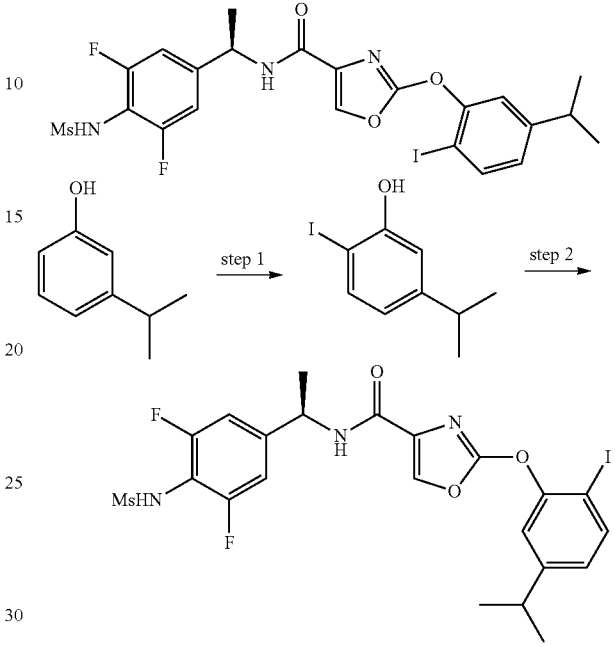

Step 1: 2-Iodo-5-isopropyl-phenol

A mixture of 3-isopropylphenol (670 mg, 4.92 mmol), KIO$_3$ (210 mg, 0.98 mmol), and I$_2$ (500 mg, 1.97 mmol) in acetic acid was stirred for 3 days at room temperature. The solvent was removed at reduced pressure. The residue was diluted with Et$_2$O and washed with aq. NaHCO$_3$, aq. Na$_2$S$_2$O$_3$, and brine. The organic layer was dried over anhydrous MgSO$_4$, filtered, and concentrated under reduced pressure. The residue was purified with flash column chromatography to give the title compound (830 mg, 64%).

$^1$H NMR (300 MHz, CDCl$_3$): δ7.54 (d, 1H, J=7.8 Hz), 6.88 (d, 1H, J=1.8 Hz), 6.57 (dd, 1H, J=8.1, 1.8 Hz), 5.21 (s, 1H), 2.84 (m, 1H), 1.22 (d, 6H, J=7.2 Hz).

Step 2: 2-(2-Iodo-5-isopropyl-phenoxy)-oxazole-4-carboxylic acid [1-(3,5-difluoro-4-methanesulfonylamino-phenyl)-ethyl]-amide This compound was prepared according to the method of example 1.

2-Iodo-5-isopropyl-phenol (84 mg, 0.32 mmol) and 2-chloro-oxazole-4-carboxylic. acid [1-(3,5-difluoro-4-methanesulfonylamino-phenyl)-ethyl]-amide (80 mg, 0.21 mmol) was reacted using K$_2$CO$_3$ (90 mg, 0.65 mmol) as described above to give the title compound (120 mg, 94%) after purification by flash chromatography on silica gel (hexane: EtOAc=1:1).

$^1$H NMR (300 MHz, CDCl$_3$): δ7.90 (s, 1H), 7.78 (d, 1H, J=8.4 Hz), 7.19 (m, 1H), 6.96 (d, 2H, J=8.1 Hz), 6.93 (m, 2H), 6.21 (s, 1H), 5.15 (m, 1H), 3.18 (s, 3H), 2.94 (m, 1H), 1.50 (d, 3H, J=7.2 Hz), 1.26 (d, 6H, J=6.9 Hz)

Example 53

2-(2-Chloro-5-trifluoromethyl-phenoxy)-oxazole-4-carboxylic acid [1-(3,5-difluoro-4-methanesulfonylamino-phenyl)-ethyl]-amide

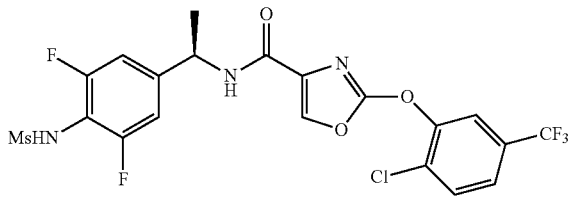

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 2-chloro-5-trifluoromethyl-phenol (52 mg, 0.26 mmol) to give the title compound (50 mg, 71%) after purification by column chromatography (gradient 12% to 100% EtOAc in n-hexane).

$^1$H NMR (300 MHz, CDCl$_3$): δ7.92 (s, 1H), 7.71 (s, 1H), 7.66 (d, 1H, J=8.7 Hz), 7.56 (d, 1H, J=8.1 Hz), 6.95 (d, 2H, J=8.7 Hz), 6.79 (d, 1H, J=7.8 Hz), 6.22 (s, 1H), 5.18~5.12 (m, 1H), 3.18 (s, 3H), 1.51 (d, 3H, J=7.2 Hz).

Example 54

2-(2-Cyclopropyl-5-trifluoromethyl-phenoxy)-oxazole-4-carboxylic acid [1-(3,5-difluoro-4-methanesulfonylamino-phenyl)-ethyl]-amide

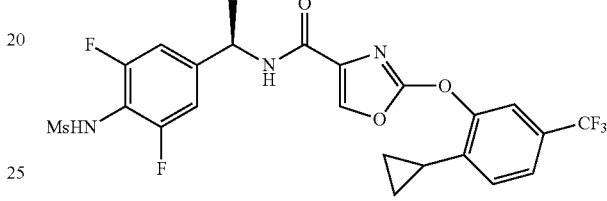

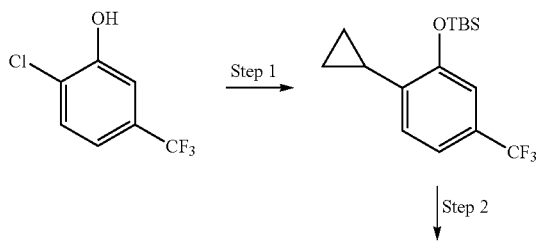

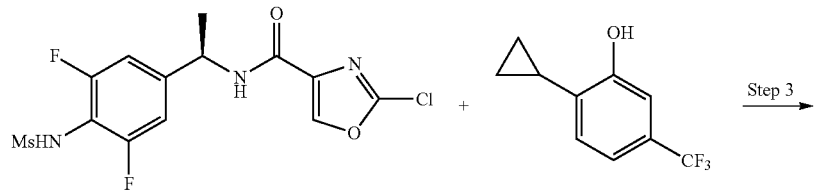

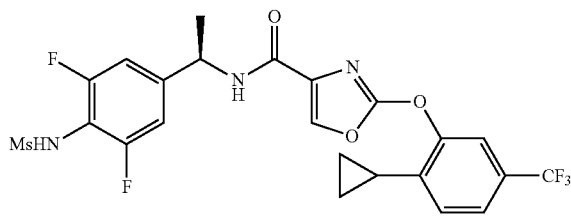

Step 1: tert-Butyl-(2-cyclopropyl-5-trifluoromethyl-phenoxy)-dimethyl-silane 2-Chloro-5-trifluoromethyl-phenol (509 mg, 2.59 mmol) was reacted with TBSC1 (467 mg, 3.1 mmol) as described above to give tert-butyl-(2-cyclopropyl-5-trifluoromethyl-phenoxy)-dimethyl-silane (800 mg, 99%) after purification by column chromatography (gradient 12% to 100% EtOAc in n-hexane).

$^1$H NMR (300 MHz, CDCl$_3$): δ7.44 (d, 1H, J=8.1 Hz), 7.14 (d, 1H, J=8.1 Hz), 7.09 (s, 1H), 1.03 (s, 9H), 0.25 (s, 6H).

Step 2: 2-Cyclopropyl-5-trifluoromethyl-phenol tert-Butyl-(2-cyclopropyl-5-trifluoromethyl-phenoxy)-dimethyl-silane (268 mg, 0.862 mmol) was reacted with cyclopropyl boronic acid (96 mg, 1.12 mmol) as described above to give 2-cyclopropyl-5-trifluoromethyl-phenol (93 mg, 53%) after purification by column chromatography (gradient 12% to 100% EtOAc in n-hexane).

$^1$H NMR (300 MHz, CDCl$_3$): δ7.03~6.97 (m, 3H), 4.92 (s, 1H), 1.81~1.72 (m, 1H), 0.92~0.86 (m, 2H), 0.85~0.52 (m, 2H).

Step 3: 2-(2-Cyclopropyl-5-trifluoromethyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with cyclopropyl-5-trifluoromethyl-phenol (53 mg, 0.26 mmol) to give the title compound (60 mg, 85%) after purification by column chromatography (gradient 12% to 100% EtOAc in n-hexane).

$^1$H NMR (300 MHz, CDCl$_3$): δ7.94 (s, 1H), 7.55 (s, 1H), 7.48 (d, 1H, J=8.1 Hz), 7.12 (d, 1H, J=8.1 Hz), 6.94 (d, 2H, J=8.1 Hz), 6.90 (d, 1H, J=10.5 Hz), 6.64 (s, 1H), 5.18~5.08 (m, 1H), 3.16 (s, 3H), 2.08~1.99 (m, 1H), 1.50 (d, 3H, J=6.9 Hz), 1.05~0.98 (m, 2H), 0.80~0.72 (m, 2H).

Example 55

2-(5,6,7,8-Tetrahydro-naphthalen-1-yloxy)-oxazole-4-carboxylic acid [1-(3,5-difluoro-4-methanesulfonylamino-phenyl)-ethyl]-amide

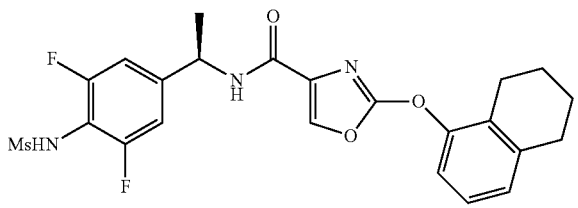

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 5,6,7,8-tetrahydro-naphthalen-1-ol (38.7 mg, 0.26 mmol) to give the title compound (57 mg, 89%) after purification by column chromatography (gradient 12% to 100% EtOAc in n-hexane).

$^1$H NMR (300 MHz, CDCl$_3$): δ7.87 (s, 1H), 7.19~7.14 (m, 1H), 7.06~7.03 (m, 2H), 6.95 (d, 2H, J=8.4 Hz), 6.30 (d, 1H, J=5.4 Hz), 6.37 (s, 1H), 5.20~5.10 (m, 1H), 3.17 (s, 3H), 2.82 (s, 2H), 2.67 (s, 2H), 1.80~1.78 (m, 4H), 1.50 (d, 3H, J=6.9 Hz).

Example 56

2-(3-Cyclobutyl-phenoxy)-oxazole-4-carboxylic acid [1-(3,5-difluoro-4-methanesulfonylamino-phenyl)-ethyl]-amide

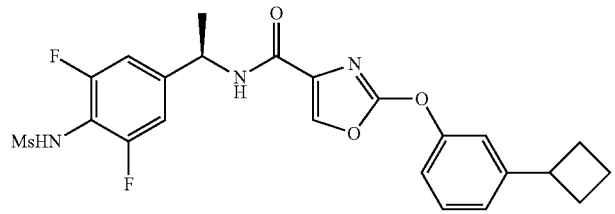

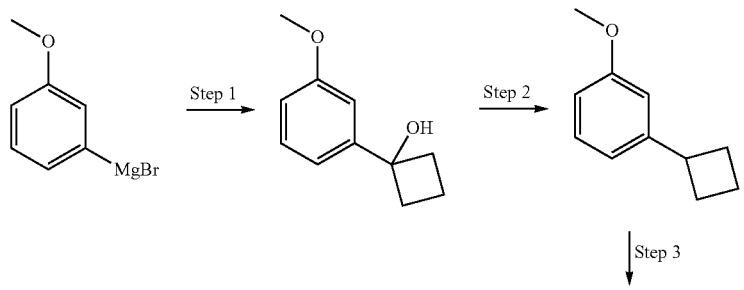

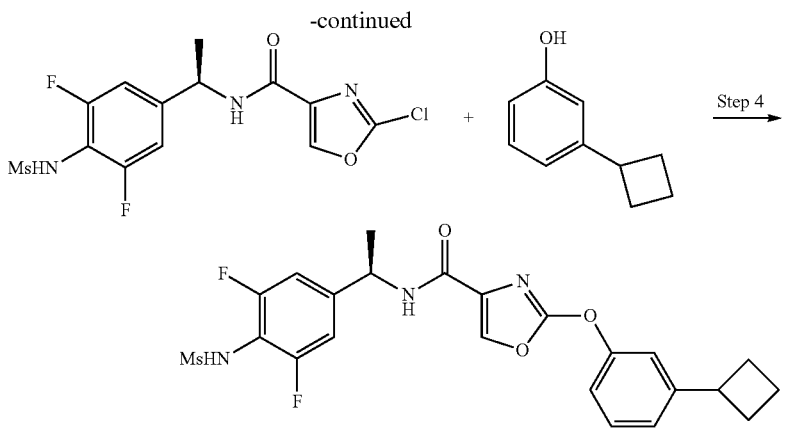

Step 1: 1-(3-Methoxy-phenyl)-cyclobutanol

To an ice-cold solution of 3-methoxyphenyl magnesium bromide (200 mg, 2.85 mmol) in Et$_2$O (2 mL) was added dropwise 1M 3-methoxyphenyl magnesium bromide (in THF, 3.13 mL, 3.13 mmol). The mixture was stirred for 1 hour at 0° C., and then diluted with Et$_2$O. The organic layer was washed with saturated ammonium chloride, water and brine, dried over anhydrous magnesium sulfate, filtered and concentrated under reduced pressure. The crude residue was purified by column chromatography to give 1-(3-methoxy-phenyl)-cyclobutanol (400 g, 72%).

$^1$H NMR (300 MHz, CDCl$_3$): δ7.32~7.25 (m, 1H), 7.08 (d, 1H, J=7.5 Hz), 7.05 (s, 1H), 6.82 (dd, 1H, J=8.1, 2.1 Hz), 3.82 (s, 3H), 2.59~2.51 (m, 2H), 2.40~2.31 (m, 2H), 2.08~1.99 (m, 2H), 1.74~1.60 (m, 1H).

Step 2: 1-Cyclobutyl-3-methoxy-benzene

A mixture of 1-(3-methoxy-phenyl)-cyclobutanol and 10% Pd/C (60 mg) in ethanol (10 ml) was hydrogenated under 45 psi hydrogen atmosphere for 3 hours. The mixture was diluted with EtOAc, filtered through a celite pad. The filtrate was concentrated under reduced pressure, and dried to give 1-cyclobutyl-3-methoxy-benzene (162 mg, 89%).

$^1$H NMR (300 MHz, CDCl$_3$): δ7.21 (t, 1H, J=7.8 Hz), 6.81 (d, 1H, J=7.8 Hz), 6.76 (s, 1H), 6.71 (d, 1H, J=7.8 Hz), 3.80 (s, 3H), 3.57~3.46 (m, 1H), 2.37~2.28 (m, 2H), 2.07~1.95 (m, 2H), 1.72~1.57 (m, 2H).

Step 3: 3-Cyclobutyl-phenol

To a suspension of 1-cyclobutyl-3-methoxy-benzene (155 mg, 0.95 mmol) in CH$_2$Cl$_2$ (2 mL) was added dropwise 1.0M-BBr$_2$ (1.05 mL, 1.05 mmol) at 0° C. The mixture was stirred for 1 hour at 0° C., treated with saturated ammonium chloride, and then extracted with CH$_2$Cl$_2$. The organic layer was dried over magnesium sulfate and concentrated in vacuo. The crude product was purified by column chromatography to give 3-cyclobutyl-phenol (100 mg, 71%).

$^1$H NMR (300 MHz, CDCl$_3$): δ7.15 (t, 1H, J=7.8 Hz), 6.77 (d, 1H, J=7.2 Hz), 6.70 (s, 1H), 6.40 (d, 1H, J=7.8 Hz), 5.16 (s, 1H), 3.55~3.43 (m, 1H), 2.38~2.27 (m, 2H), 2.18~2.15 (m, 2H), 1.87~1.78 (m, 2H).

Step 4: 2-(3-Cyclobutyl-phenoxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-cyclobutyl-phenol (38.7 mg, 0.26 mmol) to give the title compound (63 mg, 98%) after purification by column chromatography (gradient 12% to 100% EtOAc in n-hexane).

$^1$H NMR (300 MHz, CDCl$_3$): δ7.89 (s, 1H), 7.36 (t, 1H, J=7.8 Hz), 7.15-7.11 (m, 3H), 6.97~6.94 (m, 3H), 6.39 (s, 1H), 5.20~5.11 (m, 1H), 3.61~3.55 (m, 1H), 3.17 (s, 3H), 2.42~2.33 (m, 2H), 2.17~1.99 (m, 2H), 1.91-1.85 (m, 2H), 1.50 (d, 3H, J=6.9 Hz).

Example 57

2-(1-Trifluoromethyl-indan-4-yloxy)-oxazole-4-carboxylic acid [1-(3,5-difluoro-4-methanesulfonylamino-phenyl)-ethyl]-amide

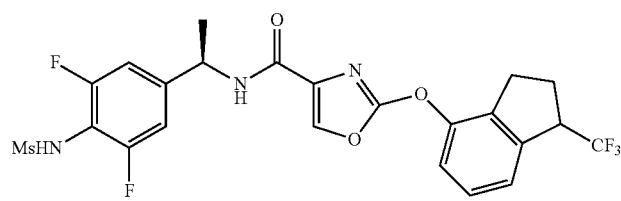

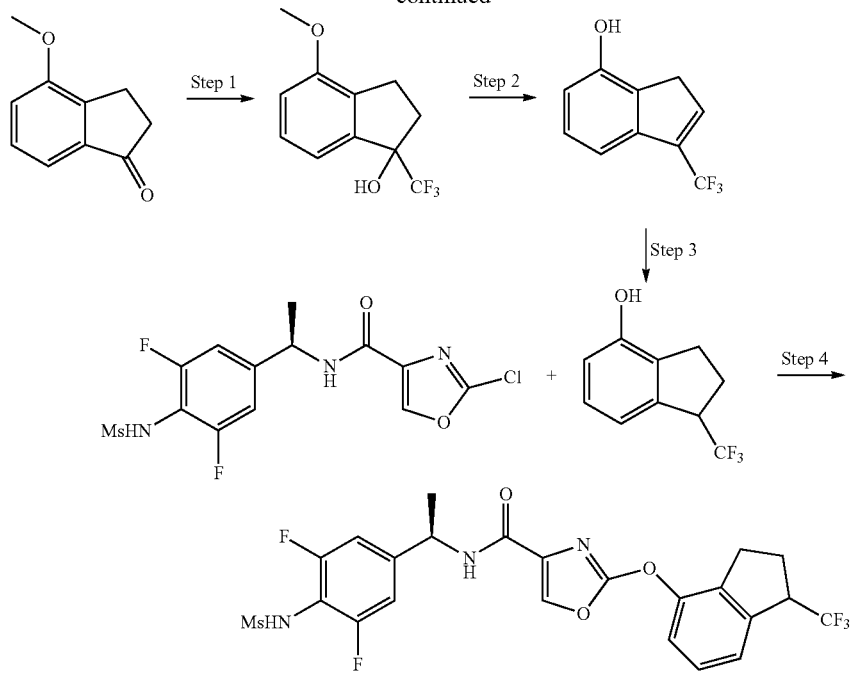

Step 1: 4-Methoxy-1-trifluoromethyl-indan-1-ol

To an ice-cold suspension of 4-methoxy-indan-1-one (200 mg, 1.23 mmol) and trimethyl(trifluoromethyl)silane (218 mg, 1.48 mmol) in THF (4 mL) was added 1M-TBAF (615 mL, 0.615 mmol) at 0° C. The mixture was stirred overnight at room temperature, and then diluted with EtOAc. The organic layer was washed with water, dried over anhydrous magnesium sulfate, filtered and concentrated tinder reduced pressure. The crude residue was purified by column chromatography to give 4-methoxy-1-trifluoromethyl-indan-1-ol (170 g, 60%).

$^1$H NMR (300 MHz, CDCl$_3$): δ7.29~7.24 (m, 1H), 7.07 (d, 1H, J=7.5 Hz), 6.84 (d, 1H, J=8.1 Hz), 3.38 (s, 3H), 3.07~2.84 (m, 2H), 2.72 (s, 1H), 2.68~2.59 (m, 1H), 2.25~2.14 (m, 1H).

Step 2: 1-Trifluoromethyl-3H-inden-4-ol

To a suspension of 4-methoxy-1-trifluoromethyl-indan-1-ol (170 mg, 0.73 mmol) in benzene (4 mL) was added p-toluenesulfonic acid (139 mg, 0.73 mmol). The mixture was stirred overnight at 80° C., and concentrated under reduced pressure. The crude residue was purified by column chromatography to give 4-methoxy-1-trifluoromethyl-3H-inden. The 4-methoxy-1-trifluoromethyl-3H-inden was dissolved in CH$_2$Cl$_2$ (2 ml) and 1M-BBr$_3$ (in CH$_2$Cl$_2$, 1.46 mL, 1.46 mmol) was added dropwise. The mixture was stirred for 1 hour at room temperature, and then washed with saturated ammonium chloride, water and brine, dried over anhydrous magnesium sulfate, filtered and concentrated under reduced pressure. The crude residue was purified by column chromatography to give 1-trifluoromethyl-3H-inden-4-ol (70 g, 48%).

$^1$H NMR (300 MHz, CDCl$_3$): δ7.24 (t, 1H, J=7.8 Hz), 7.15 (d, 1H, J=7.2 Hz), 6.99 (s, 1H), 6.75 (d, 1H, J=7.8 Hz), 7.60 (s, 1H), 3.48 (s, 2H).

Step 3: 1-Trifluoromethyl-indan-4-ol

A mixture of 1-trifluoromethyl-3H-inden-4-ol (70 mg, 0.349) and 10% Pd/C (20 mg) in methanol (2 ml) was hydrogenated under 50 psi hydrogen atmosphere for 3 hours. The mixture was dissolved in EtOAc, filtered through a celite pad. The filtrate was concentrated tinder reduced pressure, and dried to give 1-trifluoromethyl-indan-4-ol (68 mg, 97%).

$^1$H NMR (300 MHz, CDCl$_3$): δ7.12 (t, 1H, J=7.8 Hz), 7.00 (d, 1H, J=7.2 Hz), 6.74 (d, 1H, J=8.1 Hz), 4.96 (s, 1H), 3.89~3.81 (m, 1H), 3.07~2.97 (m, 1H), 2.93~2.83 (m, 1H), 2.46~2.24 (m, 2H).

Step 4: 2-(1-Trifluoromethyl-indan-4-yloxy)-oxazole-4-carboxylic acid [1-(3,5-difluoro-4-methanesulfonylamino-phenyl)-ethyl]-amide This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 1-trifluoromethyl-indan-4-ol (53 mg, 0.26 mmol) to give the title compound (62 mg, 87%) after purification by column chromatography (gradient 12% to 100% EtOAc in n-hexane).

$^1$H NMR (300 MHz, CDCl$_3$): δ7.90 (s, 1H), 7.35~7.28 (m, 2H), 6.95 (d, 2H, J=9.9 Hz), 6.90 (d, 1H, J=5.1 Hz), 6.40 (d, 1H, J=3.0 Hz), 5.19~5.09 (m, 1H), 3.99~3.88 (m, 1H), 3.17 (s, 3H), 3.10~2.99 (m, 1H), 2.93~2.85 (m, 1H), 2.48~2.27 (m, 3H), 1.49 (d, 3H, J=6.6 Hz).

Example 58

2-(3-Iodo-phenoxy)-oxazole-4-carboxylic acid [1-(3,5-difluoro-4-methanesulfonylamino-phenyl)-ethyl]-amide

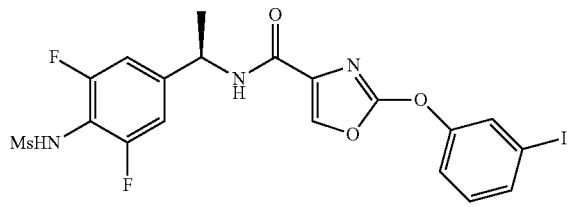

This compound was prepared according to the method of example 1.

2-Chloro-oxazole-4-carboxylic acid [1-(3,5-difluoro-4-methanesulfonylamino-phenyl)-ethyl]-amide (50 mg, 0.13 mmol) was reacted with 3-iodophenol (58 mg, 0.26 mmol) to give the title compound (68 mg, 85%) after purification by column chromatography (gradient 12% to 100% EtOAc in n-hexane).

$^1$H NMR (300 MHz, CDCl$_3$): δ7.90 (s, 1H), 7.68 (d, 1H, J=2.4 Hz), 7.64 (d, 1H, J=7.8 Hz), 7.31 (dd, 1H, J=8.7, 1.5 Hz), 7.18 (t, 1H, J=7.8 Hz), 6.97 (d, 2H, J=8.1 Hz), 6.88 (d, 1H, J=7.8 Hz), 6.28 (s, 1H), 5.22-5.11 (m, 1H), 3.18 (s, 3H), 1.52 (d, 3H, J=6.9 Hz).

Example 59

5-(3-Isopropyl-phenoxy)-furan-2-carboxylic acid [1-(3,5-difluoro-4-methanesulfonylamino-phenyl)-ethyl]-amide

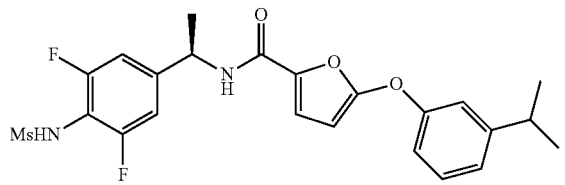

This compound was prepared according to the method of example 1.

5-Bromo-furan-2-carboxylic acid [1-(3,5-difluoro-4-methanesulfonylamino-phenyl)-ethyl]-amide (37 mg, 0.09 mmol) was reacted with 3-isopropylphenol (23 mg, 0.18 mmol) to give the title compound (7 mg, 14%) after purification by column chromatography (gradient 12% to 100% EtOAc in n-hexane).

$^1$H NMR (300 MHz, CDCl$_3$): δ7.32~7.26 (m, 2H), 7.11 (d, 1H, J=3.6 Hz), 7.09~7.07 (m, 1H), 7.01~6.98 (m, 2H), 6.92 (d, 1H, J=7.8 Hz), 6.37 (d, 1H, J=7.2 Hz), 6.20 (s, 1H), 5.54 (d, 1H, J=3.6 Hz), 5.24~5.17 (m, 1H), 3.18 (s, 3H), 3.01~2.87 (m, 1H), 1.53 (d, 3H, J=7.2 Hz) 1.24 (d, 6H, J=6.9 Hz).

Example 60

5-(4-Trifluoromethyl-phenyl)-thiophene-2-carboxylic acid 3,5-difluoro-4-methanesulfonylamino-benzylamide

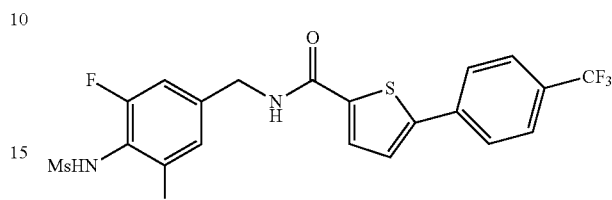

To a suspension of 5-bromo-thiophene-2-carboxylic acid 3,5-difluoro-4-methanesulfonylamino-benzylamide (100 mg, 0.235 mmol), Pd(PPh$_3$)$_4$ (4.1 mg, 0.0035 mmol), and 4-trifluoromethyl phenyl boronic acid (53.5 mg, 0.282 mmol) in toluene (1 mL) was added 2N—Na$_2$CO$_3$ (0.5 mL)/EtOH (0.5 mL). The mixture was stirred 3 hours at 110° C. and was diluted with EtOAc. The mixture was washed with 1N HCl, water and brine, dried over anhydrous magnesium sulfate, filtered, and concentrated under reduced pressure. The crude residue was purified by column chromatography (gradient 12% to 100% EtOAc in n-hexane) to give title compound (90 mg, 78%).

$^1$H NMR (300 MHz, DMSO-d$_6$): δ9.51 (s, 1H), 9.23 (t, 1H, J=5.4 Hz), 7.94 (d, 2H, J=8.1 Hz), 7.86~7.85 (m, 1H), 7.81~7.78 (m, 2H), 7.74~7.73 (m, 1H), 7.14 (d, 2H, J=8.7 Hz), 4.47 (d, 2H, J=5.4 Hz), 3.04 (s, 3H).

Example 61

5-(4-Bromo-phenyl)-2-trifluoromethyl-furan-3-carboxylic acid 3,5-difluoro-4-methanesulfonylamino-benzylamide

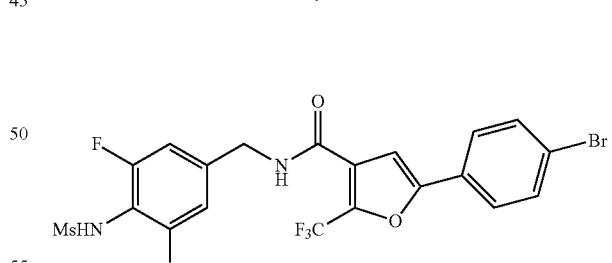

N-(4-Aminomethyl-3,5-difluoro-phenyl)-methanesulfonamide, HCl salt (41 mg, 0.15 mmol) was reacted with 5-(4-bromophenyl)-2-(trifluoromethyl)-3-furoic acid (50 mg, 0.15 mmol) as described above to give the title compound (68 mg, 81.9%) after purification by column chromatography (Hex/EtOAc=1:1)

$^1$H NMR (300 MHz, CDCl$_3$): δ7.58 (s, 4H), 6.98 (m, 3H), 6.34 (bs, 1H), 6.03 (s, 1H), 4.60 (d, 2H, J=6.3 Hz), 3.23 (s, 3H).

Example 62

5-(4-Bromo-phenyl)-2-trifluoromethyl-furan-3-carboxylic acid [1-(3,5-difluoro-4-methanesulfonylamino-phenyl)-ethyl]-amide

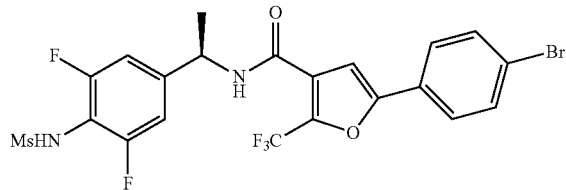

(R)—N-[4-(1-Amino-ethyl)-2-fluoro-phenyl]-methanesulfonamide, HCl salt (43 mg, 0.15 mmol) was reacted with 5-(4-bromophenyl)-2-(trifluoromethyl)-3-furoic acid (50 mg, 0.15 mmol) as described above to give the title compound (57 mg, 68.2%) after purification by column chromatography (Hex/EtOAc=3:2)
$^1$H NMR (300 MHz, CDCl$_3$): δ7.58 (s, 4H), 6.99 (m, 3H), 6.02 (s, 1H), 5.22 (m, 1H), 3.22 (s, 3H), 1.58 (m, 3H).

Example 63

5-(4-tert-Butyl-phenyl)-thiophene-2-carboxylic acid 3,5-difluoro-4-methanesulfonylamino-benzylamide

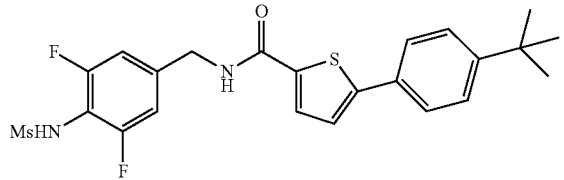

This compound was prepared according to the method of example 60.
5-Bromo-thiophene-2-carboxylic acid 3,5-difluoro-4-methanesulfonylamino-benzylamide (80 mg, 0.19 mmol) was reacted with 4-tert-butyl phenyl boronic acid (40.2 mg, 0.23 mmol) to give the title compound (64 mg, 71%) after purification by column chromatography (gradient 12% to 100% EtOAc in n-hexane).
$^1$H NMR (300 MHz, DMSO-d$_6$): δ9.42 (s, 1H), 9.06 (t, 1H, J=6.0 Hz), 7.74 (d, 1H, J=3.9 Hz), 7.57 (d, 2H, J=8.4 Hz), 7.44 (d, 1H, J=3.9 Hz), 7.39 (d, 2H, J=8.4 Hz), 7.06 (d, 2H, J=8.4 Hz), 4.40 (d, 2H, J=5.7 Hz), 2.98 (s, 3H), 1.23 (s, 9H).

Example 64

5-(3-Ethoxy-phenyl)-thiophene-2-carboxylic acid 3,5-difluoro-4-methanesulfonylamino-benzylamide

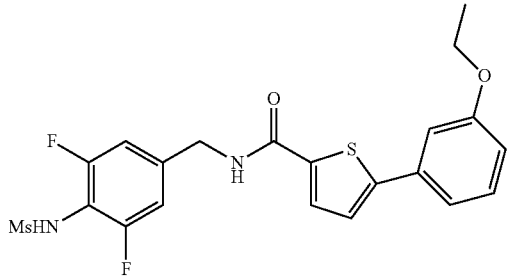

This compound was prepared according to the method of example 60.
5-Bromo-thiophene-2-carboxylic acid 3,5-difluoro-4-methanesulfonylamino-benzylamide (80 mg, 0.19 mmol) was reacted with 3-ethoxy phenyl boronic acid (37.5 mg, 0.23 mmol) to give the title compound (55 mg, 62%) after purification by column chromatography (gradient 12% to 100% EtOAc in n-hexane).
$^1$H NMR (300 MHz, DMSO-d$_6$): δ9.45 (s, 1H), 9.13 (t, 1H, J=5.4 Hz), 7.80 (d, 1H, J=3.9 Hz), 7.58 (d, 1H, J=3.6 Hz), 7.33 (d, 1H, J=7.8 Hz), 7.26~7.21 (m, 2H), 7.13 (d, 2H, J=8.4 Hz), 6.93 (d, 1H, J=8.4 Hz), 4.46 (d, 2H, J=5.7 Hz), 4.09 (q, 2H, J=7.2 Hz), 3.04 (s, 3H), 1.34 (t, 3H, J=7.2 Hz).

Example 65

5-(3-Trifluoromethyl-phenyl)-thiophene-2-carboxylic acid 3,5-difluoro-4-methanesulfonylamino-benzylamide

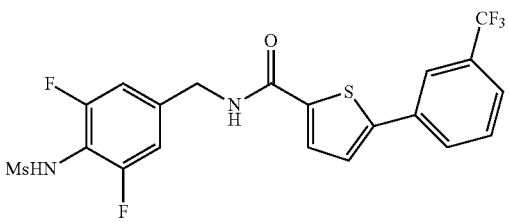

This compound was prepared according to the method of example 60.
5-Bromo-thiophene-2-carboxylic acid 3,5-difluoro-4-methanesulfonylamino-benzylamide (80 mg, 0.19 mmol) was reacted with 3-trifluoromethyl phenyl boronic acid (42 mg, 0.23 mmol) to give the title compound (27 mg, 29%) after purification by column chromatography (gradient 12% to 100% EtOAc in n-hexane).
$^1$H NMR (300 MHz, DMSO-d$_6$): δ9.50 (s, 1H), 9.20 (t, 1H, J=5.7 Hz), 8.02 (s, 1H), 8.01 (d, 1H, J=5.7 Hz), 7.85 (d, 1H, J=4.2 Hz), 7.76 (d, 1H, J=4.2 Hz), 7.71~7.66 (m, 2H), 7.14 (d, 2H, J=8.7 Hz), 4.47 (d, 2H, J=5.7 Hz), 3.05 (s, 3H).

Example 66

2-(2-Butoxy-phenyl)-oxazole-4-carboxylic acid [1-(3,5-difluoro-4-methanesulfonylamino-phenyl)-ethyl]-amide

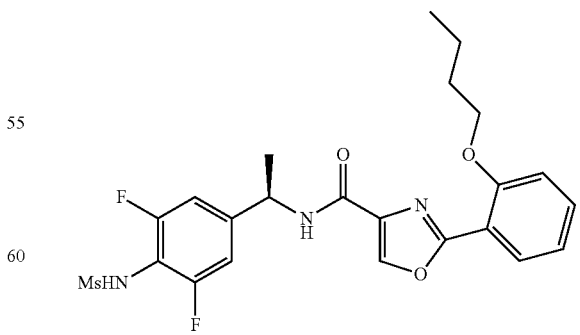

In a glass tube were placed 2-chloro-oxazole-4-carboxylic acid [1-(3,5-difluoro-4-methanesulfonylamino-phenyl)-ethyl]-amide (100 mg, 0.26 mmol), 2-butoxy phenyl boronic acid (61 mg, 0.32 mmol), 2N—Na$_2$CO$_3$ (0.5 mL), Pd(PPh$_3$)$_4$ (4.6 mg, 0.004 mmol), toluene (1.0 mL), ethanol (0.5 mL), and a magnetic stir bar. The mixture was stirred overnight at 110° C. and was diluted with EtOAc and water. The organic layer was washed with saturated ammonium chloride, water and brine, dried over anhydrous magnesium sulfate, filtered, and concentrated under reduced pressure. The crude residue was purified by column chromatography (gradient 12% to 100% EtOAc in n-hexane) to give title compound (50 mg, 39%).

$^1$H NMR (300 MHz, DMSO-d$_6$): δ9.48 (s, 1H), 8.68 (d, 1H, J=6.0 Hz), 8.67 (s, 1H), 7.87 (d, 1H, J=7.8 Hz), 7.52 (t, 1H, J=7.8 Hz), 7.26~7.20 (m, 3H), 7.08 (t, 1H, J=7.5 Hz), 5.18~5.12 (m, 1H), 4.09 (t, 2H, J=6.0 Hz), 3.04 (s, 1H), 1.75~1.66 (m, 2H), 1.49 (d, 3H, J=6.9 Hz), 1.43~1.37 (m, 2H), 0.90 (t, 3H, J=7.5 Hz).

Example 67

2-(3-Trifluoromethyl-phenyl)-oxazole-4-carboxylic acid [1-(3,5-difluoro-4-methanesulfonylamino-phenyl)-ethyl]-amide

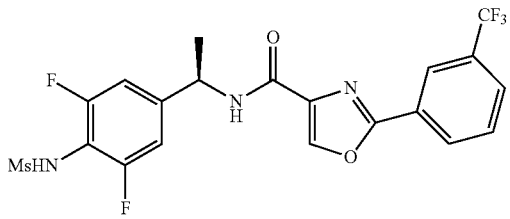

In a glass tube were placed 2-chloro-oxazole-4-carboxylic acid [1-(3,5-difluoro-4-methanesulfonylamino-phenyl)-ethyl]-amide (100 mg, 0.26 mmol), 3-trifluoromethyl phenyl boronic acid (60 mg, 0.32 mmol), 2N—Na$_2$CO$_3$ (0.5 mL), Pd(PPh$_3$)$_4$ (4.6 mg, 0.004 mmol), toluene (1.0 mL), ethanol (0.5 mL), and a magnetic stir bar. The mixture was stirred overnight at 110° C. and was diluted with EtOAc and water. The organic layer was washed with saturated ammonium chloride, water and brine, dried over anhydrous magnesium sulfate, filtered, and concentrated under reduced pressure. The crude residue was purified by column chromatography (gradient 12% to 100% EtOAc in n-hexane) to give title compound (30 mg, 29%).

$^1$H NMR (300 MHz, DMSO-d$_6$): δ9.48 (s, 1H), 8.87 (d, 1H, J=7.8 Hz), 8.78 (s, 1H), 8.33 (s, 1H), 8.33~8.30 (m, 1H), 7.97~7.94 (m, 1H), 7.85~7.81 (m, 1H), 7.26 (d, 2H, J=9.0 Hz), 5.19~5.14 (m, 1H), 3.04 (s, 3H), 1.51 (d, 3H, J=6.6 Hz).

Example 68

2-(3-Methoxy-phenyl)-oxazole-4-carboxylic acid [1-(3,5-difluoro-4-methanesulfonylamino-phenyl)-ethyl]-amide

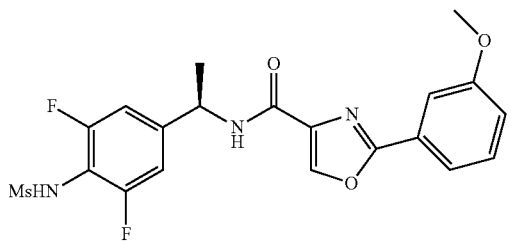

This compound was prepared according to the method of example 66.

2-Chloro-oxazole-4-carboxylic acid [1-(3,5-difluoro-4-methanesulfonylamino-phenyl)-ethyl]-amide (100 mg, 0.26 mmol) was reacted with 3-methoxy phenyl boronic acid (48 mg, 0.32 mmol) to give the title compound (15 mg, 10%) after purification by column chromatography (gradient 12% to 100% EtOAc in n-hexane).

$^1$H NMR (300 MHz, DMSO-d$_6$): δ9.41 (s, 1H), 8.75 (d, 1H, J=8.4 Hz), 8.63 (s, 1H), 7.57 (d, 1H, J=7.5 Hz), 7.49 (s, 1H), 7.43 (t, 1H, J=7.8 Hz), 7.18 (d, 2H, J=8.7 Hz), 7.09 (d, 1H, J=6.0 Hz), 5.13~5.05 (m, 1H), 3.78 (s, 3H), 2.98 (s, 3H), 1.44 (d, 3H, J=7.2 Hz).

Example 69

2-(3-Isopropyl-phenyl)-oxazole-4-carboxylic acid [1-(3,5-difluoro-4-methanesulfonylamino-phenyl)-ethyl]-amide

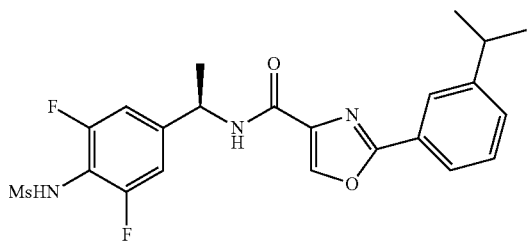

This compound was prepared according to the method of example 66.

2-Chloro-oxazole-4-carboxylic acid [1-(3,5-difluoro-4-methanesulfonylamino-phenyl)-ethyl]-amide (50 mg, 0.13 mmol) was reacted with 3-isopropyl phenyl boronic acid (43 mg, 0.26 mmol) to give the title compound (10 mg, 16%) after purification by column chromatography (gradient 12% to 100% EtOAc in n-hexane).

$^1$H NMR (300 MHz, DMSO-dd: δ9.48 (s, 1H), 8.81 (d, 1H, J=8.1 Hz), 8.69 (s, 1H), 7.91 (s, 1H), 7.86 (d, 1H, J=6.6 Hz), 7.52~7.47 (m, 2H), 7.26 (d, 2H, J=8.7 Hz), 5.18~5.13 (m, 1H), 3.04 (s, 3H), 3.03~2.95 (m, 1H), 1.50 (d, 3H, J=6.6 Hz), 1.25 (d, 6H, J=6.9 Hz).

Example 70

2-Biphenyl-3-yl-oxazole-4-carboxylic acid [1-(3,5-difluoro-4-methanesulfonylamino-phenyl)-ethyl]-amide

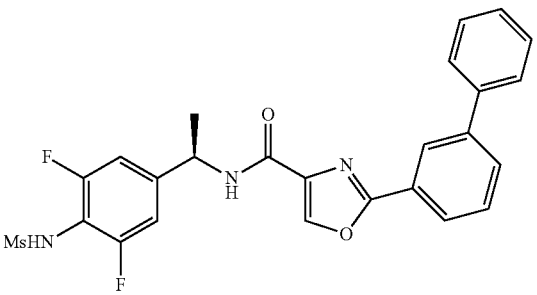

In a 5 ml glass tube were placed 2-chloro-oxazole-4-carboxylic acid [1-(3,5-difluoro-4-methanesulfonylamino-phenyl)-ethyl]-amide (100 mg, 0.26 mmol), 3-biphenyl boronic acid (104 mg, 0.53 mmol), Cs$_2$CO$_3$ (257 mg, 0.79 mmol), Pd(PPh$_3$)$_2$Cl$_2$ (15 mg, 0.021 mmol), DME (0.8 mL), ethanol (0.2 mL), and a magnetic stir bar. The vial was sealed with septum and placed into the Microwave cavity. The vial was irradiated in a Microwave synthesizer at 140° C. for 20 min. The mixture was diluted with EtOAc and washed with 1N HCl and water. The organic layer was dried over anhydrous MgSO₄ and concentrated under reduced pressure. The crude residue was purified by column chromatography (gradient 12% to 100% EtOAc in n-hexane) to give title compound (70 mg, 54%).

¹H NMR (300 MHz, CDCl₃): δ9.48 (s, 1H), 8.84 (d, 1H, J=8.1 Hz), 8.74 (s, 1H), 8.30 (s, 1H), 8.04 (d, 1H, J=7.8 Hz), 7.87 (d, 1H, J=7.5 Hz), 7.74 (d, 2H, J=7.8 Hz), 7.68 (t, 1H, J=7.8 Hz), 7.52 (t, 2H, J=7.5 Hz), 7.43 (t, 1H, J=7.2 Hz), 7.26 (d, 2H, J=8.7 Hz), 5.20~5.15 (m, 1H), 3.04 (s, 3H), 1.51 (d, 3H, J=6.9 Hz).

Example 71

2-(3-Propoxy-phenyl)-oxazole-4-carboxylic acid [1-(3,5-difluoro-4-methanesulfonylamino-phenyl)-ethyl]-amide

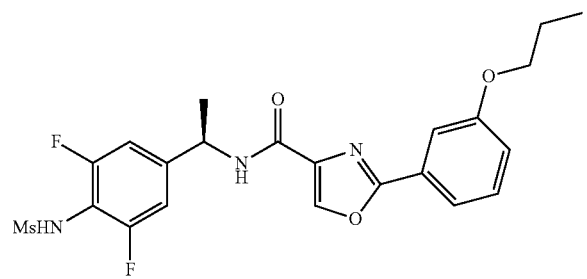

This compound was prepared according to the method of example 70.

2-Chloro-oxazole-4-carboxylic acid [1-(3,5-difluoro-4-methanesulfonylamino-phenyl)-ethyl]-amide (50 mg, 0.13 mmol) was reacted with 3-propoxy phenyl boronic acid (47 mg, 0.26 mmol) to give the title compound (10 mg, 16%) after purification by column chromatography (gradient 12% to 100% EtOAc in n-hexane).

¹H NMR (300 MHz, CDCl₃): δ69.42 (s, 1H), 8.75 (d, 1H, J=8.1 Hz), 8.63 (s, 1H), 7.54 (d, 1H, J=7.5 Hz), 7.49 (s, 1H), 7.41 (t, 1H, J=8.1 Hz), 7.19 (d, 2H, J=8.7 Hz), 7.07 (d, 1H, J=8.1 Hz), 5.12~5.04 (m, 1H), 3.95 (t, 2H, J=6.6 Hz), 2.97 (s, 3H), 1.73~1.62 (m, 2H), 1.44 (d, 3H, J=6.9 Hz), 0.93 (t, 3H, J=7.5 Hz).

Example 72

5-(3-Isopropyl-phenyl)-thiophene-2-carboxylic acid [1-(3,5-difluoro-4-methanesulfonylamino-phenyl)-ethyl]-amide

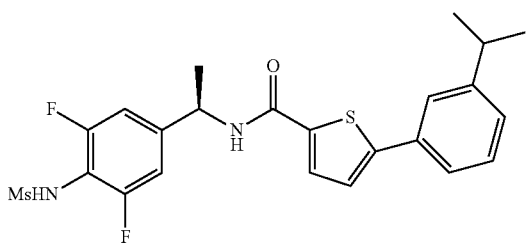

In a 5 ml glass tube were placed 5-bromo-thiophene-2-carboxylic acid [1-(3,5-difluoro-4-methanesulfonylamino-phenyl)-ethyl]-amide (50 mg, 0.12 mmol), 3-isopropyl phenyl boronic acid (37 mg, 0.23 mmol), Cs₂CO₃ (114 mg, 0.34 mmol), Pd(PPh₃)₂Cl₂ (6.4 mg, 0.009 mmol), DME (0.8 mL), ethanol (0.2 mL), and a magnetic stir bar. The vial was sealed with septum and placed into the Microwave cavity. The vial was irradiated in a Microwave synthesizer at 140° C. for 20 min. The mixture was diluted with EtOAc and washed with 1N HCl and water. The organic layer was dried over anhydrous MgSO₄ and concentrated under reduced pressure. The crude residue was purified by column chromatography (gradient 12% to 100% EtOAc in n-hexane) to give title compound (42 mg, 77%).

¹H NMR (300 MHz, CDCl₃): δ9.50 (s, 1H), 8.87 (d, 1H, J=7.8 Hz), 7.88 (d, 2H, J=3.9 Hz), 7.56 (d, 2H, J=3.9 Hz), 7.50 (d, 1H, J=7.8 Hz), 7.35 (t, 1H, J=7.8 Hz), 7.26~7.19 (m, 2H), 5.16~5.09 (m, 1H), 3.04 (s, 3H), 2.98~2.93 (m, 1H), 1.47 (d, 3H, J=6.9 Hz), 1.23 (d, 6H, J=7.2 Hz).

Example 73

5-(3-Trifluoromethyl-phenyl)-thiophene-2-carboxylic acid [1-(3,5-difluoro-4-methanesulfonylamino-phenyl)-ethyl]-amide

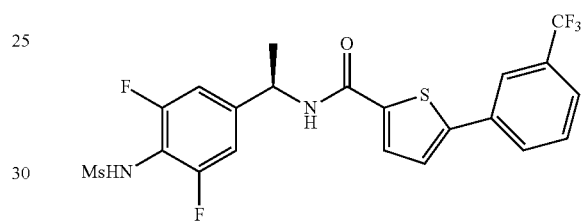

5-Bromo-thiophene-2-carboxylic acid [1-(3,5-difluoro-4-methanesulfonylamino-phenyl)-ethyl]-amide (50 mg, 0.12 mmol) was reacted with 3-trifluoromethyl phenyl boronic acid (42 mg, 0.23 mmol) as described in example 60 to give the title compound (42 mg, 77%) after purification by column chromatography (gradient 12% to 100% EtOAc in n-hexane).

¹H NMR (300 MHz, DMSO-d₆): δ9.49 (s, 1H), 8.94 (d, 1H, J=7.8 Hz), 8.02 (s, 1H), 7.99 (d, 1H, J=9.6 Hz), 7.93 (d, 1H, J=3.9 Hz), 7.76 (d, 1H, J=3.9 Hz), 7.71~7.65 (m, 2H), 7.21 (d, 2H, J=8.7 Hz), 5.15~5.07 (m, 1H), 3.04 (s, 3H), 1.47 (d, 3H, J=6.9 Hz).

Example 74

2-(4-Trifluoromethyl-phenyl)-oxazole-4-carboxylic acid [1-(3,5-difluoro-4-methanesulfonylamino-phenyl)-ethyl]-amide

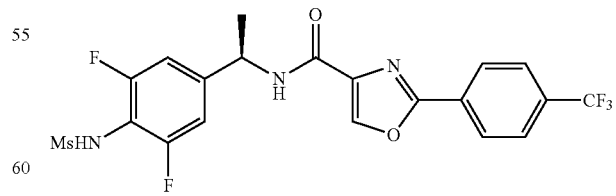

4-Trifluoromethylbenzeneboronic acid (50 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (15 mg, 24%) after purification by flash chromatography on silica gel (hexane: EtOAc=1:1).

¹H NMR (300 MHz, CDCl₃): δ8.31 (s, 1H), 8.18 (d, 2H, J=8.4 Hz), 7.76 (d, 2H, J=8.1 Hz), 7.23 (d, 1H, J=8.4 Hz), 7.04 (d, 2H, J=8.7 Hz), 6.22 (s, 1H), 5.24 (m, 1H), 3.20 (s, 3H), 1.62 (d, 3H, J=6.9 Hz).

Example 75

2-(4-tort-Butyl-phenyl)-oxazole-4-carboxylic acid [1-(3,5-difluoro-4-methanesulfonylamino-phenyl)-ethyl]-amide

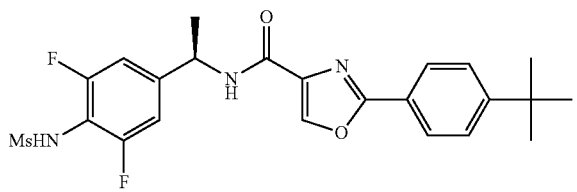

4-tert-Butylphenylboronic acid (39.2 mg, 0.22 mmol) and 2-chloro-oxazole-4-carboxylic acid [1-(3,5-difluoro-4-methanesulfonylamino-phenyl)-ethyl]-amide (42.6 mg, 0.11 mmol) was reacted using Pd(PPh₃)₂Cl₂ (6.3 mg, 0.009 mmol), Cs₂CO₃ (107.5 mg, 0.33 mmol) as described above to give the title compound (15 mg, 29%) after purification by flash chromatography on silica gel (hexane: EtOAc=1:1).

¹H NMR (300 MHz, CDCl₃): δ8.22 (s, 1H), 7.97 (d, 1H, J=8.4 Hz), 7.49 (m, 2H), 7.23 (s, 1H), 7.05 (d, 2H, J=8.7 Hz), 6.98 (m, 1H), 6.03 (s, 1H), 5.22 (m, 1H), 3.20 (s, 3H), 1.61 (d, 3H, J=6.9 Hz), 1.36 (s, 9H).

Example 76

2-(3-Acetyl-phenyl)-oxazole-4-carboxylic acid [1-(3,5-difluoro-4-methanesulfonylamino-phenyl)-ethyl]-amide

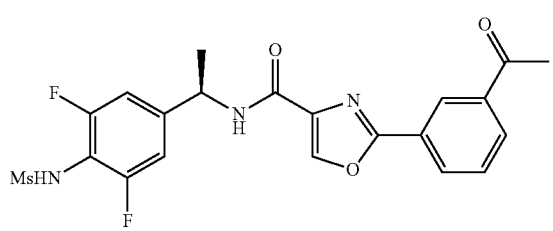

3-Acetylphenylboronic acid (42.6 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (23 mg, 38%) after purification by flash chromatography on silica gel (hexane: EtOAc=1:1).

¹H NMR (300 MHz, CDCl₃): δ8.65 (s, 1H), 8.31 (s, 1H), 8.24 (d, 1H, J=8.1 Hz), 8.09 (d, 1H, J=7.8 Hz), 7.62 (m, 1H), 7.29 (d, 1H, J=8.1 Hz), 7.04 (d, 2H, J=8.7 Hz), 6.35 (s, 1H), 5.25 (m, 1H), 3.20 (s, 3H), 2.70 (s, 3H), 1.62 (d, 3H, J=6.9 Hz)

Example 77

2-(5-Isopropyl-2-methoxy-phenyl)-oxazole-4-carboxylic acid [1-(3,5-difluoro-4-methanesulfonylamino-phenyl)-ethyl]-amide

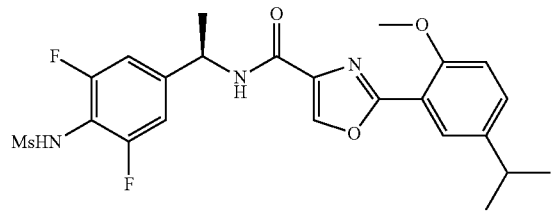

5-Isopropyl-2-methoxybenzeneboronic acid (50.5 mg, 0.26 mmol) and 2-chloro-oxazole-4-carboxylic acid [1-(3,5-difluoro-4-methanesulfonylaminophenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (12 mg, 19%) after purification by flash chromatography on silica gel (hexane: EtOAc=1:1).

¹H NMR (300 MHz, CDCl₃): δ8.28 (s, 1H), 7.76 (d, 1H, J=2.1 Hz), 7.34 (m, 1H), 7.29 (bs, 1H), 7.05 (d, 2H, J=8.4 Hz), 6.98 (d, 1H, J=8.4 Hz), 6.02 (s, 5.25 (m, 1H), 3.93 (s, 3H), 3.20 (s, 3H), 2.98 (m, 1H), 1.58 (d, 3H, J=4.2 Hz), 1.28 (d, 6H, J=6.9 Hz)

Example 78

2-Biphenyl-4-yl-oxazole-4-carboxylic acid [1-(3,5-difluoro-4-methanesulfonylamino-phenyl)-ethyl]-amide

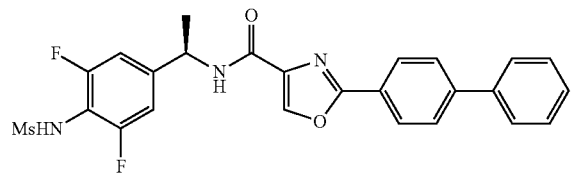

4-Biphenylboronic acid (51.5 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (20 mg, 31%) after purification by flash chromatography on silica gel (hexane: EtOAc=1:1).

¹H NMR (300 MHz, CDCl₃): δ8.27 (s, 1H), 8.12 (d, 2H, J=8.1 Hz), 7.72 (d, 2H, J=7.8 Hz), 7.64 (d, 2H, J=7.2 Hz), 7.45 (m, 3H), 7.29 (s, 1H), 7.05 (d, 2H, J=8.4 Hz), 6.20 (s, 1H), 5.25 (m, 1H), 3.20 (s, 3H), 1.62 (d, 3H, J=6.6 Hz)

Example 79

2-(2-Fluoro-3-trifluoromethyl-phenyl)-oxazole-4-carboxylic acid [1-(3,5-difluoro-4-methanesulfonylamino-phenyl)-ethyl]-amide

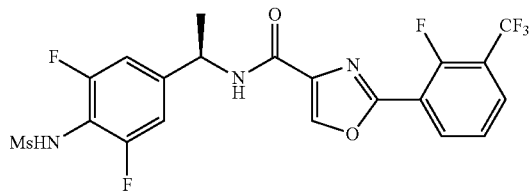

2-Fluoro-3-trifluoromethylbenzeneboronic acid (54 mg, 0.26 mmol) and 2-chloro-oxazole-4-carboxylic acid [1-(3,5-difluoro-4-methanesulfonylaminophenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (21 mg, 32%) after purification by flash chromatography on silica gel (% EtOAc in hexane=12%~80%).

$^1$H NMR (300 MHz, DMSO-d$_6$): δ9.45 (bs, 1H), 8.84 (m, 2H), 8.40 (t, 1H, J=6.9 Hz), 8.3 (t, 1H, J=6.9 Hz), 7.63 (t, 1H, J=7.5 Hz), 7.26 (d, 2H, J=9.0 Hz), 5.17 (m, 1H), 3.04 (s, 3H), 1.51 (d, 3H, J=7.2 Hz)

Example 80

2-(3-Isopropyl-phenyl)-thiazole-4-carboxylic acid [1-(3,5-difluoro-4-methanesulfonylamino-phenyl)-ethyl]-amide

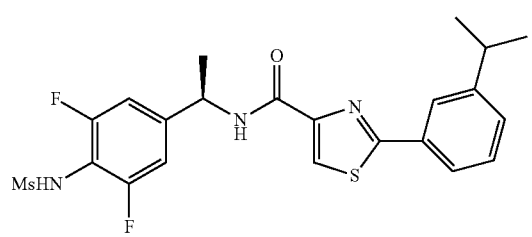

This compound was prepared according to the method of example 70

2-Chloro-thiazole-4-carboxylic acid [1-(3,5-difluoro-4-methanesulfonylamino-phenyl)-ethyl]-amide (50 mg, 0.13 mmol) was reacted with 3-isopropyl phenyl boronic acid (42 mg, 0.26 mmol) to give the title compound (28 mg, 45%) after purification by column chromatography (gradient 12% to 100% EtOAc in n-hexane).

$^1$H NMR (300 MHz, CDCl$_3$): δ8.11 (s, 1H), 7.78 (s, 1H), 7.65 (d, 1H, J=7.8 Hz), 7.47~7.34 (m, 2H), 7.05 (d, 2H, J=8.4 Hz), 6.13 (s, 1H), 5.50~5.24 (m, 2H), 3.19 (s, 3H), 3.06~2.96 (m, 1H), 1.62 (d, 3H, J=6.9 Hz), 1.31 (d, 6H, J=6.9 Hz).

Example 81

2-(3-Dimethylamino-phenyl)-oxazole-4-carboxylic acid [1-(3,5-difluoro-4-methanesulfonylamino-phenyl)-ethyl]-amide

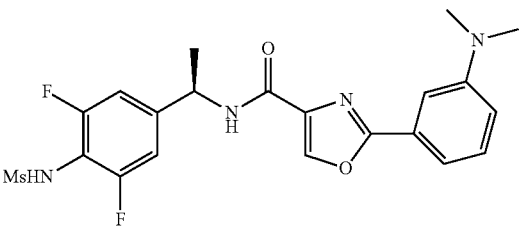

In a 5 ml glass tube were placed 2-chloro-oxazole-4-carboxylic acid [1-(3,5-difluoro-4-methanesulfonylamino-phenyl)-ethyl]-amide (50 mg, 0.13 mmol), 3-dimethylaminophenyl boronic acid (60 mg, 0.30 mmol), Cs$_2$CO$_3$ (129 mg, 0.40 mmol), Pd(PPh$_3$)$_2$Cl$_2$ (7 mg, 0.01 mmol), dimethoxyethane (0.8 mL), ethanol (0.2 mL), and a magnetic stir bar. The mixture was stirred at 140° C. for 20 minutes under microwave irradiation, acidified with 3N HCl, and extracted twice with EtOAc. The organic layer was washed with brine, dried over anhydrous magnesium sulfate, filtered, and concentrated under reduced pressure. The crude residue was triturated with ether to give title compound (10 mg, 16%).

$^1$H NMR (300 MHz, DMSO-d$_6$): δ9.48 (s, 1H), 8.80 (d, 1H, J=8.4 Hz), 8.66 (s, 1H), 7.63~7.50 (m, 2H), 7.37~7.20 (s, 3H), 6.92 (d, 1H, J=7.2 Hz), 5.20~5.11 (m, 1H), 3.04 (s, 3H), 2.98 (s, 6H), 1.51 (d, 3H, J=7.2 Hz).

Example 82

2-(3-Chloro-phenyl)-oxazole-4-carboxylic acid [1-(3,5-difluoro-4-methanesulfonylamino-phenyl)-ethyl]-amide

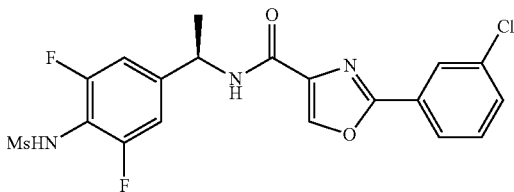

3-Chlorophenylboronic acid (40.7 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (20 mg, 34%) after purification by flash chromatography on silica gel (hexane: EtOAc=1:1). $^1$H NMR (300 MHz, CDCl$_3$): δ8.31 (s, 1H), 8.05 (s, 1H), 7.93 (d, 1H, J=7.2 Hz), 7.45 (m, 2H), 7.29 (bs, 1H), 7.01 (d, 2H, J=8.7 Hz), 6.67 (s, 1H), 5.22 (m, 1H), 3.18 (s, 3H), 1.60 (d, 3H, J=6.9 Hz)

Example 83

2-(3,5-Dichloro-phenyl)-oxazole-4-carboxylic acid [1-(3,5-difluoro-4-methanesulfonylamino-phenyl)-ethyl]-amide

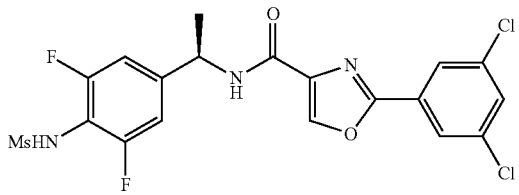

3,5-Dichlorobenzeneboronic acid (30.7 mg, 0.16 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (13 mg, 20%) after purification by flash chromatography on silica gel (hexane: EtOAc=1:1).

$^1$H NMR (300 MHz, CDCl$_3$): δ8.29 (s, 1H), 7.94 (d, 2H, J=1.5 Hz), 7.49 (s, 1H), 7.21 (d, 1H, J=7.8 Hz), 7.03 (d, 2H, J=8.4 Hz), 6.30 (s, 1H), 5.23 (m, 1H), 3.19 (s, 3H), 1.61 (d, 3H, J=6.9 Hz)

Example 84

2-(2-Chloro-phenyl)-oxazole-4-carboxylic acid [1-(3,5-difluoro-4-methanesulfonylamino-phenyl)-ethyl]-amide

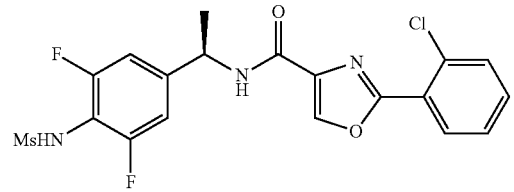

2-Chlorophenylboronic acid (40.7 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (18 mg, 30%) after purification by flash chromatography on silica gel (hexane: EtOAc=1:1).

$^1$H NMR (300 MHz, CDCl$_3$): δ8.36 (s, 1H), 7.97 (d, 1H, J=7.5 Hz), 7.4 (m, 3H), 7.28 (d, 1H, J=7.8 Hz), 7.01 (d, 2H, J=8.4 Hz), 6.54 (s, 1H), 5.23 (m, 1H), 3.18 (s, 3H), 1.58 (d, 3H, J=7.2 Hz)

Example 85

2-(2,3-Dichloro-phenyl)-oxazole-4-carboxylic acid [1-(3,5-difluoro-4-methanesulfonylamino-phenyl)-ethyl]-amide

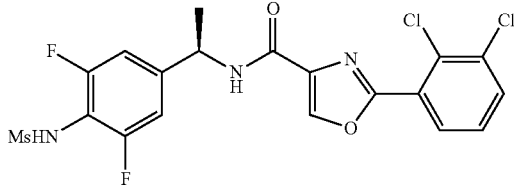

2,3-Dichlorobenzeneboronic acid (49.6 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (9 mg, 14%) after purification by flash chromatography on silica gel (hexane: EtOAc=1:1).

$^1$H NMR (300 MHz, CDCl$_3$): δ8.36 (s, 1H), 7.86 (d, 1H, J=7.8 Hz), 7.63 (d, 1H, J=8.1 Hz), 7.34 (m, 1H), 7.23 (d, 1H, J=8.1 Hz), 7.02 (d, 2H, J=8.7 Hz), 6.32 (bs, 1H), 5.24 (m, 1H), 3.19 (s, 3H), 1.59 (d, 3H, J=7.2 Hz)

Example 86

2-(3,4-Dichloro-phenyl)-oxazole-4-carboxylic acid [1-(3,5-difluoro-4-methanesulfonylamino-phenyl)-ethyl]-amide

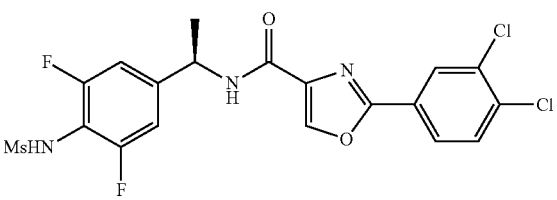

3,4-Dichlorobenzeneboronic acid (49.6 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (19 mg, 30%) after purification by flash chromatography on silica gel (hexane: EtOAc=1:1).

$^1$H NMR (300 MHz, CDCl$_3$): δ8.28 (s, 1H), 8.16 (d, 1H, J=7.8 Hz), 7.88 (d, 1H, J=8.4 Hz), 7.57 (d, 1H, J=8.4 Hz), 7.21 (d, 1H, J=7.8 Hz), 7.03 (d, 2H, J=8.4 Hz), 6.33 (s, 1H), 5.23 (m, 1H), 3.19 (s, 3H), 1.60 (d, 3H, J=6.9 Hz)

Example 87

2-(3,5-Bis-trifluoromethyl-phenyl)-oxazole-4-carboxylic acid [1-(3,5-difluoro-4-methanesulfonylamino-phenyl)-ethyl]-amide

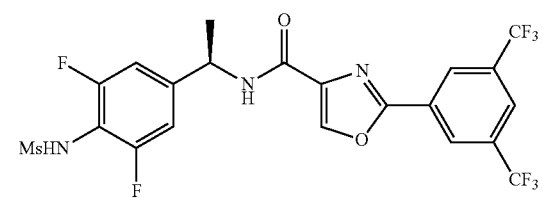

3,5-Bis(trifluoromethyl)benzeneboronic acid (67 mg, 0.26 mmol) and 2-chloro-oxazole-4-carboxylic acid [1-(3,5-difluoro-4-methanesulfonylaminophenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (14 mg, 19%) after purification by flash chromatography on silica gel (% EtOAc in hexane=12%~80%).

¹H NMR (300 MHz, DMSO-d₆): δ9.46 (bs, 1H), 8.93 (d, 1H, J=8.4 Hz), 8.87 (s, 1H), 8.60 (s, 2H), 8.29 (s, 1H), 7.24 (d, 2H, J=9.0 Hz), 5.18 (m, 1H), 3.2 (s, 3H), 1.51 (d, 3H, J=7.2 Hz)

Example 88

2-Naphthalen-1-yl-oxazole-4-carboxylic acid [1-(3,5-difluoro-4-methanesulfonylamino-phenyl)-ethyl]-amide

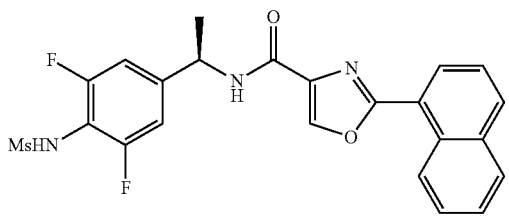

1-Naphthaleneboronic acid (44.7 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (18 mg, 29%) after purification by flash chromatography on silica gel (hexane: EtOAc=1:1).

¹H NMR (300 MHz, CDCl₃): δ9.03 (d, 1H, J=8.4 Hz), 8.37 (s, 1H), 8.20 (d, 1H, J=7.5 Hz), 8.02 (d, 1H, J=8.1 Hz), 7.94 (d, 1H, J=8.1 Hz), 7.69 (m, 1H), 7.58 (m, 2H), 7.29 (d, 1H, J=7.8 Hz), 7.07 (d, 2H, J=8.4 Hz), 6.03 (s, 1H), 5.30 (m, 1H), 3.20 (s, 3H), 1.64 (d, 3H, J=6.9 Hz)

Example 89

2-Naphthalen-2-yl-oxazole-4-carboxylic acid [1-(3,5-difluoro-4-methanesulfonylamino-phenyl)-ethyl]-amide

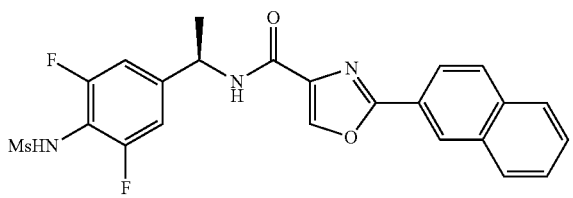

2-Naphthaleneboronic acid (44.7 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (14 mg, 23%) after purification by flash chromatography on silica gel (hexane: EtOAc=1:1).

¹H NMR (300 MHz, CDCl₃): δ8.57 (s, 1H), 8.29 (s, 1H), 8.13 (d, 1H, J=8.7 Hz), 7.95 (m, 2H), 7.98 (m, 1H), 7.57 (m, 1H), 7.29 (d, 1H, J=7.8 Hz), 7.07 (d, 2H, J=8.7 Hz), 6.01 (s, 1H), 5.27 (m, 1H), 3.20 (s, 3H), 1.63 (d, 3H, J=6.9 Hz)

Example 90

2-(2,3-Dimethyl-phenyl)-oxazole-4-carboxylic acid [1-(3,5-difluoro-4-methanesulfonylamino-phenyl)-ethyl]-amide

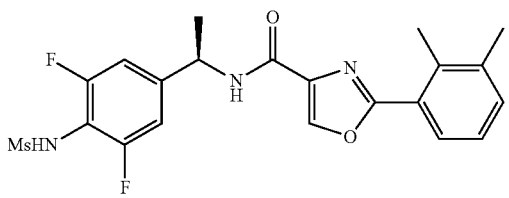

2,3-Dimethylphenylboronic acid (39 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (28 mg, 48%) after purification by flash chromatography on silica gel (hexane: EtOAc=1:1).

¹H NMR (300 MHz, CDCl₃): δ8.34 (s, 1H), 7.69 (d, 1H, J=7.5 Hz), 7.29 (d, 2H, J=7.5 Hz), 7.21 (d, 1H, J=7.8 Hz), 7.00 (d, 2H, J=8.4 Hz), 6.80 (s, 1H), 5.22 (m, 1H), 3.17 (s, 3H), 2.52 (s, 3H), 2.36 (s, 3H), 1.57 (d, 3H, J=6.9 Hz)

Example 91

2-(4-Chloro-3-trifluoromethyl-phenyl)-oxazole-4-carboxylic acid [1-(3,5-difluoro-4-methanesulfonylamino-phenyl)-ethyl]-amide

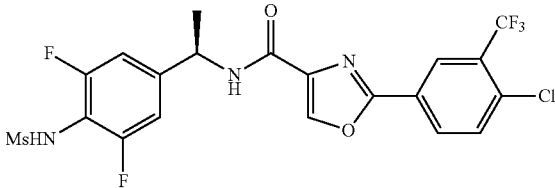

4-Chloro-3-trifluoromethylphenylboronic acid (58.3 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (17 mg, 25%) after purification by flash chromatography on silica gel (hexane: EtOAc=1:1).

¹H NMR (300 MHz, CDCl₃): δ8.39 (s, 1H), 8.34 (s, 1H), 8.14 (d, 1H, J=7.8 Hz), 7.64 (d, 1H, J=8.4 Hz), 7.23 (d, 1H, J=7.8 Hz), 7.02 (d, 2H, J=8.4 Hz), 6.58 (s, 1H), 5.23 (m, 1H), 3.19 (s, 3H), 1.61 (d, 3H, J=6.9 Hz)

Example 92

2-(4-Fluoro-3-trifluoromethyl-phenyl)-oxazole-4-carboxylic acid [1-(3,5-difluoro-4-methanesulfonylamino-phenyl)-ethyl]-amide

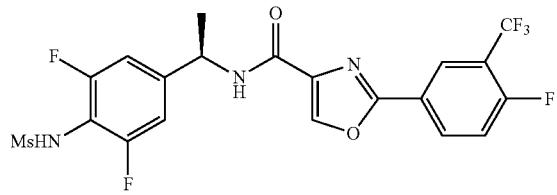

4-Fluoro-3-trifluoromethylphenylboronic acid (54.1 mg, 0.26 mmol) and 2-chloro-oxazole-4-carboxylic acid [1-(3,5-difluoro-4-methanesulfonylaminophenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (5 mg, 8%) after purification by flash chromatography on silica gel (hexane: EtOAc=1:1).

$^1$H NMR (300 MHz, CDCl$_3$): δ8.34 (d, 1H, J=6.3 Hz), 8.29 (s, 1H), 8.24 (m, 1H), 7.35 (m, 1H), 7.20 (d, 1H, J=7.8 Hz), 7.04 (d, 2H, J=8.4 Hz), 6.17 (s, 1H), 5.24 (m, 1H), 3.20 (s, 3H), 1.62 (d, 3H, J=6.9 Hz)

Example 93

2-(3,5-Bis-trifluoromethyl-phenyl)-thiazole-4-carboxylic acid [1-(3,5-difluoro-4-methanesulfonylamino-phenyl)-ethyl]-amide

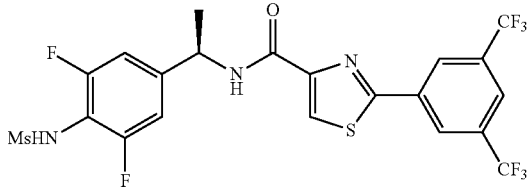

3,5-Bis(trifluoromethyl)phenylboronic acid (67.1 mg, 0.26 mmol) and 2-chloro-thiazole-4-carboxylic acid [1-(3,5-difluoro-4-methanesulfonylaminophenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (21 mg, 28%) after purification by flash chromatography on silica gel (hexane: EtOAc=1:1).

$^1$H NMR (300 MHz, CDCl$_3$): δ8.38 (s; 2H), 8.29 (bs, 1H), 7.98 (s, 1H), 7.58 (d, 1H, J=7.5 Hz), 7.06 (d, 2H, J=8.4 Hz), 6.30 (bs, 1H), 5.28 (m, 1H), 3.19 (s, 3H), 1.66 (d, 3H, J=6.6 Hz)

Example 94

2-(3-Trifluoromethyl-phenyl)-thiazole-4-carboxylic acid [1-(3,5-difluoro-4-methanesulfonylamino-phenyl)-ethyl]-amide

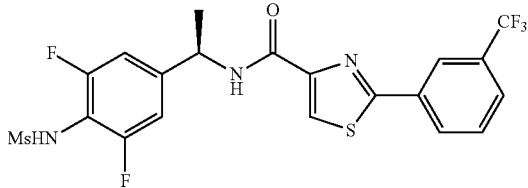

3-Trifluoromethylphenylboronic acid (62.7 mg, 0.33 mmol) and 2-chloro-thiazole-4-carboxylic acid [1-(3,5-difluoro-4-methanesulfonylamino-phenyl)-ethyl]-amide (44.6 mg, 0.11 mmol) was reacted using Pd(PPh$_3$)$_2$Cl$_2$ (10.5 mg, 0.015 mmol), Cs$_2$CO$_3$ (143.4 mg, 0.44 mmol) as described above to give the title compound (29 mg, 44%) after purification by flash chromatography on silica gel (hexane: EtOAc=1:1).

$^1$H NMR (300 MHz, CDCl$_3$): δ8.22 (s, 1H), 8.12 (d, 1H, J=7.5 Hz), 7.73 (d, 1H, J=7.8 Hz), 7.62 (m, 2H), 7.04 (d, 2H, J=8.4 Hz), 6.51 (s, 1H), 5.26 (m, 1H), 3.18 (s, 3H), 1.63 (d, 3H, J=6.9 Hz)

Example 95

5-(3-Cyclopropyl-5-trifluoromethyl-phenyl)-furan-2-carboxylic acid [1-(3,5-difluoro-4-methanesulfonylamino-phenyl)-ethyl]-amide

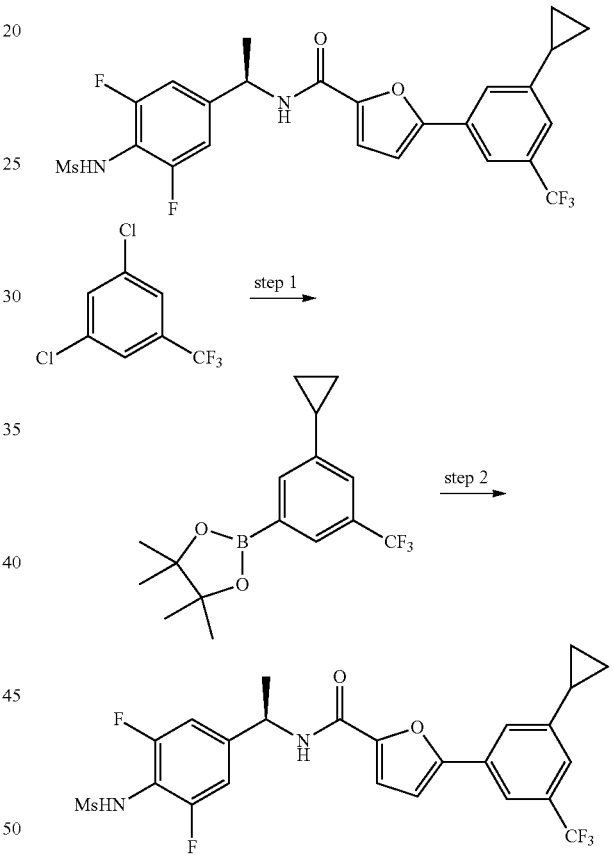

Step 1: 2-(3-Cyclopropyl-5-trifluoromethyl-phenyl)-4,4,5,5-tetramethyl-[1,3,2]dioxaborolane 3,5-Dichlorobenzotrifluoride (1.10 g, 5.1 mmol) and cyclopropylboronic acid (440 mg, 5.1 mmol) were reacted using K$_3$PO$_4$ (3.8 g, 17.9 mmol), tricyclohexylphosphine (145 mg, 0.51 mmol), Pd(OAc)$_2$ (60 mg, 0.27 mmol) as described in example 100 to give 1-chloro-3-cyclopropyl-5-trifluoromethyl-benzene (980 mg, 87%) after purification by flash chromatography on silica gel.

1-chloro-3-cyclopropyl-5-trifluoromethyl-benzene (950 mg, 4.3 mmol) and bis(pinacolo)diborane (1.2 g, 4.7 mmol) were reacted using vacuum-dried KOAc (630 mg, 6.4 mmol), Pd(dba)$_2$ (74 mg, 0.13 mmol) and tricyclohexylphosphine (90 mg, 0.32 mmol) as described in example 100 to give the title compound (1.06 g, 79%) after purification by flash chromatography on silica gel (hexane).

¹H NMR (300 MHz, CDCl₃): δ7.83 (s, 1H), 7.67 (s, 1H), 7.37 (s, 1H), 1.96 (m, 1H), 1.35 (s, 12H), 1.01 (m, 2H), 0.75 (m, 2H)

Step 2: 5-(3-Cyclopropyl-5-trifluoromethyl-phenyl)-furan-2-carboxylic acid [1-(3,5-difluoro-4-methane-sulfonylamino-phenyl)-ethyl]-amide 2-(3-Cyclopropyl-5-trifluoromethyl-phenyl)-4,4,5,5-tetramethyl-[1,3,2]dioxaborolane (120 mg, 0.26 mmol) and 5-Bromo-furan-2-carboxylic acid [1-(3,5-difluoro-4-methanesulfonylamino-phenyl)-ethyl]-amide (110 mg, 0.26 mmol) was reacted using Pd(PPh₃)₂Cl₂ (18 mg, 0.03 mmol), Cs₂CO₃ (250 mg, 0.77 mmol) as described in example 102 to give the title compound (25 mg, 18%) after purification by flash chromatography on silica gel (hexane: EtOAc=1:1).

¹H NMR (300 MHz, CDCl₃): δ7.71 (s, 1H), 7.59 (s, 1H), 7.24 (m, 2H), 7.06 (d, 2H, J=8.7 Hz), 6.82 (d, 1H, J=3.6 Hz), 6.58 (d, 1H, J=7.5 Hz), 6.17 (s, 1H), 5.28 (m, 1H), 3.20 (s, 3H), 2.03 (m, 1H), 1.61 (m, 3H), 1.10 (m, 2H), 0.81 (m, 2H)

Example 96

2-(4-Methoxy-3-trifluoromethyl-phenyl)-oxazole-4-carboxylic acid [1-(3,5-difluoro-4-methanesulfonylamino-phenyl)-ethyl]-amide

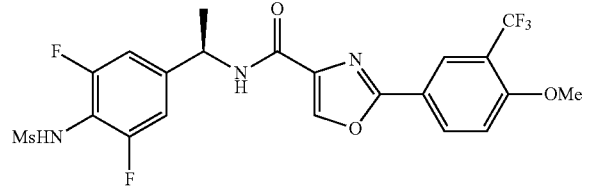

4-Methoxy-3-trifluoromethylbenzeneboronic acid (34 mg, 0.16 mmol) and 2-chloro-oxazole-4-carboxylic acid [1-(3,5-difluoro-4-methanesulfonylaminophenyl)-ethyl]-amide (30 mg, 0.078 mmol) was reacted using Pd(PPh₃)₂Cl₂ (7 mg, 0.01 mmol), Cs₂CO₃ (80 mg, 0.25 mmol) as described above to give the title compound (13 mg, 32%) after purification by flash chromatography on silica gel (% EtOAc in hexane=12%~100%).

¹H NMR (300 MHz, DMSO-d₆): δ9.42 (bs, 1H), 8.82 (d, 1H, J=8.1 Hz), 8.70 (s, 1H), 8.26 (m, 2H), 7.49 (d, 1H, J=8.7 Hz), 7.23 (d, 2H, J=8.7 Hz), 5.14 (m, 1H), 3.99 (s, 3H), 3.01 (s, 3H), 1.50 (d, 3H, J=6.9 Hz)

Example 97

2-(3-Methoxy-5-trifluoromethyl-phenyl)-oxazole-4-carboxylic acid [1-(3,5-difluoro-4-methanesulfonylamino-phenyl)-ethyl]-amide

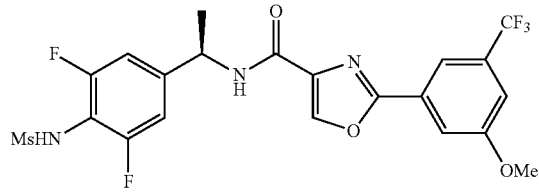

3-Methoxy-5-trifluoromethylbenzeneboronic acid (34 mg, 0.16 mmol) and 2-chloro-oxazole-4-carboxylic acid [1-(3,5-difluoro-4-methanesulfonylaminophenyl)-ethyl]-amide (30 mg, 0.078 mmol) was reacted using Pd(PPh₃)₂Cl₂ (7 mg, 0.01 mmol), Cs₂CO₃ (30 mg, 0.25 mmol) as described above to give the title compound (9 mg, 22%) after purification by flash chromatography on silica gel (% EtOAc in hexane=12%~100%).

¹H NMR (300 MHz, DMSO-d₆): δ9.47 (bs, 1H), 8.87 (d, 1H, J=8.1 Hz), 8.79 (s, 1H), 7.92 (s, 1H), 7.80 (s, 1H), 7.48 (s, 1H), 7.24 (d, 2H, J=8.7 Hz), 5.17 (m, 1H), 3.95 (s, 3H), 3.03 (s, 3H), 1.51 (d, 3H, J=6.9 Hz)

Example 98

2-(3-Methylsulfanyl-phenyl)-oxazole-4-carboxylic acid [1-(3,5-difluoro-4-methanesulfonylamino-phenyl)-ethyl]-amide

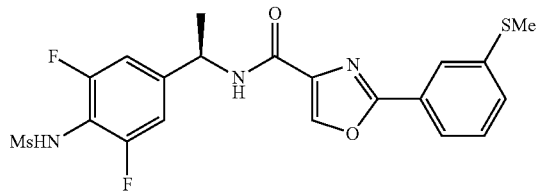

3-Methylthiobenzeneboronic acid (40 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (26 mg, 43%) after purification by flash chromatography on silica gel (% EtOAc in hexane=30%-100%).

¹H NMR (300 MHz, DMSO-d₆): δ9.48 (bs, 1H), 8.80 (d, 1H, J=8.1 Hz), 8.72 (s, 1H), 7.89 (s, 1H), 7.81 (d, 1H, J=7.5 Hz), 7.50 (m, 2H), 7.24 (d, 2H, J=9.0 Hz), 5.16 (m, 1H), 3.04 (s, 3H), 2.56 (s, 3H), 1.51 (d, 3H, J=6.9 Hz)

Example 99

2-(3,5-Dimethyl-phenyl)-oxazole-4-carboxylic acid [1-(3,5-difluoro-4-methanesulfonylamino-phenyl)-ethyl]-amide

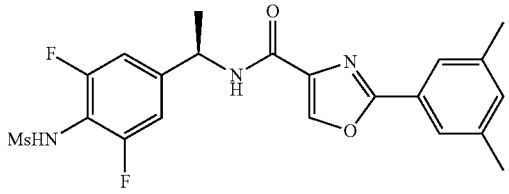

3,5-Dimethylbenzeneboronic acid (39 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh₃)₂Cl₂ (7 mg, 0.01 mmol), Cs₂CO₃ (127 mg, 0.39 mmol) as described above to give the title compound (22 mg, 38%) after purification by flash chromatography on silica gel (% EtOAc in hexane=30%~100%).

$^1$H NMR (300 MHz, DMSO-d$_6$): δ9.48 (bs, 1H), 8.74 (d, 1H, J=8.1 Hz), 8.68 (s, 1H), 7.68 (s, 2H), 7.22 (m, 3H), 5.15 (m, 1H), 3.00 (s, 3H), 2.36 (s, 6H), 1.50 (d, 3H, J=6.9 Hz)

Example 100

2-(3-Cyclopropyl-phenyl)-oxazole-4-carboxylic acid [1-(3,5-difluoro-4-methanesulfonylamino-phenyl)-ethyl]-amide

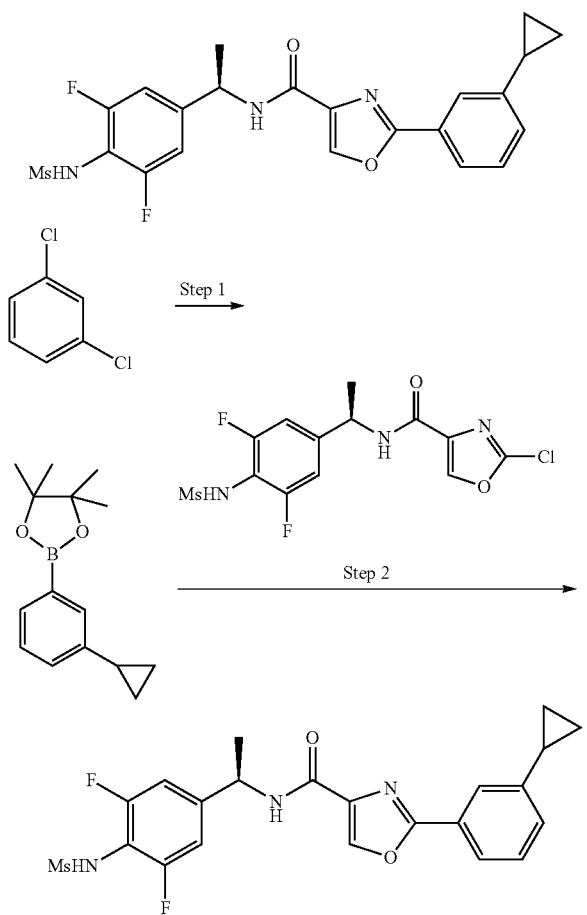

Step 1: 2-(3-Cyclopropyl-phenyl)-4,4,5,5-tetramethyl-[1,3]dioxolane

A mixture of 1,3-dichlorobenzene (1.47 g, 10.0 mmol), cyclopropylboronic acid (859 mg, 10.0 mol), K$_3$PO$_4$ (7.48 g, 35.0 mmol), tricyclohexylphosphine (280 mg, 1.00 mmol), Pd(OAc)$_2$ (144 mg, 0.50 mmol) in toluene/H$_2$O (40 ml/2 ml) was degassed under vacuum and then charged with argon. The resulting mixture was heated at 100° C. for 3 hrs, and then quenched by adding water after cooling to ambient temperature. The aqueous phase was extracted with ether and the combined organic layer was dried over anhydrous MgSO$_4$ and concentrated under reduced pressure. The crude residue was directly used to next step without further purification.

A mixture of Pd(dba)$_2$ (173 mg, 0.30 mmol) and tricyclohexylphosphine (202 mg, 0.72 mmol) was degassed under vacuum and then charged with argon, to which was added dry dioxane. The resulting mixture was stirred for 30 min at ambient temperature, to which were successively added bis(pinacolo)diborane (2.79 g, 11 mmol), vacuum-dried KOAc (1.47 g, 15.0 mmol), and the crude residue obtained above. The resulting mixture was degassed tinder vacuum, charged with argon, and then heated at 80° C. for 72 hrs. The reaction mixture was quenched by adding water after cooling to ambient temperature. The aqueous phase was extracted with benzene and the combined organic layer was dried over anhydrous MgSO$_4$ and concentrated under reduced pressure. The crude residue was purified by column chromatography (hexane~EtOAc/Hex=1/15) to give title compound (1.52 g, 62% over 2 steps).

$^1$H NMR (300 MHz, CDCl$_3$): δ7.58 (m, 2H), 7.26 (m, 1H), 7.15 (m, 1H), 1.91 (m, 1H), 1.34 (s, 12H), 0.92 (m, 2H), 0.71 (m, 2H)

Step 2: 2-(3-Cyclopropyl-phenyl)-oxazole-4-carboxylic acid [1-(3,5-difluoro-4-methanesulfonylamino-phenyl)-ethyl]-amide 2-(3-Cyclopropyl-phenyl)-4,4,5,5-tetramethyl-[1,3]dioxolane (63 mg, 0.26 mmol) and 2-chloro-oxazole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (20 mg, 33%) after purification by flash chromatography on silica gel (% EtOAc in hexane=25%~100%).

$^1$H NMR (300 MHz, DMSO-d$_6$): δ9.48 (bs, 1H), 8.79 (d, 1H, J=8.7 Hz), 8.72 (s, 1H), 8.70 (s, 1H), 7.80 (m, 2H), 7.45 (t, 1H, J=7.8 Hz), 7.26 (m, 3H), 5.16 (m, 1H), 3.01 (s, 3H), 2.01 (m. 1H), 1.51 (d, 3H, J=6.6 Hz), 1.01 (m, 2H), 0.75 (m, 2H)

Example 101

2-(3-Cyclopropyl-phenyl)-thiazole-4-carboxylic acid [1-(3,5-difluoro-4-methanesulfonylamino-phenyl)-ethyl]-amide

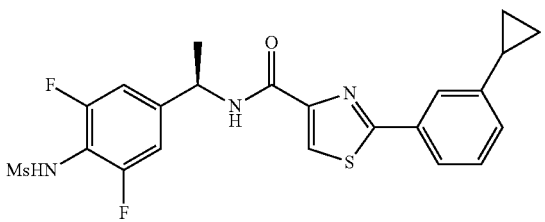

2-(3-Cyclopropyl-phenyl)-4,4,5,5-tetramethyl-[1,3]dioxolane (63 mg, 0.26 mmol) and 2-chloro-thiazole-4-carboxylic acid [1-(3,5-difluoro-4-methanesulfonylamino-phenyl)-ethyl]-amide (55 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (23 mg, 38%) after purification by flash chromatography on silica gel (% EtOAc in hexane=25%~100%).

$^1$H NMR (300 MHz, CDCl$_3$+DMSO-d$_6$): 8.10 (s, 1H), 7.72 (m, 2H), 7.22 (m, 1H), 7.07 (m, 3H), 5.10 (m, 1H), 2.96 (s, 3H), 1.90 (m, 1H), 1.52 (d, 3H, J=7.2 Hz), 0.92 (m, 2H), 0.68 (m, 2H)

Example 102

5-(3-Cyclopropyl-phenyl)-furan-2-carboxylic acid [1-(3,5-difluoro-4-methanesulfonylamino-phenyl)-ethyl]-amide

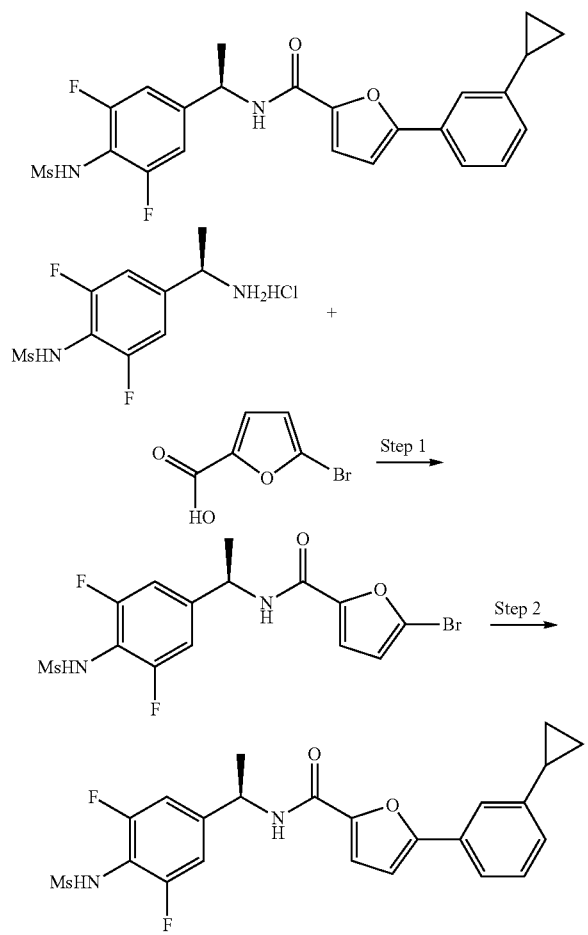

Step 1: 5-Bromo-furan-2-carboxylic acid [1-(3,5-difluoro-4-methanesulfonylamino-phenyl)-ethyl]-amide To a suspension of (R)—N-[4-(1-amino-ethyl)-2-fluoro-phenyl]-methanesulfonamide, HCl salt (1.15 g, 4.0 mmol) in THF (20 mL) was added N-methylmorpholine (550 µL, 5.0 mmol). The mixture was stirred for 5 minutes, to which were added 5-bromo-2-furoic acid (764 mg, 4.0 mmol) and DMTMM (1.38 g, 4.8 mmol). The mixture was stirred for 4 hrs at room temperature and was diluted with EtOAc and water. The aqueous layer was extracted with EtOAc and the combined organic layer was washed with brine, dried over anhydrous magnesium sulfate, filtered, and concentrated under reduced pressure. The crude residue was purified by recrystallization from n-Hex/EtOAc to give title compound (864 mg, 50%).

$^1$H NMR (300 MHz, DMSO-d$_6$): δ9.50 (bs, 1H), 8.85 (d, 1H, J=8.1 Hz), 7.18 (m, 3H), 8.70 (s, 1H), 6.76 (d, 1H, J=3.9 Hz), 5.08 (m, 1H), 3.03 (s, 3H), 1.44 (d, 3H, J=7.2 Hz)

Step 2: 5-(3-Cyclopropyl-phenyl)-furan-2-carboxylic acid [1-(3,5-difluoro-4-methanesulfonylamino-phenyl)-ethyl]-amide 2-(3-Cyclopropyl-phenyl)-4,4,5,5-tetramethyl-[1,3]dioxolane (126 mg, 0.52 mmol) and 5-bromo-furan-2-carboxylic acid [1-(3,5-difluoro-4-methanesulfonylamino-phenyl)-ethyl]-amide (110 mg, 0.26 mmol) was reacted using Pd(PPh$_3$)$_2$Cl$_2$ (14 mg, 0.02 mmol), Cs$_2$CO$_3$ (254 mg, 0.78 mmol) as described above to give the title compound (54 mg, 56%) after purification by recrystallization from n-Hex/EtOAc.

$^1$H NMR (300 MHz, DMSO-d$_6$): δ8.78 (d, 1H, J=8.4 Hz), 8.30 (s, 1H), 7.69 (d, 1H, J=7.5 Hz), 7.58 (s, 1H), 7.34 (t, 1H, J=7.8 Hz), 7.15 (m, 5H), 5.13 (m, 1H), 3.19 (s, 3H), 1.98 (m, 1H), 1.49 (d, 3H, J=6.9 Hz), 0.99 (m, 2H), 0.76 (m, 2H)

Example 103

5-(3-Trifluoromethyl-phenyl)-furan-2-carboxylic acid 3-fluoro-4-methanesulfonylamino-5-methyl-benzylamide

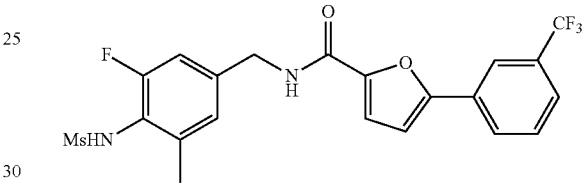

To a suspension of N-(4-aminomethyl-2-fluoro-6-methyl-phenyl)-methanesulfonamide, HCl salt (64 mg, 0.24 mmol) in THF (3 mL) was added N-methylmorpholine (52 µL, 0.47 mmol). The mixture was stirred for 5 minutes, to which were added 5-(3-trifluoromethyl-phenyl)-furan-2-carboxylic acid (51 mg, 0.20 mmol) and DMTMM (70 mg, 0.25 mmol). The mixture was stirred overnight at room temperature and was diluted with EtOAc and water. The aqueous layer was extracted with EtOAc and the combined organic layer was washed with brine, dried over anhydrous magnesium sulfate, filtered, and concentrated under reduced pressure. The crude residue was purified by recrystallization from n-Hex/EtOAc to give title compound (75 mg, 80%).

$^1$H NMR (300 MHz, DMSO-d$_6$): δ9.15 (t, 1H, J=6.0 Hz), 8.25 (m, 2H), 7.72 (m, 2H), 7.34 (d, 1H, J=3.6 Hz), 7.18 (m, 3H); 4.50 (d, 2H, J=5.7 Hz), 2.97 (s, 3H), 2.22 (d, 3H, J=2.1 Hz)

Example 104

5-(3-Trifluoromethyl-phenyl)-furan-2-carboxylic acid 3-ethynyl-5-fluoro-4-methanesulfonylamino-benzylamide

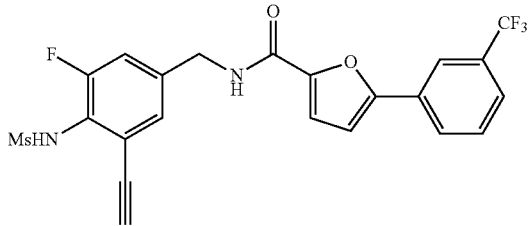

To a suspension of N-(4-aminomethyl-2-ethynyl-6-fluoro-phenyl)-methanesulfonamide, HCl salt (67 mg, 0.24 mmol)

in THF (3 mL) was added N-methylmorpholine (52 μL, 0.47 mmol). The mixture was stirred for 5 minutes, to which were added 5-(3-trifluoromethyl-phenyl)-furan-2-carboxylic acid (51 mg, 0.20 mmol) and DMTMM (70 mg, 0.25 mmol). The mixture was stirred overnight at room temperature and was diluted with EtOAc and water. The aqueous layer was extracted with EtOAc and the combined organic layer was washed with brine, dried over anhydrous magnesium sulfate, filtered, and concentrated under reduced pressure. The crude residue was purified by recrystallization from n-Hex/EtOAc to give title compound (91 mg, 95%).

$^{1}$H NMR (300 MHz, DMSO-d$_{6}$): δ9.22 (t, 1H, J=5.7 Hz), 8.24 (m, 2H), 7.72 (m, 2H), 7.30 (m, 4H), 4.51 (s, 1H), 4.48 (d, 2H, J=5.7 Hz), 3.06 (s, 3H), 2.22 (d, 3H, J=2.1 Hz)

Example 105

5-(3-Trifluoromethyl-phenyl)-furan-2-carboxylic acid 3-fluoro-4-methanesulfonylamino-5-vinyl-benzylamide

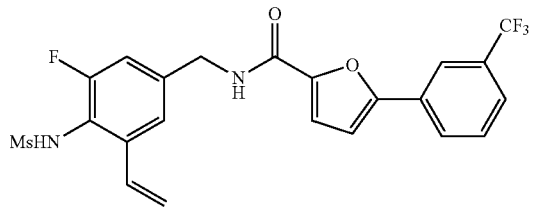

To a suspension of N-(4-aminomethyl-2-fluoro-6-vinyl-phenyl)-methanesulfonamide, HCl salt (67 mg, 0.24 mmol) in THF (3 mL) was added N-methylmorpholine (52 μL, 0.47 mmol). The mixture was stirred for 5 minutes, to which were added 5-(3-trifluoromethyl-phenyl)-furan-2-carboxylic acid (51 mg, 0.20 mmol) and DMTMM (70 mg, 0.25 mmol). The mixture was stirred overnight at room temperature and was diluted with EtOAc and water. The aqueous layer was extracted with EtOAc and the combined organic layer was washed with brine, dried over anhydrous magnesium sulfate, filtered, and concentrated under reduced pressure. The crude residue was purified by recrystallization from n-Hex/EtOAc to give title compound (85 mg, 88%).

$^{1}$H NMR (300 MHz, DMSO-d$_{6}$): δ9.22 (t, 1H, J=5.7 Hz), 8.24 (m, 2H), 7.73 (m, 2H), 7.53 (s, 1H), 7.35 (d, 1H, J=3.3 Hz), 7.26 (d, 1H, J=3.3 Hz), 7.12 (m, 2H), 5.85 (d, 1H, J=17.4 Hz), 5.42 (d, 1H, J=11.1 Hz), 4.51 (d, 2H, J=6.0 Hz), 2.99 (s, 3H)

Example 106

2-(3,5-Dicyclopropyl-phenyl)-oxazole-4-carboxylic acid [1-(3,5-difluoro-4-methanesulfonylamino-phenyl)-ethyl]-amide

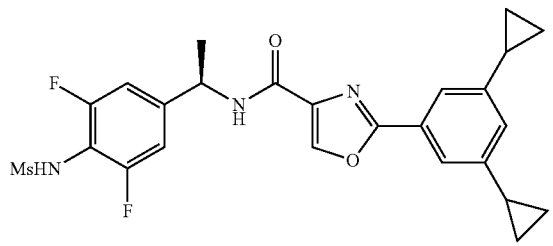

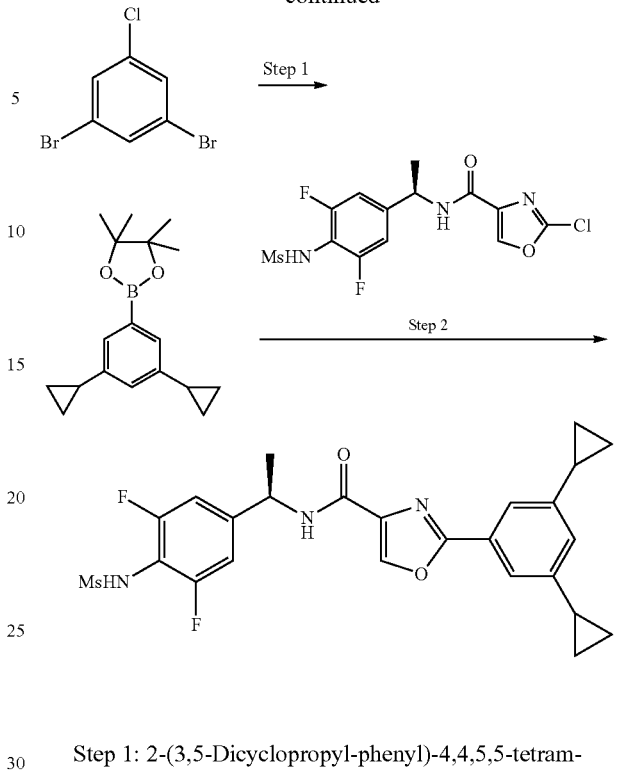

Step 1: 2-(3,5-Dicyclopropyl-phenyl)-4,4,5,5-tetramethyl-[1,3,2]dioxaborolane

1-Chloro-3,5-dibromobenzene (2.70 g, 10.0 mmol) and cyclopropylboronic acid (1.72 g, 20 mmol) were reacted using K$_{3}$PO$_{4}$ (14.9 g, 70 mmol), tricyclohexylphosphine (56 mg, 2.0 mmol), Pd(OAc)$_{2}$ (288 mg, 1.0 mmol) as described above to give 1-chloro-3,5-dicyclopropyl-benzene (1.84 g, 96%) after purification by flash chromatography on silica gel (% EtOAc in hexane=2%~10%).

$^{1}$H NMR (300 MHz, CDCl$_{3}$): 6.79 (s, 2H), 6.70 (s, 1H), 1.82 (m, 2H), 0.94 (m, 4H), 0.68 (m, 4H)

1-Chloro-3,5-dicyclopropyl-benzene (1.84 g, 9.55 mmol) and bis(pinacolo)diborane (2.79 g, 11 mmol) were reacted using vacuum-dried KOAc (1.47 g, 15.0 mmol), Pd(dba)$_{2}$ (173 mg, 0.30 mmol) and tricyclohexylphosphine (202 mg, 0.72 mmol) as described above to give the title compound (950 mg, 33%) after purification by flash chromatography on silica gel (% EtOAc in hexane=2%~10%).

$^{1}$H NMR (300 MHz, CDCl$_{3}$): δ7.30 (s, 2H), 6.88 (s, 1H), 1.87 (m, 2H), 1.33 (s, 12H), 0.92 (m, 4H), 0.70 (m, 4H)

Step 2: 2-(3,5-Dicyclopropyl-phenyl)-oxazole-4-carboxylic acid [1-(3,5-difluoro-4-methanesulfonylamino-phenyl)-ethyl]-amide 2-(3,5-Dicyclopropyl-phenyl)-4,4,5,5-tetramethyl-[1,3,2]dioxaborolane (74 mg, 0.26 mmol) and 2-chloro-oxazole-4-carboxylic acid [1-(3,5-difluoro-4-methanesulfonylamino-phenyl)-ethyl]-amide (100 mg, 0.26 mmol) was reacted using Pd(PPh$_{3}$)$_{2}$Cl$_{2}$ (14 mg, 0.02 mmol), Cs$_{2}$CO$_{3}$ (254 mg, 0.78 mmol) as described above to give the title compound (5 mg, 4%) after purification by flash chromatography on silica gel (% EtOAc in hexane=30%~70%).

$^{1}$H NMR (300 MHz, DMSO-d$_{6}$): δ9.48 (bs, 1H), 8.79 (d, 1H, J=8.4 Hz), 8.67 (s, 1H), 7.50 (s, 2H), 7.25 (d, 1H, J=8.7

Hz), 6.70 (s, 1H), 5.16 (m, 1H), 3.04 (s, 3H), 2.00 (m, 2H), 1.51 (d, 3H, J=7.2 Hz), 1.01 (m, 4H), 0.75 (m, 4H)

Example 107

2-(3,5-Dicyclopropyl-phenyl)-thiazole-4-carboxylic acid [1-(3,5-difluoro-4-methanesulfonylamino-phenyl)-ethyl]-amide

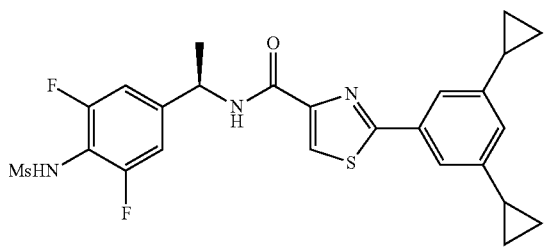

2-(3,5-Dicyclopropyl-phenyl)-4,4,5,5-tetramethyl-[1,3,2]dioxaborolane (74 mg, 0.26 mmol) and 2-chloro-thiazole-4-carboxylic acid [1-(3,5-difluoro-4-methanesulfonylamino-phenyl)-ethyl]-amide (110 mg, 0.26 mmol) was reacted using Pd(PPh$_3$)$_2$Cl$_2$ (14 mg, 0.02 mmol), Cs$_2$CO$_3$ (254 mg, 0.78 mmol) as described above to give the title compound (22 mg, 16%) after purification by flash chromatography on silica gel (% EtOAc' in hexane=30%~70%).

$^1$H NMR (300 MHz, DMSO-d$_6$): δ9.42 (bs, 1H), 8.82 (d, 1H, J=8.4 Hz), 8.29 (s, 1H), 7.53 (s, 2H), 7.24 (d, 1H, J=8.7 Hz), 6.86 (s, 1H), 5.18 (m, 1H), 3.01 (s, 3H), 2.00 (m, 2H), 1.54 (d, 3H, J=6.9 Hz), 0.99 (m, 4H), 0.78 (m, 4H)

Example 108

5-(3,5-Dicyclopropyl-phenyl)-furan-2-carboxylic acid [1-(3,5-difluoro-4-methanesulfonylamino-phenyl)-ethyl]-amide

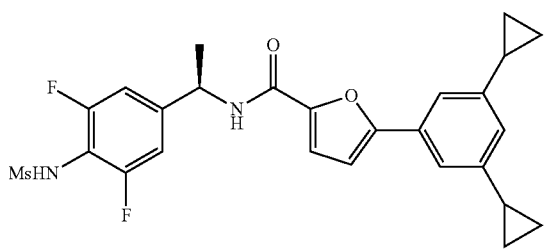

2-(3,5-Dicyclopropyl-phenyl)-4,4,5,5-tetramethyl-[1,3,2]dioxaborolane (74 mg, 0.26 mmol) and 5-bromo-furan-2-carboxylic acid [1-(3,5-difluoro-4-methanesulfonylamino-phenyl)-ethyl]-amide (110 mg, 0.26 mmol) was reacted using Pd(PPh$_3$)$_2$Cl$_2$ (14 mg, 0.02 mmol), Cs$_2$CO$_3$ (254 mg, 0.78 mmol) as described above to give the title compound (50 mg, 38%) after purification by flash chromatography on silica gel (% EtOAc in hexane=30%~70%).

$^1$H NMR (300 MHz, DMSO-d$_6$): δ9.49 (bs, 1H), 8.75 (d, 1H, J=8.1 Hz), 7.34 (s, 2H), 7.22 (m, 3H), 7.09 (d, 1H, J=3.6 Hz), 6.75 (s, 1H), 5.14 (m, 1H), 3.03 (s, 3H), 1.93 (m, 2H), 1.50 (d, 3H, J=6.6 Hz), 0.96 (m, 4H), 0.73 (m, 4H)

Example 109

(S)-5-(3-Trifluoromethyl-phenyl)-furan-2-carboxylic acid [1-(3,5-difluoro-4-methanesulfonylamino-phenyl)-ethyl]-amide

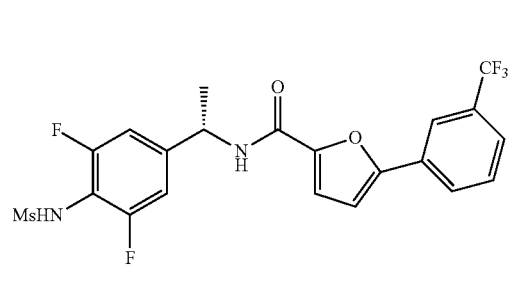

This compound was prepared according to the method of example 103, (S)—N-[4-(1-amino-ethyl)-2,6-difluoro-phenyl]-methanesulfonamide, HCl salt (62 mg, 0.215 mmol) was reacted with 5-(3-trifluoromethyl-phenyl)-furan-2-carboxylic acid (50 mg, 0.195 mmol) to give the title compound (90 mg, 95%) after purification by column chromatography (gradient 12% to 100% EtOAc in n-hexane).

$^1$H NMR (300 MHz, DMSO-d$_6$): 7.93 (s, 1H), 7.89 (d, 1H, J=7.5 Hz), 7.62-7.54 (m, 2H), 7.25 (d, 1H, J=3.6 Hz), 7.06 (d, 2H, J=8.7 Hz), 6.85 (d, 1H, J=3.6 Hz), 6.58 (d, 1H, J=7.5 Hz), 6.15 (s, 1H), 5.32~5.23 (m, 1H), 3.20 (s, 3H), 1.62 (d, 3H, J=7.2 Hz).

Example 110

5-(3-Trifluoromethyl-phenyl)-furan-2-carboxylic acid 3,5-difluoro-4-methanesulfonylamino-benzylamide

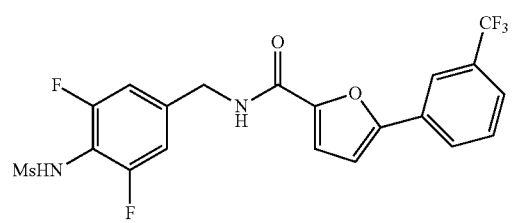

This compound was prepared according to the method of example 103.

N-(4-Aminomethyl-2,6-difluoro-phenyl)-methanesulfonamide, HCl salt (58 mg, 0.215 mmol) was reacted with 5-(3-trifluoromethyl-phenyl)-furan-2-carboxylic acid (50 mg, 0.195 mmol) to give the title compound (83 mg, 90%) after purification by column chromatography (gradient 12% to 100% EtOAc in n-hexane).

$^1$H NMR (300 MHz, DMSO-d$_6$): δ9.49 (s, 1H), 9.23 (d, 1H, J=6.0 Hz), 8.26~8.22 (m, 2H), 7.73~7.68 (m, 2H), 7.34 (d, 1H, J=3.6 Hz), 7.26 (d, 1H, J=3.6 Hz), 7.14 (d, 2H, J=8.1 Hz), 4.50 (d, 2H, J=5.4 Hz), 3.04 (s, 3H).

Example 111

5-(3-Trifluoromethyl-phenyl)-furan-2-carboxylic acid [1-(3-fluoro-4-methanesulfonylamino-phenyl)-ethyl]-amide

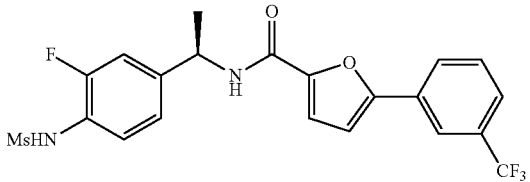

5-[3-(Trifluoromethyl)phenyl]-2-furoic acid (100 mg, 0.26 mmol) and (R)—N-[4-(1-amino-ethyl)-2-fluoro-phenyl]-methanesulfonamide, HCl salt (116 mg, 0.43 mmol) was reacted using DMTMM (130 mg, 0.47 mmol), N-methylmorpholine (60 µl, 0.55 mmol) as described above to give the title compound (130 mg, 71%) after recrystallization by ethyl acetate/hexane.

$^1$H NMR (300 MHz, CDCl$_3$): δ7.93 (s, 1H), 7.88 (d, 1H, J=7.2 Hz), 7.57 (m, 3H), 7.23 (m, 3H), 6.84 (d, 1H, J=3.9 Hz), 6.54 (d, 2H, J=7.5 Hz), 5.31 (m, 1H), 3.03 (s, 3H), 1.65 (d, 3H, J=7.2 Hz)

Example 112

5-(3-Trifluoromethyl-phenyl)-furan-2-carboxylic acid 4-methanesulfonylamino-3-methyl-benzylamide

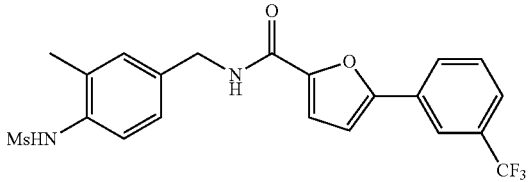

5-[3-(Trifluoromethyl)phenyl]-2-furoic acid (100 mg, 0.26 mmol) and N-(4-aminomethyl-2-methyl-phenyl)-methanesulfonamide, HCl salt (108 mg, 0.43 mmol) was reacted using DMTMM (130 mg, 0.47 mmol), N-methylmorpholine (60 µl, 0.55 mmol) as described above to give the title compound (150 mg, 71%) after recrystallization by ethyl acetate/hexane.

$^1$H NMR (300 MHz, CDCl$_3$): δ7.92 (s, 1H), 7.86 (d, 1H, J=7.2 Hz), 7.58 (m, 2H), 7.44 (d, 1H, J=7.8 Hz), 7.26 (m, 3H), 6.85 (d, 1H, J=3.3 Hz), 6.73 (m, 1H), 6.21 (s, 1H), 4.63 (d, 2H, J=5.7 Hz), 3.03 (s, 3H), 2.33 (s, 3H)

Example 113

5-(3-Trifluoromethyl-phenyl)-furan-2-carboxylic acid 4-methanesulfonylamino-3-fluoro-5-trifluomethyl-benzylamide

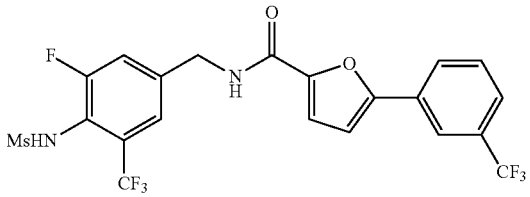

5-[3-(Trifluoromethyl)phenyl]-2-furoic acid (100 mg, 0.26 mmol) and N-(4-aminomethyl-2-fluoro-6-trifluoromethyl-phenyl)-methanesulfonamide, HCl salt (139 mg, 0.43 mmol) was reacted using DMTMM (130 mg, 0.47 mmol), N-methylmorpholine (60 µl, 0.55 mmol) as described above to give the title compound (140 mg, 68%) after purification by flash chromatography on silica gel (hexane: EtOAc=1:1).

$^1$H NMR (300 MHz, CDCl$_3$): δ7.95 (s, 1H), 7.89 (d, 1H, J=7.2 Hz), 7.58 (m, 2H), 7.48 (m, 2H), 7.29 (d, 1H, J=3.6 Hz), 6.91 (m, 1H), 6.87 (d, 1H, J=3.9 Hz), 6.18 (s, 1H), 4.70 (d, 2H, J=6.0 Hz), 3.28 (s, 3H),

Example 114

5-(3-Trifluoromethyl-5-vinyl-phenyl)-furan-2-carboxylic acid [1-(3,5-difluoro-4-methanesulfonylamino-phenyl)-ethyl]-amide

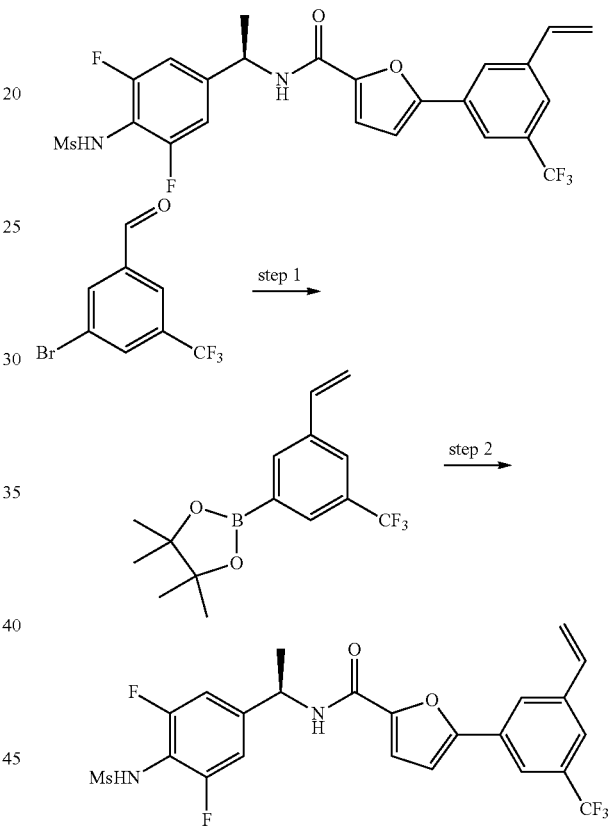

Step 1: 2-(3-Trifluoromethyl-5-vinyl-phenyl)-4,4,5,5-tetramethyl-[1,3,2]dioxaborolane 3-Bromo-5-trifluoromethylbenzaldehyde (1.10 g, 4.3 mmol) was reacted with CH$_3$PPh$_3$I (2.2 g, 5.4 mmol) and t-BuOK (710 mg, 6.3 mmol) as described above to give 1-bromo-3-trifluoromethyl-5-vinyl-benzene (850 mg, 79%) after purification by flash chromatography on silica gel 1-Bromo-3-trifluoromethyl-5-vinyl-benzene (160 mg, 0.64 mmol) and bis(pinacolo)diborane (180 mg, 0.71 mmol) were reacted using vacuum-dried KOAc (100 mg, 1.02 mmol), Pd(dba)$_2$ (10 mg, 0.02 mmol) and tricyclohexylphoaphine (13 mg, 0.05 mmol) as described above to give the title compound (135 mg, 64%) after purification by flash chromatography on silica gel (hexane).

$^1$H NMR (300 MHz, CDCl$_3$): δ7.99 (s, 1H), 7.94 (s, 1H), 7.72 (s, 1H), 6.75 (dd, 1H, J=10.8, 17.7 Hz), 5.86 (d, 1H, J=17.7 Hz), 5.36 (d, 1H, J=10.8 Hz), 1.36 (s, 12H)

Step 2: 5-(3-Trifluoromethyl-5-vinyl-phenyl)-furan-2-carboxylic acid [1-(3,5-difluoro-4-methanesulfonylamino-phenyl)-ethyl]-amide 2-(3-Trifluoromethyl-5-vinyl-phenyl)-4,4,5,5-tetramethyl-[1,3,2]dioxaborolane (135 mg, 0.45 mmol) and 5-bromo-furan-2-carboxylic acid [1-(3,5-difluoro-4-methanesulfonylamino-phenyl)-ethyl]-amide (130 mg, 0.31 mmol) was reacted using Pd(PPh$_3$)2Cl2 (20 mg, 0.03 mmol), Cs$_2$CO$_3$ (300 mg, 0.92 mmol) as described above to give the title compound (100 mg, 63%) after purification by flash chromatography on silica gel (hexane: EtOAc=1:1).

$^1$H NMR (300 MHz, CDCl$_3$): δ7.84 (s, 1H), 7.82 (s, 1H), 7.64 (s, 1H), 7.25 (m, 1H), 7.07 (d, 2H, J=8.1 Hz), 6.86 (d, 1H, J=3.3 Hz), 6.80 (dd, 1H, J=11.1, 17.7 Hz), 6.57 (d, 1H, J=7.5 Hz), 6.11 (s, 1H), 5.91 (d, 1H, J=17.4 Hz), 5.46 (d, 1H, J=10.5 Hz), 5.29 (m, 1H), 3.20 (s, 3H), 1.64 (d, 3H, J=6.6 Hz)

Example 115

2-(3-Bromo-5-cyclopropyl-phenyl)-oxazole-4-carboxylic acid [1-(3,5-difluoro-4-methanesulfonylamino-phenyl)-ethyl]-amide

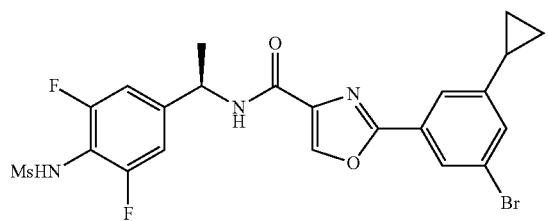

2-(3,5-Dicyclopropyl-phenyl)-4,4,5,5-tetramethyl-[1,3,2]dioxaborolane (74 mg, 0.26 mmol) and 2-chloro-oxzole-4-carboxylic acid [1-(3,5-difluoro-4-methanesulfonylamino-phenyl)-ethyl]-amide (50 mg, 0.13 mmol) was reacted using Pd(PPh$_3$)$_2$Cl$_2$ (7 mg, 0.01 mmol), Cs$_2$CO$_3$ (127 mg, 0.39 mmol) as described above to give the title compound (8 mg, 11%) after purification by flash chromatography on silica gel (% EtOAc in hexane=30%~70%).

$^1$H NMR (300 MHz, DMSO-M: 69.49 (bs, 1H), 8.82 (d, 1H, J=8.7 Hz), 8.74 (s, 1H), 7.83 (s, 1H), 7.69 (s, 1H), 7.36 (s, 1H), 7.24 (d, 2H, J=8.7 Hz), 5.16 (m, 1H), 3.02 (s, 3H), 2.09 (m, 1H), 1.50 (d, 3H, J=6.9 Hz), 1.03 (m, 2H), 0.81 (m, 2H)

Example 116

5-(3-Ethyl-5-trifluoromethyl-phenyl)-furan-2-carboxylic acid [1-(3,5-difluoro-4-methanesulfonylamino-phenyl)-ethyl]-amide

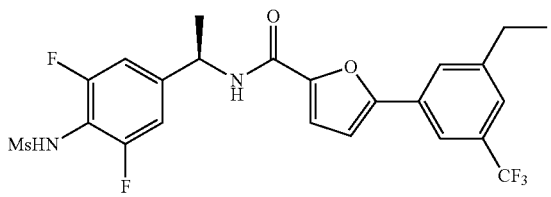

A mixture of example 114 compound (20 mg, 0.04 mmol) and 10% Pd—C (10 mg) in EtOH was hydrogenated using hydrogen balloon for 2 hours. The mixture was diluted with EtOAc, filtered through silica gel pad and washed with EtOAc. The filtrate was concentrated under reduced pressure to give the title compound (5 mg, 24%) after recrystallization with EtOAc/Hex.

$^1$H NMR (300 MHz, CDCl$_3$): δ7.76 (s, 1H), 7.68 (s, 1H), 7.44 (s, 1H), 7.25 (m, 1H), 7.07 (d, 2H, J=8.7 Hz), 6.82 (d, 1H, J=3.6 Hz), 6.56 (d, 1H, J=7.5 Hz), 6.11 (s, 1H), 5.29 (m, 1H), 3.20 (s, 3H), 2.78 (q, 2H, J=7.5 Hz), 1.64 (d, 3H, J=7.2 Hz), 0.95 (t, 3H, J=7.5 Hz)

Example 117

5-(2-Trifluoromethyl-phenyl)-furan-2-carboxylic acid 3-fluoro-4-methanesulfonylamino-benzylamide

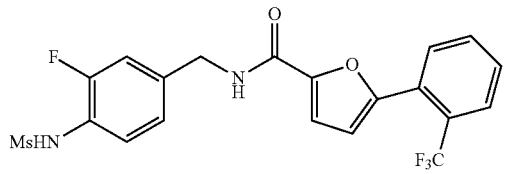

To a 25 mL round-bottomed flask was filled with Ar gas and 5-[2-(trifluoromethyl)-phenyl]-2-furoic acid (50 mg, 0.20 mmol) in THF (2 mL) was put into the flask. To the solution was added DMTMM (81 mg, 0.29 mmol) and NMM (21 µl, 0.20 mmol). The mixture was stirred at room temperature for 4 hrs, to which were added N-[4-(aminomethyl)-2-fluorophenyl]methanesulfonamide, HCl salt (60 mg, 0.24 mmol) and Et$_3$N (65 µl, 0.48 mmol). The mixture was stirred overnight at room temperature and diluted with CH$_2$Cl$_2$ and water. The organic layer was washed with water and brine, dried over anhydrous magnesium sulfate, filtered, and concentrated under reduced pressure. The crude residue was purified by column chromatography on silica gel (CH$_2$Cl$_2$:MeOH=20:1). to yield a white solid (45 mg, 51%).

$^1$H NMR (300 MHz, CDCl$_3$): δ7.78 (d, 1H, J=7.5 Hz), 7.68 (d, 1H, J=7.5 Hz), 7.62~7.57 (m, 1H), 7.55~7.47 (m, 2H), 7.17~7.12 (m, 2H), 4.60 (d, 2H, J=6.1 Hz), 2.99 (s, 3H).

Mass (FAB) 457 [M+H]+

Example 118

5-(3-Trifluoromethyl-phenyl)-furan-2-carboxylic acid 3-fluoro-4-methanesulfonylamino-benzylamide

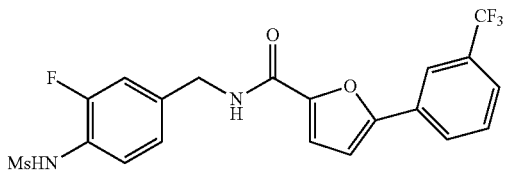

To a 5-[3-(trifluoromethyl)-phenyl]-2-furoic acid (50 mg, 0.20 mmol) was reacted with N-[4-(aminomethyl)-2-fluorophenyl]methanesulfonamide, HCl salt (60 mg, 0.24 mmol), following the general procedure to give a white solid (40 mg, 45%).

$^1$H NMR (300 MHz, CDCl$_3$): 7.91 (s, 1H), 7.85 (d, 1H, J=7.7 Hz), 7.59~7.50 (m, 3H), 7.21~7.15 (m, 2H), 6.84 (d, 2H, J=3.7 Hz), 6.51 (m, 1H), 4.63 (d, 2H, J=6.2 Hz), 3.00 (s, 3H)

Mass (FAB) 457 [M+M]+

Example 119

5-(2-Trifluoromethyl-phenyl)-furan-2-carboxylic acid [1-(3,5-difluoro-4-methanesulfonylamino-phenyl)-ethyl]-amide

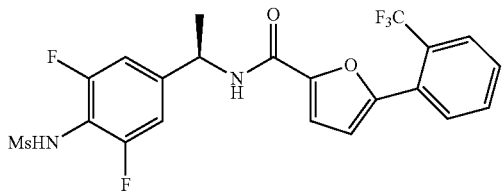

To a suspension of (R)—N-[4-(1-aminoethyl)-2,6-difluorophenyl]-methanesulfonamide, HCl salt (67 mg, 0.23 mmol) was reacted with 5-[2-(trifluoromethyl)-phenyl]-2-furoic acid (50 mg, 0.20 mmol), following the general procedure to give title compound (88 mg, 92%).

$^1$H NMR (300 MHz, CDCl$_3$): δ7.82 (m, 1H), 7.73 (m, 1H), 7.64 (m, 1H), 7.53 (m, 1H), 7.25 (d, 1H, J=3.7 Hz), 7.03~6.97 (m, 2H), 6.77 (d, 1H, J=3.7 Hz), 6.67 (d, 1H, J=3.7 Hz), 5.21 (td, 1H, J=7.1, 14.3 Hz), 3.18 (S, 3H), 1.55 (d, 3H, J=7.0 Hz)

Mass (FAB) 489 [M+H]+

Example 120

(R)-5-(3-Trifluoromethyl-phenyl)-furan-2-carboxylic acid [1-(3,5-difluoro-4-methanesulfonylamino-phenyl)-ethyl]-amide

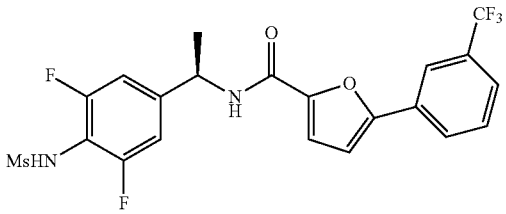

To a suspension of (R)—N-[4-(1-aminoethyl)-2,6-difluorophenyl]-methanesulfonamide, HCl salt (67 mg, 0.23 mmol) was reacted with 5-[3-(trifluoromethyl)-phenyl]-2-furoic acid (50 mg, 0.20 mmol), following the general procedure to give title compound (88 mg, 92%).

$^1$H NMR (300 MHz, CDCl$_3$): δ8.43 (m, 1H), 8.33 (m, 1H), 8.00~7.92 (m, 2H), 7.63 (d, 1H, J=3.7 Hz), 7.48~7.36 (m, 2H), 7.25 (d, 1H, J=3.7 Hz), 5.64 (m, 1H), 4.28 (d, 1H, J=11.5 Hz), 4.17~4.12 (m, 1H), 3.51 (s, 3H), 1.98 (d, 3H, J=7.0 Hz)

Mass (FAB) 489 [M+H]+

Example 121

5-(3-Trifluoromethyl-phenyl)-furan-2-carboxylic acid 3-cyano-5-fluoro-4-methanesulfonylamino-benzylamide

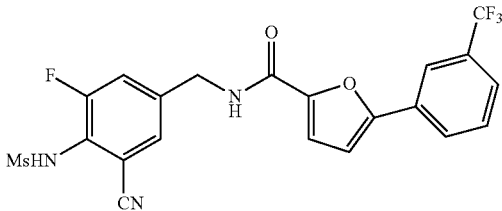

To a suspension of N-[4-(amino-methyl)-2-cyano-6-fluorophenyl]-methanesulfonamide, HCl salt (52 mg, 0.19 mmol) was reacted with 5-[3-(trifluoromethyl)-phenyl]-2-furoic acid (40 mg, 0.16 mmol), following the general procedure to give title compound (56 mg, 74%).

$^1$H NMR (300 MHz, DMSO): δ9.23 (m, 1H), 8.25~8.21 (m, 2H), 7.73~7.62 (m, 4H), 7.35 (d, 1H, J=3.7 Hz), 7.26 (d, 1H, J=3.7 Hz), 4.53 (d, 2H, J=6.1 Hz), 3.09 (s, 3H)

Mass (FAB) 482 [M+H]+

Example 122

2-(4-Trifluoromethyl-phenyl)-thiazole-5-carboxylic acid 3-fluoro-4-methanesulfonylamino-benzylamide

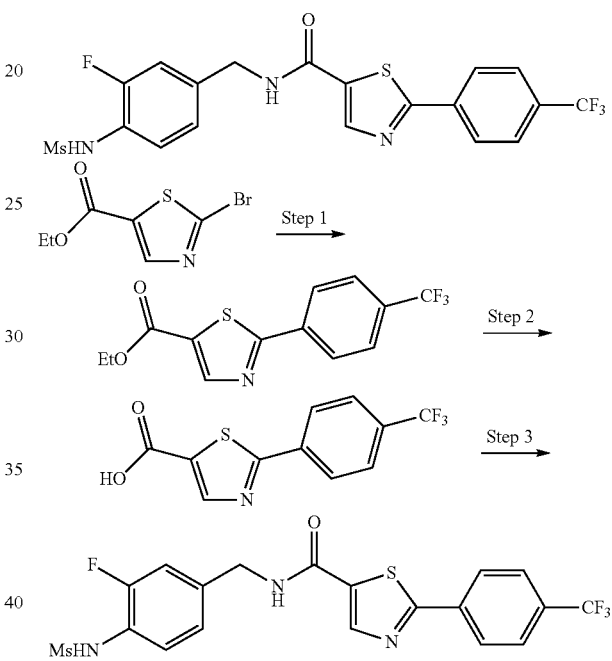

Step 1: Ethyl 2-[4-(trifluoromethyl)phenyl]thiazole-5-carboxylate

To a solution of ethyl 2-bromothiazole-5-carboxylate (39 μl, 0.26 mmol) in toluene (2 mL) were added 4-(trifluoromethyl)phenylboronic acid (60 mg, 0.32 mmol), 2M Na$_2$CO$_3$ (390 μl, 0.78 mmol), and catalytic amounts of Pd(PPh$_3$)$_4$ (61 mg, 0.05 mmol). The reaction mixture was refluxed for 6 hrs, diluted with water and extracted with EtOAc. The extracts were washed with brine, dried over anhydrous magnesium sulfate, filtered, and concentrated under reduced pressure. The crude residue was purified by column chromatography on silica gel (EtOAc/n-Hex=1:5) to give title compound (28 mg, 30%).

Step 2: 2-[4-(Trifluoromethyl)phenyl]thiazole-5-carboxylic acid

Ethyl 2-[4-(trifluoromethyl)phenyl]thiazole-5-carboxylate (28 mg, 0.09 mmol.) and LiOH (5.0 mg, 0.12 mmol) were diluted with THF/H$_2$O=1:1 (1 mL), and then stirred for 3 hrs at room temperature. The mixture was acidified with 1N HCl, concentrated under reduced pressure, and diluted with EtOAc and water. The organic layer was washed with brine, dried over anhydrous magnesium sulfate, filtered, and concentrated under reduced pressure to yield the crude title compound as a yellow solid (23 mg, 91%).

Step 3: 2-(4-Trifluoromethyl-phenyl)-thiazole-5-carboxylic acid 3-fluoro-4-methanesulfonylamino-benzylamide To a suspension of N-[4-(aminomethyl)-2-fluorophenyl]ethanesulfonamide, HCl salt (26 mg, 0.10 mmol) was reacted with 2-[4-(trifluoromethyl)phenyl]thiazole-5-carboxylic acid (23 mg, 0.08 mmol), following the general procedure to give title compound (35 mg, 88%).

$^1$H NMR (300 MHz, DMSO): δ7.70 (m, 1H), 7.51~7.38 (m, 2H), 7.17~7.08 (m, 4H), 6.69 (s, 1H), 6.36 (t, 1H, J=6.4 Hz), 4.61 (d, 2H, J=6.4 Hz), 3.00 (s, 3H).

Mass (FAB) 474 [M+H]+

Example 123

5-(3,5-Bis-trifluoromethyl-phenyl)-furan-2-carboxylic acid [1-(3,5-difluoro-4-methanesulfonylamino-phenyl)-ethyl]-amide

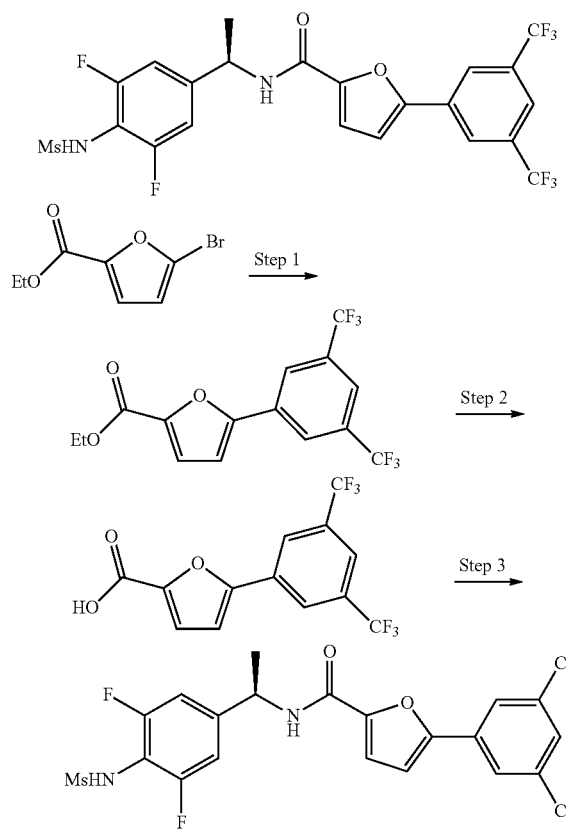

Step 1: Ethyl 5-[3,5-bis(trifluoromethyl)phenyl]furan-2-carboxylate

To a solution of ethyl 5-bromofuran-2-carboxylate (100 mg, 0.46 mmol) in benzene (5 mL) were added 3,5-bis(trifluoromethyl)phenylboronic acid (141 mg, 0.55 mmol), 2M Na$_2$CO$_3$ (6860, 1.37 mmol), and catalytic amounts of Pd(PPh$_3$)$_4$ (106 mg, 0.09 mmol). The reaction mixture was refluxed for 6 hrs, diluted with water and extracted with EtOAc. The extracts were washed with brine, dried over anhydrous magnesium sulfate, filtered, and concentrated under reduced pressure. The crude residue was purified by column chromatography on silica gel (EtOAc/n-Hex=1:5) to give title compound (61 mg, 38%).

Step 2: 5-[3,5-Bis(trifluoromethyl)phenyl]furan-2-carboxylic acid

Ethyl 5-[3,5-bis(trifluoromethyl)phenyl]furan-2-carboxylate (61 mg, 0.17 mmol) and LiOH (9.4 mg, 0.22 mmol) were diluted with THF/H$_2$O=1:1 (1.5 mL), and then stirred for 2 hrs at room temperature. The mixture was acidified with 1N HCl, concentrated under reduced pressure, and diluted with EtOAc and water. The organic layer was washed with brine, dried over anhydrous magnesium sulfate, filtered, and concentrated under reduced pressure to yield the crude title compound as a white solid (30 mg, 54%).

Step 3: 5-(3,5-Bis-trifluoromethyl-phenyl)-furan-2-carboxylic acid [1-(3,5-difluoro-4-methanesulfonylamino-phenyl)-ethyl]-amide To a suspension of (R)—N-[4-(1-Aminoethyl)-2,6-difluorophenyl]-methanesulfonamide, HCl salt (32 mg, 0.11 mmol) was reacted with 5-[3,5-bis(trifluoromethyl)phenyl]furan-2-carboxylic acid (30 mg, 0.09 mmol), following the general procedure to give title compound (23 mg, 45%).

$^1$H NMR (300 MHz, CDCl$_3$): δ8.09 (s, 2H), 7.83 (s, 1H), 7.07~7.04 (m, 2H), 6.94 (d, 1H, J=3.5 Hz), 6.52 (m, 1H), 3.19 (s, 3H), 1.64 (d, 3H, J=6.9 Hz).

Mass (FAB) 557 [M+H]+

Example 124

5-(4-Fluoro-3-trifluoromethyl-phenyl)-furan-2-carboxylic acid [1-(3,5-difluoro-4-methanesulfonylamino-phenyl)-ethyl]-amide

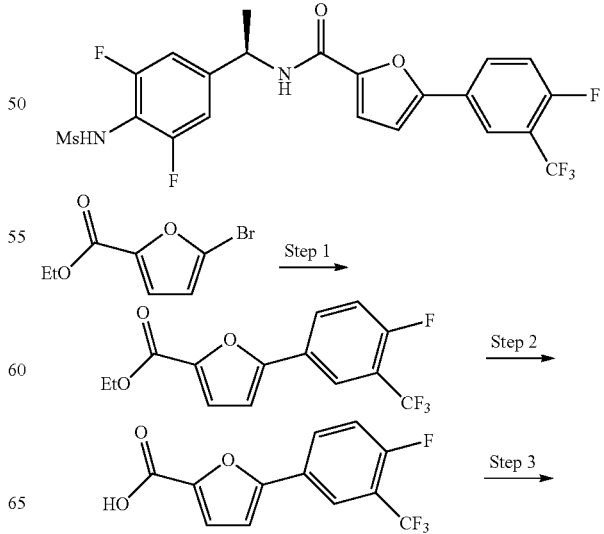

119
-continued

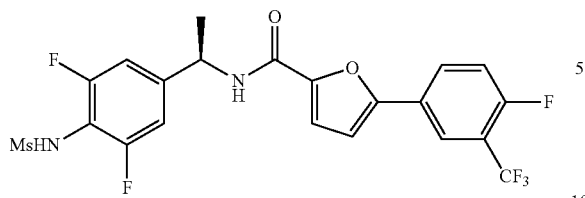

Step 1: Ethyl 5-[4-fluoro-3-(trifluoromethyl)phenyl]furan-2-carboxylate

To a solution of ethyl 5-bromofuran-2-carboxylate (150 mg, 0.69 mmol) in DME (5 mL) were added 4-fluoro-3-(trifluoromethyl)phenylboronic acid (171 mg, 0.82 mmol), 2M $Na_2CO_3$ (1.03 mL, 2.06 mol), and catalytic amounts of $Pd(Ph_3)_4$ (158 mg, 0.14 mmol). The reaction mixture was refluxed for 5 h, diluted with water and extracted with EtOAc. The extracts were washed with brine, dried over anhydrous magnesium sulfate, filtered, and concentrated under reduced pressure. The crude residue was purified by column chromatography on silica gel (EtOAc/n-Hex=1:5) to give title compound (174 mg, 70%).

Step 2: 5-[4-Fluoro-3-(trifluoromethyl)phenyl]furan-2-carboxylic acid

Ethyl 5-[4-fluoro-3-(trifluoromethyl)phenyl]furan-2-carboxylate (136 mg, 0.45 mmol.) and LiOH (25 mg, 0.59 mmol) were diluted with $THF/H_2O=1:1$ (3 mL), and then stirred for 1 hrs at room temperature. The mixture was acidified with 1N HCl, concentrated under reduced pressure, and diluted with EtOAc and water. The organic layer was washed with brine, dried over anhydrous magnesium sulfate, filtered, and concentrated under reduced pressure to yield the crude title compound as a white solid (91 mg, 73%).

Step 3: 5-(4-Fluoro-3-trifluoromethyl-phenyl)-furan-2-carboxylic acid [1-(3,5-difluoro-4-methanesulfonylamino-phenyl)-ethyl]-amide To a suspension of (R)—N-[4-(1-Aminoethyl)-2,6-difluorophenyl]-methanesulfonamide, HCl salt (56 mg, 0.20 mmol) was reacted with 5-[4-fluoro-3-(trifluoromethyl)phenyl]furan-2-carboxylic acid (45 mg, 0.16 mmol), following the general procedure to give title compound (76 mg, 91%).

$^1$H NMR (300 MHz, $CDCl_3$): δ7.90~7.85 (m, 2H), 7.03~6.94 (m, 2H, J=7.8 Hz), 6.76 (d, 1H, J=3.7 Hz), 6.65 (d, 1H, J=7.7 Hz), 6.43 (s, 1H), 5.23 (td, 1H, J=7.1, 14.3 Hz), 3.16 (s, 3H), 1.57 (d, 3H, J=7.0 Hz)

Mass (FAB) 507 [M+H]+

120

Example 125

5-(4-Fluoro-3-trifluoromethyl-phenyl)-furan-2-carboxylic acid 3-fluoro-4-methanesulfonylamino-benzylamide

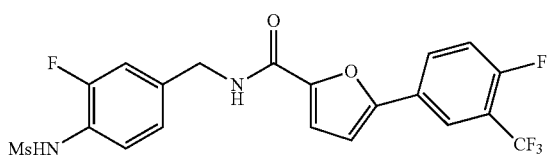

To a suspension of N-[4-(aminomethyl)-2-fluorophenyl]methanesulfonamide, HCl salt (54 mg, 0.21 mmol) was reacted with 5-[4-fluoro-3-(trifluoromethyl)phenyl]furan-2-carboxylic acid (48 mg, 0.18 mmol), following the general procedure to give title compound (74 mg, 89%).

$^1$H NMR (300 MHz, $CDCl_3$): δ7.92~7.83 (m, 2H), 7.48 (m, 1H), 7.28~7.08 (m, 3H), 6.97 (t, 1H, J=3.7 Hz), 4.61 (d, 2H, J=6.2 Hz), 4.61 (d, 2H, J=6.2 Hz), 3.01 (s, 3H)

Mass (FAB) 475 [M+H]+

Example 126

2-(3,5-Bis-trifluoromethyl-phenyl)-thiazole-5-carboxylic acid [1-(3,5-difluoro-4-methanesulfonylamino-phenyl)-ethyl]-amide

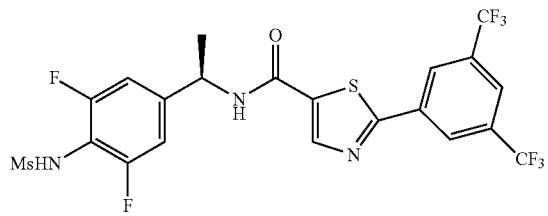

To a suspension of (R)—N-[4-(1-Aminoethyl)-2,6-difluorophenyl]-methanesulfonamide, HCl salt (35 mg, 0.12 mmol) was reacted with 2-[4-(trifluoromethyl)phenyl]thiazole-5-carboxylic acid (35 mg, 0.10 mmol), following the general procedure to give title compound (48.7 mg, 83%).

$^1$H NMR (300 MHz, DMSO): δ7.76 (s, 2H), 7.74 (s, 1H), 7.70 (br s, 1H), 6.98 (br s, 1H), 6.93 (br s, 1H), 5.13 (m, 1H), 3.10 (s, 3H), 1.48 (d, 3H, J=7.0 Hz)

LRMS (FAB+): m/z 574 (M+H$^+$).

Experimental Example

Biological Potency Test

1. $^{45}$Ca influx test

1) Separation of spinal dorsal root ganglia (DRG) in newborn rats and primary culture thereof Neonatal (2-3 clay old or younger than 2-3 day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate and 50 mg/l gentamycin were added. The DRG were incubated sequentially at 37° C. for 30 mins in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 80 membrane to obtain single cell suspension and the suspension was washed once more. This was subjected to centrifugation, then resuspended in cell culture medium at certain level of cell density. As the cell culture medium, DME/F12 medium supplemented with 10% horse serum was diluted with identical medium conditioned by C6 glioma cells 2 clays on a confluent monolayer (1:1), and NGF (Nerve Growth Factor) was added to adjust 200 ng/ml as final concentration. After the cells were grown 2 days in medium where cytosine arabinoside (Ara-C, 100 μM) was added to kill dividing nonneuronal cells, medium was changed to one without Ara-C. The resuspended cells were plated at a density of 1500-2000 neurons/well onto Terasaki plates previously coated with 10 μg/ml poly-D-ornithine.

2) $^{45}$Ca Influx Experiments

DRG nerve cells from the primary culture of 2 days were equilibrated by washing 4 times with HEPES (10 mM, pH 7.4)-buffered $Ca^{2+}$, $Mg^{2+}$-free HBSS (H-HBSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 nuns. Terasaki plates were washed five times with H-HBSS and dried at room temperature. To each well, 0.3% SDS (10 μl) was added to elute $^{45}$Ca. After the addition of scintillation cocktail of into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 μM. Results of calcium influx test are shown in Table 1.

TABLE 1

| Examples | Antagonist Calcium Uptake Test ($IC_{50}$, μM) |
| --- | --- |
| 1 | 0.15 |
| 2 | 0.41 |
| 3 | 0.49 |
| 4 | 0.080 |
| 5 | 3.6 |
| 6 | 5.0 |
| 7 | 4.3 |
| 8 | 2.7 |
| 9 | 0.44 |
| 10 | 6.4 |
| 11 | >10 |
| 12 | >10 |
| 13 | 1.4 |
| 14 | 1.5 |
| 15 | 0.60 |
| 16 | 0.77 |
| 17 | >10 |
| 18 | 2.9 |
| 19 | 0.61 |
| 20 | 67% @10 μM |
| 21 | 56% @10 μM |
| 22 | 1.9 |
| 23 | 11.9 |
| 24 | >10 |
| 25 | >10 |
| 26 | >10 |
| 27 | 1.6 |
| 28 | 0.82 |
| 29 | 0.28 |
| 30 | 0.050 |
| 31 | 2.0 |
| 32 | 0.28 |

TABLE 1-continued

| Examples | Antagonist Calcium Uptake Test ($IC_{50}$, μM) |
| --- | --- |
| 33 | 4.9 |
| 34 | 0.40 |
| 35 | 1.8 |
| 36 | 1.3 |
| 37 | 0.41 |
| 38 | 0.40 |
| 39 | 0.29 |
| 40 | 1.1 |
| 41 | 0.19 |
| 42 | 0.13 |
| 43 | 0.96 |
| 44 | 5.5 |
| 45 | 0.77 |
| 46 | 0.43 |
| 47 | 0.62 |
| 48 | 1.2 |
| 49 | 0.60 |
| 50 | 1.1 |
| 51 | 1.1 |
| 52 | 1.8 |
| 53 | 0.72 |
| 54 | 2.9 |
| 55 | 74% @1 μM |
| 56 | 0.56 |
| 57 | 0.33 |
| 58 | 0.093 |
| 59 | 1.0 |
| 60 | 6.1 |
| 61 | 2.8 |
| 62 | 0.44 |
| 63 | >10 |
| 64 | 4.1 |
| 65 | 2.7 |
| 66 | 0.75 |
| 67 | 0.36 |
| 63 | 1.7 |
| 69 | 0.16 |
| 70 | 0.87 |
| 71 | 1.2 |
| 72 | 1.4 |
| 73 | 10.5 |
| 74 | 89% @3 μM |
| 75 | 2.4 |
| 76 | >10 |
| 77 | 2.0 |
| 78 | >10 |
| 79 | 0.99 |
| 80 | 0.030 |
| 81 | 1.0 |
| 82 | 0.65 |
| 83 | 0.88 |
| 84 | 7.4 |
| 85 | 1.2 |
| 86 | 1.0 |
| 87 | 0.14 |
| 88 | 0.72 |
| 89 | 2.7 |
| 90 | 0.91 |
| 91 | 0.21 |
| 92 | 1.7 |
| 93 | 0.91 |
| 94 | 0.36 |
| 95 | 66% @1 μM |
| 96 | 1.3 |
| 97 | 1.4 |
| 98 | 1.7 |
| 99 | 2.0 |
| 100 | 0.048 |
| 101 | 0.073 |
| 102 | 0.10 |
| 103 | 84% @3 μM |
| 104 | 100% @1 μM |
| 105 | 96% @0.3 μM |
| 106 | 82% @10 μM |
| 107 | 3.0 |
| 108 | 0.52 |

TABLE 1-continued

| Examples | Antagonist Calcium Uptake Test (IC$_{50}$, μM) |
|---|---|
| 109 | 0.27 |
| 110 | 0.62 |
| 111 | 0.24 |
| 112 | 0.22 |
| 113 | 1.4 |
| 114 | 93% @3 μM |
| 115 | 0.77 |
| 116 | 0.16 |
| 117 | 0.68 |
| 118 | 0.37 |
| 119 | 0.13 |
| 120 | 0.064 |
| 121 | 0.33 |
| 122 | 8.8 |
| 123 | 0.045 |
| 124 | 0.042 |
| 125 | 0.53 |
| 126 | 0.49 |

2. Analgesic Activity Test: Mouse Writhing Test by Inducing with Phenyl-p-quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a close of 4.5 mg/kg) and 6 mins later, the number of abdominal constrictions was counted in the subsequent 6 mins period. Animals (10 animals/group) received 0.2 ml of test compounds solution in vehicle of ethanol/Tween 80/saline (Oct. 10, 1980) intraperitoneally 30 min before the injection of phenyl-p-quinone. In the case of oral administration, 0.2 ml of test compounds solution in vehicle of ethanol/Tween 80/saline (5/5/90) were administered 54 min prior to the 0.2 ml of 0.02% phenyl-p-quinone injection. A reduction in the number of writhes responding to the test drug compound relative to the number responding in saline control group was considered to be indicative of an analgesic effect. Analgesic effect was calculated by % inhibition equation (% inhibition=(C-T)/C×100), wherein C and T represent the number of writhes in control and compound-treated group, respectively. Test results of analgesic activity for writhing by phenyl-p-quinone (administration route (p.o.)) are shown in Table 2.

TABLE 2

| Example | Dose (mg/kg) | Analgesic effect (% Inhibition) |
|---|---|---|
| 1 | 3 | 21 |
| 2 | 3 | 32 |
| 4 | 3 | 28 |
| 30 | 3 | 16 |
| 32 | 3 | 32 |
| 35 | 0.3 | 29 |
| 42 | 0.3 | 30 |
| 46 | 3 | 53 |
| 67 | 3 | 43 |
| 69 | 0.3 | 35 |
| 80 | 3 | 22 |
| 87 | 3 | 59 |
| 91 | 3 | 25 |
| 93 | 3 | 41 |
| 94 | 3 | 46 |
| 100 | 3 | 35 |
| 101 | 3 | 33 |
| 102 | 3 | 58 |
| 117 | 3 | 39 |
| 118 | 3 | 42 |
| 119 | 3 | 38 |
| 120 | 3 | 60 |
| 123 | 0.3 | 21 |

INDUSTRIAL APPLICABILITY

As explained above, the compound according to the present disclosure is useful to prevent or to treat pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastroesophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis.

More specifically, the compound according to the present disclosure is useful to preventing and treating of pain, which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, and other types of headaches.

The invention claimed is:

1. A compound of the formula (I), an enantiomer thereof, or a pharmaceutically acceptable salt thereof;

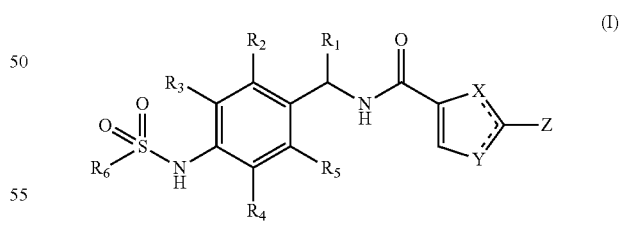

wherein,

X and Y are independently CH, N, O, or S;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;

$R_6$ is C1-C5 alkyl, halo(C1-C5) alkyl, or C2-C5 alkenyl; and

Z is wherein,

A is a single bond, CH₂, NH, or O;

B is N or CR₁₁;

----- is a single bond or a double bond;

Q₁ and Q₂ are independently O or CH₂;

U₁, U₂, U₃, and U₄ are independently CH or N, and if anyone of U₁ to U₄ is N, the rest are independently CH;

m is 1 or 2;

n is 0, 1 or 2;

R₇, R₈, R₉, R₁₀, and R₁₁ are independently hydrogen, halogen, nitro, cyano, C1-C10 alkyl, C1-C10 alkoxy, halo(C1-C10) alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio;

R₁₂ is hydrogen, halogen, C1-C3 alkyl, or halo(C1-C3) alkyl wherein ----- is a single bond, and CH₂ or CHR₁₃ wherein ----- is a double bond; and R₁₃ is C₁-C₅ alkyl.

2. The compound according to claim 1, an enantiomer thereof, or a pharmaceutically acceptable salt thereof;
wherein, if X is O or S, then Y is CH and if X is N, then Y is O or S.

3. The compound according to claim 1, an enantiomer thereof, or a pharmaceutically acceptable salt thereof;
wherein, R₁ is hydrogen, methyl, or ethyl;

R₂, R₃, R₄, and R₅ are independently hydrogen, halogen, nitro, cyano, C1-C5 alkyl, C1-C5 alkoxy, halo(C1-C5) alkyl, C2-C5 alkenyl, or C2-C5 alkynyl;

R₆ is C1-C3 alkyl, halo(C1-C3) alkyl, or vinyl; and

Z is wherein,

A is a single bond, CH₂, NH, or O;

B is CR₁₁;

----- is a single bond or a double bond;

m is 1 or 2;

R₇, R₈, R₉, R₁₀, and R₁₁ are independently hydrogen, halogen, nitro, cyano, C1-C10 alkyl, C1-C10 alkoxy, halo(C1-C10) alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio;

R₁₂ is hydrogen, C1-C3 alkyl, or halo(C1-C3) alkyl wherein ----- is a single bond, and CH₂ or CHR₁₃ wherein ----- is a double bond; and R₁₃ is C₁-C₅ alkyl.

4. The compound according to claim 1, an enantiomer thereof, or a pharmaceutically acceptable salt thereof;
wherein, R₆ is methyl, or trifluoromethyl; and Z is wherein, A is a single bond or O;

B is CR₁₁;

m is 1 or 2;

R₇, R₈, R₉, R₁₀, and R₁₁ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, aryl, C1-C5 alkylamino, di(C1-C5 alkyl)amino, C3-C6 cycloalkyl, or C1-C5 alkylthio;

R₁₂ is hydrogen, methyl, ethyl, or trifluoromethyl wherein ----- is a single bond and CH₂ or CHR₁₃ wherein ----- is a double bond; and R₁₃ is C₁-C₃ alkyl.

5. The compound according to claim 1, an enantiomer thereof, or a pharmaceutically acceptable salt thereof;
wherein, R₁ is methyl;

R₂, R₃, R₄, and R₅ are independently hydrogen, fluoro, cyano, methyl, trifluoromethyl, vinyl, or acetylenyl;

R₆ is methyl; and

Z is

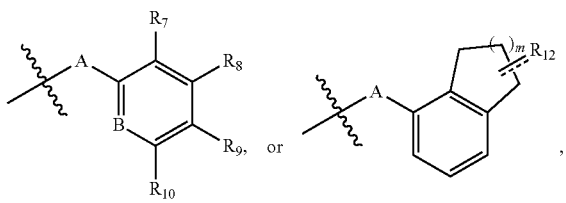

wherein,
A is a single bond or O;
B is $CR_{11}$;
----- is a single bond or a double bond;
m is 1 or 2;
$R_7, R_8, R_9, R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, phenyl, di(C1-C5 alkyl)amino, C3-C6 cycloalkyl, or C1-C5 alkylthio; and
$R_{12}$ is hydrogen, methyl, ethyl, or trifluoromethyl wherein ----- is a single bond, and $CH_2$ wherein ----- is a double bond.

6. A compound of the formula (II), an enantiomer thereof, or a pharmaceutically acceptable salt thereof;

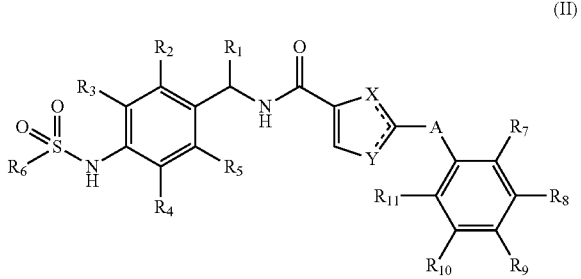

wherein,
X and Y are independently CH, N, O, or S;
A is $CH_2$, NH, or O;
$R_1$ is hydrogen, halogen, or C1-C5 alkyl;
$R_2, R_3, R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;
$R_6$ is C1-C5 alkyl, halo(C1-C5) alkyl, or C2-C5 alkenyl; and
$R_7, R_8, R_9, R_{10}$, and $R_{11}$ are independently hydrogen, halogen, nitro, cyano, C1-C10 alkyl, C1-C10 alkoxy, halo(C1-C10) alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

7. The compound according to claim 6, an enantiomer thereof, or a pharmaceutically acceptable salt thereof;
wherein,
$R_2, R_3, R_4$, and $R_5$ are independently hydrogen, halogen, cyano, methyl, ethyl, trifluoromethyl, vinyl, or acetylenyl; and
$R_7, R_8, R_9, R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, phenyl, di(C1-C5 alkyl)amino, C3-C6 cycloalkyl, or C1-C5 alkylthio.

8. The compound according to claim 6, an enantiomer thereof, or a pharmaceutically acceptable salt thereof;
wherein,
$R_2$ and $R_5$ are hydrogen;
$R_3$ and $R_4$ are independently hydrogen, fluoro, chloro, cyano, methyl, trifluoromethyl, vinyl, or acetylenyl; and
$R_7, R_8, R_9, R_{10}$, and $R_{11}$ are independently hydrogen, halogen, C1-C5 alkyl, C1-C5 alkoxy, halo(C1-C2) alkyl, C2-C5 alkenyl, C2-C5 alkynyl, phenyl, or C3-C5 cycloalkyl.

9. The compound according to claim 6, an enantiomer thereof, or a pharmaceutically acceptable salt thereof;
wherein,
$R_2$ and $R_5$ are hydrogen;
$R_3$ and $R_4$ are independently hydrogen, fluoro, cyano, methyl, trifluoromethyl, vinyl, or acetylenyl; and
$R_7, R_8, R_9, R_{10}$, and $R_{11}$ are independently hydrogen, fluoro, chloro, bromo, iodo, ethyl, isopropyl, tert-butyl, propoxy, butoxy, trifluoromethyl, 1-trifluoromethylethyl, or cyclopropyl.

10. The compound according to claim 6, an enantiomer thereof, or a pharmaceutically acceptable salt thereof;
wherein, if X is O, then Y is CH and if X is N, then Y is O or S; A is O.

11. The compound according to any one of claim 6, an enantiomer thereof, or a pharmaceutically acceptable salt thereof;
wherein, if X is O, then Y is CH and if X is N, then Y is O; and A is O.

12. The compound according to claim 6, an enantiomer thereof, or a pharmaceutically acceptable salt thereof;
wherein,
$R_1$ is hydrogen, methyl, or ethyl; and $R_6$ is methyl, or trifluoromethyl.

13. The compound according to claim 6, an enantiomer thereof, or a pharmaceutically acceptable salt thereof;
wherein,
$R_1$ is hydrogen, or methyl; $R_2$ and $R_5$ are hydrogen; $R_3$ and $R_4$ are independently hydrogen, fluoro, cyano, methyl, trifluoromethyl, vinyl, acetylenyl;
$R_6$ is methyl; and
$R_7, R_8, R_9, R_{10}$, and $R_{11}$ are independently hydrogen, fluoro, chloro, bromo, iodo, ethyl, isopropyl, tert-butyl, butoxy, trifluoromethyl, or cyclopropyl.

14. A compound of the formula (III), an enantiomer thereof, or a pharmaceutically acceptable salt thereof;

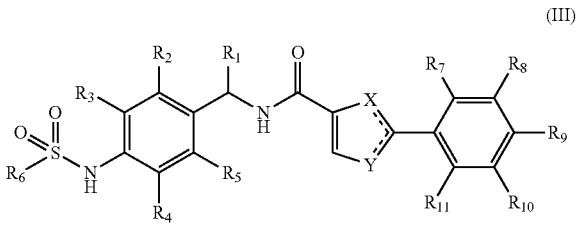

wherein,
X and Y are independently CH, N, O, or S;
$R_1$ is hydrogen, halogen, or C1-C5 alkyl;
$R_2, R_3, R_4$, and $R_5$ are independently hydrogen, halogen, nitro, cyano, C1-C5 alkyl, C1-C5 alkoxy, halo(C1-C5) alkyl, C2-C5 alkenyl, C2-C5 alkynyl, or carboxy;
$R_6$ is C1-C5 alkyl, halo(C1-C5) alkyl, or C2-C5 alkenyl; and $R_7$, $R_8$, $R_9$, $R_{10}$, and $R_{11}$ are independently hydrogen, halogen, nitro, cyano, C1-C10 alkyl, C1-C10 alkoxy, halo (C1-C10) alkyl, C2-C10 alkenyl, C2-C10 alkynyl, carboxy, C1-C10 alkoxycarbonyl, C1-C10 alkylcarbonyl, aryl, C1-C10 alkylamino, di(C1-C10 alkyl)amino, C3-C8 cycloalkyl, or C1-C10 alkylthio.

15. The compound according to claim 14, an enantiomer thereof, or a pharmaceutically acceptable salt thereof; wherein, $R_2$, $R_3$, $R_4$, and $R_5$ are independently hydrogen, halogen, cyano, methyl, ethyl, trifluoromethyl, vinyl, or acetylenyl; and $R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, phenyl, di(C1-C5 alkyl)amino, C3-C6 cycloalkyl, or C1-C5 alkylthio.

16. The compound according to claim 14, an enantiomer thereof, or a pharmaceutically acceptable salt thereof; wherein, $R_2$ and $R_5$ are hydrogen;

$R_3$ and $R_4$ are independently hydrogen, fluoro, chloro, cyano, methyl, trifluoromethyl, vinyl, or acetylenyl; and $R_7$, $R_8$, $R_9$, $R_{10}$, and $R_{11}$ are independently hydrogen, halogen, C1-C5 alkyl, C1-C5 alkoxy, halo(C1-C2) alkyl, C2-C5 alkenyl, C2-C5 alkynyl, phenyl, or C3-C5 cycloalkyl.

17. The compound according to claim 14, an enantiomer thereof, or a pharmaceutically acceptable salt thereof; wherein, $R_2$ and $R_5$ are hydrogen;

$R_3$ and $R_4$ are independently hydrogen, fluoro, cyano, methyl, trifluoromethyl, vinyl, or acetylenyl; and $R_7$, $R_8$, $R_9$, $R_{10}$, and $R_{11}$ are independently hydrogen, fluoro, chloro, bromo, iodo, ethyl, isopropyl, tert-butyl, propoxy, butoxy, trifluoromethyl, 1-trifluoromethylethyl, or cyclopropyl.

18. The compound according to claim 14, an enantiomer thereof, or a pharmaceutically acceptable salt thereof;

wherein, if X is O, then Y is CH and if X is N, then Y is O or S.

19. The compound according to claim 14, an enantiomer thereof, or a pharmaceutically acceptable salt thereof;

wherein, if X is O, then Y is CH and if X is N, then Y is O.

20. The compound according to claim 14, an enantiomer thereof, or a pharmaceutically acceptable salt thereof;

wherein, $R_1$ is hydrogen, methyl, or ethyl; and $R_6$ is methyl, or trifluoromethyl.

21. The compound according to claim 14, an enantiomer thereof, or a pharmaceutically acceptable salt thereof; wherein, $R_1$ is hydrogen, or methyl;

$R_2$ and $R_5$ are hydrogen;

$R_3$ and $R_4$ are independently hydrogen, fluoro, cyano, methyl, trifluoromethyl, vinyl, or acetylenyl;

$R_6$ is methyl; and $R_7$, $R_8$, $R_9$, $R_{10}$, and $R_{11}$ are independently hydrogen, fluoro, chloro, bromo, iodo, ethyl, isopropyl, tert-butyl, butoxy, trifluoromethyl, or cyclopropyl.

22. A compound of the formula (IV), an enantiomer thereof, or a pharmaceutically acceptable salt thereof;

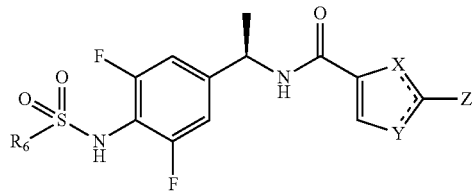

(IV)

wherein, if X is O, then Y is CH and if X is N, then Y is O;

$R_6$ is methyl, ethyl, or trifluoromethyl; and

Z is

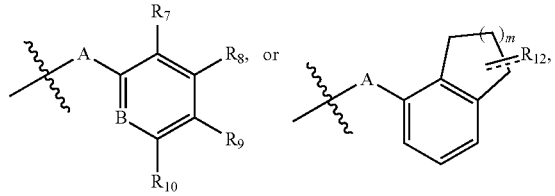

wherein,

A is a single bond or O;

B is CH or $CR_{11}$;

----- is a single bond or double bond;

m is 1 or 2;

$R_7$, $R_8$, $R_9$, $R_{10}$, and $R_{11}$ are independently hydrogen, halogen, nitro, cyano, C1-C5 alkyl, C1-C5 alkoxy, halo(C1-C5) alkyl, C2-C5 alkenyl, C2-C5 alkynyl, carboxy, C1-C5 alkoxycarbonyl, C1-C5 alkylcarbonyl, phenyl, di(C1-C5 alkyl)amino, C3-C6 cycloalkyl, or C1-C5 alkylthio;

$R_{12}$ is hydrogen, methyl, ethyl, or trifluoromethyl wherein ----- is a single bond, and $CH_2$ or $CHR_{13}$ wherein ----- is a double bond; and $R_{13}$ is C1-C5 alkyl.

23. The compound according to claim 22, an enantiomer thereof, or a pharmaceutically acceptable salt thereof; wherein, $R_6$ is methyl;

$R_7$, $R_8$, $R_9$, $R_{10}$, and $R_{11}$ are independently hydrogen, halogen, C1-C5 alkyl, C1-C5 alkoxy, halo(C1-C2) alkyl, C2-C5 alkenyl, C2-C5 alkynyl, phenyl, or C3-C5 cycloalkyl;

$R_{12}$ is hydrogen, methyl, or trifluoromethyl wherein ----- is a single bond, and $CH_2$ or $CHR_{13}$ wherein ----- is a double bond; and $R_{13}$ is C1-C3 alkyl.

24. The compound according to claim 22, an enantiomer thereof, or a pharmaceutically acceptable salt thereof; wherein, $R_6$ is methyl;

$R_7$, $R_8$, $R_9$, $R_{10}$, and $R_{11}$ are independently hydrogen, fluoro, chloro, bromo, iodo, ethyl, isopropyl, tert-butyl, butoxy, trifluoromethyl, or cyclopropyl; and $R_{12}$ is hydrogen, methyl, ethyl, or trifluoromethyl wherein ----- is a single bond, and $CH_2$ wherein ----- is a double bond.

25. The compound according to claim 1, an enantiomer thereof, or a pharmaceutically acceptable salt thereof, wherein the compound is selected from the group consisting of:

2-(3-tert-Butyl-phenoxy)-oxazole-4-carboxylic acid [1-(3,5-difluoro-4-methanesulfonylamino-phenyl)-ethyl]-amide, 2-(3-Trifluoromethyl-phenoxy)-oxazole-4-carboxylic acid [1-(3,5-difluoro-4-methanesulfonylamino-phenyl)-ethyl]-amide, 2-(2-Isopropyl-phenoxy)-oxazole-4-carboxylic acid [1-(3,5-difluoro-4-methanesulfonylamino-phenyl)-ethyl]-amide, 2-(3-Isopropyl-phenoxy)-oxazole-4-carboxylic acid [1-(3,5-difluoro-4-methanesulfonylamino-phenyl)-ethyl]-amide, 2-(3-Ethyl-phenoxy)-oxazole-4-carboxylic acid [1-(3,5-difluoro-4-methanesulfonylamino-phenyl)-ethyl]-amide, 2-(1-Methyl-indan-4-yloxy)-oxazole-4-carboxylic acid [1-(3,5-difluoro-4-methanesulfonylamino-phenyl)-ethyl]-amide, 2-(3-Cyclopropyl-phenoxy)-oxazole-4-carboxylic acid [1-(3,5-difluoro-4-methanesulfonylamino-phenyl)-ethyl]-amide, 2-(2,2-Dimethyl-2,3-dihydro-benzofuran-7-yloxy)-oxazole-4-carboxylic acid [1-(3,5-difluoro-4-methanesulfonylamino-phenyl)-ethyl]-amide, 2-(5-Methylene-5,6,7,8-tetrahydro-naphthalen-1-yloxy)-oxazole-4-carboxylic acid [1-(3,5-difluoro-4-methanesulfonylamino-phenyl)-ethyl]-amide, 2-(1-Ethyl-indan-4-yloxy)-oxazole-4-carboxylic acid [1-(3,5-difluoro-4-methanesulfonylamino-phenyl)-ethyl]-amide, 2-(5-Methyl-5,6,7,8-tetrahydro-naphthalen-1-yloxy)-oxazole-4-carboxylic acid [1-(3,5-difluoro-4-methanesulfonylamino-phenyl)-ethyl]-amide, 2-(2-Propyl-5-trifluoromethyl-phenoxy)-oxazole-4-carboxylic acid [1-(3,5-difluoro-4-methanesulfonylamino-phenyl)-ethyl]-amide, 2-(2-Propyl-3-trifluoromethyl-phenoxy)-oxazole-4-carboxylic acid [1-(3,5-difluoro-4-methanesulfonylamino-phenyl)-ethyl]-amide, 2-(2-Cyclopropyl-3-trifluoromethyl-phenoxy)-oxazole-4-carboxylic acid [1-(3,5-difluoro-4-methanesulfonylamino-phenyl)-ethyl]-amide, 2-(5,6,7,8-Tetrahydro-naphthalen-1-yloxy)-oxazole-4-carboxylic acid [1-(3,5-difluoro-4-methanesulfonylamino-phenyl)-ethyl]-amide, 2-(3-Cyclobutyl-phenoxy)-oxazole-4-carboxylic acid [1-(3,5-difluoro-4-methanesulfonylamino-phenyl)-ethyl]-amide, 2-(1-Trifluoromethyl-indan-4-yloxy)-oxazole-4-carboxylic acid [1-(3,5-difluoro-4-methanesulfonylamino-phenyl)-ethyl]-amide, 2-(3-Iodo-phenoxy)-oxazole-4-carboxylic acid [1-(3,5-difluoro-4-methanesulfonylamino-phenyl)-ethyl]-amide, 5-(4-Bromo-phenyl)-2-trifluoromethyl-furan-3-carboxylic acid [1-(3,5-difluoro-4-methanesulfonylamino-phenyl)-ethyl]-amide, 2-(3-Trifluoromethyl-phenyl)-oxazole-4-carboxylic acid [1-(3,5-difluoro-4-methanesulfonylamino-phenyl)-ethyl]-amide, 2-(3-Isopropyl-phenyl)-oxazole-4-carboxylic acid [1-(3,5-difluoro-4-methanesulfonylamino-phenyl)-ethyl]-amide, 2-(4-Trifluoromethyl-phenyl)-oxazole-4-carboxylic acid [1-(3,5-difluoro-4-methanesulfonylamino-phenyl)-ethyl]-amide, 2-(3-Isopropyl-phenyl)-thiazole-4-carboxylic acid [1-(3,5-difluoro-4-methanesulfonylamino-phenyl)-ethyl]-amide, 2-(3,5-Bis-trifluoromethyl-phenyl)-oxazole-4-carboxylic acid [1-(3,5-difluoro-4-methanesulfonylamino-phenyl)-ethyl]-amide, 2-(4-Chloro-3-trifluoromethyl-phenyl)-oxazole-4-carboxylic acid [1-(3,5-difluoro-4-methanesulfonylamino-phenyl)-ethyl]-amide, 2-(3-Trifluoromethyl-phenyl)-thiazole-4-carboxylic acid [1-(3,5-difluoro-4-methanesulfonylamino-phenyl)-ethyl]-amide, 2-(3-Cyclopropyl-phenyl)-oxazole-4-carboxylic acid [1-(3,5-difluoro-4-methanesulfonylamino-phenyl)-ethyl]-amide, 2-(3-Cyclopropyl-phenyl)-thiazole-4-carboxylic acid [1-(3,5-difluoro-4-methanesulfonylamino-phenyl)-ethyl]-amide, 5-(3-Cyclopropyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid 3-fluoro-4-methanesulfonylamino-5-methyl-benzylamide, 5-(3-Trifluoromethyl-phenyl)-furan-2-carboxylic acid 3-ethynyl-5-fluoro-4-methanesulfonylamino-benzylamide, 5-(3-Trifluoromethyl-phenyl)-furan-2-carboxylic acid 3-fluoro-4-methanesulfonylamino-5-vinyl-benzylamide, 5-(3,5-Dicyclopropyl-phenyl)-furan-2-carboxylic acid [1-(3,5-difluoro-4-methanesulfonylamino-phenyl)-ethyl]-amide, (S)-5-(3-Trifluoromethyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid [1-(3-fluoro-4-methanesulfonylamino-phenyl)-ethyl]-amide, 5-(3-Trifluoromethyl-phenyl)-furan-2-carboxylic acid 4-methanesulfonylamino-3-methyl-benzylamide, 5-(3-Trifluoromethyl-5-vinyl-phenyl)-furan-2-carboxylic acid [1-(3,5-difluoro-4-methanesulfonylamino-phenyl)-ethyl]-amide, 5-(3-Ethyl-5-trifluoromethyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid 3-fluoro-4-methanesulfonylamino-benzylamide, 5-(2-Trifluoromethyl-phenyl)-furan-2-carboxylic acid [1-(3,5-difluoro-4-methanesulfonylamino-phenyl)-ethyl]-amide, (R)-5-(3-Trifluoromethyl-phenyl)-furan-2-carboxylic acid [1-(3,5-difluoro-4-methanesulfonylamino-phenyl)-ethyl]-amide, 5-(3-Trifluoromethyl-phenyl)-furan-2-carboxylic acid 3-cyano-5-fluoro-4-methanesulfonylamino-benzylamide, 5-(3,5-Bis-trifluoromethyl-phenyl)-furan-2-carboxylic acid [1-(3,5-difluoro-4-methanesulfonylamino-phenyl)-ethyl]-amide, 5-(4-Fluoro-3-trifluoromethyl-phenyl)-furan-2-carboxylic acid [1-(3,5-difluoro-4-methanesulfonylamino-phenyl)-ethyl]-amide, and 5-(4-Fluoro-3-trifluoromethyl-phenyl)-furan-2-carboxylic acid 3-fluoro-4-methanesulfonylamino-benzylamide.

26. The compound according to claim 1, an enantiomer thereof, or a pharmaceutically acceptable salt thereof, wherein the compound is selected from the group consisting of;

- 2-(3-tert-Butyl-phenoxy)-oxazole-4-carboxylic acid [1-(3,5-difluoro-4-methanesulfonylamino-phenyl)-ethyl]-amide,
- 2-(3-Isopropyl-phenoxy)-oxazole-4-carboxylic acid [1-(3,5-difluoro-4-methanesulfonylamino-phenyl)-ethyl]-amide,
- 2-(1-Methyl-indan-4-yloxy)-oxazole-4-carboxylic acid [1-(3,5-difluoro-4-methanesulfonylamino-phenyl)-ethyl]-amide,
- 2-(3-Cyclopropyl-phenoxy)-oxazole-4-carboxylic acid [1-(3,5-difluoro-4-methanesulfonylamino-phenyl)-ethyl]-amide,
- 2-(2-Propyl-5-trifluoromethyl-phenoxy)-oxazole-4-carboxylic acid [1-(3,5-difluoro-4-methanesulfonylamino-phenyl)-ethyl]-amide,
- 2-(2-Propyl-3-trifluoromethyl-phenoxy)-oxazole-4-carboxylic acid [1-(3,5-difluoro-4-methanesulfonylamino-phenyl)-ethyl]-amide,
- 2-(3-Iodo-phenoxy)-oxazole-4-carboxylic acid [1-(3,5-difluoro-4-methanesulfonylamino-phenyl)-ethyl]-amide,
- 2-(3-Isopropyl-phenyl)-oxazole-4-carboxylic acid [1-(3,5-difluoro-4-methanesulfonylamino-phenyl)-ethyl]-amide,
- 2-(3-Isopropyl-phenyl)-thiazole-4-carboxylic acid [1-(3,5-difluoro-4-methanesulfonylamino-phenyl)-ethyl]-amide
- 2-(3,5-Bis-trifluoromethyl-phenyl)-oxazole-4-carboxylic acid [1-(3,5-difluoro-4-methanesulfonylamino-phenyl)-ethyl]-amide,
- 2-(4-Chloro-3-trifluoromethyl-phenyl)-oxazole-4-carboxylic acid [1-(3,5-difluoro-4-methanesulfonylamino-phenyl)-ethyl]-amide,
- 2-(3-Cyclopropyl-phenyl)-oxazole-4-carboxylic acid [1-(3,5-difluoro-4-methanesulfonylamino-phenyl)-ethyl]-amide,
- 2-(3-Cyclopropyl-phenyl)-thiazole-4-carboxylic acid [1-(3,5-difluoro-4-methanesulfonylamino-phenyl)-ethyl]-amide,
- 5-(3-Cyclopropyl-phenyl)-furan-2-carboxylic acid [1-(3,5-difluoro-4-methanesulfonylamino-phenyl)-ethyl]-amide,
- 5-(3-Trifluoromethyl-phenyl)-furan-2-carboxylic acid 3-ethynyl-5-fluoro-4-methanesulfonylamino-benzylamide,
- 5-(3-Trifluoromethyl-phenyl)-furan-2-carboxylic acid 3-fluoro-4-methanesulfonylamino-5-vinyl-benzylamide,
- 5-(3-Trifluoromethyl-phenyl)-furan-2-carboxylic acid [1-(3-fluoro-4-methanesulfonylamino-phenyl)-ethyl]-amide,
- 5-(3-Trifluoromethyl-5-vinyl-phenyl)-furan-2-carboxylic acid [1-(3,5-difluoro-4-methanesulfonylamino-phenyl)-ethyl]-amide,
- 5-(3-Ethyl-5-trifluoromethyl-phenyl)-furan-2-carboxylic acid [1-(3,5-difluoro-4-methanesulfonylamino-phenyl)-ethyl]-amide,
- 5-(2-Trifluoromethyl-phenyl)-furan-2-carboxylic acid [1-(3,5-difluoro-4-methanesulfonylamino-phenyl)-ethyl]-amide,
- (R)-5-(3-Trifluoromethyl-phenyl)-furan-2-carboxylic acid [1-(3,5-difluoro-4-methanesulfonylamino-phenyl)-ethyl]-amide,
- 5-(3,5-Bis-trifluoromethyl-phenyl)-furan-2-carboxylic acid [1-(3,5-difluoro-4-methanesulfonylamino-phenyl)-ethyl]-amide, and
- 5-(4-Fluoro-3-trifluoromethyl-phenyl)-furan-2-carboxylic acid [1-(3,5-difluoro-4-methanesulfonylamino-phenyl)-ethyl]-amide.

27. A pharmaceutical composition comprising the compound according to claim 1, an enantiomer thereof, or a pharmaceutically acceptable salt thereof, as an active ingredient and a pharmaceutically acceptable carrier.

28. A method for treating a condition selected from the group consisting of pain, inflammatory disease of the joints, neuropathies, HIV related neuropathy, nerve injury, neurodegeneration, stroke, urinary bladder hypersensitivity including urinary incontinence, cystitis, stomach duodenal ulcer, irritable bowel syndrome (IBS), inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases, hair growth-related disorders, rhinitis, and pancreatitis, comprising administering a compound according to claim 1 to a subject in need thereof.

29. The method according to claim 28, wherein the pain is a condition selected from the group consisting of osteoarthritis, rheumatoid arthritis, ankylosing spondylitis, diabetic neuropathic pain, post-operative pain, dental pain, non-inflammatory musculoskeletal pain including fibromyalgia, myofascial pain syndrome and back pain, visceral pain, migraine, and other types of headaches.

* * * * *